(12) United States Patent
Lee et al.

(10) Patent No.: US 7,514,257 B2
(45) Date of Patent: Apr. 7, 2009

(54) ZINC FINGER TRANSCRIPTION FACTOR DIFFERENTIATION PROTEINS

(75) Inventors: Dong-Ki Lee, Daejeon (KR); Yangsoon Lee, Daejeon (KR); Jin-Soo Kim, Daejeon (KR)

(73) Assignee: ToolGen, Inc. (KR)

( * ) Notice: Subject to any disclaimer, the term of this patent is extended or adjusted under 35 U.S.C. 154(b) by 712 days.

(21) Appl. No.: 10/669,861

(22) Filed: Sep. 24, 2003

(65) Prior Publication Data

US 2004/0209277 A1 Oct. 21, 2004

Related U.S. Application Data

(63) Continuation-in-part of application No. 10/314,669, filed on Dec. 9, 2002, now abandoned.

(60) Provisional application No. 60/338,441, filed on Dec. 7, 2001, provisional application No. 60/376,053, filed on Apr. 26, 2002, provisional application No. 60/400,904, filed on Aug. 2, 2002, provisional application No. 60/401,089, filed on Aug. 5, 2002.

(51) Int. Cl.
*C12N 5/10* (2006.01)
*C12N 5/16* (2006.01)
*C12N 5/18* (2006.01)
*C07K 14/435* (2006.01)

(52) U.S. Cl. .................. 435/325; 435/354; 530/350

(58) Field of Classification Search ............. None
See application file for complete search history.

(56) References Cited

U.S. PATENT DOCUMENTS

| | | | |
|---|---|---|---|
| 5,773,583 A | 6/1998 | Sukhatme | |
| 5,789,538 A | 8/1998 | Rebar et al. | |
| 5,866,325 A | 2/1999 | Sukhatme | |
| 5,882,941 A | 3/1999 | Essigmann et al. | |
| 6,007,988 A | 12/1999 | Choo et al. | |
| 6,013,453 A | 1/2000 | Choo et al. | |
| 6,107,059 A | 8/2000 | Hart | |
| 6,140,466 A | 10/2000 | Barbas et al. | |
| 6,242,568 B1 | 6/2001 | Barbas, III et al. | |
| 6,326,166 B1 | 12/2001 | Pomerantz et al. | |
| 6,453,242 B1 | 9/2002 | Eisenberg et al. | |
| 6,492,117 B1 | 12/2002 | Choo et al. | |
| 6,503,717 B2 | 1/2003 | Case et al. | |
| 6,511,808 B2 | 1/2003 | Wolffe et al. | |
| 6,534,261 B1 | 3/2003 | Cox et al. | |
| 6,599,692 B1 | 7/2003 | Case et al. | |
| 6,607,882 B1 | 8/2003 | Cox, III et al. | |
| 6,689,558 B2 | 2/2004 | Case | |
| 6,824,978 B1 | 11/2004 | Cox, III et al. | |
| 2002/0045158 A1 | 4/2002 | Case | |
| 2002/0061512 A1 | 5/2002 | Kim et al. | |
| 2002/0081614 A1 | 6/2002 | Case et al. | |
| 2002/0164575 A1 | 11/2002 | Case et al. | |
| 2002/0173006 A1 | 11/2002 | Kim et al. | |
| 2003/0021776 A1 | 1/2003 | Rebar et al. | |
| 2003/0044404 A1 | 3/2003 | Rebar et al. | |
| 2003/0044787 A1 | 3/2003 | Joung et al. | |
| 2003/0059767 A1 | 3/2003 | Barbas et al. | |
| 2003/0165997 A1 | 9/2003 | Kim et al. | |
| 2003/0166131 A1 | 9/2003 | Case et al. | |
| 2003/0194727 A1 | 10/2003 | Kim et al. | |
| 2004/0204345 A1 | 10/2004 | Cox, III et al. | |
| 2004/0209277 A1 | 10/2004 | Lee et al. | |
| 2004/0214766 A1 | 10/2004 | Alitalo et al. | |
| 2005/0130304 A1 | 6/2005 | Cox, III et al. | |
| 2005/0215502 A1 | 9/2005 | Cox, III et al. | |
| 2005/0239203 A1 | 10/2005 | Case et al. | |

FOREIGN PATENT DOCUMENTS

| | | |
|---|---|---|
| WO | WO 01/40798 | 6/2001 |
| WO | WO 01/59450 | 8/2001 |

OTHER PUBLICATIONS

GenBank Accession No. BAA31413, GI: 3298249, Feb. 13, 1999.*
GenBank Accession No. AAS67595, GI: 45548943, Nov. 30, 2004.*
GenBank Accession No. P17022, GI: 85681864, Feb. 7, 2006.*
Guo et al. Molecular cloning and expression analysis of a novel human gene ZNF18, Yi Chuan, vol. 27, No. 4, pp. 523-530, Jul. 2005, Abstract Only.*
Bellefroid et al. X-MyT1, a Xenopus C2HC-type zinc finger protein with a regulatory function in neuronal differentiation. Cell. vol. 87, No. 7, pp. 1191-1202, Dec. 1996.*
Lamar et al. Identification of NKL, a novel Gli-Kruppel zinc-finger protein that promotes neuronal differentiation. Development. vol. 128, No. 8, pp. 1335-1346, Apr. 15, 2001.*
Klein et al. klumpfuss, a Drosophila gene encoding a member of the EGR family of transcription factors, is involved in bristle and leg development. Development. vol. 124, No. 16, pp. 3123-3134, Aug. 1997.*
Dreyer et al. LMX1B transactivation and expression in nail-patella syndrome. Human Molecular Genetics, vol. 9, No. 7, pp. 1067-1074, 2000.*
Curtiss et al. DeLIMiting development. BioEssays, vol. 20, pp. 58-69, 1998.*
Cross et al. FGF and VEGF funciton in angiogenesis: signalling pathways, biological responses and therapeutic inhibition. Trends in Pharmacological Sciences, vol. 22, No. 4, Apr. 2001.*

(Continued)

*Primary Examiner*—Celine X Qian
*Assistant Examiner*—Jennifer Dunston
(74) *Attorney, Agent, or Firm*—Fish & Richardson P.C.

(57) ABSTRACT

The disclosure describes artificial chimeric transcription factors that include at least one zinc finger domain and that can regulate cellular differentiation, for example, a neuronal cell phenotype or an osteoblast phenotype.

15 Claims, 27 Drawing Sheets

OTHER PUBLICATIONS

Liu et al. Design of polydactyl zinc-finger proteins for unique addressing within complex genomes. PNAS, vol. 94, pp. 5525-5530, May 1997.*

Ansari, (Mar. 2003) "Fingers reach for the genome," Nat. Biotechnology, 21:242-43.

Bae et al., (Feb. 2003) "Human zinc fingers as building blocks in the construction of artificial transcription factors," Nat. Biotechnology, Epub doi:10.1038/nbt796, pp. 1-6.

Beerli et al., (1998) "Toward controlling gene expression at will: Specific regulation of the erbB-2/HER-2 promoter by using polydactyl zinc finger proteins constructed from modular building blocks", Proc. Natl. Acad. Sci. USA 95:14628-14633.

Beerli et al. (2000) "Positive and negative regulation of endogenous genes by designed transcription factors,"Proc. Nat. Acad. U.S.A. 97:1495-1500.

Desjarlais et al., (1993) "Use of a Zinc-finger Consensus Sequence Framework and Specificity Rules to Design Specific DNA Binding Proteins," Proc. Natl. Acad. Sci. USA, 90:2256-2260.

Liang et al. (2002) J Biol Chem. 277(22):20087-94. Epub Mar. 23, 2002.

Liu et al. (2001) J Biol Chem. 276(14):11323-34. Epub Jan. 5, 2001.

Wilson et al. (1993) "A genetic method for defining DNA-binding domains: application to the nuclear receptor NGFI-B" Proc. Natl. Acad. Sci. USA 90:9186.

Bartsevich & Juliano, "Regulation of the MDR1 gene by transcriptional repressors selected using peptide combinatorial libraries", Mol. Pharmacol. 58:1-10 (2000).

Beerli et al. (2000) "Chemically Regulated Zinc Finger Transcription Factors," The Journal of Biological Chemistry, 275(42):32617-32627.

Brent & Ptashne, "A eukaryotic transcriptional activator bearing the DNA specificity of a prokaryotic repressor", Cell 43:729-736 (1985).

Chevray & Nathans, "Protein interaction cloning in yeast: Identification of mammalian proteins that react with the leucine zipper of Jun", Proc. Natl. Acad. Sci. 89:5789-5793 (1992).

Choo & Klug, "Physical basis of a protein-DNA recognition code", Curr. Opin. Struct. Biol. 7:117-125 (1997).

Chrast et al. (2000) "Mice trisomic for a bacterial artificial chromosome with the single-minded 2 gene (Sim2) show phenotypes similar to some of those present in the partial trisomy 16 mouse models of Down syndrome," Human Molecular Genetics, 9(12):1853-1864.

Corbi et al. (2000) "The artificial zinc finger coding gene 'Jazz' binds the utrophin promoter and activates transcription," Gene Therapy, 7(12):1076-1083.

Desjarlais & Berg, "Length-encoded multiplex binding site determination: Application to zinc finger proteins", Proc. Natl. Acad Sci. 91:11099-11103 (1994).

Dreier et al., "Development of zinc finger domains for recognition of the 5'-ANN-3' family of DNA sequences and their use in the construction of artificial transcription factors", J. Biol. Chem. 276:29466-29478 (2001).

Elrod-Erickson et al., "High-resolution structures of variant Zif268-DNA complexes: implications for understanding zinc finger-DNA recognition", Structure 6:451-464 (1998).

Gogos et al., "Recognition of diverse sequences by class I zinc fingers: Asymmetries and indirect effects on specificity in the interaction between CF2II and A+T-rich sequence elements", Proc. Natl. Acad. Sci. USA 93:2159-2164 (1996).

Higashi et al. (2002) "The p53-activated Gene, PAG608, Requires a Zinc Finger Domain for Nuclear Localization and Oxidative Stress-induced Apoptosis," The Journal of Biological Chemistry, 277(44):42224-42232.

Hsu et al., "Multiple zinc finger forms resulting from developmentally regulated alternative splicing of a transcription factor gene", Science 257:1946-1950 (1992).

Hudson, Jr. et al., "The complete set of predicted genes from Saccharomyces cerevisiae in a readily usable form", Genome Res. 7:1169-1173 (1997).

Imanishi et al. (2000) "DNA-Bending Finger: Artificial Design of 6-Zinc Finger Peptides with Polyglycine Linker and Induction of DNA Bending," Biochemistry, 39(15):4383-4390.

Isalan et al., "A rapid, generally applicable method to engineer zinc fingers illustrated by targeting the HIV-1 promoter", Nat. Biotechnol. 19:656-660 (2001).

Jamieson et al., "In vitro selection of zinc fingers with altered DNA-binding specificity", Biochemistry 33:5689-5695 (1994).

Kamiuchi et al. (1998) "Artificial Nine Zinc-Finger Peptide with 30 Base Pair Binding Sites," Biochemistry, 37(39):13827-13834.

Lee et al (2000) "Efficient generation of midbrain and hindbrain neurons from mouse embryonic stem cells," Nat Biotech 18:675-679.

Liu et al., "Validated zinc finger protein designs for all 16 GNN DNA triplet targets", J. Biol. Chem. 277:3850-3856 (2002).

Niwa et al. (2000) "Quantitative expression of Oct-3/4 defines differentiation, dedifferentiation or selfl-renewal of ES cells," Nat Genet 24:372-376.

Pabo et al., "Design and selection of novel $Cys_2His_2$ zinc finger proteins", Annu. Rev. Biochem. 70:313-340 (2001).

Pavletich & Pabo, "Zinc finger-DNA recognition: Crystal structure of a Zif268-DNA complex at 2.1 Å", Science 252:809-817 (1991).

Phillips et al. (2000) "The Genetic Program of Hematopoietic Stem Cells," Science 288:1635-1640.

Ren et al., "PPARγ knockdown by engineered transcription factors: exogenous PPARγ2 but not PPARγ1 reactivates adipogenesis", Genes & Dev. 16:27-32 (2002).

Reubinoff et al. (2001) "Neural progenitors from human embryonic stem cells," Nat Biotech 19:1134-1140.

Segal et al., "Toward controlling gene expression at will: Selection and design of zinc finger domains recognizing each of the 5'-GNN-3' DNA target sequences", Proc. Natl. Acad. Sci. 96:2758-2763 (1999).

Sera & Uranga, "Rational design of artificial zinc-finger proteins using a nondegenerate recognition code table", Biochemistry 41:7074-7081 (2002).

Taylor et al., "Designing zinc-finger ADR1 mutants with altered specificity of DNA binding to T in UASI sequences", Biochemistry 34:3222-3230 (1995).

Wagner et al. (1999) "Induction of a midbrain dopaminergic phenotype in Nurr1-overexpressing neural stem cells by type 1 astrocytes," Nat Biotech 17:653-659.

Wang & Reed, "Molecular cloning of the olfactory neuronal transcription factor Olf-1 by genetic selection in yeast", Nature 364:121-126 (1993).

Wolfe et al., "Beyond the "recognition": Structures of two $Cys_2His_2$ zinc finger/TATA box complexes", Structure 8:717-723 (2001).

Wolfe et al., "Analysis of zinc fingers optimized via phage display: Evaluating the utility of a recognition code", J. Mol. Biol. 285:1917-1934 (1999).

Zhang et al., "Synthetic zinc finger transcription factor action at an endogenous chromosomal site: Activation of the human erythropoietin gene", J. Biol. Chem. 275:33850-33860 (2000).

Zhang et al. (2001) "In vitro differentiation of transplantable neural precursors from human embryonic stem cells," Nat Biotech 19:1129-1133.

\* cited by examiner

A partial directory of zinc finger-DNA interactions

| 3-bp sequence | zinc finger |
|---|---|
| GAA | QSNR |
| GAC | CSNR |
| GAG | RSNR |
| GAT | ISNR |
| GCA | QSSR |
| GCC | - |
| GCG | RDER |
| GCT | VSTR |

FIG. 10A

NEURO1-P65 (ALSO CALLED 08_D1)
QSNR1-QSNK-CSNR1-p65

NUCLEIC ACID SEQUENCE
ATGGTGTACCCCTACGACGTGCCCGACTACGCCGAATTGCCTCCAAAAAAGAAGAGAAAGGTAGGG
ATCCgaattcccggggaaaaaccgTTTGAGTGTAAAGATTGCGGGAAAGCTTTCATTCAGAAGTCA
AACCTCATCAGACACCAGAGAACTCACaccggggaaaaaccgTACAAGTGTGAAGAATGTGGCAAA
GCTTTTACCCAATCCTCAAACCTTACTAAACATAAGAAAATTCATaccggggaaaaaccgTATAAA
TGTAAGCAATGTGGGAAAGCTTTTGGATGTCCCTCAAACCTTCGAAGGCATGGAAGGACTCACacc
ggtgaaaaagcggccgctaaattcTACCTGCCAGATACAGACGATCGTCACCGGATTGAGGAGAAA
CGTAAAAGGACATATGAGACCTTCAAGAGCATCATGAAGAAGAGTCCTTTCAGCGGACCCACCGAC
CCCCGGCCTCCACCTCGACGCATTGCTGTGCCTTCCCGCAGCTCAGCTTCTGTCCCCAAGCCAGCA
CCCCAGCCCTATCCCTTTACGTCATCCCTGAGCACCATCAACTATGATGAGTTTCCCACCATGGTG
TTTCCTTCTGGGCAGATCAGCCAGGCCTCGGCCTTGGCCCCGGCCCCTCCCCAAGTCCTGCCCCAG
GCTCCAGCCCCTGCCCCTGCTCCAGCCATGGTATCAGCTCTGGCCCAGGCCCCAGCCCCTGTCCCA
GTCCTAGCCCCAGGCCCTCCTCAGGCTGTGGCCCCACCTGCCCCCAAGCCCACCCAGGCTGGGGAA
GGAACGCTGTCAGAGGCCCTGCTGCAGCTGCAGTTTGATGATGAAGACCTGGGGGCCTTGCTTGGC
AACAGCACAGACCCAGCTGTGTTCACAGACCTGGCATCCGTCGACAACTCCGAGTTTCAGCAGCTG
CTGAACCAGGGCATACCTGTGGCCCCCCACACAACTGAGCCCATGCTGATGGAGTACCCTGAGGCT
ATAACTCGCCTAGTGACAGCCCAGAGGCCCCCCGACCCAGCTCCTGCTCCACTGGGGGCCCCGGGG
CTCCCCAATGGCCTCCTTTCAGGAGATGAAGACTTCTCCTCCATTGCGGACATGGACTTCTCAGCC
CTGCTGAGTCAG TAA (SEQ ID NO:1)

PROTEIN SEQUENCE
MVYPYDVPDYAELPPKKKRKVGIRIPGEKP*FECKDCGKAFIQKSNLIRHQRTHT*GEKP*YKCEECGK*
*AFTQSSNLTKHKKIHT*GEKP*YKCKQCGKAFGCPSNLRRHGRTHT*GEKAAAKFYLPDTDDRHRIEEK
RKRTYETFKSIMKKSPFSGPTDPRPPPRRIAVPSRSSASVPKPAPQPYPFTSSLSTINYDEFPTMV
FPSGQISQASALAPAPPQVLPQAPAPAPAPAMVSALAQAPAPVPVLAPGPPQAVAPPAPKPTQAGE
GTLSEALLQLQFDDEDLGALLGNSTDPAVFTDLASVDNSEFQQLLNQGIPVAPHTTEPMLMEYPEA
ITRLVTAQRPPDPAPAPLGAPGLPNGLLSGDEDFSSIADMDFSALLSQ (SEQ ID NO:2)

FIG. 14

OSTEO1-P65 (ALSO CALLED S045-15-D11 )
RDKR-QTHR1-VSTR-RDKR-p65

NUCLEIC ACID SEQUENCE
ATGGTGTACCCCTACGACGTGCCCGACTACGCCGAATTGCCTCCAAAAAAGAAGAGAAAGGTAGGG
ATCCgaattcccggggaaaaaccgTATGTATGCGATGTAGAGGGATGTACGTGGAAATTTGCCCGC
TCAGATAAGCTCAACAGACACAAGAAAAGGCACaccggggaaaaaccgTATGAGTGTCACGATTGC
GGAAAGTCCTTTAGGCAGAGCACCCACCTCACTCGGCACCGGAGGATCCACaccggggaaaaaccg
TATGAGTGTAATTACTGTGGAAAAACCTTTAGTGTGAGCTCAACCCTTATTAGACATCAGAGAATC
CACaccggggaaaaaccgTATGTATGCGATGTAGAGGGATGTACGTGGAAATTTGCCCGCTCAGAT
AAGCTCAACAGACACAAGAAAAGGCACaccggtgaaaaagcggccgctaaattcTACCTGCCAGAT
ACAGACGATCGTCACCGGATTGAGGAGAAACGTAAAAGGACATATGAGACCTTCAAGAGCATCATG
AAGAAGAGTCCTTTCAGCGGACCCACCGACCCCCGGCCTCCACCTCGACGCATTGCTGTGCCTTCC
CGCAGCTCAGCTTCTGTCCCCAAGCCAGCACCCCAGCCCTATCCCTTTACGTCATCCCTGAGCACC
ATCAACTATGATGAGTTTCCCACCATGGTGTTTCCTTCTGGGCAGATCAGCCAGGCCTCGGCCTTG
GCCCCGGCCCCTCCCCAAGTCCTGCCCCAGGCTCCAGCCCTGCCCCTGCTCCAGCCATGGTATCA
GCTCTGGCCCAGGCCCCAGCCCCTGTCCCAGTCCTAGCCCCAGGCCCTCCTCAGGCTGTGGCCCCA
CCTGCCCCCAAGCCCACCCAGGCTGGGGAAGGAACGCTGTCAGAGGCCCTGCTGCAGCTGCAGTTT
GATGATGAAGACCTGGGGGCCTTGCTTGGCAACAGCACAGACCCAGCTGTGTTCACAGACCTGGCA
TCCGTCGACAACTCCGAGTTTCAGCAGCTGCTGAACCAGGGCATACCTGTGGCCCCCCACACAACT
GAGCCCATGCTGATGGAGTACCCTGAGGCTATAACTCGCCTAGTGACAGCCCAGAGGCCCCCCGAC
CCAGCTCCTGCTCCACTGGGGGCCCCGGGGCTCCCCAATGGCCTCCTTTCAGGAGATGAAGACTTC
TCCTCCATTGCGGACATGGACTTCTCAGCCCTGCTGAGTCAG TAA (SEQ ID NO:3)

PROTEIN SEQUENCE
MVYPYDVPDYAELPPKKKRKVGIRIPGEKP*YVCDVEGCTWKFARSDKLNRHKKRH*TGEKP
*YECHDCGKSFRQSTHLTRHRRIH*TGEKP*YECNYCGKTFSVSSTLIRHQRIH*TGEKP*YVCD
VEGCTWKFARSDKLNRHKKRH*TGEKAAAKFYLPDTDDRHRIEEKRKRTYETFKSIMKKSP
FSGPTDPRPPPRRIAVPSRSSASVPKPAPQPYPFTSSLSTINYDEFPTMVFPSGQISQAS
ALAPAPPQVLPQAPAPAPAPAMVSALAQAPAPVPVLAPGPPQAVAPPAPKPTQAGEGTLS
EALLQLQFDDEDLGALLGNSTDPAVFTDLASVDNSEFQQLLNQGIPVAPHTTEPMLMEYP
EAITRLVTAQRPPDPAPAPLGAPGLPNGLLSGDEDFSSIADMDFSALLSQ (SEQ ID NO:4)

FIG. 15

08_D04_p65:
RSHR-RDHT-VSSR-p65

NUCLEIC ACID SEQUENCE
ATGGTGTACCCCTACGACGTGCCCGACTACGCCGAATTGCCTCCAAAAAAGAAGAGAAAGGTAGGG
ATCCgaattcccggggaaaaaccgTATAAGTGCATGGAGTGTGGGAAGGCTTTTAACCGCAGGTCA
CACCTCACACGGCACCAGCGGATTCACaccggggaaaaaccgTTCCAGTGTAAAACTTGTCAGCGA
AAGTTCTCCCGGTCCGACCACCTGAAGACCCACACCAGGACTCATaccggggaaaaaccgTATACA
TGTAAACAGTGTGGGAAAGCCTTCAGTGTTTCCAGTTCCCTTCGAAGACATGAAACCACTCACacc
ggtgaaaaagcggccgctaaattcTACCTGCCAGATACAGACGATCGTCACCGGATTGAGGAGAAA
CGTAAAAGGACATATGAGACCTTCAAGAGCATCATGAAGAAGAGTCCTTTCAGCGGACCCACCGAC
CCCCGGCCTCCACCTCGACGCATTGCTGTGCCTTCCCGCAGCTCAGCTTCTGTCCCCAAGCCAGCA
CCCCAGCCCTATCCCTTTACGTCATCCCTGAGCACCATCAACTATGATGAGTTTCCCACCATGGTG
TTTCCTTCTGGGCAGATCAGCCAGGCCTCGGCCTTGGCCCCGGCCCCTCCCCAAGTCCTGCCCCAG
GCTCCAGCCCCTGCCCCTGCTCCAGCCATGGTATCAGCTCTGGCCCAGGCCCCAGCCCCTGTCCCA
GTCCTAGCCCCAGGCCCTCCTCAGGCTGTGGCCCCACCTGCCCCCAAGCCCACCCAGGCTGGGGAA
GGAACGCTGTCAGAGGCCCTGCTGCAGCTGCAGTTTGATGATGAAGACCTGGGGGCCTTGCTTGGC
AACAGCACAGACCCAGCTGTGTTCACAGACCTGGCATCCGTCGACAACTCCGAGTTTCAGCAGCTG
CTGAACCAGGGCATACCTGTGGCCCCCCACACAACTGAGCCCATGCTGATGGAGTACCCTGAGGCT
ATAACTCGCCTAGTGACAGCCCAGAGGCCCCCCGACCCAGCTCCTGCTCCACTGGGGGCCCCGGGG
CTCCCCAATGGCCTCCTTTCAGGAGATGAAGACTTCTCCTCCATTGCGGACATGGACTTCTCAGCC
CTGCTGAGTCAG TAA (SEQ ID NO:5)

PROTEIN SEQUENCE
MVYPYDVPDYAELPPKKKRKVGIRIPGEKP*YKCMECGKAFNRRSHLTRHQRIHT*GEKP*FQCKTCQR*
*KFSRSDHLKTHTRTHT*GEKP*YTCKQCGKAFSVSSSLRRHETTHT*GEKAAAKF*YLPDTDDRHRIEEK
RKRTYETFKSIMKKSPFSGPTDPRPPPRRIAVPSRSSASVPKPAPQPYPFTSSLSTINYDEFPTMV
FPSGQISQASALAPAPPQVLPQAPAPAPAPAMVSALAQAPAPVPVLAPGPPQAVAPPAPKPTQAGE
GTLSEALLQLQFDDEDLGALLGNSTDPAVFTDLASVDNSEFQQLLNQGIPVAPHTTEPMLMEYPEA
ITRLVTAQRPPDPAPAPLGAPGLPNGLLSGDEDFSSIADMDFSALLSQ (SEQ ID NO:6)

FIG. 16

Name: P_B08
QSNR1-DSNR-DSNR-p65

NUCLEIC ACID SEQENCE
ATGGTGTACCCCTACGACGTGCCCGACTACGCCGAATTGCCTCCAAAAAAGAAGAGAAAGGTAGGG
ATCCgaattcccggggaaaaaccgTTTGAGTGTAAAGATTGCGGGAAAGCTTTCATTCAGAAGTCA
AACCTCATCAGACACCAGAGAACTCACaccggggaaaaaccgTATGCTTGCCCTGTCGAGTCCTGC
GATCGCCGCTTTTCTGATTCGTCGAACCTTACCCGCCATATCCGCATCCACaccggggaaaaaccg
TATGCTTGCCCTGTCGAGTCCTGCGATCGCCGCTTTTCTGATTCGTCGAACCTTACCCGCCATATC
CGCATCCACaccggtgaaaaagcggccgctaaattcTACCTGCCAGATACAGACGATCGTCACCGG
ATTGAGGAGAAACGTAAAAGGACATATGAGACCTTCAAGAGCATCATGAAGAAGAGTCCTTTCAGC
GGACCCACCGACCCCCGGCCTCCACCTCGACGCATTGCTGTGCCTTCCCGCAGCTCAGCTTCTGTC
CCCAAGCCAGCACCCCAGCCCTATCCCTTTACGTCATCCCTGAGCACCATCAACTATGATGAGTTT
CCCACCATGGTGTTTCCTTCTGGGCAGATCAGCCAGGCCTCGGCCTTGGCCCCGGCCCCTCCCCAA
GTCCTGCCCCAGGCTCCAGCCCCTGCCCCTGCTCCAGCCATGGTATCAGCTCTGGCCCAGGCCCCA
GCCCCTGTCCCAGTCCTAGCCCCAGGCCCTCCTCAGGCTGTGGCCCCACCTGCCCCCAAGCCCACC
CAGGCTGGGGAAGGAACGCTGTCAGAGGCCCTGCTGCAGCTGCAGTTTGATGATGAAGACCTGGGG
GCCTTGCTTGGCAACAGCACAGACCCAGCTGTGTTCACAGACCTGGCATCCGTCGACAACTCCGAG
TTTCAGCAGCTGCTGAACCAGGGCATACCTGTGGCCCCCCACACAACTGAGCCCATGCTGATGGAG
TACCCTGAGGCTATAACTCGCCTAGTGACAGCCCAGAGGCCCCCCGACCCAGCTCCTGCTCCACTG
GGGGCCCCGGGGCTCCCCAATGGCCTCCTTTCAGGAGATGAAGACTTCTCCTCCATTGCGGACATG
GACTTCTCAGCCCTGCTGAGTCAG TAA (SEQ ID NO:7)

PROTEIN SEQUENCE
MVYPYDVPDYAELPPKKKRKVGIRIPGEKPFECKDCGKAFIQKSNLIRHQRTHTGEKPYACPVESC
DRRFSDSSNLTRHIRIHTGEKPYACPVESCDRRFSDSSNLTRHIRIHTGEKAAAKFYLPDTDDRHR
IEEKRKRTYETFKSIMKKSPFSGPTDPRPPPRRIAVPSRSSASVPKPAPQPYPFTSSLSTINYDEF
PTMVFPSGQISQASALAPAPPQVLPQAPAPAPAPAMVSALAQAPAPVPVLAPGPPQAVAPPAPKPT
QAGEGTLSEALLQLQFDDEDLGALLGNSTDPAVFTDLASVDNSEFQQLLNQGIPVAPHTTEPMLME
YPEAITRLVTAQRPPDPAPAPLGAPGLPNGLLSGDEDFSSIADMDFSALLSQ (SEQ ID NO:8)

FIG. 17

Name: K_D10

QSHV-WSNR-WSNR-RDNQ-kid

NUCLEIC ACID SEQUENCE

ATGGTGTACCCCTACGACGTGCCCGACTACGCCGAATTGCCTCCAAAAAAGAAGAGAAAGGTAGGG
ATCCgaattcccggggaaaaaccgTATGAGTGTGATCACTGTGGAAAATCCTTTAGCCAGAGCTCT
CATCTGAATGTGCACAAAAGAACTCACaccggggaaaaaccgTACAGATGTGAGGAATGTGGCAAA
GCCTTTAGGTGGCCCTCAAACCTTACTAGACATAAGAGAATTCACaccggggaaaaaccgTACAGA
TGTGAGGAATGTGGCAAAGCCTTTAGGTGGCCCTCAAACCTTACTAGACATAAGAGAATTCACacc
ggggaaaaaccgTTTGCCTGCCCTGAGTGTCCTAAGCGCTTCATGAGATCCGACAACCTGACCCAG
CATATCAAGACCCACaccggtgaaaaagcggccgctaaattcGTGTCAGTGACATTTGAAGATGTG
GCTGTGCTCTTTACTCGGGACGAGTGGAAGAAGCTGGATCTGTCTCAGAGAAGCCTGTACCGTGAG
GTGATGCTGGAGAATTACAGCAACCTGGCCTCCATGGCAGGATTCCTGTTTACCAAACCAAAGGTG
ATCTCCCTGTTGCAGCAAGGAGAGGATCCCTGGTAA (SEQ ID NO:9)

PROTEIN SEQUENCE

MVYPYDVPDYAELPPKKKRKVGIRIPGEKPYECDHCGKSFSQSSHLNVHKRTHTGEKPYRCEECGK
AFRWPSNLTRHKRIHTGEKPYRCEECGKAFRWPSNLTRHKRIHTGEKPFACPECPKRFMRSDNLTQ
HIKTHTGEKAAAKFVSVTFEDVAVLFTRDEWKKLDLSQRSLYREVMLENYSNLASMAGFLFTKPKV
ISLLQQGEDPW (SEQ ID NO:10)

FIG. 18

Name: K_F02
DSAR2-RDKR-RDER1-QTHR1-kid

NUCLEIC ACID SEQUENCE
ATGGTGTACCCCTACGACGTGCCCGACTACGCCGAATTGCCTCCAAAAAAGAAGAGAAAGGTAGGG
ATCCgaattcccggggaaaaaccgTACTCCTGTGGCATTTGTGGCAAATCCTTCTCTGACTCCAGT
GCCAAAAGGAGACACTGCATTCTACACaccggggaaaaaccgTATGTATGCGATGTAGAGGGATGT
ACGTGGAAATTTGCCCGCTCAGATAAGCTCAACAGACACAAGAAAAGGCACaccggggaaaaaccg
TATGTATGCGATGTAGAGGGATGTACGTGGAAATTTGCCCGCTCAGATGAGCTCAACAGACACAAG
AAAAGGCACaccggggaaaaaccgTATGAGTGTCACGATTGCGGAAAGTCCTTTAGGCAGAGCACC
CACCTCACTCGGCACCGGAGGATCCACaccggtgaaaaagcggccgctaaattcGTGTCAGTGACA
TTTGAAGATGTGGCTGTGCTCTTTACTCGGGACGAGTGGAAGAAGCTGGATCTGTCTCAGAGAAGC
CTGTACCGTGAGGTGATGCTGGAGAATTACAGCAACCTGGCCTCCATGGCAGGATTCCTGTTTACC
AAACCAAAGGTGATCTCCCTGTTGCAGCAAGGAGAGGATCCCTGGTAA (SEQ ID NO:11)

PROTEIN SEQUENCE
MVYPYDVPDYAELPPKKKRKVGIRIPGEKPYSCGICGKSFSDSSAKRRHCILHTGEKPYVCDVEGC
TWKFARSDKLNRHKKRHTGEKPYVCDVEGCTWKFARSDELNRHKKRHTGEKPYECHDCGKSFRQST
HLTRHRRIHTGEKAAAKFVSVTFEDVAVLFTRDEWKKLDLSQRSLYREVMLENYSNLASMAGFLFT
KPKVISLLQQGEDPW (SEQ ID NO:12)

FIG. 19

Name: K 44_11_D01

QSHV-QSNI-QTHR1-CSNR1-KID

NUCLEIC ACID SEQUENCE

ATGGTGTACCCCTACGACGTGCCCGACTACGCCGAATTGCCTCCAAAAAAGAAGAGAAAGGTAGGG
ATCCgaattcccggggaaaaaccgTATGAGTGTGATCACTGTGGAAAATCCTTTAGCCAGAGCTCT
CATCTGAATGTGCACAAAAGAACTCACaccggggaaaaaccgTACATGTGCAGTGAGTGTGGGCGA
GGCTTCAGCCAGAAGTCAAACCTCATCATACACCAGAGGACACAccggggaaaaaccgTATGAG
TGTCACGATTGCGGAAAGTCCTTTAGGCAGAGCACCCACCTCACTCGGCACCGGAGGATCCACacc
ggggaaaaaccgTATAAATGTAAGCAATGTGGGAAAGCTTTTGGATGTCCCTCAAACCTTCGAAGG
CATGGAAGGACTCACaccggtgaaaaagcggccgctaaattcGTGTCAGTGACATTTGAAGATGTG
GCTGTGCTCTTTACTCGGGACGAGTGGAAGAAGCTGGATCTGTCTCAGAGAAGCCTGTACCGTGAG
GTGATGCTGGAGAATTACAGCAACCTGGCCTCCATGGCAGGATTCCTGTTTACCAAACCAAAGGTG
ATCTCCCTGTTGCAGCAAGGAGAGGATCCCTGGTAA (SEQ ID NO:13)

PROTEIN SEQUENCE

MVYPYDVPDYAELPPKKKRKVGIRIPGEKPYECDHCGKSFSQSSHLNVHKRTHTGEKPYMCSECGR
GFSQKSNLIIHQRTHTGEKPYECHDCGKSFRQSTHLTRHRRIHTGEKPYKCKQCGKAFGCPSNLRR
HGRTHTGEKAAAKFVSVTFEDVAVLFTRDEWKKLDLSQRSLYREVMLENYSNLASMAGFLFTKPKV
ISLLQQGEDPW (SEQ ID NO:14)

FIG. 20

Name: K 44_11_G12
QSHV-VSTR-RDNQ-QTHR1-kid

NUCLEIC ACID SEQUENCE
ATGGTGTACCCCTACGACGTGCCCGACTACGCCGAATTG CCTCCAAAAAAGAAGAGAA
AGGTA GGGATCCgaattcccggggaaaaaccgTATGAGTGTGATCACTGTGGAAAATCCTTTAGCC
AGAGCTCTCATCTGAATGTGCACAAAAGAACTCACaccggggaaaaaccgTATGAGTGTAATTA
CTGTGGAAAAACCTTTAGTGTGAGCTCAACCCTTATTAGACATCAGAGAATCCACaccggg
gaaaaaccgTTTGCCTGCCCTGAGTGTCCTAAGCGCTTCATGAGATCCGACAACCTGACCCA
GCATATCAAGACCCACaccggggaaaaaccgTATGAGTGTCACGATTGCGGAAAGTCCTTTAGG
CAGAGCACCCACCTCACTCGGCACCGGAGGATCCACaccggtgaaaaagcggccgctaaattcGTGTC
AGTGACATTTGAAGATGTGGCTGTGCTCTTTACTCGGGACGAGTGGAAGAAGCTGGATC
TGTCTCAGAGAAGCCTGTACCGTGAGGTGATGCTGGAGAATTACAGCAACCTGGCCTCC
ATGGCAGGATTCCTGTTTACCAAACCAAAGGTGATCTCCCTGTTGCAGCAAGGAGAGGA
TCCCTGGTAA (SEQ ID NO:15)

PROTEIN SEQUENCE
MVYPYDVPDYAELPPKKKRKVGIRIPGEKP YECDHCGKSFSQSSHLNVHKRTH TGEKP YECNYCGK
TFSVSSTLIRHQRIH TGEKP FACPECPKRFMRSDNLTQHIKTH TGEKP YECHDCGKSFRQSTHLTR
HRRIH TGEKAAAKF VSVTFEDVAVLFTRDEWKKLDLSQRSLYREVMLENYSNLASMAGFLFTKPKV
ISLLQQGEDPW (SEQ ID NO:16)

RDHT-RSHR-QSHR2-p65

NUCLEIC ACID SEQUENCE
ATGGTGTACCCCTACGACGTGCCCGACTACGCCGAATTG CCTCCAAAAAAGAAGAGAAAGGTA GGG
ATCCgaattcccggggaaaaaaccgTTCCAGTGTAAAACTTGTCAGCGAAAGTTCTCCCGGTCCGAC
CACCTGAAGACCCACACCAGGACTCATaccggggaaaaaaccgTATAAGTGCATGGAGTGTGGGAAG
GCTTTTAACCGCAGGTCACACCTCACACGGCACCAGCGGATTCACaccggggaaaaaaccgTATAAA
TGCGGCCAGTGTGGGAAGTTCTACTCGCAGGTCTCCCACCTCACCCGCCACCAGAAAATCCACacc
ggtgaaaaagcggccgctaaattcTACCTGCCAGATACAGACGATCGTCACCGGATTGAGGAGAAA
CGTAAAAGGACATATGAGACCTTCAAGAGCATCATGAAGAAGAGTCCTTTCAGCGGACCCACCGAC
CCCCGGCCTCCACCTCGACGCATTGCTGTGCCTTCCCGCAGCTCAGCTTCTGTCCCCAAGCCAGCA
CCCCAGCCCTATCCCTTTACGTCATCCCTGAGCACCATCAACTATGATGAGTTTCCCACCATGGTG
TTTCCTTCTGGGCAGATCAGCCAGGCCTCGGCCTTGGCCCCGGCCCCTCCCCAAGTCCTGCCCCAG
GCTCCAGCCCCTGCCCCTGCTCCAGCCATGGTATCAGCTCTGGCCCAGGCCCCAGCCCCTGTCCCA
GTCCTAGCCCCAGGCCCTCCTCAGGCTGTGGCCCCACCTGCCCCCAAGCCCACCCAGGCTGGGGAA
GGAACGCTGTCAGAGGCCCTGCTGCAGCTGCAGTTTGATGATGAAGACCTGGGGGCCTTGCTTGGC
AACAGCACAGACCCAGCTGTGTTCACAGACCTGGCATCCGTCGACAACTCCGAGTTTCAGCAGCTG
CTGAACCAGGGCATACCTGTGGCCCCCCACACAACTGAGCCCATGCTGATGGAGTACCCTGAGGCT
ATAACTCGCCTAGTGACAGCCCAGAGGCCCCCCGACCCAGCTCCTGCTCCACTGGGGGCCCCGGGG
CTCCCCAATGGCCTCCTTTCAGGAGATGAAGACTTCTCCTCCATTGCGGACATGGACTTCTCAGCC
CTGCTGAGTCAG TAA (SEQ ID NO:17)

PROTEIN SEQUENCE
MVYPYDVPDYAELPPKKKRKVGIRIPGEKP*FQCKTCQRKFSRSDHLKTHTRTHT*GEKP*YKCMECGK*
*AFNRRSHLTRHQRIHT*GEKP*YKCGQCGKFYSQVSHLTRHQKIHT*GEKAAAKFYLPDTDDRHRIEEK
RKRTYETFKSIMKKSPFSGPTDPRPPPRRIAVPSRSSASVPKPAPQPYPFTSSLSTINYDEFPTMV
FPSGQISQASALAPAPPQVLPQAPAPAPAPAMVSALAQAPAPVPVLAPGPPQAVAPPAPKPTQAGE
GTLSEALLQLQFDDEDLGALLGNSTDPAVFTDLASVDNSEFQQLLNQGIPVAPHTTEPMLMEYPEA
ITRLVTAQRPPDPAPAPLGAPGLPNGLLSGDEDFSSIADMDFSALLSQ (SEQ ID NO:18)

FIG. 22

F121_p65
QSHT-RSHR-RDHT-p65

NUCLEIC ACID SEQUENCE

ATGGTGTACCCCTACGACGTGCCCGACTACGCCGAATTGCCTCCAAAAAAGAAGAGAAAGGTAGGG
ATCCgaattcccggggaaaaaccgTACAAATGTGAAGAATGTGGCAAAGCCTTTAGGCAGTCCTCA
CACCTTACTACACATAAGATAATTCATaccggggaaaaaccgTATAAGTGCATGGAGTGTGGGAAG
GCTTTTAACCGCAGGTCACACCTCACACGGCACCAGCGGATTCACaccggggaaaaaccgTTCCAG
TGTAAAACTTGTCAGCGAAAGTTCTCCCGGTCCGACCACCTGAAGACCCACACCAGGACTCATacc
ggtgaaaaagcggccgctaaattcTACCTGCCAGATACAGACGATCGTCACCGGATTGAGGAGAAA
CGTAAAAGGACATATGAGACCTTCAAGAGCATCATGAAGAAGAGTCCTTTCAGCGGACCCACCGAC
CCCCGGCCTCCACCTCGACGCATTGCTGTGCCTTCCCGCAGCTCAGCTTCTGTCCCCAAGCCAGCA
CCCCAGCCCTATCCCTTTACGTCATCCCTGAGCACCATCAACTATGATGAGTTTCCCACCATGGTG
TTTCCTTCTGGGCAGATCAGCCAGGCCTCGGCCTTGGCCCCGGCCCCTCCCCAAGTCCTGCCCCAG
GCTCCAGCCCCTGCCCCTGCTCCAGCCATGGTATCAGCTCTGGCCCAGGCCCCAGCCCCTGTCCCA
GTCCTAGCCCCAGGCCCTCCTCAGGCTGTGGCCCCACCTGCCCCCAAGCCCACCCAGGCTGGGGAA
GGAACGCTGTCAGAGGCCCTGCTGCAGCTGCAGTTTGATGATGAAGACCTGGGGGCCTTGCTTGGC
AACAGCACAGACCCAGCTGTGTTCACAGACCTGGCATCCGTCGACAACTCCGAGTTTCAGCAGCTG
CTGAACCAGGGCATACCTGTGGCCCCCCACACAACTGAGCCCATGCTGATGGAGTACCCTGAGGCT
ATAACTCGCCTAGTGACAGCCCAGAGGCCCCCCGACCCAGCTCCTGCTCCACTGGGGGCCCCGGGG
CTCCCCAATGGCCTCCTTTCAGGAGATGAAGACTTCTCCTCCATTGCGGACATGGACTTCTCAGCC
CTGCTGAGTCAG TAA (SEQ ID NO:19)

PROTEIN SEQUENCE
MVYPYDVPDYAELPPKKKRKVGIRIPGEKP*YKCEECGKAFRQSSHLTTHKIIH*TGEKP*YKCMECGK
AFNRRSHLTRHQRIH*TGEKP*FQCKTCQRKFSRSDHLKTHTRTH*TGEKAAAKFYLPDTDDRHRIEEK
RKRTYETFKSIMKKSPFSGPTDPRPPPRRIAVPSRSSASVPKPAPQPYPFTSSLSTINYDEFPTMV
FPSGQISQASALAPAPPQVLPQAPAPAPAPAMVSALAQAPAPVPVLAPGPPQAVAPPAPKPTQAGE
GTLSEALLQLQFDDEDLGALLGNSTDPAVFTDLASVDNSEFQQLLNQGIPVAPHTTEPMLMEYPEA
ITRLVTAQRPPDPAPAPLGAPGLPNGLLSGDEDFSSIADMDFSALLSQ (SEQ ID NO:20)

RDHT-QSNV2-QTHR1-QFNR-kid

ATGGTGTACCCCTACGACGTGCCCGACTACGCCGAATTGCCTCCAAAAAAGAAGAGAAAGGTA
GGGATCCgaattcccgggggaaaaaccgTTCCAGTGTAAAACTTGTCAGCGAAAGTTCTCCCGG
TCCGACCACCTGAAGACCCACACCAGGACTCATaccggggaaaaaccgTATGTTTGCTCAAAA
TGTGGGAAAGCCTTCACTCAGAGTTCAAATCTGACTGTACATCAAAAAATCCACaccggggaa
aaaccgTATGAGTGTCACGATTGCGGAAAGTCCTTTAGGCAGAGCACCCACCTCACTCGGCAC
CGGAGGATCCACaccggggaaaaaccgTATAAGTGTCATCAATGTGGGAAAGCCTTTATTCAA
TCCTTTAACCTTCGAAGACATGAGAGAACTCACaccggtgaaaaagcggccgctaaattcGTG
TCAGTGACATTTGAAGATGTGGCTGTGCTCTTTACTCGGGACGAGTGGAAGAAGCTGGATCTG
TCTCAGAGAAGCCTGTACCGTGAGGTGATGCTGGAGAATTACAGCAACCTGGCCTCCATGGCA
GGATTCCTGTTTACCAAACCAAAGGTGATCTCCCTGTTGCAGCAAGGAGAGGATCCCTGGTAA
(SEQ ID NO:259)

MVYPYDVPDYAELPPKKKRKVGIRIPGEKP*FQCKTCQRKFSRSDHLKTHTRTH*TGEKP*YVCSK
CGKAFTQSSNLTVHQKIH*TGEKP*YECHDCGKSFRQSTHLTRHRRIH*TGEKP*YKCHQCGKAFIQ
SFNLRRHERTH*TGEKAAAKF*VSVTFEDVAVLFTRDEWKKLDLSQRSLYREVMLENYSNLASMA
GFLFTKPKVISLLQQGEDPW* (SEQ ID NO:260)

QSHV-QSSR1-QTHR1-kid

ATGGTGTACCCCTACGACGTGCCCGACTACGCCGAATTGCCTCCAAAAAAGAAGAGAAAGGTA
GGGATCCgaattcccggggaaaaaccgTATGAGTGTGATCACTGTGGAAAATCCTTTAGCCAG
AGCTCTCATCTGAATGTGCACAAAAGAACTCACaccggggaaaaaccgTATAAGTGCCCTGAT
TGTGGGAAGAGTTTTAGTCAGAGTTCCAGCCTCATTCGCCACCAGCGGACACAccggggaa
aaaccgTATGAGTGTCACGATTGCGGAAAGTCCTTTAGGCAGAGCACCCACCTCACTCGGCAC
CGGAGGATCCACaccggtgaaaaagcggccgctaaattcGTGTCAGTGACATTTGAAGATGTG
GCTGTGCTCTTTACTCGGGACGAGTGGAAGAAGCTGGATCTGTCTCAGAGAAGCCTGTACCGT
GAGGTGATGCTGGAGAATTACAGCAACCTGGCCTCCATGGCAGGATTCCTGTTTACCAAACCA
AAGGTGATCTCCCTGTTGCAGCAAGGAGAGGATCCCTGGTAA (SEQ ID NO:261)

MVYPYDVPDYAELPPKKKRKVGIRIPGEKPYECDHCGKSFSQSSHLNVHKRTHTGEKP
YKCPDCGKSFSQSSSLIRHQRTHTGEKPYECHDCGKSFRQSTHLTRHRRIHTGEKAAA
KFVSVTFEDVAVLFTRDEWKKLDLSQRSLYREVMLENYSNLASMAGFLFTKPKVISLL
QQGEDPW (SEQ ID NO:64)

FIG. 25

ZINC FINGER TRANSCRIPTION FACTOR DIFFERENTIATION PROTEINS

CROSS-REFERENCE TO RELATED APPLICATIONS

This application is a continuation-in-part of 10/314,669, now abandoned filed Dec. 9, 2002, which claims the benefit of priority of U.S. Ser. No. 60/338,441, filed Dec. 7, 2001; U.S. Ser. No. 60/376,053, filed Apr. 26, 2002; U.S. Ser. No. 60/400,904, filed Aug. 2, 2002; and U.S. Ser. No. 60/401,089, filed Aug. 5, 2002, the contents of each of which is hereby incorporated by reference in their entirety for all purposes.

BACKGROUND

Most genes are regulated at the transcriptional level by polypeptide transcription factors that bind to specific DNA sites within the gene, typically in promoter or enhancer regions. These proteins activate or repress transcriptional initiation by RNA polymerase at the promoter, thereby regulating expression of the target gene. Many transcription factors, both activators and repressors, include structurally distinct domains that have specific functions, such as DNA binding, dimerization, or interaction with the transcriptional machinery. The DNA binding portion of the transcription factor itself can be composed of independent structural domains that contact DNA. The three-dimensional structures of many DNA-binding domains, including zinc finger domains, homeodomains, and helix-turn-helix domains, have been determined from NMR and X-ray crystallographic data. Effector domains such as activation domains or repression domains retain their function when transferred to DNA-binding domains of heterologous transcription factors (Brent and Ptashne, (1985) *Cell* 43:729-36; Dawson et al., (1995) *Mol. Cell Biol.* 15:6923-31).

Artificial transcription factors can be produced that are chimeras of zinc finger domains. For example, WO 01/60970 (Kim et al.) describes methods for determining the specificity of zinc finger domains and for constructing artificial transcription factors that recognize particular target sites. One application for artificial transcription factors is to alter the expression of a particular target gene. Target sites are identified in the regulatory region of the target gene, and artificial transcription factors are engineered to recognize one or more of the target sites. When such artificial transcription factors are introduced into cells, they may bind to the corresponding target sites and modulate transcription. This strategy for controlling the expression of a target gene is sometimes referred to as the "target-driven" approach for identifying transcription factors.

SUMMARY

In one aspect, the invention features a method that includes: (1) providing a library of cells, the library comprising a plurality of cells that each have a heterologous nucleic acid that expresses an artificial, chimeric polypeptide comprising a first and a second binding domain, wherein the first and second binding domain are heterologous to each other, and the first and second binding domain of each member of the plurality differ from those of the other members of the plurality; and (2) identifying, from the library, a cell that has a trait that is altered relative to a reference cell. The binding domains can be, for example, independently folded modules, e.g., zinc finger domains. In many embodiments, the binding domains are DNA binding domain. Typically, the reference cell is a cell which does not include a library nucleic acid or which includes a control nucleic acid. The reference cell may be a parental cell from which the library of cells was made, or a derivative thereof.

The trait can be any detectable phenotype, e.g., a phenotype that can be observed, selected, inferred, and/or quantitated. As used herein, a chimeric protein includes at least two binding domains that are heterologous to each other. The two binding domains can be from different naturally occurring proteins. The two regions can also be from the same naturally occurring protein, but are positioned in a different configuration in the chimeric protein relative to the corresponding naturally occurring protein. In one embodiment, a naturally occurring sequence is a sequence whose sequence was determined on or before Dec. 7, 2001; Apr. 26, 2002; Aug. 2, 2002; Aug. 5, 2002, or Dec. 9, 2002. The sequences of a number of genomes, for example, were determined on or before these dates.

In many embodiments, the cell does not include a reporter gene. In other words, the cells can be screened without having, a priori, information about a target gene whose regulation is altered by expression of the chimeric polypeptide. In addition, the cell may include a reporter gene as an additional indicator of a marker that is related or unrelated to the trait. Likewise, one or more target genes may be known prior to the screening.

In another example, the trait is production of a compound (e.g., a natural or artificial compound. The compound can be an antibiotic, an anti-proliferative drug, an analgesic, a protein and so on.

In yet another example, the trait is resistance to an environmental condition, e.g., heavy metals, salinity, environmental toxins, biological toxins, pathogens, parasites, other environmental extremes (e.g., desiccation, heat, cold), and so forth. In a related example, the trait is stress resistance (e.g., to heat, cold, extreme pH, chemicals, such as ammonia, drugs, osmolarity, and ionizing radiation). In yet another example, the trait is drug resistance. The change in the trait can be in either direction, e.g., towards sensitivity or further resistance.

In yet another example, the cell is a plant, animal (e.g., mammalian), fungal, or bacterial cell. For mammals, the trait can be cell proliferation, production of a cytokine, hormone, or signaling molecule, activation of a cell signaling pathway, activation of a physiological pathway (e.g., glucose homeostasis, metabolism, obesity).

The DNA binding domains can be, for example, zinc finger domains. Typically, the first zinc finger domain varies among nucleic acids of the library, and the second zinc finger domain also varies among nucleic acids of the plurality. The nucleic acid can also express at least a third DNA binding domain, e.g., a third zinc finger domain.

The zinc finger domains of each expressed polypeptide can be identical to zinc finger domains from different naturally occurring proteins, or can be variants of naturally-occurring proteins, e.g., mutants at the DNA contacting positions. The naturally-occurring protein can be any eukaryotic zinc finger protein: for example, a fungal (e.g., yeast), plant, or animal protein (e.g., a mammalian protein, such as a human or murine protein). Each polypeptide can further include a third, fourth, fifth, and/or sixth zinc finger domain. Each zinc finger domain can be a mammalian, e.g., human zinc finger domain.

Optionally, the nucleic acids of the plurality of cells encode a sufficient number of different zinc finger domains to recognize at least 10, 20, 30, 40, or 50 different 3-base pair DNA sites. In one embodiment, the nucleic acids the nucleic acids of the plurality encode a sufficient number of different zinc finger domains to recognize no more than 30, 20, 10, or 5 different 3-base pair DNA sites.

The polypeptide expressed from each nucleic acid of the library of cells can also include a functional transcriptional regulatory domain, e.g., a transcription activation, repression domain methylation domain, acetylation domain, or deacetylation domain. Also many chimeric polypeptides are functional without fusion to a particular transcriptional regulatory domain. The nucleic acid encoding the polypeptide can be operably linked to a constitutive or inducible promoter.

The method can further include isolating the nucleic acid from the identified cell. The nucleic acid can be sequenced. The polypeptide encoded by the nucleic acid can be isolated. The method can further include identifying a nucleic acid binding site specifically recognized by the polypeptide. The binding site can be identified, e.g., by a computer string or profile search of a sequence database, particularly, a database of regulatory sequences or by selecting in vitro nucleic acids that bind to the polypeptide (e.g., SELEX). A computer database of nucleic acid sequences can be analyzed to identify occurrences of the identified nucleic acid binding site or sites similar to the identified binding site.

The method can include analyzing the expression of one or more endogenous genes or the level/activity of one or more endogenously expressed polypeptides in the identified cell, e.g., using mRNA profiling (e.g., using microarray analysis), 2-D gel electrophoresis, an array of protein ligands (e.g., antibodies), and/or mass spectroscopy. Also, a single or small number of genes or proteins can also be profiled. In one embodiment, the profile is compared to a database of reference profiles. In another embodiment, regulatory regions of genes whose expression is altered by expression of the identified chimeric polypeptide are compared to identify candidate sites that determine coordinate regulation that results directly or indirectly from expression of the chimeric polypeptide.

The method can also include cultivating the cell to exploit the altered trait. For example, if the altered trait is increased production of a metabolite, the method can include cultivating the cell to produce the metabolite. The cell can be the cell isolated from the library, or a cell into which the nucleic acid encoding the chimeric polypeptide has been re-introduced. Expression of the chimeric polypeptide can be tuned, e.g., using an inducible promoter, in order to finely vary the trait, or another conditional promoter (e.g., a cell type specific promoter). A cell containing the nucleic acid encoding the chimeric polypeptide can be introduced into an organism (e.g., ex vivo treatment), or used to make a transgenic organism.

In one embodiment, at least some library members encode proteins having different regulatory domains. For example, some library members can include an activation domain, and other members, an inhibitory domain. A particular combination of DNA binding domains, for example, may be represented in the library in one instance as a fusion to an activation domain, and in another instance as a fusion to a repression domain. In another example, some library members include an activation domain, whereas others do not have a regulatory domain.

The following are some exemplary phenotypes: expansion of stem cells populations (e.g., hematopoietic stem cells, neuronal stem cells, epidermal stem cells, or cord blood stem cells) and other cells having a limited ability to expand in vitro; inhibition of stem cell differentiations not differentiate; increased pluripotency of a cell (e.g., a differentiated cell or a stem cell); altered stress resistance (e.g., increased or decreased resistance to a condition such as heat, cold, extreme pH, chemicals such as ammonia which can be produced during cell culture, drugs, salt (osmality), ionizing irradiation, etc.); sensitivity to ionizing irradiation or a toxic agent (e.g., an anticancer drug cells), e.g., increased sensitivity in cancer cells; ability to support viral infection/replication (e.g., hepatitis C replication); ability to resist a pathogen, e.g., a virus, bacteria, or protist; enhancement of RNAi efficiency in cells; enhancing transfection efficiency; retardation or delay of the aging process in cells or organisms; growth in a serum-free, chemically-defined media, in the absence of added growth factors; reduction or elimination of inclusion body formation; and enhanced protein secretion in a cell.

Exemplary applications of these methods include: identifying essential genes in a pathogen (e.g., a pathogenic microbe), identifying genes (of the host or pathogen) required for pathogenesis of microbes, identifying targets of drug candidates, gene discovery in signal transduction pathways, microbial engineering and industrial biotechnology, increasing yield of metabolites of commercial interests, and modulating growth behavior (e.g. improving growth of a microorganism, or reducing growth of a cancer cell).

In another aspect, the invention features a cultured cell that includes (a) a gene (endogenous or exogenous) encoding a protein, and (b) an artificial transcription factor, wherein the cell produces the protein at a higher level than does an identical cell that comprises the gene but not the transcription factor, and wherein the transcription factor exerts its effect on production of the protein in a manner other than by binding to a regulatory region operably linked to the gene. The term "artificial" means not naturally-occurring. The term "gene" means a "coding sequence", either cDNA or genomic (i.e., with introns), and either endogenous or exogenous (transiently or stably transfected).

The artificial transcription factor can include a chimeric DNA binding domain that includes at least two, three, or four zinc finger domains. The artificial transcription factor can further include a regulatory domain (list of activation and repression domain in summary). At least one or two of the individual zinc finger domains may be naturally-occurring (e.g., mammalian, plant, or human). In one embodiment, all the zinc finger domains present are naturally occurring.

The artificial transcription factor can be encoded by a heterologous gene of the cell. The heterologous gene encoding the heterologous transcription factor can be regulated by an inducible promoter. The cell can further include at least a second artificial transcription factor.

For example, (i) the artificial transcription factor causes the cell or a culture cell lacking the first gene, but otherwise identical to produce a second protein encoded by a second gene operably linked to a regulatory region other than the regulatory region operably linked to the first gene at a higher level than does an identical cell including the second gene but not the transcription factor, and (ii) the transcription factor exerts its effect on production of the second protein in a manner other than by binding to a regulatory region operably linked to the second gene. In another example, (i) the cell further includes a second gene encoding a second protein, (ii) the cell produces the second protein at a higher level than does an identical cell including the second gene but not the transcription factor, and (iii) the transcription factor exerts its effect on production of the second protein in a manner other than by binding to a regulatory region operably linked to the second gene. The regulatory region operably linked to the first gene can be different from the regulatory region operably linked to the second gene.

The first and second transcription factors are selected from the group consisting of:
  a) a polypeptide including the amino acid sequence of SEQ ID NO:21 (FECKDCGKAFIQKSNLIRHQRTHT-GEKPYACPVESCDRRFSDSSNLTRHIRIHTGEKP YACPVESCDRRFSDSSNLTRHIRIH);
  b) a polypeptide including the amino acid sequence of SEQ ID NO:22 (SCGICGKSFSDSSAKRRHCILHTGEK-PYVCDVEGCTWKFARSDKLNRHKKRHTGEK PYVCDVEGCTWKFARSDELNRHKKRHT-GEKPYECHDCGKSFRQSTHLTRHRRIH)
  c) a polypeptide including the amino acid sequence of SEQ ID NO:23 (YECDHCGKSFSQSSHLNVHKRTHT-GEKPYRCEECGKAFRWPSNLTRHKRIHTGEKP YRCEECGKAFRWPSNLTRHKRIHTGEKP-FACPECPKRFMRSDNLTQHIKTH).

In another aspect, the invention features a method of producing a protein. The method includes providing a cell described herein (e.g., above); culturing the cell under conditions that permit production of the protein at a level higher (e.g., at least two, three, five, ten, or a hundred fold) than the level produced by an identical cell that includes the gene but not the transcription factor; detecting the protein produced by the cell and/or purifying the expressed protein from the cell and/or from a medium that surrounds the cell. The gene can be an endogenous or exogenous gene. An endogenous gene can be a naturally occurring gene or a gene that is genetically altered relative to a naturally-occurring gene (e.g., by insertion or modification of regulatory sequences). Examples of endogenous genes include genes encoding a hormone, a cell surface receptor, an antibody, a growth factor, an adhesion protein, a neurotransmitter, and an enzyme. An exogenous gene can be operably linked to a viral promoter, e.g., a CMV or adenovirus promoter. The cell can be a mammalian cell.

The method can further include introducing the cell into a subject. The method can further include formulating the purified protein with a pharmaceutically acceptable carrier.

The method can include one or more of the following features: the transcription factor is present in the cell in an amount effective to increase production of a luciferase marker protein encoded by a gene operably linked to a CMV promoter at least 1.1, or 2 fold; the transcription factor is present in the cell in an amount effective to increase production of a secreted alkaline phosphatase marker protein encoded by a gene operably linked to an SV40 promoter at least 2, 5, 7, 10 fold; the transcription factor directly alters the expression of a plurality of endogenous genes; the transcription factor alters the rate of division of the cell; the transcription factor competes for binding to a naturally-occurring DNA binding site specifically recognized by PB08, K_F02, or K_D10, and has a dissociation constant for a DNA site of less than 50 nM; the transcription factor specifically recognizes a DNA site that partially overlaps the DNA binding site specifically recognized by PB08, K_F02, or K_D10; the transcription factor includes two consecutive zinc finger domains that have motifs selected from the group consisting of: QSNR-DSNR; DSNR-DSNR; DSAR-RDKR; RDKR-RDER; RDER-QTHR; QSHV-WSNR; WSNR-WSNR; WSNR-RDNQ, QSNR-QSNK; QSNK-CSNR, wherein each four letter identifier identifies the amino acid present at the −1, +2, +3, and +6 DNA contacting residues of a zinc finger domain and non-DNA contacting residues may vary. In one embodiment, the non-DNA contacting residues are identical to a set of non-DNA contacting residues described herein, for example the following specific zinc finger domains QSNR1-DSNR; DSNR-DSNR; DSAR2-RDKR; RDKR-RDER1; RDER1-QTHR1; QSHV-WSNR; WSNR-WSNR; WSNR-RDNQ, QSNR1-QSNK; QSNK-CSNR1. It is also possible to use a transcription factor includes two consecutive zinc finger domains that are specific zinc finger domains described herein and that conform to the foregoing motifs. In one embodiment, the transcription factor includes the amino acid sequence of SEQ ID NO:21, 22, or 23.

The transcription factor can include an amino acid sequence that differs by 1 to 8 amino acid substitutions, insertions, or deletions of SEQ ID NO:21, 22, or 23. The substitution may be at a position other than a DNA contacting residue, e.g., between a metal coordinating cysteine and position −1. The substitutions can be conservative substitutions. The transcription factor includes an amino acid encoded by a nucleic acid sequence in FIGS. 17, 18, and 19.

In another example, the transcription factor includes one or more of the following three zinc finger domains (e.g., two or all three of following from N- to C terminus):

a) Cys-$X_{2-5}$-Cys-$X_3$-$X_a$-X-Gln-X-Ser-Asn-$X_b$-X-Arg-His-$X_{3-5}$-His; (SEQ ID NO: 24)

b) Cys-$X_{2-5}$-Cys-$X_3$-$X_a$-X-Asp-X-Ser-Asn-$X_b$-X-Arg-His-$X_{3-5}$-His; and (SEQ ID NO: 25)

c) Cys-$X_{2-5}$-Cys-$X_3$-$X_a$-X-Asp-X-Ser-Asn-$X_b$-X-Arg-His-$X_{3-5}$-His, (SEQ ID NO: 26)

e.g., with between one and three substitutions at the invariant positions.

In another example, the transcription factor includes at least one, two, three or all four of the following four zinc finger domains (in this order):

a) Cys-$X_{2-5}$-Cys-$X_3$-$X_a$-X-Asp-X-Ser-Ala-$X_b$-X-Arg-His-$X_{3-5}$-His; (SEQ ID NO: 27)

b) Cys-$X_{2-5}$-Cys-$X_3$-$X_a$-X-Arg-X-Asp-Lys-$X_b$-X-Arg-His-$X_{3-5}$-His; (SEQ ID NO: 28)

c) Cys-$X_{2-5}$-Cys-$X_3$-$X_a$-X-Arg-X-Asp-Glu-$X_b$-X-Arg-His-$X_{3-5}$-His; and (SEQ ID NO: 29)

d) Cys-$X_{2-5}$-Cys-$X_3$-$X_a$-X-Gln-X-Thr-His-$X_b$-X-Arg-His-$X_{3-5}$-His, (SEQ ID NO: 30)

e.g., with between one and three substitutions at the invariant positions.

In another example, the transcription factor at least one, two, three or all four of the following four zinc finger domains (in this order):

a) Cys-$X_{2-5}$-Cys-$X_3$-$X_a$-X-Gln-X-Ser-His-$X_b$-X-Val-His-$X_{3-5}$-His; (SEQ ID NO: 31)

b) Cys-$X_{2-5}$-Cys-$X_3$-$X_a$-X-Trp-X-Ser-Asn-$X_b$-X-Arg-His-$X_{3-5}$-His; (SEQ ID NO: 32)

c) Cys-$X_{2-5}$-Cys-$X_3$-$X_a$-X-Trp-X-Ser-Asn-$X_b$-X-Arg-His-$X_{3-5}$-His; and (SEQ ID NO: 33)

-continued d) Cys-X$_{2-5}$-Cys-X$_3$-X$_a$-X-Arg-X-Asp- (SEQ ID NO: 34)
   Asn-X$_b$-X-Lys-His-X$_{3-5}$-His, e.g., with between one and three substitutions at the invariant positions. In the above listings, X$_a$ is any amino acid, or optionally phenylalanine or tyrosine; and X$_b$ is any amino acid, or optionally, a hydrophobic amino acid.

In another aspect, the invention features a method of producing a target protein that includes expressing a nucleic acid encoding the target protein in a cell (e.g., in vitro or in vivo), wherein the cell includes a heterologous, artificial transcription factor that increase the amount of protein produced relative to a cell that does not include the heterologous transcription factor. In one embodiment, the heterologous transcription factor causes the increase by a mechanism other than by directly regulating transcription of the gene encoding the target protein. For example, the heterologous transcription factor does not bind to a transcriptional regulatory region that directly regulates the nucleic acid encoding the target gene. The transcription factor can be introduced into the cell as a protein or by introduction and transcription of a nucleic acid encoding it. The method can include other features described herein.

In still another aspect, the invention features a method of identifying a transcription factor. The method includes: providing a nucleic acid library that includes a plurality of nucleic acids, each encoding a different artificial transcription factor, each transcription factor including at least two zinc finger domains that are chimeric with respect to each other; introducing a member of the library into each of a plurality of cells; identifying a cell from the plurality that has enhanced production of a first target protein, wherein the first target protein is encoded by a gene operably linked to a first transcriptional regulatory sequence; and evaluating the ability of the member of the library to enhance production of a second target protein encoded by a gene operably linked to a second transcriptional regulatory sequence that is different from the first transcriptional regulatory sequence.

The method can include one or more of the following features: the first and second target proteins are the same; the cells into which the library members are introduced each includes the gene encoding the second target protein operably linked to the second transcriptional regulatory sequence; the cell is a eukaryotic cell; the first and/or second transcriptional regulatory sequences includes a viral regulatory sequence; the method further includes preparing a host cell that includes a gene encoding transcription factor encoded by a member of the library that enhances production of the first and the second target protein; the method further includes producing a third target protein, different from the first and second target protein from the host cell; and the evaluating includes evaluating the identified cell. The second or third target protein can be, for example, a secreted protein, e.g., erythropoietin, thrombopoietin, a growth factor, an interleukin, or a chemokine. In another example, the target protein is an enzyme, e.g., that catalyzes a reaction in a metabolite producing pathway. Other features described herein can also be included.

In a related aspect, the invention features a method of identifying a protein chimera. The method includes: providing a nucleic acid library that comprises a plurality of nucleic acids, each encoding a different artificial protein chimera that comprises at least two zinc finger domains; providing a test cell that produces a given level of a first target protein under a specific condition; wherein the first target protein is encoded by a gene operably linked to a first transcriptional regulatory sequence; introducing each member of the plurality into a replicate of the test cell to provide a plurality of transformed cells; identifying, from the plurality of transformed cells or progeny cells thereof, a cell that produces, under the specific condition, a level of the first target protein that differs from the given level; and evaluating the ability of the member of the library in the identified cell to enhance production of a second target protein, encoded by a gene operably linked to a second transcriptional regulatory sequence, different from the first transcriptional regulatory sequence. Other features described herein can also be included.

In another aspect, the invention features a host cell, whose genetic material includes: a heterologous gene that encodes an artificial transcription factor that increases production of a target protein encoded by a target gene at least 30% relative to an otherwise identical control host cell lacking the heterologous gene. In one embodiment, the transcription factor does not directly regulate transcription of the target protein. In another embodiment, the transcription factor directly regulates transcription of the target protein. The host cell can include a sequence or a reporter construct such as a sequence encoding lacZ, secreted alkaline phosphatase (SEAP), GFP, luciferase etc) operably linked to a promoter (e.g., a viral promoter). The cell can include other features described herein.

In another aspect, the invention features a host cell, whose genetic material includes a heterologous gene that encodes a polypeptide that includes at least two, three, or four zinc finger domains, binds to an naturally-occurring DNA site, e.g., with an equilibrium dissociation constant of less than 50 nM, and competes with PB08, K_F02, or K_D10 for binding to the naturally-occurring DNA binding site. The cell can include other features described herein.

In another aspect, the invention features a host cell, whose genetic material includes a first heterologous gene that encodes a target protein, and a second heterologous gene that encodes an artificial transcription factor that increases production of the target protein at least 30% relative to an otherwise identical control host cell lacking the second heterologous gene, wherein the transcription factor does not directly regulate transcription of the target protein. The cell can include other features described herein.

In still another aspect, the invention features an isolated polypeptide that includes: the sequence: X$_a$-X-Cys-X$_{2-5}$-Cys-X$_3$-X$_a$-X$_5$-X$_b$-X-Arg-His-X$_{3-5}$-His-X$_{1-6}$-X$_a$-X-Cys-X$_{2-5}$-Cys-X$_3$-X$_a$-X$_5$-X$_b$-X-Arg-His-X$_{3-5}$-His-X$_{1-6}$-X$_a$-X-Cys-X$_{2-5}$-Cys-X$_3$-X$_a$-X$_5$-X$_b$-X-Arg-His-X$_{3-5}$-His (SEQ ID NO:35), and that has one or more of the following effects when present at an effective concentration in a human 293 cell: a) increases expression of a gene encoding a luciferase operably linked to a CMV promoter at least 2 fold; b) increases expression of a gene encoding SEAP operably linked to a SV40 promoter at least 2 fold and c) increases or decreases the rate of cell division at least 50%.

In another aspect, the invention features a method of altering the differentiated state of a metazoan cell, the method including: expressing an artificial transcription factor in the cell in an amount effective to alter the differentiated state of the cell. In one embodiment, the differentiated state can be characterized by a neuronal phenotype (e.g., neurite extension, synapse formation, or neuronal marker expression) or an osteoblasts phenotype (e.g., osteoblasts marker expression). In one embodiment, the differentiated state is altered so as to increase the pluripotency of the cell, e.g., to make it less differentiated, e.g., functional as a stem cell or a precursor cell. In one embodiment, the differentiated state is altered from one differentiated state to another (e.g., from a myogenic cell state to an osteoblast state, from a neuronal state to a glial state, and so forth). In one embodiment, the artificial transcription factor induces neurite extension. The cell can be, for example, a stem cell, a neuronal cell, a neural crest cell, or a neuronal progenitor cell. The artificial transcription factor can be a transcription factor described herein, e.g., Neuro1-p65 or a Neuro1 related molecule (see below). The artificial transcription factor can compete for binding to a natural DNA binding site with Neuro1-p65. The artificial transcription factor may bind to the same site as Neuro1-p65 or a site that overlaps a DNA site bound by Neuro1-p65.

In another embodiment, the artificial transcription factor induces an osteoblasts-specific marker, e.g., in an initially non-osteoblast cell, e.g., a myoblast.

In another aspect, the invention features a method of identifying a transcription factor. The method includes: providing a nucleic acid library that includes a plurality of nucleic acids, each encoding a different artificial transcription factor, each transcription factor including at least two zinc finger domains; introducing a member of the library into each of a plurality of cells; and identifying a cell from the plurality that has an altered differentiated state. The method can include one or more of the following features: the cell is a stem cell; the cell is a neuronal cell, a neural crest cell, or a neuronal progenitor cell; and the differentiated state includes neuronal outgrowth or neurite formation. Other features can also be included.

In still another aspect, the invention features a method of identifying a plurality of transcription factors. The method includes: providing a nucleic acid library that includes a plurality of nucleic acids, each encoding a different artificial transcription factor, each transcription factor including at least two zinc finger domains; identifying a first member of the library which alters a given trait of a cell; and screening cells to identify a cell in which the given trait is further altered, wherein each screened cell expresses the transcription factor encoded by the first member of the library and a transcription factor encoded by second member of the same nucleic acid library or another nucleic acid library of artificial transcription factors. The method can include additional rounds of screening in the presence of the first and second transcription factors. In some cases, the method includes identifying a second member of the library that reverses the change in phenotypic state effected by the first member. The method can include other features described herein.

In another aspect, the invention features a method of preparing a modified cell, the method including providing a nucleic acid library that includes a plurality of nucleic acids, each encoding a different artificial transcription factor, each transcription factor including at least two zinc finger domains; identifying a first and a second member of the library which alters a given trait of a cell; and preparing a cell that can express first and second polypeptides, the first and second polypeptides being encoded respectively by the first and second identified library members. The method can also be extended to additional member, e.g., a third member. The method can further include evaluating the given trait for the prepared cell.

The method can further include one or more of the following features: the preparing includes introducing a first gene encoding the first polypeptide and a second gene encoding the second polypeptide into the cell; the first and second gene are components of the same nucleic acid; wherein the preparing includes fusing a first cell that includes a first gene encoding the first polypeptide to a second cell that includes a second gene encoding the second polypeptide; the given trait is production of a metabolite; the given trait is production of a target polypeptide; the production includes secretion. Other features described herein can also be used.

The following method relates to using viruses to screening organismal properties of a ZFP library. A method of identifying a transcription factor can include: providing a nucleic acid library that includes a plurality of nucleic acids, each encoding a different artificial transcription factor, each transcription factor including at least two zinc finger domains; packaging each member of the library into a virus or viral particle that infects mammalian cells to form a plurality of viruses or viral particles; introducing the plurality of viruses or viral particles into a plurality of non-human mammalian subjects; and identifying a subject from the plurality that has an altered phenotype. For example, each subject has a detectable disorder; the plurality of viruses or viral particles is divided into pools, and each pool is introduced into one of the subjects from the plurality of subjects; the plurality of viruses or viral particles includes separate samples, each sample having packaged within a single nucleic acid of the nucleic acid library, and a single sample is introduced into each subject.

In one aspect, the invention features a modified cell that includes a heterologous nucleic acid encoding an artificial transcription factor that confers stress resistance to the modified cell relative to a reference cell that is substantially identical to the modified cell and that lacks the heterologous nucleic acid and the artificial transcription factor. For example, the artificial transcription factor includes at least two zinc finger domains. One or more of the zinc finger domains can be naturally occurring, e.g., a naturally occurring domain in Table 1. In another embodiment, one or more of the zinc finger domains can include at least 17, 18, 19, 20, 21, 22, 23, 24, or 25 amino acids that are identical to a zinc finger domain sequence in Table 1 or are at least 70, 75, 80, 85, 90, or 95% identical to a zinc finger domain sequence in Table 1. For example, the DNA contacting residues can be among the identical amino acids. Exemplary artificial transcription factors include transcription factors that have one or more consecutive motifs as described herein, e.g., a thermotolerant or solvent tolerant protein described herein.

The modified cell can be a prokaryotic or eukaryotic cell. The stress resistance can include one or more the following traits: heat resistance, solvent resistance, heavy metal resistance, osmolarity resistance, resistance to extreme pH, chemical resistance, cold resistance, and resistance to a genotoxic agent, resistance to radioactivity. Stress resistance enables a resistant cell to survive or grow in a condition in which a non-resistant cell would die or fail to grow. For example, the modified cell can express the artificial transcription factor and resist stress to a greater extent than a substantially identical culture cell that lacks the artificial transcription factor. The invention also provides such artificial proteins, and proteins that alter sensitivity of the cell to a toxic agent relative to an identical cell that does not contain the nucleic acid.

In another aspect, the method includes a method of producing a cellular product. The method includes providing a modified cell that includes a heterologous nucleic acid encoding an artificial transcription factor; maintaining the modified cell under conditions in which the artificial transcription factor is produced; and recovering a product produced by the cultured cell, wherein the product is other than the artificial transcription factor. For example, the artificial transcription factor can confer stress resistance, or another property described herein, e.g., altered protein production, altered metabolite production, and so forth. For example, the artificial transcription factor includes at least two zinc finger domains. One or more of the zinc finger domains can be naturally occurring, e.g., a naturally occurring domain in Table 1. In another embodiment, one or more of the zinc finger domains can include at least 18, 19, 20, 21, 22, 23, 24, or 25 amino acids that are identical to a zinc finger domain sequence in Table 1 or are at least 70, 75, 80, 85, 90, or 95% identical to a zinc finger domain sequence in Table 1. Exemplary artificial transcription factors include transcription factors that have one or more consecutive motifs (e.g., at least two, three or four consecutive motifs, or at least three motifs in the same pattern, including non-consecutive patterns) as described herein.

Exemplary products include a metabolite or a protein (e.g., an endogenous or heterologous protein. For example, the modified cell includes a nucleic acid encoding a heterologous protein, other than the artificial transcription factor, and the product is the heterologous protein. In another example, the modified cell further includes a second nucleic acid encoding a heterologous protein, and the heterologous protein participates in production of the metabolite. The modified cell can be maintained at a temperature between 20° C. and 40° C. or greater than 37° C. In one embodiment, the modified cell is maintained under conditions which would inhibit the growth of a substantially identical cell that lacks the artificial transcription factor.

In one embodiment, the zinc finger domain includes a set of DNA contacting residues that correspond to DNA contacting residues of a zinc finger domain listed in Table 15. In a related embodiment, the artificial transcription factor includes an array of at least three zinc finger domains, wherein the DNA contacting residues of each of the zinc finger domains of the array correspond respectively to DNA contacting residues of any three consecutive zinc finger domains listed in a row of Table 15. In still another embodiment, the artificial transcription factor competes with a protein that includes the array of zinc finger domains listed in a row of Table 15.

In another aspect, the invention features a cell that contains a gene (e.g., an endogenous or heterologous gene) encoding a target protein and a heterologous nucleic acid that includes a sequence encoding an artificial protein chimera that (1) increases the amount of the protein produced by the cell relative to a cell that does not include the heterologous nucleic acid, and (2) does not bind to a transcriptional regulatory region that directly regulates transcription of the gene encoding the target protein. For example, the artificial transcription factor includes at least two zinc finger domains, and, e.g., binds DNA. One or more of the zinc finger domains can be naturally occurring, e.g., a naturally occurring domain in Table 1. In another embodiment, one or more of the zinc finger domains can include at least 18, 19, 20, 21, 22, 23, 24, or 25 amino acids that are identical to a zinc finger domain sequence in Table 1 or are at least 70, 75, 80, 85, 90, or 95% identical to a zinc finger domain sequence in Table 1. Exemplary artificial transcription factors include transcription factors that have one or more consecutive motifs as described herein, In one embodiment, the cell is a eukaryotic cell, and the artificial protein chimera competes with PB08, K_F02, or K_D10 for binding to a genomic DNA site.

In one embodiment, the artificial protein chimera alters (e.g., increases or decrease) the rate of cell cycle progression by the cell. The invention also provides such artificial transcription factors.

The cell can be used in a method of producing a protein, the method including: providing the cell, and maintaining the cell under conditions in which the artificial protein chimera increases the amount of the target protein produced by the cell relative to a cell that does not include the heterologous nucleic acid. For example, the protein is a secreted protein, a cytoplasmic protein, or a nuclear protein.

In another aspect, the invention features a cell that contains an endogenous gene encoding a secreted protein and a heterologous nucleic acid that includes a sequence encoding an artificial transcription factor that increases the amount of the secreted protein produced by the cell relative to a cell that does not include the heterologous nucleic acid. In one embodiment, the cell is a eukaryotic cell, and the secreted protein is insulin. In one embodiment, the artificial transcription factor specifically binds to an endogenous DNA site that is also specifically bound by 08_D04_p65. In another embodiment, the artificial transcription factor specifically binds to an endogenous DNA site and the artificial transcription factor competes with 08_D04_p65 for binding to the endogenous DNA site. For example, the artificial transcription factor includes an amino acid sequence as follows:

$CX_{(2-5)}CXXXBXRXSHJXRX_{(3-5)}HX_{(1-6)}$ (SEQ ID NO: 45)

$BXCX_{(2-5)}CXXXBXRXDHJXTHX_{(3-5)}H$; or $CX_{(2-5)}CXXXBXRXDHJXTHX_{(3-5)}HX_{(1-6)}$ (SEQ ID NO: 46)

$BXCX_{(2-5)}CXXXBXVXSSJXRHX_{(3-5)}H$ where B is phenylalanine or tyrosine; and J is a hydrophobic amino acid.

The cell can be used in a method of producing a secreted protein (e.g., insulin). For example, the cell is maintained under conditions in which the artificial transcription factor increases the amount of insulin produced by the cell relative to a cell that does not include the heterologous nucleic acid. Similarly, the invention provides an artificial transcription factor including at least two zinc finger domains, wherein the artificial transcription factor induces expression of an endogenous insulin gene in a mammalian cell that does not express an endogenous insulin gene in the absence of the artificial transcription factor.

In another aspect, the invention features an artificial transcription factor that alters sensitivity of the cell to a toxic agent (e.g., a drug, e.g., an anti-fungal drug, e.g., ketoconazole) relative to an identical cell that does not contain the nucleic acid. The sensitivity can be increased or decreased. In one embodiment, the cell is a fungal cell. For example, the artificial transcription factor includes at least two zinc finger domains, e.g., at least three. One or more of the zinc finger domains can be naturally occurring, e.g., a naturally occurring domain in Table 1. Exemplary artificial transcription factors include transcription factors that have one or more consecutive motifs as described herein. For example, the artificial transcription factor binds to an endogenous DNA site and the artificial transcription factor competes with a zinc finger protein listed in Table 5 for binding to the endogenous DNA site.

In another aspect, the invention features a method of altering the drug resistance of a fungal cell. The method includes altering the expression or activity of a protein that is at least 70% identical to AQY1, YJR147W, YLL052C, YLL053C, or YPL091W in the cell. The expression can be altered, e.g., using a transcription factor.

In still another aspect, the invention features a method of identifying an artificial chimeric protein that alters the sensitivity of a cell to a toxic agent, the method including: providing a nucleic acid library that includes a plurality of nucleic acids, each nucleic acid of the plurality encoding a chimeric protein that includes an array of at least three zinc finger domains wherein at least two adjacent zinc finger domains do not occur adjacent to each other in a naturally occurring protein; introducing members of the library into replicates of a test cell to yield transformed cells; cultivating the transformed cells in the presence of a toxic agent; and identifying, from the transformed cells, a cell whose sensitivity to the toxic agent is altered relative to the test cell. For example, the test cell is a fungal cell, and the toxic agent is an anti-fungal agent. In another example, the test cell is a cancer cell, and the toxic agent is an anti-mitotic agent. The chimeric protein encoded by each nucleic acid of the plurality can include a transcriptional regulatory domain.

The method can further include constructing a nucleic acid that encodes a second chimeric protein that includes the array of zinc finger domains of the chimeric protein encoded by the library member in the selected cell, but does not include the transcriptional regulatory domain of the chimeric protein encoded by the library member in the identified cell. The method can further include constructing a nucleic acid that encodes a second chimeric protein that includes (i) the array of zinc finger domains of the chimeric protein encoded by the library member in the selected cell, and (ii) a transcriptional regulatory domain, other than the transcriptional regulatory domain of the chimeric protein encoded by the library member in the identified cell.

In another aspect, the invention features a nucleic acid that includes a sequence encoding an artificial transcription factor including three zinc finger domains, wherein expression of the artificial transcription factor induces a neuronal phenotype in at least one vertebrate cell. In one example, at least one of the zinc finger domains has the sequence:

Cys-$X_{2-5}$-Cys-$X_{3-Xa}$-X-Gln-X-Ser- (SEQ ID NO: 250)
Asn-$X_b$-X-Arg-His-$X_{3-5}$-His

Cys-$X_{2-5}$-Cys-$X_3$-$X_a$-X-Gln-X-Ser- (SEQ ID NO: 251)
Asn-$X_b$-X-Lys-His-$X_{3-5}$-His; or

Cys-$X_{2-5}$-Cys-$X_3$-$X_a$-X-Cys-X-Ser- (SEQ ID NO: 252)
Asn-$X_b$-X-Arg-His-$X_{3-5}$-His, wherein $X_a$ is phenylalanine or tyrosine; and $X_b$ is a hydrophobic amino acid. For example, the artificial transcription factor includes the sequence: Cys-$X_{2-5}$-Cys-$X_3$-$X_a$-X-Gln-X-Ser-Asn-$X_b$-X-Arg-His-$X_{3-5}$-His-$X_{1-6}$-$X_a$-X-Cys-$X_{2-5}$-Cys-$X_3$-$X_a$-X-Gln-X-Ser-Asn-$X_b$-X-Lys-His-$X_{3-5}$-His-$X_{1-6}$-$X_a$-X-Cys-$X_{2-5}$-Cys-X3-$X_a$-X-Cys-X-Ser-Asn-$X_b$-X-Arg-His-$X_{3-5}$-His (SEQ ID NO:253), wherein $X_a$ is phenylalanine or tyrosine; and $X_b$ is a hydrophobic amino acid.

One method includes providing a vertebrate cell (e.g., a mammalian cell, a human) that contains the nucleic acid; and maintaining the vertebrate cell under conditions in which the artificial transcription factor is produced and neurite formation is induced. In one example, the vertebrate cell is a stem cell prior to production of the artificial transcription factor.

In another aspect, the invention features a nucleic acid that includes a sequence encoding an artificial transcription factor included of three zinc finger domains, wherein expression of the artificial transcription factor induces oosteogenesis in at least one vertebrate cell. For example, at least one of the zinc finger domains has the sequence:

Cys-$X_{2-5}$-Cys-$X_3$-Xa-X-Arg-X-Asp- (SEQ ID NO: 254)
Lys-$X_b$-X-Arg-His-$X_{3-5}$-His;

Cys-$X_{2-5}$-Cys-$X_3$-Xa-X-Gln-X-Thr- (SEQ ID NO: 255)
His-$X_b$-X-Arg-His-$X_{3-5}$-His;

Cys-$X_{2-5}$-Cys-$X_3$-Xa-X-Val-X-Ser- (SEQ ID NO: 256)
Thr-$X_b$-X-Arg-His-$X_{3-5}$-His; or

Cys-$X_{2-5}$-Cys-$X_3$-Xa-X-Arg-X-Asp- (SEQ ID NO: 257)
Lys-$X_b$-X-Arg-His-$X_{3-5}$-His, wherein $X_a$ is phenylalanine or tyrosine; and $X_b$ is a hydrophobic amino acid; or the artificial transcription factor includes the amino acid sequence:
CYS-$X_{2-5}$-CYS-$X_3$-$X_a$-X-Arg-X-Asp-Lys-$X_b$-X-Arg-His-$X_{3-5}$-His-$X_{1-6}$-$X_a$-X-CYS-$X_{2-5}$-Cys-$X_3$-$X_a$-X-Gln-X-Thr-His-$X_b$-X-Arg-His-$X_{3-5}$-His-$X_{1-6}$-$X_a$-X-Cys-$X_{2-5}$-Cys-$X_3$-$X_a$-X-Val-X-Ser-Thr-$X_b$-X-Arg-His-$X_{3-5}$-His-$X_{1-6}$-$X_a$-X-Cys-$X_{2-5}$-Cys-$X_3$-$X_a$-X-Arg-X-Asp-Lys-$X_b$-X-Arg-His-$X_{3-5}$-His (SEQ ID NO:258), wherein $X_a$ is phenylalanine or tyrosine; and $X_b$ is a hydrophobic amino acid.

One method includes providing a vertebrate cell that contains the nucleic acid; and maintaining the vertebrate cell under conditions in which the artificial transcription factor is produced and oosteogenesis is induced.

In another aspect, the invention features a method of altering the differentiative capacity of a stem cell. The method includes: providing a stem cell and a nucleic acid that includes a sequence encoding an artificial transcription factor includes of a plurality of zinc finger domains, wherein the artificial transcription factor alters the differentiative capacity of the stem cell; introducing the nucleic into the stem cell; and maintaining the stem cell under conditions in which the artificial transcription factor is produced thereby altering the differentiative capacity of the stem cell. For example, the artificial transcription factor induces differentiation of the stem cell. In another example, the artificial transcription factor enhances self-renewal potential of the stem cell. The stem cell can be an embryonic stem cell, a vertebrate stem cell, a plant stem cell, a hematopoietic stem cell, a neuronal progenitor cell or muscular progenitor cell.

In still another aspect, the invention features a method that includes: providing a nucleic acid library that includes a plurality of nucleic acids, each encoding a different artificial transcription factor, each artificial transcription including an array of at least two zinc finger domains and a regulatory domain that activates or represses transcription; providing cell that have a given trait; introducing members of the nucleic acid library into the cells; identifying a member of the library that alters the given trait; and preparing a coding nucleic acid that includes a sequence encoding a DNA binding polypeptide that includes the array of zinc finger domains from the identified member, but does not include a regulatory domain identical to the regulatory domain of the identified member. For example, the DNA binding polypeptide is lacks the regulatory domain of the identified member. In another example, the DNA binding polypeptide includes a regulatory domain that is mutated relative to the regulatory domain of the identified member. In one embodiment, the DNA binding polypeptide includes a regulatory domain of opposite functionality relative to the regulatory domain of the identified member.

The method can further include introducing the coding nucleic acid into a cell and assessing the given trait of the cell. The step of identifying can include identifying cells having a property selected from the group consisting of: resistance to a given environmental condition; differentiation; dedifferentiation; proliferation; apoptosis; serum-independence; pathogen resistance; and pathogen sensitivity.

In another aspect, the invention features an isolated nucleic acid encoding an artificial transcription factor that improves solubility of a heterologous, over-expressed protein in a cell that produces the artificial transcription factor. For example, the artificial transcription factor includes a plurality of zinc finger domains. The cell can be a bacterial cell or a eukaryotic cell. In one example, the protein is a mammalian protein, e.g., AKT protein. In one embodiment, the plurality of zinc finger domains include domains: QSTR-DSAR-RDHT-WSNR or VSTR-DGNV-QSNR-QSNK (where each set of four amino acids corresponds to the DNA contacting residues of a zinc finger domain and non-DNA contacting residues may vary). The invention also features a modified cell that includes a heterologous nucleic acid described herein. The invention also provides a method of producing a heterologous target protein. The method includes providing the modified cell wherein the modified cell includes a second nucleic acid that includes a sequence encoding a heterologous target protein; and maintaining the modified cell under conditions wherein the artificial transcription factor and the heterologous target protein are produced. The modified cell can be a cultured cell or an in vivo cell, e.g., in a subject.

In another aspect, the invention features a method of transferring an altered trait from a first cell to a second cell. The method includes: providing a nucleic acid library that includes a plurality of nucleic acids, each encoding a different artificial protein chimera that includes at least two zinc finger domains; introducing members of the nucleic acid library into first cells that have a given trait to provide transformed cells; identifying an altered cell from the transformed cells in which a member of the library alters the given trait; recovering a nucleic acid library member from the identified, altered cell; introducing the nucleic acid library member into second cells, wherein the second cells differ from the first cells by a phenotypic trait other than the given trait; and evaluating a second cell that includes the nucleic acid library member and expresses the artificial protein chimera that the nucleic acid library member encodes. For example, the first and second cells are eukaryotic, e.g., yeast cells or mammalian cells. The first and second cells can differ by the proliferative properties or differentiative properties. For example, the first cells are cancer cells, and the second cells are non-cancerous, or vice versa. The evaluated second cell can be evaluated for an alteration to the given trait.

In other aspects, the invention features a nucleic acid including a sequence encoding an artificial transcription factor included of three zinc finger domains. For example, expression of the artificial transcription factor alters a property of at least one eukaryotic cell, wherein the property is selected from the group consisting of viral replication, virus production, and viral infectivity; expression of the artificial transcription factor alters an ability of a eukaryotic cell to regulate a stem cell that is co-cultured with the eukaryotic cell or that is cultured in media conditioned by the eukaryotic cell; expression of the artificial transcription factor alters an ability of a mammalian culture cell (e.g., a CHO cell) to glycosylate a secreted protein (e.g., an antibody); and expression of the artificial transcription factor alters the ability of a cell to take up exogenous nucleic acid.

In still another aspect, the invention features a method of identifying a transcription factor. The method includes: providing a nucleic acid library that includes a plurality of nucleic acids, each encoding a different artificial transcription factor, each transcription factor including at least two zinc finger domains; introducing members of the nucleic acid library into cells that have a given trait; identifying a member of the library which alters the given trait; and preparing a second library that includes a plurality of nucleic acids, each encoding (1) a variant that differs from the artificial protein chimera corresponding to the identified member by between one and six amino acid substitutions, insertions, or deletions, (2) a protein chimera that comprises the zinc finger domains of the artificial protein chimera corresponding to the identified member and an additional zinc finger domain, wherein the additional zinc finger domain varies among the members of the second library, (3) a variant of the artificial protein chimera corresponding to the identified member, wherein the variant has a subset of the zinc finger domain positions replaced with other zinc finger domains and at least one invariant zinc finger domain that is identical to the zinc finger domain at a corresponding position in the artificial protein chimera corresponding to the identified member, and/or (4) a variant of the artificial protein chimera corresponding to the identified member, wherein, among the members of the second library, one or more zinc finger domain positions are varied such that the particular domain in the artificial protein chimera corresponding to the identified member at that position occurs at a frequency greater than other zinc finger domains at that position. The method can include other features described herein.

In another aspect, the invention features a method of identifying a transcription factor, the method includes: providing a nucleic acid library that includes a plurality of nucleic acids, each encoding a different artificial transcription factor, each transcription factor including a DNA binding component having at least two zinc finger domains and a first regulatory domain that activates or represses transcription; introducing members of the nucleic acid library into cells that have a given trait; identifying a member of the library which alters the given trait; and preparing a nucleic acid that encodes the DNA binding component of the identified member and a second regulatory domain that differs from the first regulatory domain. A related method includes identifying a transcription factor that lacks a regulatory domain, and adding one; or removing a regulatory domain from a transcription factor that includes one. Some transcription factors can function without a transcriptional regulatory domain. The invention also features an artificial transcription factor that comprises a plurality of zinc finger domains and a first regulatory domain. The artificial transcription factor produces a first trait when produced in a cell, but produces a second trait if the first regulatory domain is inactivated and a second regulatory domain, of opposite functionality from the first, is included.

In one example, the first regulatory domain activates transcription and the second regulatory domain represses transcription. In another example, the first regulatory domain represses transcription and the second regulatory domain activates transcription. In still another example, the first regulatory domain activates transcription to a first extent and the second regulatory domain activates transcription to an extent at least 50% less than the first extent. The method can further include introducing the prepared nucleic acid into a test cell and assessing the test cell, e.g., the given trait of the test cell. In one embodiment, the identified member increases the rate of cell division, and the prepared nucleic acid encodes a transcription factor that decreases the rate of cell division. In another embodiment, the identified member causes resistance to a compound, and the prepared nucleic acid encodes a transcription factor that causes sensitivity to the compound.

In still another aspect, the invention features a method of identifying a transcription factors, the method including: providing a nucleic acid library that includes first and second pluralities of nucleic acids, wherein each nucleic acid of the first plurality encodes a different artificial transcription factor that includes at least two zinc finger domains and a regulatory domain that activates transcription, and each nucleic acid of the second plurality encodes a different artificial transcription factor that includes at least two zinc finger domains and a regulatory domain that represses transcription; introducing members of the nucleic acid library into cells that have a given trait; and identifying a member of the library which alters the given trait.

The invention also features a method that includes evaluating the phenotype of a chimeric artificial zinc finger protein in a first cell, expressing the protein in a second cell, and evaluating a phenotype of the second cell. For example, the method can include identifying a member of a transcription factor library that alters a given phenotype in a first cell (a yeast strain or a human cell line such as 293 cells, for example) and then expressing the member in a different cell (a different yeast strain or HeLa cells, for example). The first cell may be more amenable for screening than other strains or cell lines.

In another aspect, the invention features a method of altering the sensitivity of a fungal strain to an anti-fungal agent. The method includes: introducing a nucleic acid encoding an artificial chimeric protein that comprises at least three zinc finger domains into a fungal cell; and maintaining the fungal cell under conditions that allow for expression of the introduced nucleic acid in the cell. For example, the fungal cell is a yeast cell, e.g., *Candida, Pichia, Hanseula, Histoplasma*, or *Cryptococcus*. In one embodiment, the artificial chimeric protein comprises the amino acid sequence of the zinc finger array of a protein selected from K1 through K11 (see Example 3).

The method can include one or more of the following features: the artificial chimeric protein comprises a transcriptional regulatory domain (e.g., an activation or repression domain); expression of the artificial chimeric protein in the cell alters the transcript level of a water transporter; expression of the artificial chimeric protein in a *S. cerevisiae* cell alters the transcript level of the YLL053C gene or the PDR5 gene; the artificial chimeric protein competes a polypeptide selected from K1 through K11 for binding to a specific DNA site.

In another aspect, the invention features a method of altering the sensitivity of a fungal strain to an anti-fungal agent. The method includes altering the activity or expression of a protein that comprises an amino acid sequence of at least 50 amino acids that is at least 30, 50, 60, 70, 80, 90, or 95% identical to YLL053C, AQY1, YJR147W, YLL052C, or YPL091W. For example, the fungal cell is a yeast cell, e.g., *Candida, Pichia, Hanseula, Histoplasma*, or *Cryptococcus*. In one embodiment, the activity or expression is increased to reduce sensitivity, i.e., increase resistance. In another embodiment, the activity or expression is reduced to increase sensitivity. Altering the activity or expression can include expressing an artificial transcription factor, contacting the cell with a double-stranded RNA (dsRNA) that includes a sequence of at least 20 nucleotides complementary to YLL053C, AQY1, YJR147W, YLL052C, or YPL091W gene, or contacting the cell with a chemical compound.

A related method includes screening a test compound (e.g., a small organic compound) for interaction with such a protein, e.g., to identify an inhibitor of a YLL053C/AQY1-related protein or screening a test compound for ability to alter the activity or expression of AQY1, YJR147W, YLL052C, YLL053C or YPL091W.

In another aspect, the invention features a method of identifying an artificial chimeric protein that alters the sensitivity of a fungal strain to an anti-fungal agent. The method includes: providing a nucleic acid library that comprises a plurality of nucleic acids, each nucleic acid of the plurality comprising a coding sequence that encodes an artificial, chimeric protein that comprises an array of at least three zinc finger domains wherein at least two adjacent zinc finger domains do not occur adjacent to each other in a naturally occurring protein; introducing each nucleic acid of the plurality into a fungal cell to yield transformed fungal cells; maintaining (e.g., culturing) the transformed fungal cells in the presence of an anti-fungal agent; and selecting a cell from the transformed fungal cells whose sensitivity to the anti-fungal agent is altered relative to a control fungal cell.

The method can include one or more of the following features: the control fungal cell is not transformed or is transformed with a reference nucleic acid; the chimeric protein encoded by each nucleic acid of the plurality comprises a transcriptional regulatory domain; the fungal cell is a pathogenic fungal cell, e.g., a *Candida, Histoplasma*, or *Cryptococcus*.

The method can further include, for example, constructing a nucleic acid that encodes a second chimeric protein that comprises (i) the array of zinc finger domains of the chimeric protein encoded by the library member in the selected cell, and (ii) a transcriptional regulatory domain, other than the transcriptional regulatory domain of the chimeric protein encoded by the library member in the selected cell. The method can include other features described herein.

In a further aspect, the invention features a method of identifying an agent that counters resistance of a fungal cell to an anti-fungal agent. The method includes: contacting a test compound to a polypeptide that includes YJR147W, YLL052C, YLL053C or YPL091W; and evaluating interaction between the test compound and the polypeptide, wherein an interaction indicates that the test compound may be useful as an agent to counter resistance to an anti-fungal agent. The method can further include contacting a fungal cell with the test compound and the anti-fungal agent, e.g., and evaluating viability or growth of the cell. The cell can be a cell that is resistant to the anti-fungal agent (e.g., ketoconazole).

In another aspect, the invention features a method of identifying a target gene that is regulated by artificial transcription factors. The method includes: providing a nucleic acid library that comprises a plurality of nucleic acids, each encoding a different artificial transcription factor, each transcription factor comprising at least two zinc finger domains; introducing each member of the plurality into a replicate of a test cell to provide a plurality of transformed cells; identifying a plurality of phenotypically altered cells from the plurality of transformed cells, wherein each phenotypically altered cell has an altered phenotype relative to the test cell; and identifying one or more transcripts or proteins whose abundance is similarly altered in at least two phenotypically altered cells of the plurality relative to the test cell.

In one embodiment, the method further includes, in a test cell, altering the activity of a transcript or protein whose abundance is similarly altered in at least two phenotypically altered cells, e.g., by genetic alteration (e.g., mutation or overexpression) or otherwise (e.g., RNA interference, antisense, or antibody binding). In some cases, the activity of a plurality of transcripts or proteins is altered.

In one embodiment, the similarly altered transcripts or proteins are identified by profiling transcripts or protein abundance in each phenotypically altered cell of the plurality to provide a profile for each phenotypically altered cell; and comparing the profiles to each other. Profiles can be obtained using, for example, a nucleic acid or protein array, SAGE tags, differential display, or subtractive hybridization.

In one embodiment, the cell is a cancer cell, e.g., a human cancer cell. One or more of the identified transcripts can be a transcript that is absent from the cell in the absence of any artificial transcription factors.

A polypeptide encoded by one of the identified transcripts can be used as a target polypeptide for screening to find test compounds that interact with the target. The test compound can be evaluated to determine if they enhance or inhibit activity of the target polypeptide. In one embodiment, the test compound is a small molecule having a molecular weight of less than 10, 5, or 2 kDa.

With respect to all methods described herein, a library of nucleic acids that encode chimeric zinc finger proteins can be used. The term "library" refers to a physical collection of similar, but non-identical biomolecules. The collection can be, for example, together in one vessel or physically separated (into groups or individually) in separate vessels or on separate locations on a solid support. Duplicates of individual members of the library may be present in the collection. A library can include at least 10, $10^2$, $10^3$, $10^5$, $10^7$, or $10^9$ different members, or fewer than $10^{13}$, $10^{12}$, $10^{10}$, $10^9$, $10^7$, $10^5$, or $10^3$ different members.

A first exemplary library includes a plurality of nucleic acids, each nucleic acid encoding a polypeptide comprising at least a first, second, and third zinc finger domains. As used herein, "first, second and third" denotes three separate domains that can occur in any order in the polypeptide: e.g., each domain can occur N-terminal or C-terminal to either or both of the others. The first zinc finger domain varies among nucleic acids of the plurality. The second zinc finger domain varies among nucleic acids of the plurality. At least 10 different first zinc finger domains are represented in the library. In one implementation, at least 0.5, 1, 2, 5%, 10%, or 25% of the members of the library have one or both of the following properties: (1) each represses transcription of at least one p1G reporter plasmid at least 1.25 fold in vivo; and (2) each binds at least one target site with a dissociation constant of no more than 7, 5, 3, 2, 1, 0.5, or 0.05 nM. The first and second zinc finger domains can be from different naturally-occurring proteins or are positioned in a configuration that differs from their relative positions in a naturally-occurring protein. For example, the first and second zinc finger domains may be adjacent in the polypeptide, but may be separated by one or more intervening zinc finger domains in a naturally occurring protein.

A second exemplary library includes a plurality of nucleic acids, each nucleic acid encoding a polypeptide that includes at least first and second zinc finger domains. The first and second zinc finger domains of each polypeptide (1) are identical to zinc finger domains of different naturally occurring proteins (and generally do not occur in the same naturally occurring protein or are positioned in a configuration that differs from their relative positions in a naturally-occurring protein), (2) differ by no more than four, three, two, or one amino acid residues from domains of naturally occurring proteins, or (3) are non-adjacent zinc finger domains from a naturally occurring protein. Identical zinc finger domains refer to zinc finger domains that are identical at each amino acid from the first metal coordinating residue (typically cysteine) to the last metal coordinating residue (typically histidine). The first zinc finger domain varies among nucleic acids of the plurality, and the second zinc finger domain varies among nucleic acids of the plurality. The naturally occurring protein can be any eukaryotic zinc finger protein: for example, a fungal (e.g., yeast), plant, or animal protein (e.g., a mammalian protein, such as a human or murine protein). Each polypeptide can further include a third, fourth, fifth, and/or sixth zinc finger domain. Each zinc finger domain can be a mammalian, e.g., human, zinc finger domain.

Other types of libraries can also be used, e.g., including mutated zinc finger domains.

In some embodiments, a library of nucleic acids encoding zinc finger proteins or a library of such proteins themselves can include members with different regulatory domains. For example, the library can include at least 10% of members with an activation domain, and at least another 10% of members with a repression domain. In another example, at least 10% have an activation domain or repression domain; another at least 10% has no regulatory domain. In still another example, some include an activation domain; others, a repression domain; still others, no regulatory domain at all. Other percentages, e.g., at least 20, 25, 30, 40, 50, 60% can also be used.

1. Neuro1-p65 and Related Molecules

In still another aspect, the invention features an artificial polypeptide that includes: the sequence:

$CX_{(2-5)}CXXXBXQXSNJXRHX_{(3-5)}$   (SEQ ID NO: 36)

$HX_{(1-6)}BXCX_{(2-5)}CXXXBXQXSNJ$ $XKHX_{(3-5)}HX_{(1-6)}BXCX_{(2-5)}CX$ $XXBXCXSNJXRHX_{(3-5)}H$, where B is any amino acid, or optionally phenylalanine or tyrosine; and J is any amino acid, or optionally, a hydrophobic amino acid. This array is also abbreviated as: QSNR-QSNK-CSNR. Other exemplary artificial polypeptides include:

$CX_{(2-5)}CXXXBXQXSNJXRHX_{(3-5)}HX_{(1-6)}$   (SEQ ID NO: 37)

$BXCX_{(2-5)}CXXXBXQXSNJXKHX_{(3-5)}H$, and $CX_{(2-5)}CXXXBXQXSNJXKHX_{(3-5)}HX_{(1-6)}$   (SEQ ID NO: 38)

$BXCX_{(2-5)}CXXXBXCXSNJXRHX_{(3-5)}H$.

The polypeptide can, for example, induce neurites when present at an effective concentration in a mouse Neuro2a cell. For example, the isolated polypeptide can include an amino acid sequence that is identical to the zinc finger array within SEQ ID NO:2 or that differs by no more than 8, 6, 4, 3, or 2 substitutions within the zinc finger domains present in SEQ ID NO:2. The substitutions can be conservative substitutions. The isolated polypeptide can have a sequence that is at least 80, 85, 90, 95, or 97% identical to the zinc finger array within SEQ ID NO:2. In one embodiment, the polypeptide can specifically bind to a target DNA site. For example, the polypeptide can compete with the Neuro1-p65 chimeric ZFP (SEQ ID NO:2) for binding to a target DNA site, e.g., a site bound with a $K_d$ of less than 10 nM. The polypeptide can further include a transcriptional regulatory domain, e.g., an activation or repression domain. The polypeptide can include one, two, or three or more additional zinc finger domains.

Also featured are nucleic acids encoding the above polypeptides. For example, the isolated polypeptide that includes the amino acid of SEQ ID NO:2 can be encoded by a nucleic acid sequence that includes the sequence of SEQ ID NO:1. Featured nucleic acids can include operably linked regulatory sequences, e.g., a promoter sequence, an enhancer sequence, an insulator sequence, untranslated regulatory regions, a polyA addition site, and so forth. In one embodiment, the coding nucleic acid is operably linked to a conditional promoter such as an inducible promoter or a cell-type specific promoter. The nucleic acid can be included in a vector or integrated into a chromosome.

In addition, the invention features host cells (e.g., mammalian host cells) that include a polypeptide described above. The host cell can include a nucleic acid described above and express the nucleic acid. For example, the host cell can be a neuronal cell that extends neurites (e.g., at least in part as a consequence of the polypeptide).

2. Osteo1-p65 and Related Molecules

In still another aspect, the invention features an artificial polypeptide that includes: the sequence:

CX$_{(2-5)}$CXXXBXRXDKJXRHX$_{(3-5)}$    (SEQ ID NO: 39)

HX$_{(1-6)}$BXCX$_{(2-5)}$CXXXBXQXTHJ

XRHX$_{(3-5)}$HX$_{(1-6)}$BXCX$_{(2-5)}$CX

XXBXVXSTJXRHX$_{(3-5)}$HX$_{(1-6)}$BX

CX$_{(2-5)}$CXXXBXRXDKJXRHX$_{(3-5)}$H, where B is any amino acid, or optionally phenylalanine or tyrosine; and J is any amino acid, or optionally, a hydrophobic amino acid. This array is also abbreviated as: RDKR-QTHR-VSTR-RDKR (where each set of four amino acids corresponds to the DNA contacting residues of a zinc finger domain and non-DNA contacting residues may vary).

Other exemplary artificial polypeptides include:

CX$_{(2-5)}$CXXXBXRXDKJXRHX$_{(3-5)}$    (SEQ ID NO: 40)

HX$_{(1-6)}$BXCX$_{(2-5)}$CXXXBXQXTHJ

XRHX$_{(3-5)}$HX$_{(1-6)}$BXCX$_{(2-5)}$CX

XXBXVXSTJXRHX$_{(3-5)}$H;

CX$_{(2-5)}$CXXXBXQXTHJXRHX$_{(3-5)}$    (SEQ ID NO: 41)

HX$_{(1-6)}$BXCX$_{(2-5)}$CXXXBXVXSTJ

XRHX$_{(3-5)}$HX$_{(1-6)}$BXCX$_{(2-5)}$CX

XXBXRXDKJXRHX$_{(3-5)}$H;

CX$_{(2-5)}$CXXXBXRXDKJXRHX$_{(3-5)}$    (SEQ ID NO: 42)

HX$_{(1-6)}$BXCX$_{(2-5)}$CXXXBXQXTHJ

XRHX$_{(3-5)}$H; and

CX$_{(2-5)}$CXXXBXVXSTJXRHX$_{(3-5)}$    (SEQ ID NO: 43)

HX$_{(1-6)}$BXCX$_{(2-5)}$CXXXBXRXDKJ

XRHX$_{(3-5)}$H.

The polypeptide can, for example, induce alkaline phosphatase or other indicators of osteoblasts differentiation, when present at an effective concentration in a C2C12 myo-blast cell line cell. For example, the isolated polypeptide can include an amino acid sequence that is identical to the zinc finger array within SEQ ID NO:4 or that differs by no more than 8, 6, 4, 3, or 2 substitutions within the zinc finger domains present in SEQ ID NO:4. The substitutions can be conservative substitutions. The isolated polypeptide can have a sequence that is at least 80, 85, 90, 95, or 97% identical to the zinc finger array within SEQ ID NO:4. In one embodiment, the polypeptide can specifically bind to a target DNA site. For example, the polypeptide can compete with the Osteo1-p65 chimeric ZFP (SEQ ID NO:4) for binding to a target DNA site, e.g., a site bound with a $K_d$ of less than 10 nM. The polypeptide can further include a transcriptional regulatory domain, e.g., an activation or repression domain. The polypeptide can include one, two, or three or more additional zinc finger domains.

Also featured are nucleic acids encoding the above polypeptides. For example, the isolated polypeptide that includes the amino acid of SEQ ID NO:4 can be encoded by a nucleic acid sequence that includes the sequence of SEQ ID NO:3.

The nucleic acid of SEQ ID NO:3 is as follows:

ATGGTGTACCCCTACGACGTGCCCGACTACG (SEQ ID NO: 3)

CCGAATTGCCTCCAAAAAGAAGAGAAAGGTAGGGA

TCCGAATTCCCGGGGAAAAACCGTATGTATGCGATG

TAGAGGGATGTACGTGGAAATTTGCCCGCTCAGATA

AGCTCAACAGACACAAGAAAAGGCACACCGGGGAAA

AACCGTATGAGTGTCACGATTGCGGAAAGTCCTTTA

GGCAGAGCACCCACCTCACTCGGCACCGGAGGATCC

ACACCGGGGAAAAACCGTATGAGTGTAATTACTGTG

GAAAAACCTTTAGTGTGAGCTCAACCCTTATTAGAC

ATCAGAGAATCCACACCGGGGAAAAACCGTATGTAT

GCGATGTAGAGGGATGTACGTGGAAATTTGCCCGCT

CAGATAAGCTCAACAGACACAAGAAAAGGCACACCG

GTGAAAAAGCGGCCGCTAAATTCTACCTGCCAGATA

CAGACGATCGTCACCGGATTGAGGAGAAACGTAAAA

GGACATATGAGACCTTCAAGAGCATCATGAAGAAGA

GTCCTTTCAGCGGACCCACCGACCCCCGGCCTCCAC

CTCGACGCATTGCTGTGCCTTCCCGCAGCTCAGCTT

CTGTCCCCAAGCCAGCACCCCAGCCCTATCCCTTTA

CGTCATCCCTGAGCACCATCAACTATGATGAGTTTC

CCACCATGGTGTTTCCTTCTGGGCAGATCAGCCAGG

CCTCGGCCTTGGCCCCGGCCCCTCCCCAAGTCCTGC

CCCAGGCTCCAGCCCCTGCCCCTGCTCCAGCCATGG

TATCAGCTCTGGCCCAGGCCCCAGCCCCTGTCCCAG

TCCTAGCCCCAGGCCCTCCTCAGGCTGTGGCCCCAC

CTGCCCCCAAGCCCACCCAGGCTGGGAAGGAACGC

TGTCAGAGGCCCTGCTGCAGCTGCAGTTTGATGATG

-continued
AAGACCTGGGGGCCTTGCTTGGCAACAGCACAGACC

CAGCTGTGTTCACAGACCTGGCATCCGTCGACAACT

CCGAGTTTCAGCAGCTGCTGAACCAGGGCATACCTG

TGGCCCCCCACACAACTGAGCCCATGCTGATGGAGT

ACCCTGAGGCTATAACTCGCCTAGTGACAGCCCAGA

GGCCCCCCGACCCAGCTCCTGCTCCACTGGGGGCCC

CGGGGCTCCCCAATGGCCTCCTTTCAGGAGATGAAG

ACTTCTCCTCCATTGCGGACATGGACTTCTCAGCCC

TGCTGAGTCAG TAA

The amino acid sequence of SEQ ID NO:4 is as follows:

MVYPYDVPDYAELPPKKKRKVGIRIPGEKPYVCDVEGCTWKFARSDKLNR

HKKRHTGEKPYECHDCGKSFRQSTHLTRHRRIHTGEKPYECNYCGKTFSV

SSTLIRHQRIHTGEKPYVCDVEGCTWKFARSDKLNRHKKRHTGEKAAAKF

YLPDTDDRHRIEEKRKRTYETFKSIMKKSPFSGPTDPRPPPRRIAVPSRS

SASVPKPAPQPYPFTSSLSTINYDEFPTMVFPSGQISQASALAPAPPQVL

PQAPAPAPAPAMVSALAQAPAPVPVLAPGPPQAVAPPAPKPTQAGEGTLS

EALLQLQFDDEDLGALLGNSTDPAVFTDLASVDNSEFQQLLNQGIPVAPH

TTEPMLMEYPEAITRLVTAQRPPDPAPAPLGAPGLPNGLLSGDEDFSSIA

DMDFSALLSQ.

Featured nucleic acids can include operably linked regulatory sequences, e.g., a promoter sequence, an enhancer sequence, an insulator sequence, untranslated regulatory regions, a polyA addition site, and so forth. In one embodiment, the coding nucleic acid is operably linked to a conditional promoter such as an inducible promoter or a cell-type specific promoter. The nucleic acid can be included in a vector or integrated into a chromosome.

In addition, the invention features host cells (e.g., mammalian host cells) that include a polypeptide described above. The host cell can include a nucleic acid described above and express the nucleic acid. For example, the host cell can be a stem cell that has the phenotype of an osteoblasts, e.g., at least partially as a consequence of the artificial chimeric polypeptide.

3. 08 D04-p65 and Related Molecules

In still another aspect, the invention features an artificial polypeptide that includes: the sequence:

$CX_{(2-5)}CXXXBXRXSHJXRHX_{(3-5)}HX_{(1-6)}$ (SEQ ID NO:44)

$BXCX_{(2-5)}CXXXBXRXDHJXTHX_{(3-5)}HX_{(1-6)}$ $BXCX_{(2-5)}CXXXBXVXSSJXRHX_{(3-5)}H,$ where B is any amino acid, or optionally phenylalanine or tyrosine; and J is any amino acid, or optionally, a hydrophobic amino acid. This array is also abbreviated as: RSHR-RDHT-VSSR. Other exemplary artificial polypeptides include:

$CX_{(2-5)}CXXXBXRXSHJXRHX_{(3-5)}HX_{(1-6)}$ (SEQ ID NO:45)

$BXCX_{(2-5)}CXXXBXRXDHJXTHX_{(3-5)}H;$ and $CX_{(2-5)}CXXXBXRXDHJXTHX_{(3-5)}HX_{(1-6)}$ (SEQ ID NO:46)

$BXCX_{(2-5)}CXXXBXVXSSJXRHX_{(3-5)}H$

The polypeptide can, for example, induce insulin gene expression, e.g., when present at an effective concentration in a human 293 cell. For example, the isolated polypeptide can include an amino acid sequence that is identical to the zinc finger array within SEQ ID NO:6 or that differs by no more than 8, 6, 4, 3, or 2 substitutions within the zinc finger domains present in SEQ ID NO:6. The substitutions can be conservative substitutions. The isolated polypeptide can have a sequence that is at least 80, 85, 90, 95, or 97% identical to the zinc finger array within SEQ ID NO:6. In one embodiment, the polypeptide can specifically bind to a target DNA site. For example, the polypeptide can compete with the 08_D04-p65 chimeric ZFP (SEQ ID NO:6) for binding to a target DNA site, e.g., a site bound with a $K_d$ of less than 10 nM. The polypeptide can further include a transcriptional regulatory domain, e.g., an activation or repression domain. The polypeptide can include one, two, or three or more additional zinc finger domains.

Also featured are nucleic acids encoding the above polypeptides. For example, the isolated polypeptide that includes the amino acid of SEQ ID NO:6 can be encoded by a nucleic acid sequence that includes the sequence of SEQ ID NO:5. Featured nucleic acids can include operably linked regulatory sequences, e.g., a promoter sequence, an enhancer sequence, an insulator sequence, untranslated regulatory regions, a polyA addition site, and so forth. In one embodiment, the coding nucleic acid is operably linked to a conditional promoter such as an inducible promoter or a cell-type specific promoter. The nucleic acid can be included in a vector or integrated into a chromosome.

In addition, the invention features host cells (e.g., mammalian host cells) that include a polypeptide described above. The host cell can include a nucleic acid described above and express the nucleic acid. For example, the host cell can be a human cell that expresses the insulin gene, e.g., at least partially as a consequence of the artificial chimeric polypeptide. The invention also features a method of producing insulin that includes culturing a cell described herein in vitro, or of producing insulin in a subject by introducing a polypeptide described above or a nucleic acid encoding the polypeptide into a cell of the subject.

4. P B08 and Related Molecules

In still another aspect, the invention features an artificial polypeptide that includes: the sequence:

$CX_{(2-5)}CXXXBXQXSNJXRHX_{(3-5)}HX_{(1-6)}$ (SEQ ID NO:47)

$BXCX_{(2-5)}CXXXBXDXSNJXRHX_{(3-5)}HX_{(1-6)}$ $BXCX_{(2-5)}CXXXBXDXSNJXRHX_{(3-5)}H,$ where B is any amino acid, or optionally phenylalanine or tyrosine; and J is any amino acid, or optionally, a hydrophobic amino acid. This array is also abbreviated as: QSNR-DSNR-DSNR. Other exemplary artificial polypeptides include:

$CX_{(2-5)}CXXXBXQXSNJXRHX_{(3-5)}HX_{(1-6)}$ (SEQ ID NO:48)

$BXCX_{(2-5)}CXXXBXDXSNJXRHX_{(3-5)}H$;
and $CX_{(2-5)}CXXXBXDXSNJXRHX_{(3-5)}HX_{(1-6)}$ (SEQ ID NO:49)

$BXCX_{(2-5)}CXXXBXDXSNJXRHX_{(3-5)}H$.

The polypeptide can, for example, increase expression of a heterologous polypeptide, e.g., a reporter polypeptide encoded by a SV40-SEAP reporter construct in a 293 cell when present at an effective concentration. For example, the isolated polypeptide can include an amino acid sequence that is identical to the zinc finger array within SEQ ID NO:8 or that differs by no more than 8, 6, 4, 3, or 2 substitutions within the zinc finger domains present in SEQ ID NO:8. The substitutions can be conservative substitutions. The isolated polypeptide can have a sequence that is at least 80, 85, 90, 95, or 97% identical to the zinc finger array within SEQ ID NO:8. In one embodiment, the polypeptide can specifically bind to a target DNA site. For example, the polypeptide can compete with the P_B08 chimeric ZFP (SEQ ID NO:8) for binding to a target DNA site, e.g., a site bound with a $K_d$ of less than 10 nM. The polypeptide can further include a transcriptional regulatory domain, e.g., an activation or repression domain. The polypeptide can include one, two, or three or more additional zinc finger domains.

Also featured are nucleic acids encoding the above polypeptides. For example, the isolated polypeptide that includes the amino acid of SEQ ID NO:8 can be encoded by a nucleic acid sequence that includes the sequence of SEQ ID NO:7. Featured nucleic acids can include operably linked regulatory sequences, e.g., a promoter sequence, an enhancer sequence, an insulator sequence, untranslated regulatory regions, a polyA addition site, and so forth. In one embodiment, the coding nucleic acid is operably linked to a conditional promoter such as an inducible promoter or a cell-type specific promoter. The nucleic acid can be included in a vector or integrated into a chromosome.

In addition, the invention features host cells (e.g., mammalian host cells) that include a polypeptide described above. The host cell can include a nucleic acid described above and express the nucleic acid. For example, the host cell can be a mammalian cell that has increased heterologous polypeptide production.

5. K D10 and Related Molecules

In still another aspect, the invention features an artificial polypeptide that includes: the sequence:

$CX_{(2-5)}CXXXBXQXSHJXVHX_{(3-5)}HX_{(1-6)}$ (SEQ ID NO:50)

$BXCX_{(2-5)}CXXXBXWXSNJXRHX_{(3-5)}HX_{(1-6)}$ $BXCX_{(2-5)}CXXXBXWXSNJXRHX_{(3-5)}HX_{(1-6)}$ $BXCX_{(2-5)}CXXXBXRXDNJXQHX_{(3-5)}H$, where B is any amino acid, or optionally phenylalanine or tyrosine; and J is any amino acid, or optionally, a hydrophobic amino acid. This array is also abbreviated as: QSHV-WSNR-WSNR-RDNQ. Other exemplary artificial polypeptides include:

$CX_{(2-5)}CXXXBXWXSNJXRHX_{(3-5)}HX_{(1-6)}$ (SEQ ID NO:51)

$BXCX_{(2-5)}CXXXBXWXSNJXRHX_{(3-5)}HX_{(1-6)}$ $BXCX_{(2-5)}CXXXBXRXDNJXQHX_{(3-5)}H$; and $CX_{(2-5)}CXXXBXQXSHJXVHX_{(3-5)}HX_{(1-6)}$ (SEQ ID NO:52)

$BXCX_{(2-5)}CXXXBXWXSNJXRHX_{(3-5)}HX_{(1-6)}$ $BXCX_{(2-5)}CXXXBXWXSNJXRHX_{(3-5)}H$.

The polypeptide can decrease the cell proliferation when present at an effective concentration in a mammalian cell, e.g., by at least 30, 40, 50, or 60%. Cell proliferation may be assessed by cell number after a predefined incubation time. For example, the isolated polypeptide can include an amino acid sequence that is identical to the zinc finger array within SEQ ID NO:10 or that differs by no more than 8, 6, 4, 3, or 2 substitutions within the zinc finger domains present in SEQ ID NO:10. The substitutions can be conservative substitutions. The isolated polypeptide can have a sequence that is at least 80, 85, 90, 95, or 97% identical to the zinc finger array within SEQ ID NO:10. In one embodiment, the polypeptide can specifically bind to a target DNA site. For example, the polypeptide can compete with the K_D10 chimeric ZFP (SEQ ID NO:10) for binding to a target DNA site, e.g., a site bound with a $K_d$ of less than 10 nM. The polypeptide can further include a transcriptional regulatory domain, e.g., an activation or repression domain. The polypeptide can include one, two, or three or more additional zinc finger domains.

Also featured are nucleic acids encoding the above polypeptides. For example, the isolated polypeptide that includes the amino acid of SEQ ID NO:10 can be encoded by a nucleic acid sequence that includes the sequence of SEQ ID NO:9. Featured nucleic acids can include operably linked regulatory sequences, e.g., a promoter sequence, an enhancer sequence, an insulator sequence, untranslated regulatory regions, a polyA addition site, and so forth. In one embodiment, the coding nucleic acid is operably linked to a conditional promoter such as an inducible promoter or a cell-type specific promoter. The nucleic acid can be included in a vector or integrated into a chromosome.

In addition, the invention features host cells (e.g., eukaryotic, e.g., mammalian host cells) that include a nucleic acid described herein, e.g., a nucleic acid encoding polypeptide described herein. The host cell can also express the nucleic acid. For example, the host cell can be a mammalian cell that has a reduced proliferation rate relative to an otherwise identical cell that does not include the polypeptide.

6. K F02 and Related Molecules

In still another aspect, the invention features an artificial polypeptide that includes: the sequence:

$CX_{(2-5)}CXXXBXDXSAJXRHX_{(3-5)}HX_{(1-6)}$ (SEQ ID NO:53)

$BXCX_{(2-5)}CXXXBXRXDKJXRHX_{(3-5)}HX_{(1-6)}$ $BXCX_{(2-5)}CXXXBXRXDEJXRHX_{(3-5)}HX_{(1-6)}$ $BXCX_{(2-5)}CXXXBXQXTHJXRHX_{(3-5)}H$, where B is any amino acid, or optionally phenylalanine or tyrosine; and J is any amino acid, or optionally, a hydrophobic amino acid. This array is also abbreviated as: DSAR-RDKR-RDER-QTHR (where each set of four amino acids corresponds to the DNA contacting residues of a zinc finger domain and non-DNA contacting residues may vary).

Other exemplary artificial polypeptides include:

CX$_{(2-5)}$CXXXBXRXDKJXRHX$_{(3-5)}$HX$_{(1-6)}$ (SEQ ID NO:54)

BXCX$_{(2-5)}$CXXXBXRXDEJXRHX$_{(3-5)}$HX$_{(1-6)}$

BXCX$_{(2-5)}$CXXXBXQXTHJXRHX$_{(3-5)}$;
and

CX$_{(2-5)}$CXXXBXDXSAJXRHX$_{(3-5)}$HX$_{(1-6)}$ (SEQ ID NO:55)

BXCX$_{(2-5)}$CXXXBXRXDKJXRHX$_{(3-5)}$HX$_{(1-6)}$

BXCX$_{(2-5)}$CXXXBXRXDEJXRHX$_{(3-5)}$H.

The polypeptide can increase cell proliferation, e.g., by at least 50, 100, or 120%, in a mammalian cell, e.g., a 293 cell. For example, the isolated polypeptide can include an amino acid sequence that is identical to the zinc finger array within SEQ ID NO:12 or that differs by no more than 8, 6, 4, 3, or 2 substitutions within the zinc finger domains present in SEQ ID NO:12. The substitutions can be conservative substitutions. The isolated polypeptide can have a sequence that is at least 80, 85, 90, 95, or 97% identical to the zinc finger array within SEQ ID NO:12. In one embodiment, the polypeptide can specifically bind to a target DNA site. For example, the polypeptide can compete with the K_F02 chimeric ZFP (SEQ ID NO:12) for binding to a target DNA site, e.g., a site bound with a $K_d$ of less than 10 nM. The polypeptide can further include a transcriptional regulatory domain, e.g., an activation or repression domain. The polypeptide can include one, two, or three or more additional zinc finger domains.

Also featured are nucleic acids encoding the above polypeptides. For example, the isolated polypeptide that includes the amino acid of SEQ ID NO:12 can be encoded by a nucleic acid sequence that includes the sequence of SEQ ID NO:11. Featured nucleic acids can include operably linked regulatory sequences, e.g., a promoter sequence, an enhancer sequence, an insulator sequence, untranslated regulatory regions, a polyA addition site, and so forth. In one embodiment, the coding nucleic acid is operably linked to a conditional promoter such as an inducible promoter or a cell-type specific promoter. The nucleic acid can be included in a vector or integrated into a chromosome.

In addition, the invention features host cells (e.g., mammalian host cells) that include a nucleic acid described above. The host cell can include a nucleic acid described above and express the nucleic acid. For example, the host cell can be a mammalian cell that has an increased rate of cell proliferation relative to an otherwise identical cell that does not include the polypeptide.

7. K12 A11 and Related Molecules

In still another aspect, the invention features an artificial polypeptide that includes: the sequence:

CX$_{(2-5)}$CXXXBXRXDHJXTHX$_{(3-5)}$HX$_{(1-6)}$ (SEQ ID NO:56)

BXCX$_{(2-5)}$CXXXBXQXSNJXVHX$_{(3-5)}$HX$_{(1-6)}$

BXCX$_{(2-5)}$CXXXBXQXTHJXRHX$_{(3-5)}$HX$_{(1-6)}$

BXCX$_{(2-5)}$CXXXBXQXFNJXRHX$_{(3-5)}$H, where B is any amino acid, or optionally phenylalanine or tyrosine; and J is any amino acid, or optionally, a hydrophobic amino acid. This array is also abbreviated as:

RDHT-QSNV-QTHR-QFNR (where each set of four amino acids corresponds to the DNA contacting residues of a zinc finger domain and non-DNA contacting residues may vary).

Other exemplary polypeptides include:

CX$_{(2-5)}$CXXXBXRXDHJXTHX$_{(3-5)}$HX$_{(1-6)}$ (SEQ ID NO:57)

BXCX$_{(2-5)}$CXXXBXQXSNJXVHX$_{(3-5)}$HX$_{(1-6)}$

BXCX$_{(2-5)}$CXXXBXQXTHJXRHX$_{(3-5)}$H;
and

CX$_{(2-5)}$CXXXBXQXSNJXVHX$_{(3-5)}$HX$_{(1-6)}$ (SEQ ID NO:58)

BXCX$_{(2-5)}$CXXXBXQXTHJXRHX$_{(3-5)}$HX$_{(1-6)}$

BXCX$_{(2-5)}$CXXXBXQXFNJXRHX$_{(3-5)}$H

The polypeptide can increase heterologous gene expression, e.g., a gene operable linked to a strong promoter such as a viral promoter, in a mammalian cell. For example, the isolated polypeptide can include an amino acid sequence that is identical to the zinc finger array within SEQ ID NO:260 or that differs by no more than 8, 6, 4, 3, or 2 substitutions within the zinc finger domains present in SEQ ID NO:260. The substitutions can be conservative substitutions. The isolated polypeptide can have a sequence that is at least 80, 85, 90, 95, or 97% identical to the zinc finger array within SEQ ID NO:260. In one embodiment, the polypeptide can specifically bind to a target DNA site. For example, the polypeptide can compete with the K12_A11 chimeric ZFP (SEQ ID NO:260) for binding to a target DNA site, e.g., a site bound with a $K_d$ of less than 10 nM. The polypeptide can further include a transcriptional regulatory domain, e.g., an activation or repression domain. The polypeptide can include one, two, or three or more additional zinc finger domains. Since the K12_A11 chimeric ZFP includes a repression domain it is unlikely to increase heterologous gene expression by directly binding to the promoter of the heterologous gene.

Also featured are nucleic acids encoding the above polypeptides. For example, the isolated polypeptide that includes the amino acid of SEQ ID NO:260 can be encoded by a nucleic acid sequence that includes the sequence of SEQ ID NO:259. Featured nucleic acids can include operably linked regulatory sequences, e.g., a promoter sequence, an enhancer sequence, an insulator sequence, untranslated regulatory regions, a polyA addition site, and so forth. In one embodiment, the coding nucleic acid is operably linked to a conditional promoter such as an inducible promoter or a cell-type specific promoter. The nucleic acid can be included in a vector or integrated into a chromosome.

In addition, the invention features host cells (e.g., mammalian host cells) that include a nucleic acid described above. The host cell can include a nucleic acid described above and express the nucleic acid.

8. K44-16-E12 and Related Molecules

In still another aspect, the invention features an artificial polypeptide that includes: the sequence:

CX$_{(2-5)}$CXXXBXQXSHJXVHX$_{(3-5)}$HX$_{(1-6)}$ (SEQ ID NO:59)

BXCX$_{(2-5)}$CXXXBXQXSSJXRHX$_{(3-5)}$HX$_{(1-6)}$

BXCX$_{(2-5)}$CXXXBXQXTHJXRHX$_{(3-5)}$H, where B is any amino acid, or optionally phenylalanine or tyrosine; and J is any amino acid, or optionally, a hydrophobic amino acid. This array is also abbreviated as: QSHV-QSSR-QTHR (where each set of four amino acids corresponds to the DNA contacting residues of a zinc finger domain and non-DNA contacting residues may vary).

Other exemplary polypeptides include:

$CX_{(2-5)}CXXXBXQXSSJXRHX_{(3-5)}HX_{(1-6)}$ (SEQ ID NO:60)

$BXCX_{(2-5)}CXXXBXQXTHJXRHX_{(3-5)}H$; and $CX_{(2-5)}CXXXBXQXSHJXVHX_{(3-5)}HX_{(1-6)}$ (SEQ ID NO:61)

$BXCX_{(2-5)}CXXXBXQXSSJXRHX_{(3-5)}H$.

The polypeptide can increase heterologous gene expression, e.g., a gene operable linked to a strong promoter such as a viral promoter, in a mammalian cell. For example, the isolated polypeptide can include an amino acid sequence that is identical to the zinc finger array within SEQ ID NO: 64 or that differs by no more than 8, 6, 4, 3, or 2 substitutions within the zinc finger domains present in SEQ ID NO: 64. The substitutions can be conservative substitutions. The isolated polypeptide can have a sequence that is at least 80, 85, 90, 95, or 97% identical to the zinc finger array within SEQ ID NO: 64. In one embodiment, the polypeptide can specifically bind to a target DNA site. For example, the polypeptide can compete with the K44-16-E12 chimeric ZFP (SEQ ID NO: 64) for binding to a target DNA site, e.g., a site bound with a $K_d$ of less than 10 nM. The polypeptide can further include a transcriptional regulatory domain, e.g., an activation or repression domain. The polypeptide can include one, two, or three or more additional zinc finger domains. Since the K44-16-E12 chimeric ZFP includes a repression domain it is unlikely to increase heterologous gene expression by directly binding to the promoter of the heterologous gene.

Also featured are nucleic acids encoding the above polypeptides. For example, the isolated polypeptide that includes the amino acid of SEQ ID NO: 64 can be encoded by a nucleic acid sequence that includes the sequence of SEQ ID NO:261. Featured nucleic acids can include operably linked regulatory sequences, e.g., a promoter sequence, an enhancer sequence, an insulator sequence, untranslated regulatory regions, a polyA addition site, and so forth. In one embodiment, the coding nucleic acid is operably linked to a conditional promoter such as an inducible promoter or a cell-type specific promoter. The nucleic acid can be included in a vector or integrated into a chromosome.

In addition, the invention features host cells (e.g., mammalian host cells) that include a nucleic acid described above. The host cell can include a nucleic acid described above and express the nucleic acid. For example, the host cell can be a mammalian cell (e.g., a 293 cell that has the phenotype of increased heterologous protein production (e.g., both a secreted and intracellular reporter protein encoded by genes operably linked to the CMV promoter).

9. F104 p65 and Related Molecules

In still another aspect, the invention features an artificial polypeptide that includes: the sequence:

$CX_{(2-5)}CXXXBXRXDHJXTHX_{(3-5)}HX_{(1-6)}$ (SEQ ID NO:65)

$BXCX_{(2-5)}CXXXBXRXSHJXRHX_{(3-5)}HX_{(1-6)}$ $BXCX_{(2-5)}CXXXBXQXSHJXRHX_{(3-5)}H$, where B is any amino acid, or optionally phenylalanine or tyrosine; and J is any amino acid, or optionally, a hydrophobic amino acid. This array is also abbreviated as: RDHT-RSHR-QSHR. Other exemplary artificial polypeptides include:

$CX_{(2-5)}CXXXBXRXSHJXRHX_{(3-5)}HX_{(1-6)}$ (SEQ ID NO:66)

$BXCX_{(2-5)}CXXXBXQXSHJXRHX_{(3-5)}H$; and $CX_{(2-5)}CXXXBXRXDHJXTHX_{(3-5)}HX_{(1-6)}$ (SEQ ID NO:67)

$BXCX_{(2-5)}CXXXBXRXSHJXRHX_{(3-5)}H$.

For example, the isolated polypeptide can include an amino acid sequence that is identical to the zinc finger array within SEQ ID NO:18 or that differs by no more than 8, 6, 4, 3, or 2 substitutions within the zinc finger domains present in SEQ ID NO:18. The substitutions can be conservative substitutions. The isolated polypeptide can have a sequence that is at least 80, 85, 90, 95, or 97% identical to the zinc finger array within SEQ ID NO:18. In one embodiment, the polypeptide can specifically bind to a target DNA site. For example, the polypeptide can compete with the F104_p65 chimeric ZFP (SEQ ID NO:18) for binding to a target DNA site, e.g., a site bound with a $K_d$ of less than 10 nM. The polypeptide can further include a transcriptional regulatory domain, e.g., an activation or repression domain. The polypeptide can include one, two, or three or more additional zinc finger domains. The polypeptide can be used to alter the expression of one or more endogenous genes in a cell, e.g., a mammalian cell.

Also featured are nucleic acids encoding the above polypeptides. For example, the isolated polypeptide that includes the amino acid of SEQ ID NO:18 can be encoded by a nucleic acid sequence that includes the sequence of SEQ ID NO:17. Featured nucleic acids can include operably linked regulatory sequences, e.g., a promoter sequence, an enhancer sequence, an insulator sequence, untranslated regulatory regions, a polyA addition site, and so forth. In one embodiment, the coding nucleic acid is operably linked to a conditional promoter such as an inducible promoter or a cell-type specific promoter. The nucleic acid can be included in a vector or integrated into a chromosome.

In addition, the invention features host cells (e.g., mammalian host cells) that include a nucleic acid described above. The host cell can include a nucleic acid described above and express the nucleic acid.

10. F121 p65 and Related Molecules

In still another aspect, the invention features an artificial polypeptide that includes: the sequence:

$CX_{(2-5)}CXXXBXQXSHJXTHX_{(3-5)}HX_{(1-6)}$ (SEQ ID NO:68)

$BXCX_{(2-5)}CXXXBXRXSHJXRHX_{(3-5)}HX_{(1-6)}$ $BXCX_{(2-5)}CXXXBXRXDHJXTHX_{(3-5)}H$, where B is any amino acid, or optionally phenylalanine or tyrosine; and J is any amino acid, or optionally, a hydrophobic amino acid. This array is also abbreviated as: QSHT-RSHR-RDHT. Other exemplary polypeptides include:

CX$_{(2-5)}$CXXXBXRXSHJXRHX$_{(3-5)}$HX$_{(1-6)}$ (SEQ ID NO:69)

BXCX$_{(2-5)}$CXXXBXRXDHJXTHX$_{(3-5)}$H;
and

CX$_{(2-5)}$CXXXBXQXSHJXTHX$_{(3-5)}$HX$_{(1-6)}$ (SEQ ID NO:70)

BXCX$_{(2-5)}$CXXXBXRXSHJXRHX$_{(3-5)}$H.

For example, the isolated polypeptide can include an amino acid sequence that is identical to the zinc finger array within SEQ ID NO:20 or that differs by no more than 8, 6, 4, 3, or 2 substitutions within the zinc finger domains present in SEQ ID NO:20. The substitutions can be conservative substitutions. The isolated polypeptide can have a sequence that is at least 80, 85, 90, 95, or 97% identical to the zinc finger array within SEQ ID NO:20. In one embodiment, the polypeptide can specifically bind to a target DNA site. For example, the polypeptide can compete with the F121_p65 chimeric ZFP (SEQ ID NO:20) for binding to a target DNA site, e.g., a site bound with a $K_d$ of less than 10 nM. The polypeptide can further include a transcriptional regulatory domain, e.g., an activation or repression domain. The polypeptide can include one, two, or three or more additional zinc finger domains. The polypeptide can be used, for example, to regulate expression of endogenous genes such as insulin-like growth factor 2.

Also featured are nucleic acids encoding the above polypeptides. For example, the isolated polypeptide that includes the amino acid of SEQ ID NO:20 can be encoded by a nucleic acid sequence that includes the sequence of SEQ ID NO:19. Featured nucleic acids can include operably linked regulatory sequences, e.g., a promoter sequence, an enhancer sequence, an insulator sequence, untranslated regulatory regions, a polyA addition site, and so forth. In one embodiment, the coding nucleic acid is operably linked to a conditional promoter such as an inducible promoter or a cell-type specific promoter. The nucleic acid can be included in a vector or integrated into a chromosome.

In addition, the invention features host cells (e.g., mammalian host cells) that include a nucleic acid described above. The host cell can include a nucleic acid described above and express the nucleic acid.

11. K44-11-D01 and K44-11-G12 and Related Molecules

In still another aspect, the invention features an artificial polypeptide that includes: the sequence:

CX$_{(2-5)}$CXXXBXQXSHJXVHX$_{(3-5)}$HX$_{(1-6)}$ (SEQ ID NO:62)

BXCX$_{(2-5)}$CXXXBXQXSNJXIHX$_{(3-5)}$HX$_{(1-6)}$

BXCX$_{(2-5)}$CXXXBXQXTHJXRHX$_{(3-5)}$HX$_{(1-6)}$

BXCX$_{(2-5)}$CXXXBXCXSNJXRHX$_{(3-5)}$H,

CX$_{(2-5)}$CXXXBXQXSHJXVHX$_{(3-5)}$HX$_{(1-6)}$ (SEQ ID NO:63)

BXCX$_{(2-5)}$CXXXBXVXSTJXRHX$_{(3-5)}$HX$_{(1-6)}$

BXCX$_{(2-5)}$CXXXBXRXDNJXQHX$_{(3-5)}$HX$_{(1-6)}$

BXCX$_{(2-5)}$CXXXBXQXTHJXRHX$_{(3-5)}$H, where B is any amino acid, or optionally phenylalanine or tyrosine; and J is any amino acid, or optionally, a hydrophobic amino acid. These arrays are also abbreviated as: QSHV-QSNI-QTHR-CSNR and QSHV-VSTR-RDNQ-QTHR (where each set of four amino acids corresponds to the DNA contacting residues of a zinc finger domain and non-DNA contacting residues may vary).

For example, the isolated polypeptide can include an amino acid sequence that is identical to the zinc finger array within SEQ ID NO:14 or 16 or that differs by no more than 8, 6, 4, 3, or 2 substitutions within the zinc finger domains present in SEQ ID NO:14 or 16. The substitutions can be conservative substitutions. The isolated polypeptide can have a sequence that is at least 80, 85, 90, 95, or 97% identical to the zinc finger array within SEQ ID NO:14 or 16. In one embodiment, the polypeptide can specifically bind to a target DNA site. For example, the polypeptide can compete with the K44-11-D01 or K44-11-G12 chimeric ZFP (SEQ ID NO:14 or 16) for binding to a target DNA site, e.g., a site bound with a $K_d$ of less than 10 nM. The polypeptide can further include a transcriptional regulatory domain, e.g., an activation or repression domain. The polypeptide can include one, two, or three or more additional zinc finger domains. The polypeptide can be used, for example, to regulate protein production or otherwise increase SEAP activity in 293 cells.

Also featured are nucleic acids encoding the above polypeptides. For example, the isolated polypeptide that includes the amino acid of SEQ ID NO:14 or 16 can be encoded by a nucleic acid sequence that includes the sequence of SEQ ID NO:13 or 15. Featured nucleic acids can include operably linked regulatory sequences, e.g., a promoter sequence, an enhancer sequence, an insulator sequence, untranslated regulatory regions, a polyA addition site, and so forth. In one embodiment, the coding nucleic acid is operably linked to a conditional promoter such as an inducible promoter or a cell-type specific promoter. The nucleic acid can be included in a vector or integrated into a chromosome.

In addition, the invention features host cells (e.g., mammalian host cells) that include a nucleic acid described above. The host cell can include a nucleic acid described above and express the nucleic acid.

As used herein, the "dissociation constant" refers to the equilibrium dissociation constant of a polypeptide for binding to a 28-basepair double-stranded DNA that includes one 9-basepair target site. The dissociation constant is determined by gel shift analysis using a purified protein that is bound in 20 mM Tris pH 7.7, 120 mM NaCl, 5 mM MgCl$_2$, 20 µM ZnSO$_4$, 10% glycerol, 0.1% Nonidet P-40, 5 mM DTT, and 0.10 mg/mL BSA (bovine serum albumin) at room temperature. Additional details are provided in Example 10 and Rebar and Pabo (1994) *Science* 263:671-673.

As used herein, the term "screen" refers to a process for evaluating members of a library to find one or more particular members that have a given property. In a direct screen, each member of the library is evaluated. For example, each cell is evaluated to determine if it is extending neurites. In another type of screen, termed a "selection," each member is not directly evaluated. Rather the evaluation is made by subjecting the members of the library to conditions in which only members having a particular property are retained. Selections may be mediated by survival (e.g., drug resistance) or binding to a surface (e.g., adhesion to a substrate). Such selective processes are encompassed by the term "screening."

The term "base contacting positions," "DNA contacting positions," or "nucleic acid contacting positions" refers to the four amino acid positions of a zinc finger domain that structurally correspond to the positions of amino acids arginine 73, aspartic acid 75, glutamic acid 76, and arginine 79 of ZIF268.

```
Glu Arg Pro Tyr Ala Cys Pro Val Glu Ser Cys Asp Arg Arg Phe Ser   (SEQ ID NO:71)
 1           5                  10                 15

Arg Ser Asp Glu Leu Thr Arg His Ile Arg Ile His Thr Gly Gln Lys
            20                  25                 30

Pro Phe Gln Cys Arg Ile Cys Met Arg Asn Phe Ser Arg Ser Asp His
            35                  40                 45

Leu Thr Thr His Ile Arg Thr His Thr Gly Glu Lys Pro Phe Ala Cys
         50                  55              60

Asp Ile Cys Gly Arg Lys Phe Ala Arg Ser Asp Glu Arg Lys Arg His
 65              70                  75                 80

Thr Lys Ile His Leu Arg Gln Lys Asp
                 85
```

These positions are also referred to as positions −1, 2, 3, and 6, respectively. To identify positions in a query sequence that correspond to the base contacting positions, the query sequence is aligned to the zinc finger domain of interest such that the cysteine and histidine residues of the query sequence are aligned with those of finger 3 of Zif268. The ClustalW WWW Service at the European Bioinformatics Institute (Thompson et al. (1994) *Nucleic Acids Res.* 22:4673-4680) provides one convenient method of aligning sequences.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; a group of amino acids having acidic side chains is aspartic acid and glutamic acid; and a group of amino acids having sulfur-containing side chains is cysteine and methionine. Depending on circumstances, amino acids within the same group may be interchangeable. Some additional conservative amino acids substitution groups are: valine-leucine-isoleucine; phenylalanine-tyrosine; lysine-arginine; alanine-valine; aspartic acid-glutamic acid; and asparagine-glutamine.

The term "heterologous polypeptide" refers either to a polypeptide with a non-naturally occurring sequence (e.g., a hybrid polypeptide) or a polypeptide with a sequence identical to a naturally occurring polypeptide but present in a milieu in which it does not naturally occur.

The terms "hybrid" and "chimera" refer to a non-naturally occurring polypeptide that comprises amino acid sequences derived from either (i) at least two different naturally occurring sequences, or non-contiguous regions of the same naturally occurring sequence, wherein the non-contiguous regions are made contiguous in the hybrid; (ii) at least one artificial sequence (i.e., a sequence that does not occur naturally) and at least one naturally occurring sequence; or (iii) at least two artificial sequences (same or different). Examples of artificial sequences include mutants of a naturally occurring sequence and de novo designed sequences. An "artificial sequence" is not present among naturally occurring sequences. With respect to any artificial sequence (e.g., protein or nucleic acid) described herein, the invention also refers to a sequence with the same elements, but which is not presenting each of the following organisms whose genomes are sequenced: *Homo sapiens, Mus musculus, Arabidopsis thaliana, Drosophila melanogaster, Escherichia coli, Saccharomyces cerevisiae,* and *Oryza sativa.* A molecule with such a sequence can be expressed as a heterologous molecule in a cell of one of the afore-mentioned organisms.

The invention also includes sequences (not necessarily termed "artificial") which are made by a method described herein, e.g., a method of joining nucleic acid sequences encoding different zinc finger domains or a method of phenotypic screening. The invention also features a cell that includes such a sequence.

As used herein, the term "hybridizes under stringent conditions" refers to conditions for hybridization in 6× sodium chloride/sodium citrate (SSC) at 45° C., followed by two washes in 0.2×SSC, 0.1% SDS at 65° C.

The term "binding preference" refers to the discriminative property of a polypeptide for selecting one nucleic acid binding site relative to another. For example, when the polypeptide is limiting in quantity relative to two different nucleic acid binding sites, a greater amount of the polypeptide will bind the preferred site relative to the other site in an in vivo or in vitro assay described herein.

A "reference cell" refers to any cell of interest. In one example, the reference cell is a parental cell for a cell that expresses a zinc finger protein, e.g., a cell that is substantially identical to the zinc finger protein expressing cell, but which does not produce the zinc finger protein.

A "transformed" or "transfected" cell refers to a cell that includes a heterologous nucleic acid. The cell can be made by introducing (e.g., transforming, transfecting, or infecting, e.g., using a viral particle) a nucleic acid into the cell or the cell can be a progeny or derivative of a cell thus made.

Among other advantages, many of the methods and compositions relate to the identification and use of new and useful chimeric proteins, e.g., chimeric transcription factors. Some embodiments may include one or more of the following advantages: i) Endogenous genes can be either up- or down-regulated. Any given artificial chimeric transcription factor can be converted to transcriptional activator by fusing to appropriate transcriptional activation domains or to transcriptional repressor by fusing to repression domains. Moreover, even without a transcriptional regulatory domain, chimeric transcription factors can be potent repressors, e.g., when they bind to sites near the TATA box and the initiator element. Moreover, it is possible to screen a library that includes both activators and repressors with different DNA binding specificity. ii) Gene expression can be finely regulated. Depending on the DNA-binding affinity, chimeric transcription factors can cause a range of effects, e.g., moderate to strong activation and repression. This may lead to diverse phenotypes that are not necessarily obtained by completely inactivation or high level over-expressed of a particular target gene. For example, in some cases, broad specificity may be an advantage where the coordinated action of several genes is required to drive a desired phenotype. In other cases, narrow specificity is desired. One method for flexibly controlling specificity is by adding or removing zinc finger domains. 3-finger ZFPs theoretically regulate more genes than 6-finger ZFPs. iii) ZFP library approach is universally applicable. Since transcriptional regulatory mechanisms are highly conserved and because all known organism use DNA and transcription for life, chimeric proteins that bind to DNA can be used to regulate any desired cell. Further, as described herein, many methods do not require a priori information (e.g., genome sequence) of the cell in order to identify useful chimeric proteins. iv) Artificial chimeric proteins can be used as a tool to dissect pathways within a cell. For example, target genes responsible for the phenotypic changes in selected clones can be identified, e.g., as described herein. v) A ZFP-TF may mimic the function of a master regulatory protein, such as a master regulatory transcription factor. For example, the ZFP-TF may bind to the same site as the master regulatory, or to an overlapping site. vi) The level of gene expression change, thus the extent of the phenotype generated by ZFP-TF, can be precisely controlled by altering the expression level of ZFP-TF in cells.

All patents, patent applications, and references cited herein are incorporated by reference in their entirety. The following patent applications: WO 01/60970 (Kim et al.); U.S. Ser. No. 60/338,441, filed Dec. 7, 2001; U.S. Ser. No. 60/313,402, filed Aug. 17, 2001; U.S. Ser. No. 60/374,355, filed Apr. 22, 2002; U.S. Ser. No. 60/376,053, filed Apr. 26, 2002; U.S. Ser. No. 60/400,904, filed Aug. 2, 2002; U.S. Ser. No. 60/401,089, filed Aug. 5, 2002; and U.S. Ser. No. 10/223,765, filed Aug. 19, 2002, are expressly incorporated by reference in their entirety for all purposes. The details of one or more embodiments of the invention are set forth in the accompanying drawings and the description below. Any feature described herein can be used in combination with another compatible feature also described herein. Other features, objects, and advantages of the invention will be apparent from the description and drawings, and from the claims.

DESCRIPTION OF THE DRAWINGS

FIG. 8A. pcDNA3 (empty vector)-transfected Neuro2A cells without retinoic acid (RA) treatment. FIG. 8B. Neuro1-p65 (also called 08_D01-65) expression without RA treatment. FIG. 8C. pcDNA3(empty vector)-transfected Neuro2A cells with 10 μM RA. FIG. 8D. Neuro1-p65 expression with 10 μM RA.

FIG. 10A is a truncated table listing ZFP DNA binding specificities.

FIG. 14 lists the coding nucleic acid (SEQ ID NO:1) and amino acid (SEQ ID NO:2) sequences for Neuro 1-p65, a protein that can induce neurites. Neuro 1-p65 includes the zinc finger domains QSNR-QSNK-CSNR and the p65 activation domain. Other artificial proteins with at least two or three consecutive zinc finger domains that have the same pattern of DNA contacting residues as domains in QSNR-QSNK-CSNR-p65 may also induce neurites.

FIG. 15 lists the coding nucleic acid (SEQ ID NO:3) and amino acid (SEQ ID NO:4) sequences for Osteo1-p65, a protein that can induce oosteocytes. Osteo1-p65 includes the zinc finger domains RDKR-QTHR1-VSTR-RDKR and the p65 activation domain. Other artificial proteins with at least two or three consecutive zinc finger domains that have the same pattern of DNA contacting residues as domains in RDKR-QTHR1-VSTR-RDKR-p65 may also induce oosteocytes.

FIG. 16 lists the coding nucleic acid (SEQ ID NO:5) and amino acid (SEQ ID NO:6) sequences for 08_D04_p65, a protein that can enhance insulin production (See FIG. 9). 08_D04_p65 includes the zinc finger domains RSHR-RDHT-VSSR and the p65 activation domain. Other artificial proteins with at least two or three consecutive zinc finger domains that have the same pattern of DNA contacting residues as domains in RSHR-RDHT-VSSR may also enhance insulin production.

FIG. 17 lists the coding nucleic acid (SEQ ID NO:7) and amino acid (SEQ ID NO:8) sequences for P_B08, a protein that can enhances SV40-SEAP. P_B08 includes the zinc finger domains QSNR1-DSNR-DSNR and the p65 activation domain. Other artificial proteins with at least two or three consecutive zinc finger domains that have the same pattern of DNA contacting residues as domains in QSNR-DSNR-DSNR may also enhances SV40-SEAP.

FIG. 18 lists the coding nucleic acid (SEQ ID NO:9) and amino acid (SEQ ID NO:10) sequences for K_D10, a protein that can decrease cell proliferation. K_D10 includes the zinc finger domains QSHV-WSNR-WSNR-RDNQ and the kid repression domain. Other artificial proteins with at least two or three consecutive zinc finger domains that have the same pattern of DNA contacting residues as domains in QSHV-WSNR-WSNR-RDNQ may also decrease cell proliferation.

FIG. 19 lists the coding nucleic acid (SEQ ID NO:11) and amino acid (SEQ ID NO:12) sequences for K_F02, a protein that can enhance cell proliferation. K_F02 includes the zinc finger domains DSAR2-RDKR-RDER1-QTHR1 and the kid repression domain. Other artificial proteins with at least two or three consecutive zinc finger domains that have the same pattern of DNA contacting residues as domains in DSAR2-RDKR-RDER1-QTHR1-kid may also enhance cell proliferation.

FIG. 20 lists the coding nucleic acid (SEQ ID NO:13) and amino acid (SEQ ID NO:14) sequences for K44_11_D01, a protein that can enhance protein expression. K44_11_D01 includes the zinc finger domains QSHV-QSNI-QTHR1-CSNR1 and the kid repression domain. Other artificial proteins with at least two or three consecutive zinc finger domains that have the same pattern of DNA contacting residues as domains in QSHV-QSNI-QTHR1-CSNR1 may also enhance protein expression.

FIG. 21 lists the coding nucleic acid (SEQ ID NO:15) and amino acid (SEQ ID NO:16) sequences for K44-11-G12, a protein that can enhance protein expression. K44-11-G12 includes the zinc finger domains QSHV-VSTR-RDNQ-QTHR1 and the kid repression domain. Other artificial proteins with at least two or three consecutive zinc finger domains that have the same pattern of DNA contacting residues as domains in QSHV-VSTR-RDNQ-QTHR1 may also enhance protein expression.

FIG. 22 lists the coding nucleic acid (SEQ ID NO:17) and amino acid (SEQ ID NO:18) sequences for F104_p65. F104_p65 includes the zinc finger domains RDHT-RSHR-QSHR2-p65.

FIG. 23 lists the coding nucleic acid (SEQ ID NO:19) and amino acid (SEQ ID NO:20) sequences for F121_p65. F121_p65 includes the zinc finger domains QSHT-RSHR-RDHT-p65. Other artificial proteins with at least two or three consecutive zinc finger domains that have the same pattern of DNA contacting residues as domains in QSHT-RSHR-RDHT may also increase transcription of insulin-like growth factor 2

FIG. 24 lists the coding nucleic acid (SEQ ID NO:259) and amino acid (SEQ ID NO:260) sequences for K12_A11, which includes the zinc finger domains RDHT-QSNV2-QTHR1-QFNR-kid.

FIG. 25 lists the coding nucleic acid (SEQ ID NO:261) and amino acid (SEQ ID NO:64) sequences for K44-16-E12, which includes the zinc finger domains QSHV-QSSR1-QTHR1-kid.

Figure 1:
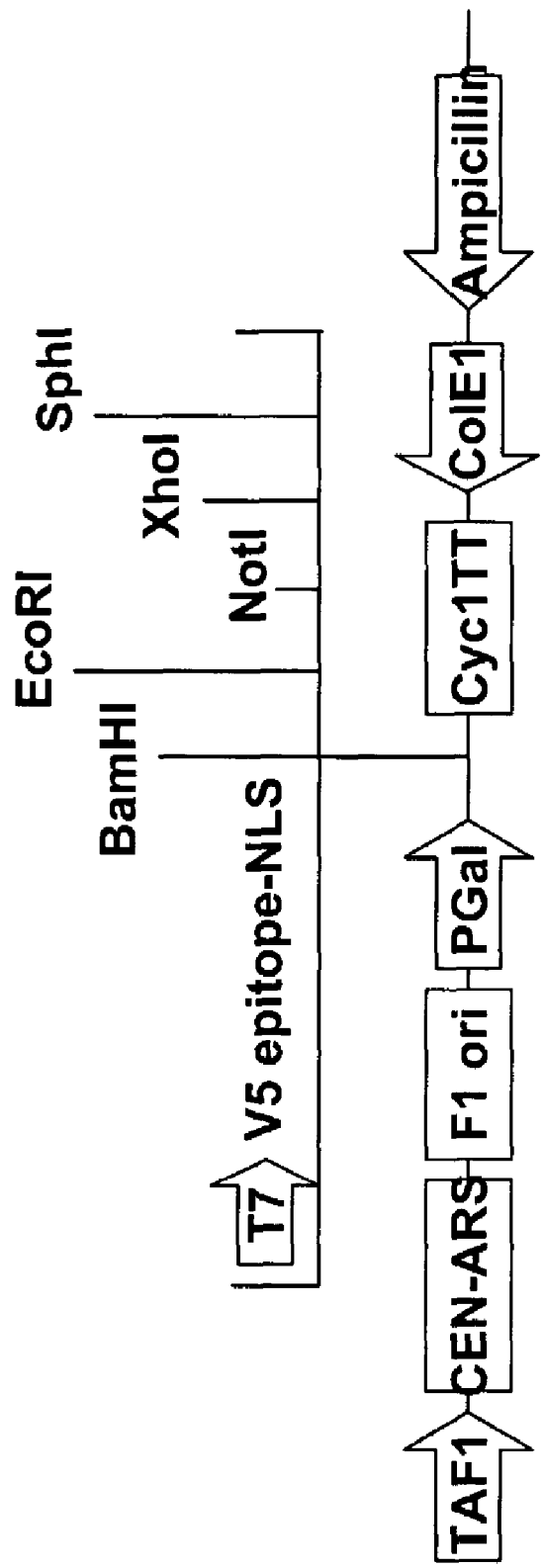
FIG. 1 is a diagram of a region of the yeast plasmid pYTC-Lib.
Figure 2:
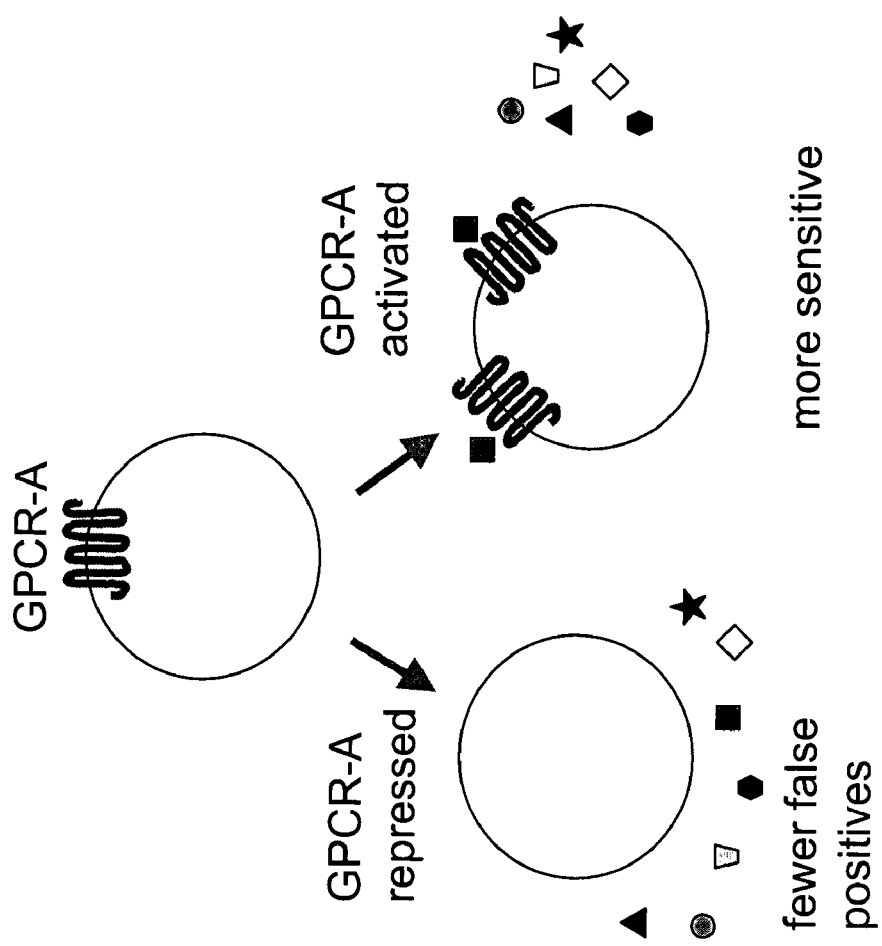
FIG. 2 is a schematic of an exemplary target-driven approach.
Figure 3A:
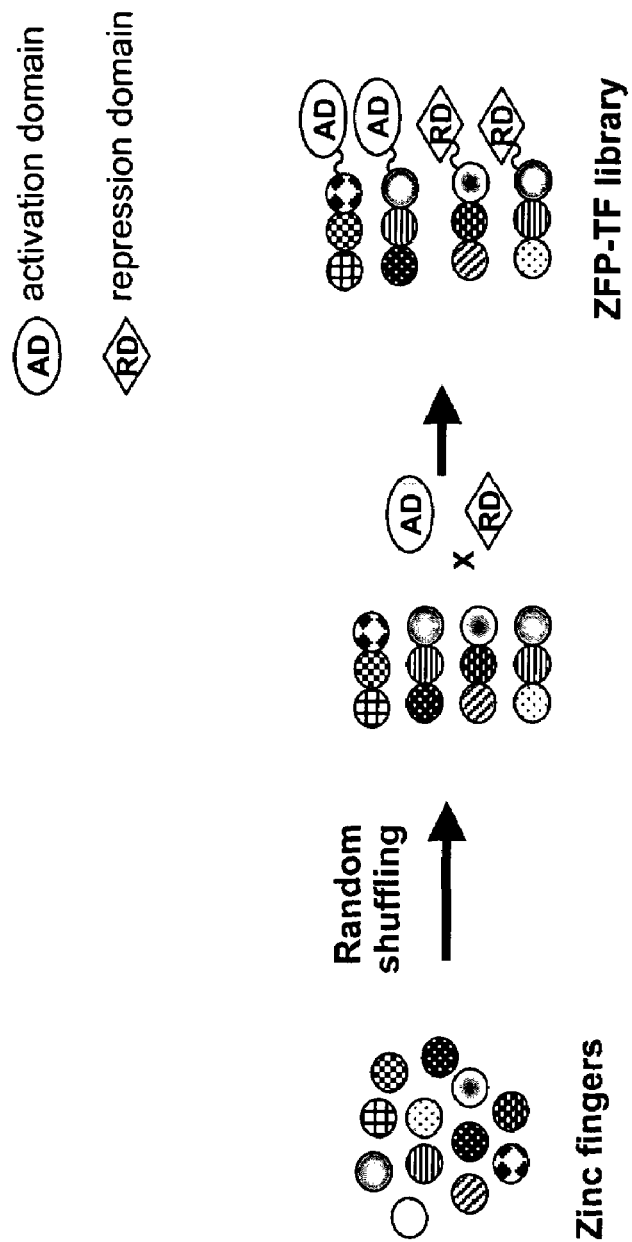
FIG. 3A is a schematic of a method for preparing an exemplary zinc finger protein library.
Figure 3B:
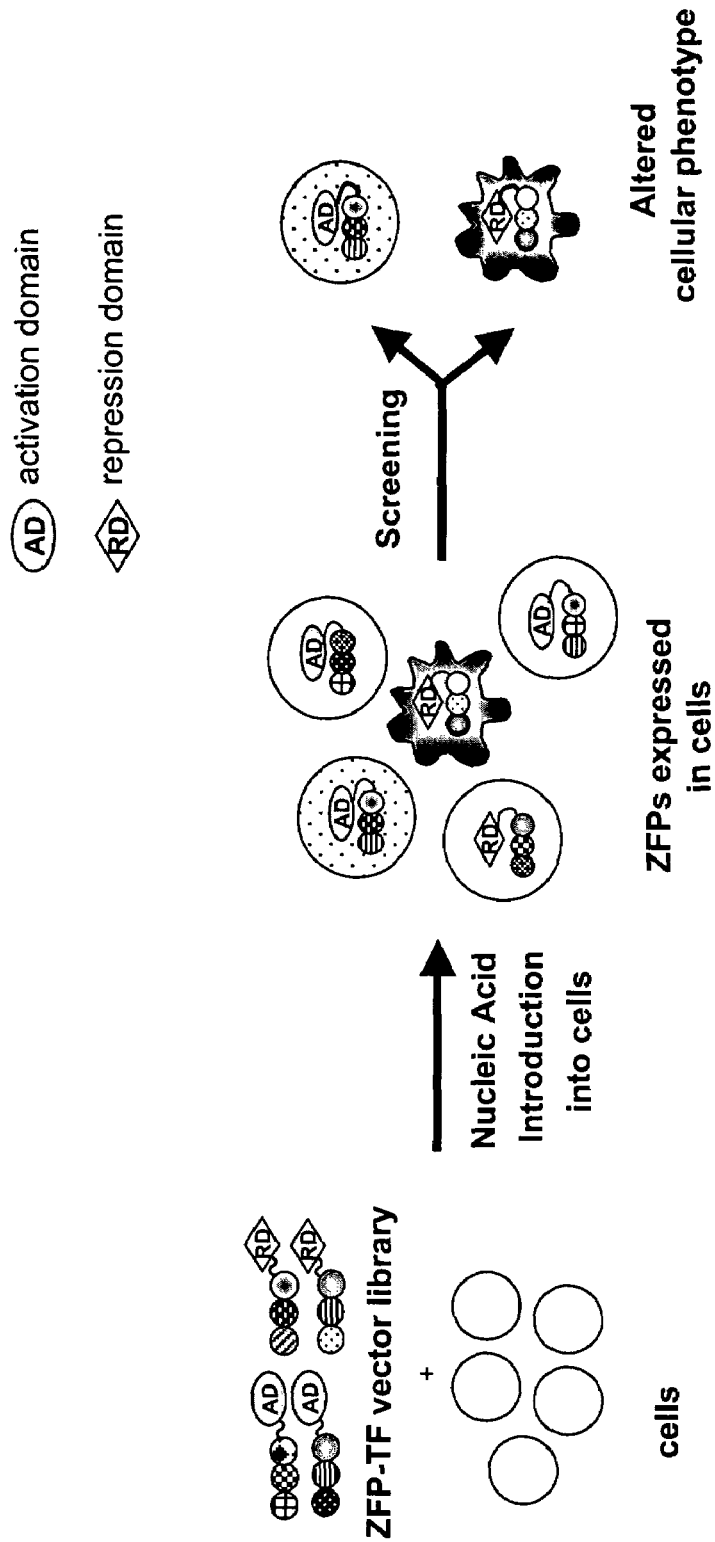
FIG. 3B is a schematic of an exemplary phenotype-driven approach.

DNA sequences in the FIGS. 14 to 25 include a sequence encoding a HA tag (gray underlined), and a sequence encoding a nuclear localization signal (boxed). The initiation and stop codons are underlined and two restriction sites used for cloning of zinc finger domains, EcoRI and NotI, are indicated as bold letters. Shaded letters indicate sequences encoding a regulatory domain, e.g., a p65 or kid domain. Small letters indicated the linker sequences. With respect to the amino acid sequences, italicized and shaded letters indicate zinc finger domains and shaded letters, not italicized indicate a regulatory domain, e.g., a Kid or p65 domain.

DETAILED DESCRIPTION

In one aspect of the invention, a library of nucleic acids that encode different artificial, chimeric proteins is screened to identify a chimeric protein that alters a phenotypic trait of a cell or organism. The chimeric protein can be identified without a priori knowledge of a particular target gene or pathway.

In one example, each nucleic acid of the library encodes an artificial polypeptide that includes a plurality of zinc finger domains. A nucleic acid library that encodes different chimeric proteins can be prepared, for example, as described in the sections below. Members of the library are introduced into cells in culture or cells in an organism. After an interval to allow for expression of the encoded polypeptides, cells or organisms which have an altered phenotypic trait are identified. The library nucleic acid in at least one of these phenotypically altered cells is recovered, thus identifying an artificial chimeric polypeptide that produces the phenotypic effect.

Although this method is generally described below in the context of chimeras of zinc finger domains, it is easily adapted to other structural domains, including other DNA binding domains and cell signaling domains.

Library Construction: 1. Exemplary Structural Domains

The nucleic acid library is constructed so that it includes nucleic acids that each encode and can express an artificial protein that is a chimera of one or more structural domains. In some aspects, the structural domains are nucleic acid binding domains that vary in specificity such that the library encodes a population of proteins with different binding specificities.

A variety of structural domains are known to bind nucleic acids with high affinity and high specificity. For reviews of structural motifs which recognize double stranded DNA, see, e.g., Pabo and Sauer (1992) *Annu. Rev. Biochem.* 61:1053-95; Patikoglou and Burley (1997) *Annu. Rev. Biophys. Biomol. Struct.* 26:289-325; Nelson (1995) *Curr Opin Genet Dev.* 5:180-9. A few non-limiting examples of nucleic acid binding domains include:

Zinc fingers. Zinc fingers are small polypeptide domains of approximately 30 amino acid residues in which there are four amino acids, either cysteine or histidine, appropriately spaced such that they can coordinate a zinc ion (For reviews, see, e.g., Klug and Rhodes, (1987) *Trends Biochem. Sci.* 12:464-469 (1987); Evans and Hollenberg, (1988) *Cell* 52:1-3; Payre and Vincent, (1988) *FEBS Lett.* 234:245-250; Miller et al., (1985) *EMBO J.* 4:1609-1614; Berg, (1988) *Proc. Natl. Acad. Sci. U.S.A.* 85:99-102; Rosenfeld and Margalit, (1993) *J. Biomol. Struct. Dyn.* 11:557-570). Hence, zinc finger domains can be categorized according to the identity of the residues that coordinate the zinc ion, e.g., as the $Cys_2$-$His_2$ class, the $Cys_2$-$Cys_2$ class, the $Cys_2$-CysHis class, and so forth. The zinc coordinating residues of $Cys_2$-$His_2$ zinc fingers are typically spaced as follows: $X_a$-X-C-$X_{2-5}$-C-$X_3$-$X_a$-$X_5\psi$-$X_2$-H-$X_{3-5}$-H (SEQ ID NO:72), where $\psi$ (psi) is a hydrophobic residue (Wolfe et al., (1999) *Annu. Rev. Biophys. Biomol. Struct.* 3:183-212), wherein "X" represents any amino acid, wherein $X_a$ is phenylalanine or tyrosine, the subscript indicates the number of amino acids, and a subscript with two hyphenated numbers indicates a typical range of intervening amino acids. Typically, the intervening amino acids fold to form an anti-parallel β-sheet that packs against an α-helix, although the anti-parallel β-sheets can be short, non-ideal, or non-existent. The fold positions the zinc-coordinating side chains so they are in a tetrahedral conformation appropriate for coordinating the zinc ion. The base contacting residues are at the N-terminus of the finger and in the preceding loop region.

For convenience, the primary DNA contacting residues of a zinc finger domain are numbered: −1, 2, 3, and 6 based on the following example:

$$X_a\text{-}X\text{-}C\text{-}X_{2\text{-}5}\text{-}C\text{-}X_3\text{-}X_a\text{-}X\text{-}C\text{-}X\text{-}S\text{-}N\text{-}X_b\text{-}X\text{-}R\text{-}H\text{-}X_{3\text{-}5}\text{-}H,$$   (SEQ ID NO: 73)

where $X_a$ is typically phenylalanine or tyrosine, and $X_b$ is typically a hydrophobic residue. As noted in the example above, the DNA contacting residues are Cys (C), Ser (S), Asn (N), and Arg (R). The above motif can be abbreviated CSNR As used herein, such abbreviation refers to a class of sequences which include a domain corresponding to the motif as wells as a species whose sequence includes a particular polypeptide sequence, typically a sequence listed in Table 1 that conforms to the motif. Where two sequences in Table 1 have the same motif, a number may be used to indicate the sequence. In certain embodiments, a sequence listed in Table 2 (if different from Table 1) that conforms to the motif may also be used.

A zinc finger protein typically consists of a tandem array of three or more zinc finger domains. For example, zinc finger domains whose motifs are listed consecutively are not interspersed with other folded domains, but may include a linker, e.g., a flexible linker described herein between domains. For an implementation that includes a specific zinc finger protein or array thereof described herein, the invention also features a related implementation that includes a corresponding zinc finger protein or array thereof having an array with zinc fingers that have the same DNA contacting residues as the specific zinc finger protein or array thereof. The corresponding zinc finger protein may differ by at least one, two, three, four, or five amino acids from the disclosed specific zinc finger protein, e.g., at an amino acid position that is not a DNA contacting residue. Other related implementations include a corresponding protein that has at least one, two, or three zinc fingers that have the same DNA contacting residues, e.g., in the same order.

The zinc finger domain (or "ZFD") is one of the most common eukaryotic DNA-binding motifs, found in species from yeast to higher prants and to humans. By one estimate, there are at least several thousand zinc finger domains in the human genome alone, possibly at least 4,500. Zinc finger domains can be isolated from zinc finger proteins. Non-limiting examples of zinc finger proteins include CF2-II, Kruppel, WT1, basonuclin, BCL-6/LAZ-3, erythroid Kruppel-like transcription factor, Sp1, Sp2, Sp3, Sp4, transcriptional repressor YY1, EGR1/Krox24, EGR2/Krox20, EGR3/Pilot, EGR4/AT133, Evi-1, GLI1, GLI2, GLI3, HIV-EP1/ZNF40, HIV-EP2, KR1, ZfX, ZfY, and ZNF7.

Computational methods described below can be used to identify all zinc finger domains encoded in a sequenced genome or in a nucleic acid database. Any such zinc finger domain can be utilized. In addition, artificial zinc finger domains have been designed, e.g., using computational methods (e.g., Dahiyat and Mayo, (1997) *Science* 278:82-7).

It is also noteworthy that at least some zinc finger domains bind to ligands other than DNA, e.g., RNA or protein. Thus, a chimera of zinc finger domains or of a zinc finger domain and another type of domain can be used to recognize a variety of target compounds, not just DNA.

WO 01/60970, U.S. Ser. No. 60/374,355, filed Apr. 22, 2002, and U.S. Ser. No. 10/223,765, filed Aug. 19, 2002, describe exemplary zinc finger domains which can be used to construct an artificial zinc finger protein. See also the Table 1, below.

Homeodomains. Homeodomains are eukaryotic domains that consist of a N-terminal arm that contacts the DNA minor groove, followed by three α-helices that contact the major groove (for a review, see, e.g., Laughon, (1991) *Biochemistry* 30:11357-67). The third α-helix is positioned in the major groove and contains critical DNA-contacting side chains. Homeodomains have a characteristic highly-conserved motif present at the turn leading into the third α-helix. The motif includes an invariant tryptophan that packs into the hydrophobic core of the domain. Homeodomains are commonly found in transcription factors that determine cell identity and provide positional information during organismal development. Such classical homeodomains can be found in the genome in clusters such that the order of the homeodomains in the cluster approximately corresponds to their expression pattern along a body axis. Homeodomains can be identified by alignment with a homeodomain, e.g., Hox-1, or by alignment with a homeodomain profile or a homeodomain hidden Markov Model (HMM; see below), e.g., PF00046 of the Pfam database or "HOX" of the SMART database, or by the Prosite motif PDOC00027 as mentioned above.

Helix-turn-helix proteins. This DNA binding motif is common among many prokaryotic transcription factors. There are many subfamilies, e.g., the LacI family, the AraC family, to name but a few. The two helices in the name refer to a first α-helix that packs against and positions a second α-helix in the major groove of DNA. These domains can be identified by alignment with a HMM, e.g., HTH_ARAC, HTH_ARSR, HTH_ASNC, HTH_CRP, HTH_DEOR, HTH_DTXR, HTH_GNTR, HTH_ICLR, HTH_LACI, HTH_LUXR, HTH_MARR, HTH_MERR, and HTH_XRE profiles available in the SMART database.

Library Construction: 2. Identification of Structural Domains

A variety of methods can be used to identify structural domains. Nucleic acids encoding identified domains are used to construct the nucleic acid library. Further, nucleic acid encoding these domains can also be varied (e.g., mutated) to provide additional domains that are encoded by the library.

Computational Methods. To identify additional naturally-occurring structural domains, the amino acid sequence of a known structural domain can be compared to a database of known sequences, e.g., an annotated database of protein or nucleic acid sequences. In another implementation, databases of uncharacterized sequences, e.g., unannotated genomic, EST or full-length cDNA sequence; of characterized sequences, e.g., SwissProt or PDB; and of domains, e.g., Pfam, ProDom (Corpet et al. (2000) *Nucleic Acids Res.* 28:267-269), and SMART (Simple Modular Architecture Research Tool, Letunic et al. (2002) *Nucleic Acids Res* 30, 242-244) can provide a source of structural domain sequences. Nucleic acid sequence databases can be translated in all six reading frames for the purpose of comparison to a query amino acid sequence. Nucleic acid sequences that are flagged as encoding candidate nucleic acid binding domains can be amplified from an appropriate nucleic acid source, e.g., genomic DNA or cellular RNA. Such nucleic acid sequences can be cloned into an expression vector. The procedures for computer-based domain identification can be interfaced with an oligonucleotide synthesizer and robotic systems to produce nucleic acids encoding the domains in a high-throughput platform. Cloned nucleic acids encoding the candidate domains can also be stored in a host expression vector and shuttled easily into an expression vector, e.g., into a translational fusion vector with other domains (of a similar or different type), either by restriction enzyme mediated subcloning or by site-specific, recombinase mediated subcloning (see U.S. Pat. No. 5,888,732). The high-throughput platform can be used to generate multiple microtitre plates containing nucleic acids encoding different candidate chimeras.

Detailed methods for the identification of domains from a starting sequence or a profile are well known in the art. See, for example, Prosite (Hofmann et al., (1999) *Nucleic Acids Res.* 27:215-219), FASTA, BLAST (Altschul et al., (1990) *J. Mol. Biol.* 215:403-10.), etc. A simple string search can be done to find amino acid sequences with identity to a query sequence or a query profile, e.g., using Perl to scan text files. Sequences so identified can be about 30%, 40%, 50%, 60%, 70%, 80%, 90%, or greater identical to an initial input sequence.

Domains similar to a query domain can be identified from a public database, e.g., using the XBLAST programs (version 2.0) of Altschul et al., (1990) *J. Mol. Biol.* 215:403-10. For example, BLAST protein searches can be performed with the XBLAST parameters as follows: score=50, wordlength=3. Gaps can be introduced into the query or searched sequence as described in Altschul et al., (1997) *Nucleic Acids Res.* 25(17):3389-3402. Default parameters for XBLAST and Gapped BLAST programs are available at National Center for Biotechnology Information (NCBI), National Institutes of Health, Bethesda Md.

The Prosite profiles PS00028 and PS50157 can be used to identify zinc finger domains. In a SWISSPROT release of 80,000 protein sequences, these profiles detected 3189 and 2316 zinc finger domains, respectively. Profiles can be constructed from a multiple sequence alignment of related proteins by a variety of different techniques. Gribskov and coworkers (Gribskov et al., (1990) *Meth. Enzymol.* 183:146-159) utilized a symbol comparison table to convert a multiple sequence alignment supplied with residue frequency distributions into weights for each position. See, for example, the PROSITE database and the work of Luethy et al., (1994) *Protein Sci.* 3:139-1465.

Hidden Markov Models (HMM's) representing a DNA binding domain of interest can be generated or obtained from a database of such models, e.g., the Pfam database, release 2.1. A database can be searched, e.g., using the default parameters, with the HMM in order to find additional domains (see, e.g., Bateman et al. (2002) *Nucleic Acids Research* 30:276-280). Alternatively, the user can optimize the parameters. A threshold score can be selected to filter the database of sequences such that sequences that score above the threshold are displayed as candidate domains. A description of the Pfam database can be found in Sonhammer et al., (1997) *Proteins* 28(3):405-420, and a detailed description of HMMs can be found, for example, in Gribskov et al., (1990) *Meth. Enzymol.* 183:146-159; Gribskov et al., (1987) *Proc. Natl. Acad. Sci. USA* 84:4355-4358; Krogh et al., (1994) *J. Mol. Biol.* 235:1501-1531; and Stultz et al., (1993) *Protein Sci.* 2:305-314.

The SMART database of HMM's (Simple Modular Architecture Research Tool, Schultz et al., (1998) *Proc. Natl. Acad. Sci. USA* 95:5857 and Schultz et al., (2000) *Nucl. Acids Res* 28:231) provides a catalog of zinc finger domains (ZnF_C2H2; ZnF_C2C2; ZnF_C2HC; ZnF_C3H1; ZnF_C4; ZnF_CHCC; ZnF_GATA; and ZnF_NFX) identified by profiling with the hidden Markov models of the HMMer2 search program (Durbin et al., (1998) *Biological sequence analysis: probabilistic models of proteins and nucleic acids*. Cambridge University Press).

Hybridization-based Methods. A collection of nucleic acids encoding various forms of a structural domain can be analyzed to profile sequences encoding conserved amino- and carboxy-terminal boundary sequences. Degenerate oligonucleotides can be designed to hybridize to sequences encoding such conserved boundary sequences. Moreover, the efficacy of such degenerate oligonucleotides can be estimated by comparing their composition to the frequency of possible annealing sites in known genomic sequences. If desired, multiple rounds of design can be used to optimize the degenerate oligonucleotides.

Comparison of known $Cys_2$-$His_2$ zinc fingers, for example, revealed a common sequence in the linker region between adjacent fingers in natural sequence (Agata et al., (1998) *Gene* 213:55-64). Degenerate oligonucleotides that anneal to nucleic acid encoding the conserved linker region were used to amplify a plurality of zinc finger domains. The amplified nucleic acid encoding the domains can be used to construct nucleic acids that encode a chimeric array of zinc fingers.

Library Construction: 3. Nucleic Acids Encoding Structural Domains

Nucleic acids that are used to assemble the library can be obtained by a variety of methods. Some component nucleic acids of the library can encode naturally occurring domains. In addition, some component nucleic acids are variants that are obtained by mutation or other randomization methods. The component nucleic acids, typically encoding just a single domain, can be joined to each other to produce nucleic acids encoding a fusion of the different domains.

Isolation of a natural repertoire of domains. A library of domains can be constructed by isolation of nucleic acid sequences encoding domains from genomic DNA or cDNA of eukaryotic organisms such as humans. Multiple methods are available for doing this. For example, a computer search of available amino acid sequences can be used to identify the domains, as described above. A nucleic acid encoding each domain can be isolated and inserted into a vector appropriate for the expression in cells, e.g., a vector containing a promoter, an activation domain, and a selectable marker. In another example, degenerate oligonucleotides that hybridize to a conserved motif are used to amplify, e.g., by PCR, a large number of related domains containing the motif. For example, Kruppel-like $Cys_2His_2$ zinc fingers can be amplified by the method of Agata et al., (1998) *Gene* 213:55-64. This method also maintains the naturally occurring zinc finger domain linker peptide sequences, e.g., sequences with the pattern: Thr-Gly-(Glu/Gln)-(Lys/Arg)-Pro-(Tyr/Phe) (SEQ ID NO:74). Moreover, screening a collection limited to domains of interest, unlike screening a library of unselected genomic or cDNA sequences, significantly decreases library complexity and reduces the likelihood of missing a desirable sequence due to the inherent difficulty of completely screening large libraries.

The human genome contains numerous zinc finger domains, many of which are uncharacterized and unidentified. It is estimated that there are thousands of genes encoding proteins with zinc finger domains (Pellegrino and Berg, (1991) *Proc. Natl. Acad. Sci. USA* 88:671-675). These human zinc finger domains represent an extensive collection of diverse domains from which novel DNA-binding proteins can be constructed. Many exemplary human zinc finger domains are described in WO 01/60970, U.S. Ser. No. 60/374,355, filed Apr. 22, 2002, and U.S. Ser. No. 10/223,765, filed Aug. 19, 2002. See also Table 1 below.

TABLE 1

Exemplary Zinc Finger Domains

| ZFD | Amino acid sequence | SEQ ID NO: | Target subsite(s) |
|---|---|---|---|
| CSNR1 | YKCKQCGKAFGCPSNLRRHGRTH | 75 | GAA > GAC > GAG |
| CSNR2 | YQCNICGKCFSCNSNLHRHQRTH | 76 | GAA > GAC > GAG |
| DSAR2 | YSCGICGKSFSDSSAKRRHCILH | 77 | GTC |
| DSCR | YTCSDCGKAFRDKSCLNRHRRTH | 78 | GCC |
| HSNK | YKCKECGKAFNHSSNFNKHHRIH | 79 | GAC |
| HSSR | FKCPVCGKAFRHSSSLVRHQRTH | 80 | GTT |
| ISNR | YRCKYCDRSFSISSNLQRHVRNIH | 81 | GAA > GAT > GAC |
| ISNV | YECDHCGKAFSIGSNLNVHRRIH | 82 | AAT |
| KSNR | YGCHLCGKAFSKSSNLRRHEMIH | 83 | GAG |
| QAHR | YKCKECGQAFRQRAHLIRHHKLH | 84 | GGA |
| QFNR | YKCHQCGKAFIQSFNLRRHERTH | 85 | GAG |
| QGNR | FQCNQCGASFTQKGNLLRHIKLH | 86 | GAA |
| QSHR1 | YACHLCGKAFTQSSHLRRHEKTH | 87 | GGA > GAA > AGA |
| QSHR2 | YKCGQCGKFYSQVSHLTRHQKIH | 88 | GGA |
| QSHR3 | YACHLCGKAFTQCSHLRRHEKTH | 89 | GGA > GAA |
| QSHR4 | YACHLCAKAFIQCSHLRRHEKTH | 90 | GGA > GAA |
| QSHR5 | YVCRECGRGFRQHSHLVRHKRTH | 91 | GGA > AGA > GAA > CGA |
| QSHT | YKCEECGKAFRQSSHLTTHKIIH | 92 | AGA, CGA > TGA > GGA |
| QSHV | YECDHCGKSFSQSSHLNVHKRTH | 93 | CGA > AGA > TGA |
| QSNI | YMCSECGRGFSQKSNLIIHQRTH | 94 | AAA, CAA |
| QSNK | YKCEECGKAFTQSSNLTKHKKIH | 95 | GAA > TAA > AAA |
| QSNR1 | FECKDCGKAFIQKSNLIRHQRTH | 96 | GAA |
| QSNR2 | YVCRECRRGFSQKSNLIRHQRTH | 97 | GAA |
| QSNR3 | YECEKCGKAFNQSSNLTRHKKSH | 98 | GAA |
| QSNV1 | YECNTCRKTFSQKSNLIVHQRTH | 99 | AAA > CAA |
| QSNV2 | YVCSKCGKAFTQSSNLTVHQKIH | 100 | AAA > CAA |
| QSNV3 | YKCDECGKNFTQSSNLIVHKRIH | 101 | AAA |
| QSNV4 | YECDVCGKTFTQKSNLGVHQRTH | 102 | AAA |
| QSNT | YECVQCGKGFTQSSNLITHQRVH | 103 | AAA |
| QSSR1 | YKCPDCGKSFSQSSSLIRHQRTH | 104 | GTA > GCA |
| QSSR2 | YECQDCGRAFNQNSSLGRHKRTH | 105 | GTA |
| QSSR3 | YECNECGKFFSQSSSLIRHRRSH | 106 | GTA > GCA |
| QSTR | YKCEECGKAFNQSSTLTRHKIVH | 107 | GTA > GCA |
| QSTV | YECNECGKAFAQNSTLRVHQRIH | 108 | ACA |
| QTHQ | YECHDCGKSFRQSTHLTQHRRIH | 109 | AGA > CGA, TGA |

TABLE 1-continued

Exemplary Zinc Finger Domains

| ZFD | Amino acid sequence | SEQ ID NO: | Target subsite(s) |
|---|---|---|---|
| QTHR1 | YECHDCGKSFRQSTHLTRHRRIH | 110 | GGA > AGA, GAA |
| QTHR2 | HKCLECGKCFSQNTHLTRHQRT | 111 | GGA |
| RDER1 | YVCDVEGCTWKFARSDELNRHKKRH | 112 | GCG > GTG, GAC |
| RDER2 | YHCDWDGCGWKFARSDELTRHYRKH | 113 | GCG > GTG |
| RDER3 | YRCSWEGCEWRFARSDELTRHFRKH | 114 | GCG > GTG |
| RDER4 | FSCSWKGCERRFARSDELSRHRRTH | 115 | GCG > GTG |
| RDER5 | FACSWQDCNKKFARSDELARHYRTH | 116 | GCG |
| RDER6 | YHCNWDGCGWKFARSDELTRHYRKH | 117 | GCG > GTG |
| RDHR1 | FLCQYCAQRFGRKDHLTRHMKKSH | 118 | GAG, GGG |
| RDHT | FQCKTCQRKFSRSDHLKTHTRTH | 119 | AGG, CGG, GGG, TGG |
| RDKI | FACEVCGVRFTRNDKLKIHMRKH | 120 | GGG |
| RDKR | YVCDVEGCTWKFARSDKLNRHKKRH | 121 | GGG > AGG |
| RSHR | YKCMECGKAFNRRSHLTRHQRIH | 122 | GGG |
| RSNR | YICRKCGRGFSRKSNLIRHQRTH | 123 | GAG > GTG |
| RTNR | YLCSECDKCFSRSTNLIRHRRTH | 124 | GAG |
| SSNR | YECKECGKAFSSGSNFTRHQRIH | 125 | GAG > GAC |
| VSNV | YECDHCGKAFSVSSNLNVHRRIH | 126 | AAT > CAT > TAT |
| VSSR | YTCKQCGKAFSVSSSLRRHETTH | 127 | GTT > GTG > GTA |
| VSTR | YECNYCGKTFSVSSTLIRHQRIH | 128 | GCT > GCG |
| WSNR | YRCEECGKAFRWPSNLTRHKRIH | 129 | GGT > GGA |

If each zinc finger domain recognizes a unique 3- to 4-bp sequence, the total number of domains required to bind every possible 3- to 4-bp sequence is only 64 to 256 ($4^3$ to $4^4$). It is possible that the natural repertoire of the human genome contains a sufficient number of unique zinc finger domains to span all possible recognition sites. These zinc finger domains are a valuable resource for constructing artificial chimeric DNA-binding proteins. A nucleic acid library can include nucleic acids encoding proteins that include naturally occurring zinc finger domains, artificial mutants of such domains, and combinations thereof.

Mutated Domains. In one implementation, the library includes nucleic acids encoding at least one structural domain that is an artificial variant of a naturally-occurring sequence. In one embodiment, such variant domains are assembled from a degenerate patterned library. In the case of a nucleic acid binding domains, positions in close proximity to the nucleic acid binding interface or adjacent to a position so located can be targeted for mutagenesis. A mutated test zinc finger domain, for example, can be constrained at any mutated position to a subset of possible amino acids by using a patterned degenerate library. Degenerate codon sets can be used to encode the profile at each position. For example, codon sets are available that encode only hydrophobic residues, aliphatic residues, or hydrophilic residues. The library can be selected for full-length clones that encode folded polypeptides. Cho et al. ((2000) *J. Mol. Biol.* 297(2):309-19) provides a method for producing such degenerate libraries using degenerate oligonucleotides, and also provides a method of selecting library nucleic acids that encode full-length polypeptides. Such nucleic acids can be easily inserted into an expression plasmid, e.g., using convenient restriction enzyme cleavage sites.

Selection of the appropriate codons and the relative proportions of each nucleotide at a given position can be determined by simple examination of a table representing the genetic code, or by computational algorithms. For example, Cho et al., supra, describe a computer program that accepts a desired profile of protein sequence and outputs a preferred oligonucleotide design that encodes the sequence.

See also Zhang et al, (2000) *J. Biol. Chem.* 275:33850-33860; Rebar and Pabo (1994) *Science* 263:671-673; Segal (1999) *Proc. Natl. Acad. Sci. USA* 96:2758; Gogus et al., (1996) *Proc. Natl. Acad. Sci. USA.* 93:2159-2164; Drier et al., (2001) *J. Biol. Chem.* 276: 29466-29478; Liu et al. (2001) *J. Biol. Chem.* 276(14):11323-11334; and Hsu et al., (1992) *Science* 257:1946-50 for some available zinc finger domains.

In one embodiment, a chimeric protein can include one or more of the zinc finger domains that have at least 18, 19, 20, 21, 22, 23, 24, or 25 amino acids that are identical to a zinc finger domain sequence in Table 1 or are at least 70, 75, 80, 85, 90, or 95% identical to a zinc finger domain sequence in Table 1. For example, the DNA contacting residues can be identical.

Library Construction: 4. A Library of Chimeric Zinc Finger Proteins

A library of nucleic acids encoding diverse chimeric zinc finger proteins can be formed by serial ligation, e.g., as described in Example 1. The library can be constructed such that each nucleic acid encodes a protein that has at least three, four, or five zinc finger domains. In some implementations, particularly for large libraries, each zinc finger coding segment can be designed to randomly encode any one of a set of zinc finger domains. The set of zinc finger domains can be selected to represent domains with a range of specificities, e.g., covering 30, 40, 50 or more of the 64 possible 3-basepair subsites. The set can include at least about 12, 15, 20, 25, 30, 40 or 50 different zinc finger domains. Some or all of these domains can be domains isolated from naturally occurring proteins. Moreover, because there may be little or no need for more than one zinc finger domain for a given 3-basepair subsite, it may be possible to generate a library using a small number of component domains, e.g., less than 500, 200, 100, or even less than 64 total component domains.

One exemplary library includes nucleic acids that encode a chimeric zinc finger protein having three fingers and 30 possible domains at each finger position. In its fully represented form, this library includes 27,000 sequences (i.e., the result of $30^3$). The library can be constructed by serial ligation in which a nucleic acid from a pool of nucleic acids encoding all 30 possible domains is added at each step.

In one embodiment, the library can be stored as a random collection. In another embodiment, individual members can be isolated, stored at an addressable location (e.g., arrayed), and sequenced. After high throughput sequencing of 40 to 50 thousand constructed library members, missing chimeric combinations can be individually assembled in order to obtain complete coverage. Once arrayed, e.g., in microtitre plates, each individual member can be recovered later for further analysis, e.g., for a phenotypic screen. For example, equal amounts of each arrayed member can be pooled and then transformed into a cell. Cells with a desired phenotype are selected and characterized. In another example, each member is individually transformed into a cell, and the cell is characterized, e.g., using a nucleic acid microarray to determine if the transcription of endogenous genes is altered (see "Profiling Regulatory Properties of a Chimeric Zinc Finger Protein," below).

Introducing Nucleic Acid Libraries into Cells

Library nucleic acids can be introduced into cells by a variety of methods. In one example, the library is stored as a random pool including multiple replicates of each library nucleic acid. An aliquot of the pool is transformed into cells. In another embodiment, individual library members are stored separately (e.g., in separate wells of a microtitre plate or at separate addresses of an array) and are individually introduced into cells.

In still another embodiment, the library members are stored in pools that have a reduced complexity relative to the library as a whole. For example, each pool can include $10^3$ different library members from a library of $10^5$ or $10^6$ different members. When a pool is identified as having a member that causes a particular effect, the pool is deconvolved to identify the individual library member that mediates the phenotypic effect. This approach is useful when recovery of the altered cell is difficult, e.g., in a screen for chimeric proteins that cause apoptosis.

Library nucleic acids can be introduced into cells by a variety of methods. Exemplary methods include electroporation (see, e.g., U.S. Pat. No. 5,384,253); microprojectile bombardment techniques (see, e.g., U.S. Pat. Nos. 5,550,318; 5,538,880; and 5,610,042; and WO 94/09699); liposome-mediated transfection (e.g., using LIPOFECTAMINE™ (Invitrogen) or SUPERFECT™ (QIAGEN GmbH); see, e.g., Nicolau et al.,*Methods Enzymol.,* 149:157-176, 1987.); calcium phosphate or DEAE-Dextran mediated transformation (see, e.g., Rippe et al., (1990) *Mol. Cell Biol.,* 10:689-695); direct microinjection or sonication loading; receptor mediated transfection (see, e.g., EP 273 085); and *Agrobacterium*-mediated transformation (see, e.g., U.S. Pat. Nos. 5,563,055 and 5,591,616). The term "transform," as used herein, encompasses any method that introduces an exogenous nucleic acid into a cell.

It is also possible to use a viral particle to deliver a library nucleic acid into a cell in vitro or in vivo. In one embodiment, viral packaging is used to deliver the library nucleic acids to cells within an organism. In another embodiment, the library nucleic acids are introduced into cells in vitro, after which the cells are transferred into an organism.

After introduction of the library nucleic acids, the library nucleic acids are expressed so that the chimeric proteins encoded by the library are produced by the cells. Constant regions of the library nucleic acid can provide necessary regulatory and supporting sequences to enable expression. Such sequences can include transcriptional promoters, transcription terminators, splice site donors and acceptors, untranslated regulatory regions (such as polyA addition sites), bacterial origins of replication, markers for indicating the presence of the library nucleic acid or for selection of the library nucleic acid.

Screening Nucleic Acid Libraries Encoding Chimeric Proteins

In a screen, the cells or organisms are evaluated to identify ones that have an altered phenotype. This process can be adapted to the phenotype of interest. As the number of possible phenotypes is vast, so too are the possibilities for screening. Numerous genetic screens and selections have been conducted to identify mutants or overexpressed naturally occurring genes that result in particular phenotypes. Any of these methods can be adapted to identify useful members of a nucleic acid library encoding chimeric proteins. A screen can include evaluating each cell or organism that includes a library nucleic acid or a selection, e.g., evaluating cells or organisms that survive or otherwise withstand a particular treatment.

Exemplary methods for evaluating cells include microscopy (e.g., light, confocal, fluorescence, scanning electron, and transmission electron), fluorescence based cell sorting, differential centrifugation, differential binding, immunoassays, enzymatic assays, growth assays, and in vivo assays.

Some screens involve particular environmental conditions. Cells that are sensitive or resistant to the condition are identified.

Some screens require detection of a particular behavior of a cell (e.g., chemotaxis, morphological changes, or apoptosis), or a particular behavior of an organism (e.g., phototaxis by a plant, mating behavior by a *Drosophila,* and so forth). In one embodiment, the cells or organisms can be evaluated directly, e.g., by visual inspection, e.g., using a microscope and optionally computer software to automatically detect altered cells. In another embodiment, the cells or organisms can be evaluated using an assay or other indicator associated with the desired phenotype.

Some screens relate to cell proliferation. Cells that proliferate at a different rate relative to a reference cell (e.g., a normal cell) are identified. In addition, cells that have an altered response to a proliferative signal (e.g., a growth factors or other mitogen) can be identified. The cells may be more or less sensitive to the signal.

Screens that relate to cell differentiation can also be used. The screening and use of chimeric zinc finger proteins can be used to modulate the differentiative and proliferative capacity of a variety of cells, including stem cells, such as ES cells and somatic stem cells, both human and otherwise. Zinc finger proteins can be found that direct ES cells to differentiate into a restricted lineage, such as neuronal progenitor cells or hematopoietic stem cells. It should be also possible to screen for zinc finger proteins that can direct differentiation of stem cells toward a defined post-mitotic cell subtype, for example, directing differentiation of ES cells and/or neural stem cells to dopaminergic or cholinergic neurons.

Among other phenotypes to evaluate differentiation, it is possible to look at expression of marker genes and marker proteins. Examples of such markers include:

FLK1 for endothelial cells (Cho et al., (2001) *Blood* 98:3635-42; Nishikawa et al.,*Development* 125: 1747-1757), vascular smooth muscle cell-specific myosin heavy chain for smooth muscle (Drab et al., (1997) *FASEB J* 11:905-15)

Bone-specific alkaline phosphatase (BAP) and osteocalci for osteoblasts, (Demers et al., (2000) *Cancer* 88:2919-26)

CD4, CD8, and CD45 for white blood cells (Ody et al., (2000) *Blood* 96:3988-90, Martin et al., (2000) *Blood* 96:2511-9)

Flk-2 and CD34 for hematopoietic stem cells, (Julie et al., *Proc. Natl. Acad. Sci. USA,* 2001,Vol. 98, Issue 25, 14541-14546, Woodward & Jenkinson. *Eur J Immunol* 2001 November;31(11):3329-38, George A A et al., *Blood* 2001 June 15;97(12):3925-30)

CFU for hematopoietic stem cells, MSC progenitors (Frimberger et al., *Exp Hematol* 2001 May; 29(5):643-52)

Muc-18 (CD146) for bone marrow fibroblasts, (Filshie et al., (1998) *Leukemia* 12:414-21)

collagen type II, collagen type IV and chondrocyte expressed protein-68 for chondrocytes (Carlberg et al., (2001) *Differentiation* 67:128-38, Steck et al., (2001) *Biochem J* 353:169-74)

adipocyte lipid-binding protein (ALBP) and fatty acid transporter for adipocytes (Amri, et al., (1995) *J. Biol. Chem.* 270:2367-2371, Bastie et al., (1999) *J Biol Chem* 274:21920-5, Frohnert et al., (1999) *J. Biol. Chem.* 274, 3970-3977, Teboul et al., (2001) *Biochem. J.* 360:305-312)

CD133 for neural stem cells (Uchida N et al., (2000) *Proc. Natl. Acad. Sci. USA* 97:14720-5)

GFAP for astrocytes (Dai et al., (2001) *Genes Dev* 15:1913-25)

microtubule-associated protein-2 for neurons (Roy et al., (2000) *Nat Med* 6:271-7)

It is also possible to screen mammalian cells for other properties, such as anti-tumorigenesis, altered apoptosis, and anti-viral phenotypes. For example, by selecting for cells that are resistant to viral infection or virus production, it is possible to identify artificial chimeric proteins that can be used as anti-viral agents.

Similarly changes in cell signaling pathways can be detected by the use of probes correlated with activity or inactivity of the pathway or by observable indications correlated with activity or inactivity of the pathway.

Some screens relate to production of a compound of interest, e.g., a metabolite, a secreted protein, and a post-translationally modified protein. For example, cells can be identified that produce an increased amount of a compound. In another example, cells can be identified that produce a reduced amount of a compound, e.g., an undesired byproduct. Cells of interest can be identified by a variety of means, including the use of a responder cell, microarrays, chemical detection assays, and immunoassays.

More examples of particular embodiments include:

1) Protein solubility: In *E. coli*, many heterologous proteins are expressed as inclusion bodies. We identified chimeric zinc finger proteins that increase the soluble fraction of a human protein expressed in *E. coli*. See Example 12. Accordingly, the invention features an artificial transcription factor or a chimeric zinc finger protein that alters (e.g., increases) the solubility of a heterologous protein expressed (e.g., overexpressed in a cell).

2) Glycosylation: Therapeutic proteins including antibodies are often produced in CHO cells. However, such proteins do not have optimal glycosylation pattern. In one embodiment, a library encoding chimeric proteins is screened to identify a CHO cell that is modified so that a secreted protein, e.g., an antibody, includes one or more (e.g., all) glycosylations that characterize an antibody produced by a B cell. Accordingly, the invention features an artificial transcription factor or a chimeric zinc finger protein that alters glycosylation of a secreted protein, e.g., a protein secreted by a CHO cell, e.g., an antibody secreted by a CHO cell.

3) Viral titer: In one embodiment, a library encoding chimeric proteins is screened to identify a chimeric protein that increases or decreases viral titer in a cell culture. Viruses can be used as a delivery vehicle, e.g., a gene delivery vehicle. For example, therapeutic viruses are now being developed to cure certain type of cancer (e.g. an adenovirus). Increasing the viral titer is useful for preparing viruses for therapy. On the other hand suppressing viral production in a cell culture and in vivo is useful for treating viral disease. Accordingly, the invention features an artificial transcription factor or a chimeric zinc finger protein that alters (e.g., increases or decreases) virus production in a cell, e.g., a eukaryotic or mammalian cell.

4) Transformation efficiency: Genetic engineering in many eukaryotic cell lines or prokaryotic organisms is limited by low transfection or transformation efficiency. Artificial transcription factors can be selected that modify cells so that transfection or transformation efficiency is improved. A selection for such a factor can be performed by a transformation with a reporter or marker at limiting concentrations, followed by selection of those cells that take up the reporter. Accordingly, the invention features an artificial transcription factor or a chimeric zinc finger protein that alters (e.g., increases) the DNA uptake efficiency or tolerance of DNA uptake procedures of a cell.

5) Feeder cells. It is possible to identify artificial transcription factors and other chimeras that modify the properties of a culture cell so that the culture cell can support proliferation or differentiation of a stem cells, e.g., thereby producing a feeder cell. The culture cell can be a human or mammalian cell. The cells can be screened (e.g., by pooling library members) to identify a cell which causes a stem cell cultivated in the same milieu (e.g, the same well) to proliferate or differentiation. The artificial transcription factor may activate key cytokines and growth factors, which are secreted to the media. The media can be used to induce differentiation or proliferate (e.g., by supporting self-renewal) the stem cell. Accordingly, the invention features an artificial transcription factor or a chimeric zinc finger protein that alters (e.g., increases) the ability of a mammalian cell to condition media or otherwise alter the behavior of a stem cell, e.g., regulate proliferation or differentiation of a stem cell.

It is also possible to screen for an artificial transcription factor using one type of cell and then to express the artificial transcription factor in a second type of cell. This process an be used to generally transfer the phenotypic change induced by the transcription factoring a first cell into a second cell. For example, we determined the expression profiles of a particular zinc finger protein in two widely different cell lines; human embryonic kidney 293 cell, which is non-cancerous, and human cervical cancer cell HeLa. We found that the profiles were strikingly similarity. Similarly, in yeast we demonstrated that a phenotype induced by a ZFP in one strain can be transferred to a different strain.

Stem Cells

The approaches described here, while generally applicable to any cell, are also particularly useful for regulating the behavior of stem cells from any metazoan organism. Stem cells are cells with the capacity self-renewal and also the potential for differentiation. The self-renewal can be prolonged, and even indefinite. Stem cells can produce highly differentiated descendants (Watt and Hogan (2000) *Science* 287:1427-1430). Recent success in culturing human embryonic stem cells has provided a potential source of cells for cell-based therapies. However, maintaining, replicating, and differentiating stem cells can, at least in some cases, be difficult. ES cells, for example, have a tendency to differentiate randomly in vitro.

A library of chimeric transcription factors can be used to identify proteins that can control cell differentiation, e.g., stem cell differentiation. For example, one may identify chimeric transcription factors that direct the differentiation of stem cells towards a defined post-mitotic cell subtype (for example, a dopaminergic or cholinergic neuron).

Proteins can be identified that increase the potential for self-renewal, that prevent differentiation, or that direct the extent and character of differentiation. These proteins are generally identified by introducing nucleic acids encoding artificial zinc finger proteins into stem cells or stem cell progenitors, and evaluating the phenotype of the cell.

A means to control the differentiative and proliferative potential of stem cells would enable, among other things, the provision of a large supply of undifferentiated cells, and the regulated differentiation toward a specific cell types. Such control can be tailored to a therapeutic use or other applications (e.g., development of transgenic animals, in vitro cell culture, and so forth).

In other examples, one can identify chimeric transcription factors that direct embryonic stem (ES) cells to differentiate into a restricted lineage. Thus, one may produce neuronal progenitor cells or hematopoietic stem cells from ES cells. It is also possible to identify chimeric proteins, e.g., chimeric ZFPs, that cause 1) a differentiated cell to adopt a different differentiated state or 2) a differentiated cell to a adopt a non-differentiated state, e.g., thereby generating a stem cell or a pluripotent progenitor cell.

The identification method does not require information about a particular target gene. Target genes can be identified after screening, e.g., by transcript or protein profiling to identify genes whose expression or activity is altered by an identified chimeric transcription factor. The identification of genes regulated by ZFP-TFs will advance understanding of cell differentiation.

Production of Cellular Products

The invention features artificial transcription factors (e.g., chimeric zinc finger proteins) that alter the ability of a cell to produce a cellular product, e.g., a protein or metabolite. A cellular product can be an endogenous or heterologous molecule. For example, it is possible to identify an artificial transcription factor that increases the ability of a cell to produce proteins, e.g., particular proteins (e.g., particular endogenous proteins), overexpressed proteins, heterologous proteins, or mis-folded proteins.

In one embodiment, cells are screened for their ability to produce a reporter protein, e.g., a protein that can be enzymatically or fluorescently detected. In one example, the reporter protein is insoluble when overexpressed in a reference cell. For example, bacterial cells can be screened for artificial transcription factors that reduce inclusion bodies. In another example, the reporter protein is secreted, e.g., by a prokaryotic or eukaryotic cell. Cells can be screened for higher secretory through-put, or improved post-translational modification, e.g., glycosylation, phosphorylation, or proteolytic processing.

In one embodiment, cells are screened for their ability to alter (e.g., increase or decrease) the activity of two different reporter proteins. The reporter proteins may differ, e.g., by activity, localization (e.g., secreted/cytoplasmic/nuclear), size, solubility, isoelectric point, oligomeric state, post-translational regulation, translational regulation, and transcriptional regulation (e.g., the gene encoding them may be regulated by different regulatory sequences). The invention includes artificial transcription factors (e.g., zinc finger proteins) that alter at least two different reporter genes that differ by these properties, and zinc finger proteins that selectively regulate a reporter gene, or a class of reporter genes defined by one of these properties.

Because the phenotypic screening method can be used to isolate the artificial transcription factor, it is not necessary to know a priori how the zinc finger protein mediates increased protein production. Possible mechanisms, which can be verified, include alteration of one or more of the following: translation machinery, transcript processing, transcription, secretion, protein degradation, stress resistance, catalytic activity, e.g., metabolite production. In one example, an artificial transcription factor may modulate expression of one or more enzymes in a metabolic pathway and thereby enhance production of a cellular product such as a metabolite or a protein.

Iterative Design

Once a chimeric DNA binding protein is identified, its ability to alter a phenotypic trait of a cell can be further improved by a variety of strategies. Small libraries, e.g., having about 6 to 200 or 50 to 2000 members, or large libraries can be used to optimize the properties of a particular identified chimeric protein.

In a first exemplary implementation of an iterative design, mutagenesis techniques are used to alter the original chimeric DNA binding protein. The techniques are applied to construct a second library whose members include members that are variants of an original protein, for example, a protein identified from a first library. Examples of these techniques include: error-prone PCR (Leung et al. (1989) *Technique* 1:11-15), recombination, DNA shuffling using random cleavage (Stemmer (1994) *Nature* 389-391), Coco et al. (2001) *Nature Biotech.* 19:354, site-directed mutagenesis (Zollner et al. (1987) *Nucl Acids Res* 10:6487-6504), cassette mutagenesis (Reidhaar-Olson (1991) *Methods Enzymol.* 208:564-586) incorporation of degenerate oligonucleotides (Griffiths et al. (1994) *EMBO J.* 13:3245); serial ligation, pooling specific library members from a prefabricated and arrayed library, recombination (e.g., sexual PCR and "DNA Shuffling™" (Maxygen, Inc., CA)), or by combinations of these methods.

In one embodiment, a library is constructed that mutates a set of amino acid positions. For example, for a chimeric zinc finger protein, the set of amino acid positions may be positions in the vicinity of the DNA contacting residues, but not the DNA contacting residues themselves. In another embodiment, the library varies each encoded domain in a chimeric protein, but to a more limited extent than the initial library from which the chimeric DNA binding protein was identified. For a chimeric zinc finger protein, the nucleic acids that encode a particular domain can be varied among other zinc finger domains whose recognition specificity is known to be similar to that of the domain present in the original chimeric protein.

Some techniques include generating new chimeric DNA binding proteins from nucleic acids encoding domains of at least two chimeric DNA binding proteins that are known to have a particular functional property. These techniques, which include DNA shuffling and standard domain swapping, create new combinations of domains. See, e.g., U.S. Pat. No. 6,291,242. DNA shuffling can also introduce point mutations in addition to merely exchanging domains. The shuffling reaction is seeded with nucleic acid sequences encoding chimeric proteins that induces a desired phenotype. The nucleic acids are shuffled. A secondary library is produced from the shuffling products and screened for members that induce the desired phenotype, e.g., under similar or more stringent conditions. If the initial library is comprehensive such that chimeras of all possible domain combinations are screened, DNA shuffling of domains isolated from the same initial library may be of no avail. DNA shuffling may be useful in instances where coverage is comprehensive and also in instances where comprehensive screening may not be practical.

In a second exemplary implementation of an iterative design, a chimeric DNA binding protein that produces a desired phenotype is altered by varying each domain. Domains can be varied sequentially, e.g., one-by-one, or greater than one at a time.

The following example refers to an original chimeric protein that includes three zinc finger domains: fingers I, II, and III and that produces a desired phenotype. A second library is constructed such that each nucleic acid member of the second library encodes the same finger II and finger III as the initially identified protein. However, the library includes nucleic acid members whose finger I differs from finger I of the original protein. The difference may be a single nucleotide that alters the amino acid sequence of the encoded chimeric protein or may be more substantial. The second library can be constructed, e.g., such that the base-contacting residues of finger I are varied, or that the base-contacting residues of finger I are maintained but that adjacent residues are varied. The second library can also to include a large enough set of zinc finger domains to recognize at least 20, 30, 40, or 60 different trinucleotide sites.

The second library is screened to identify members that alter a phenotype of a cell or organism. The extent of alteration can be similar to that produced by the original protein or greater than that produced by the original protein.

Concurrently, or subsequently, a third library can be constructed that varies finger II, and a fourth library can be constructed that varies finger III. It may not be necessary to further improve a chimeric protein by varying all domains, if the chimeric protein or already identified variants are sufficient. In other cases, it is desirable to re-optimize each domain.

If other domains are varied concurrently, improved variants from each particular library can be recombined with each other to generate still another library. This library is similarly screened.

In a third exemplary implementation of an iterative design, the method includes adding, substituting, or deleting a domain, e.g., a zinc finger domain or a regulatory domain. An additional zinc finger domain may increase the specificity of a chimeric protein and may increase its binding affinity. In some cases, increased binding affinity may enhance the phenotype that the chimeric protein produces. An additional regulatory domain, e.g., a second activation domain or a domain that recruits an accessory factor, may also enhance the phenotype that the chimeric protein produces. A deletion may improve or broaden the specificity of the activity of the chimeric protein, depending on the contribution of the domain that is deleted, and so forth.

In a fourth exemplary implementation of an iterative design, the method includes co-expressing the original chimeric protein and a second chimeric DNA binding protein in a cell. The second chimeric protein can be also identified by screening a nucleic acid library that encodes different chimeras. In one embodiment, the second chimeric protein is identified by screening the library in a cell that expresses the original chimeric protein. In another embodiment, the second chimeric protein is identified independently.

Profiling Regulatory Properties of a Chimeric Zinc Finger Protein

A chimeric transcription factor that alters a phenotype of a cell can be further characterized to identify the endogenous genes that it directly or indirectly regulates. Typically, the chimeric transcription factor is produced within the cell. At an appropriate time, e.g., before, during, or after the phenotypic change occurs, the cell is analyzed to determine the levels of transcripts or proteins present in the cell or in the medium surrounding the cell. For example, mRNA can be harvested from the cell and analyzed using a nucleic acid microarray.

Nucleic acid microarrays can be fabricated by a variety of methods, e.g., photolithographic methods (see, e.g., U.S. Pat. No. 5,510,270), mechanical methods (e.g., directed-flow methods as described in U.S. Pat. No. 5,384,261), and pin based methods (e.g., as described in U.S. Pat. No. 5,288,514). The array is synthesized with a unique capture probe at each address, each capture probe being appropriate to detect a nucleic acid for a particular expressed gene.

The mRNA can be isolated by routine methods, e.g., including DNase treatment to remove genomic DNA and hybridization to an oligo-dT coupled solid substrate (e.g., as described in *Current Protocols in Molecular Biology*, John Wiley & Sons, N.Y). The substrate is washed, and the mRNA is eluted. The isolated mRNA is then reversed transcribed and optionally amplified, e.g., by rtPCR, e.g., as described in (U.S. Pat. No. 4,683,202). The nucleic acid can be labeled during amplification or reverse transcription, e.g., by the incorporation of a labeled nucleotide. Examples of preferred labels include fluorescent labels, e.g., red-fluorescent dye Cy5 (Amersham) or green-fluorescent dye Cy3 (Amersham).

Alternatively, the nucleic acid can be labeled with biotin, and detected after hybridization with labeled streptavidin, e.g., streptavidin-phycoerythrin (Molecular Probes).

The labeled nucleic acid is then contacted to the array. In addition, a control nucleic acid or a reference nucleic acid can be contacted to the same array. The control nucleic acid or reference nucleic acid can be labeled with a label other than the sample nucleic acid, e.g., one with a different emission maximum. Labeled nucleic acids are contacted to an array under hybridization conditions. The array is washed, and then imaged to detect fluorescence at each address of the array.

A general scheme for producing and evaluating profiles includes detecting hybridization at each address of the array. The extent of hybridization at an address is represented by a numerical value and stored, e.g., in a vector, a one-dimensional matrix, or one-dimensional array. The vector x has a value for each address of the array. For example, a numerical value for the extent of hybridization at a particular address is stored in variable $x_a$. The numerical value can be adjusted, e.g., for local background levels, sample amount, and other variations. Nucleic acid is also prepared from a reference sample and hybridized to the same or a different array. The vector y is construct identically to vector x. The sample expression profile and the reference profile can be compared, e.g., using a mathematical equation that is a function of the two vectors. The comparison can be evaluated as a scalar value, e.g., a score representing similarity of the two profiles. Either or both vectors can be transformed by a matrix in order to add weighting values to different genes detected by the array.

The expression data can be stored in a database, e.g., a relational database such as a SQL database (e.g., Oracle or Sybase database environments). The database can have multiple tables. For example, raw expression data can be stored in one table, wherein each column corresponds to a gene being assayed, e.g., an address or an array, and each row corresponds to a sample. A separate table can store identifiers and sample information, e.g., the batch number of the array used, date, and other quality control information.

Genes that are similarly regulated can be identified by clustering expression data to identify coregulated genes. Such cluster may be indicative of a set of genes coordinately regulated by the chimeric zinc finger protein. Genes can be clustered using hierarchical clustering (see, e.g., Sokal and Michener (1958) *Univ. Kans. Sci. Bull.* 38:1409), Bayesian clustering, k-means clustering, and self-organizing maps (see, Tamayo et al. (1999) *Proc. Natl. Acad. Sci. USA* 96:2907).

The similarity of a sample expression profile to a reference expression profile (e.g., a control cell) can also be determined, e.g., by comparing the log of the expression level of the sample to the log of the predictor or reference expression value and adjusting the comparison by the weighting factor for all genes of predictive value in the profile.

Proteins can also be profiled in a cell that has an active chimeric protein with in it. One exemplary method for profiling proteins includes 2-D gel electrophoresis and mass spectroscopy to characterize individual protein species. Individual "spots" on the 2-D gel are proteolyzed and then analyzed on the mass spectrometer. This method can identify both the protein component and, in many cases, translational modifications.

The protein and nucleic acid profiling methods can not only provide information about the properties of the chimeric protein, but also information about natural mechanisms operating within the cell. For example, the proteins or nucleic acids upregulated by expression of the chimeric protein may be the natural effectors of the phenotypic change caused by expression of the chimeric protein.

In addition, other methods can be used to identify target genes and proteins that are directly or indirectly regulated by the artificial chimeric protein. In one example, alterations that compensate (e.g., suppress) the phenotypic effect of the artificial chimeric protein are characterized. These alterations include genetic alterations such as mutations in chromosomal genes and overexpression of a particular gene, as well as other alterations, such as RNA interference (e.g., by double-stranded RNA).

In a particular example, a chimeric ZFP is isolated that causes a growth defect or lethality when conditionally expressed in a cell, e.g., a pathogenic bacteria or fungi. Such a ZFP can be identified by transforming the cell with the ZFP libraries that include nucleic acids encoding ZFPs, expression of the nucleic acids being controlled by an inducible promoter. Transformants are cultured on non-inducible media and then replica-plated on both inducible and non-inducible plates. Colonies that grow normally on non-inducible plate, but show defective growth on inducible plate are identified as "conditional lethal" or "conditional growth defective" colonies.

(a) Identification of Target Genes Using a cDNA Library

A cDNA expression library is then transformed into the "conditional lethal" or "conditional growth defective" strains described above. Transformants are plated on inducible plates. Colonies that survive, despite the presence and expression of the ZFP that causes the defect, are isolated. The nucleic acid sequences of cDNAs that complement the defect are characterized. These cDNA can be transcripts of direct or indirect target genes that are regulated by chimeric ZFP that mediates the defect.

(b) Identification of Target Genes Using a Secondary ZFP Library

A second chimeric protein that suppresses the effect of the first chimeric protein is identified. The targets of the second chimeric protein (in the presence or absence of the first chimeric protein) are identified.

For example, a ZFP library is transformed into "conditional lethal" or "conditional growth defective" colonies (which include a first chimeric ZFP that causes the defect). Transformants are plated on inducible plates. Colonies that can survive by the expression of introduced ZFP are identified as "suppressed strains". Target genes of the second ZFPs can be characterized by DNA microarray analysis. The comparative analysis can be done between four strains: 1) no ZFP; 2) the first ZFP alone; 3) the second ZFP alone; and 4) the first and second ZFP. For example, genes that are regulated in opposing directions by the first and second chimeric ZFPs are candidates for targets that mediate the growth-defective phenotype. This method can be applied to any phenotype, not just a growth defect.

(c) Co-Regulated Genes Identified By Expression Profiling Analysis

A candidate target of a chimeric ZFP can be identified by expression profiling. Subsequently, to determine if the candidate target mediates the phenotype of the chimeric ZFP, the candidate target can be independently over-expressed or inhibited (e.g., by genetic deletion or RNA interference). In addition, it may be possible to apply this analysis to multiple candidate targets since in at least some cases more than one candidate may need to be perturbed to cause the phenotype. An example of this approach is provided in Example 3 (Ketoconazole resistance).

(d) Time-Course Analysis

Figure 13:
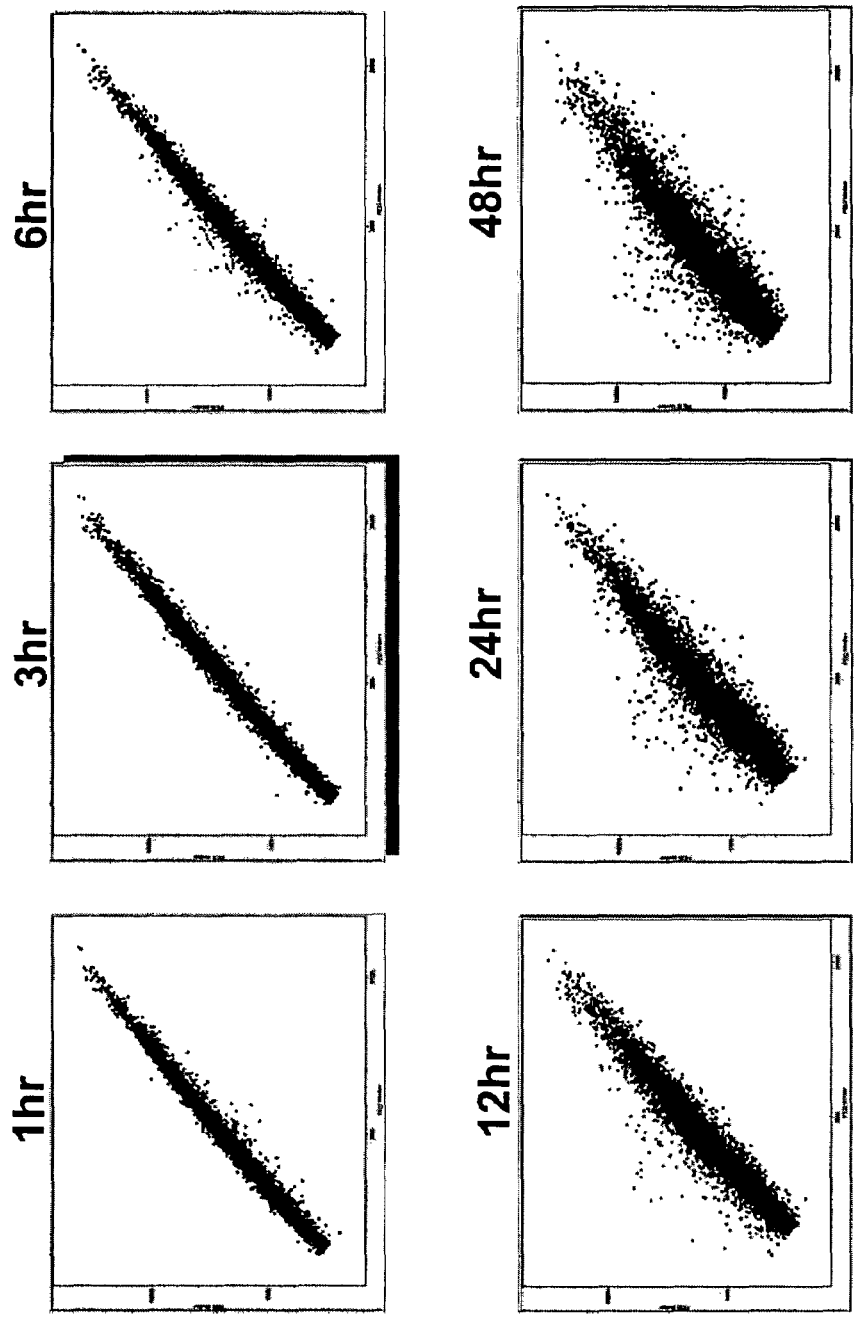
FIG. 13 depicts comparative microarray data at various time points for cells in which the F104-p65 ZFP is present.

The targets of a chimeric ZFP can be identified by a characterizing changes in gene expression with respect to time after a cell is exposed to the chimeric ZFP. For example, a gene encoding the chimeric ZFP can be attached to an inducible promoter. An exemplary inducible promoter is regulated by a small molecule such as doxycycline. The gene encoding the chimeric ZFP is introduced into cells. mRNA samples are obtained from cells at various times after induction of the inducible promoter. See, e.g., FIG. 13, which depicts genes that are activated and repressed in the course of induction of the ZFP F104-p65.

(e) Identification of Primary Target Genes of ZFP-TFs From Mammalian Cells Using Protein Transduction and cDNA Microarray Technologies.

It is also possible to introduce a chimeric protein into a cell by transduction. The protein is provided to the extracellular milieu and the cell transduces the protein into itself. Thus, the cell does not have to include a gene encoding the chimeric protein. This approach may obviate concerns about exogenous nucleic acid integration, propagation, and so forth. Levels of the protein can be precisely controlled. In one embodiment, the chimeric ZFP is fused to protein transduction domain of Tat or VP22.

To analyze the effects of a transduced chimeric protein in culture cells, the chimeric protein is added to the culture media, e.g., as a fusion to a protein transduction domain. Detection of regulated target genes can be enhanced by addition of an inhibitor of protein synthesis such as cycloheximide. Thus, translation of the primary target genes is blocked, and genes that would be regulated by proteins encoded by the primary target genes would be detected. The identity of primary target genes can be found by DNA microarray analysis.

The use of cyclohexamide to identify primary target genes can also be used when the chimeric protein is encoded by a heterologous nucleic acid in the cell. For example, expression of the heterologous nucleic acid can be induced for less than 30, 20, 15, 10, or 5 minutes, and then cyclohexamide can be added.

(f) Activity Analysis

The function of a potential target gene can be evaluated by inhibiting activity of the target gene, e.g., by RNA interference (RNAi) with double-stranded RNAs (dsRNA), antisense technology, ribozymes, or targeted genetic mutation. A cell or organism in which activity of the target gene is reduced can be evaluated and compared to a control cell or organism that is not treated with RNAi. In another example, a cell or organism that expresses the artificial zinc finger protein believed to regulate the target gene is treated with RNAi. The ability of the artificial zinc finger protein to induce a phenotype is evaluated in the presence and absence of RNAi. In some cases, if the potential target gene is indeed a critical target, the RNAi treatment inactivating the potential target may attenuate the phenotype induced by the artificial zinc finger protein.

dsRNA can be produced by transcribing a cassette in both directions, for example, by including a T7 promoter on either side of the cassette. The insert in the cassette is selected so that it includes a sequence complementary to the potential target gene. See also, the HiScribe™ RNAi Transcription Kit (New England Biolabs, MA) and Fire, A. (1999) *Trends Genet.* 15, 358-363. dsRNA can be digested into smaller fragments. See, e.g., U.S. patent application 2002-0086356. dsRNAs can be used to silence gene expression in mammalian cells. See, e.g., Clemens, et al. (2000) *Proc. Natl. Sci. USA* 97, 6499-6503; Billy, E. et al. (2001) *Proc. Natl. Sci. USA* 98, 14428-14433; Elbashir et al. (2001) *Nature.* 411(6836):494-8; Yang, D. et al. (2002) *Proc. Natl. Acad. Sci. USA* 99, 9942-9947.

Target DNA Site Identification

With respect to chimeric DNA binding proteins, a variety of methods can be used to determine the target site of a chimeric DNA binding protein that produces a phenotype of interest. Such methods can be used, alone or in combination, to find such a target site.

In one embodiment, information from expression profile is used to identify the target site recognized by a chimeric zinc finger protein. The regulatory regions of genes that are co-regulated by the chimeric zinc finger protein are compared to identify a motif that is common to all or many of the regulatory regions.

In another embodiment, biochemical means are used to determine what DNA site is bound by the chimeric zinc finger protein. For example, chromatin immuno-precipitation experiments can be used to isolate nucleic acid to which the chimeric zinc finger protein is bound. The isolated nucleic acid is PCR amplified and sequence. See, e.g., Gogus et al. (1996) *Proc. Natl. Acad. Sci. USA.* 93:2159-2164. The SELEX method is another exemplary method that can be used. Further, information about the binding specificity of individual zinc finger domains in the chimeric zinc finger protein can be used to predict the target site. The prediction can be validated or can be used to guide interpretation of other results (e.g., from chromatin immunoprecipitation, in silico analysis of co-regulated genes, and SELEX).

Figure 10B:
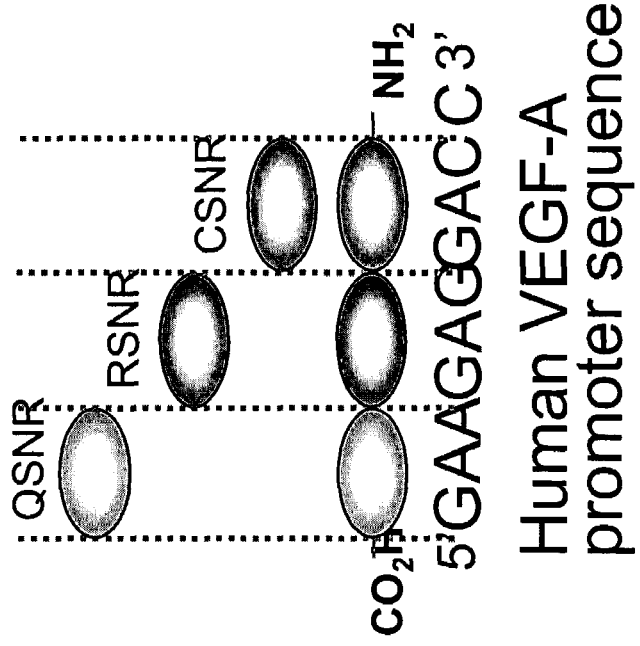
FIG. 10B is a schematic illustrating the correspondence between zinc finger domains and the recognition site sequence (SEQ ID NO:130).
Figure 11:
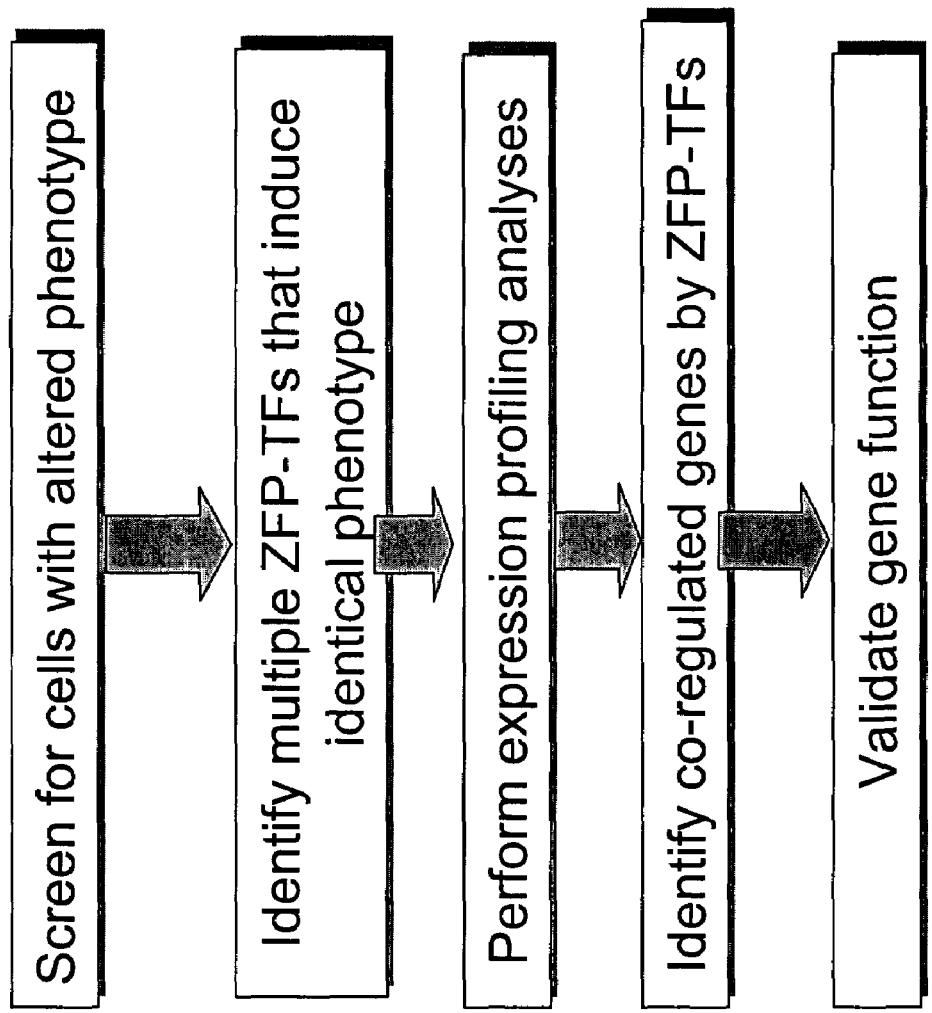
FIG. 11 is a flowchart for a method of identifying targets of artificial ZFPs.
Figure 12:
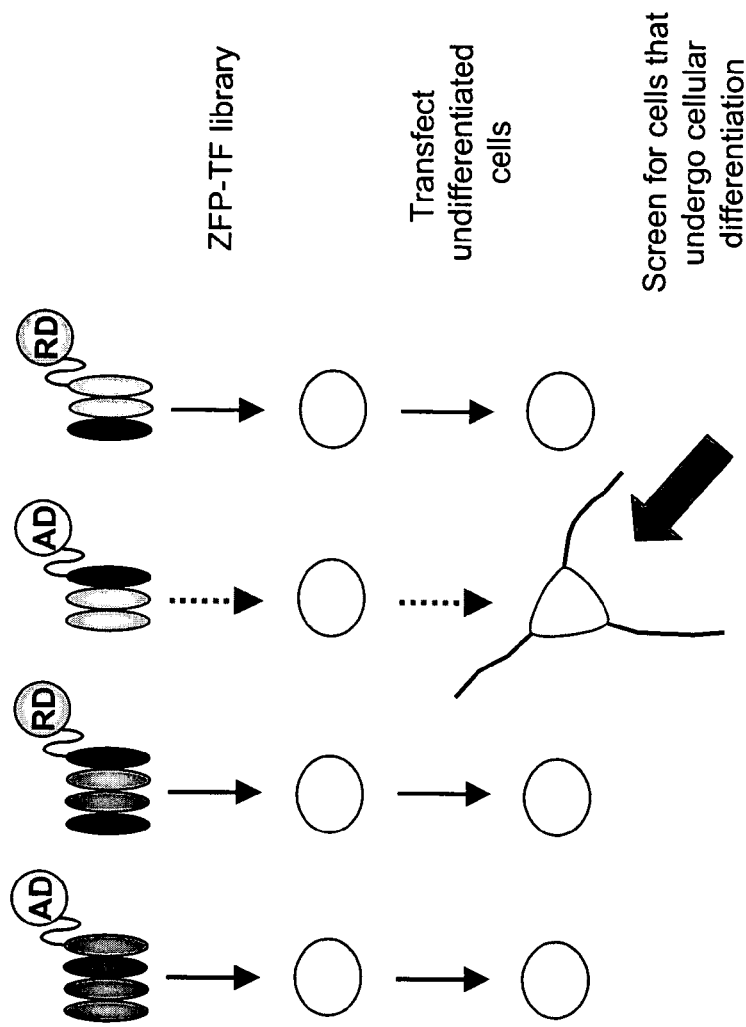
FIG. 12 is a schematic of a method of identifying ZFPs that induce differentiation.

In still another embodiment, a potential target site is inferred based on information about the binding specificity of each component zinc finger. For example, as shown in FIGS. 10A and 10B, a chimera that includes the zinc finger domains, from N- to C-terminus: CSNR, RSNR, and QSNR is expected to recognize the target site 5'-GAAGAGGACC-3' (SEQ ID NO:130). The domains CSNR, RSNR, and QSNR have the following respective DNA binding specificities GAC, GAG, and GAA. The expected target site is formed by considering the domains in C terminal to N-terminal order and concatenating their recognition specificities to obtain one strand of the target site in 5' to 3' order.

Although in most cases, chimeric zinc finger proteins are likely to function as transcriptional regulators, it is possible that in some cases the chimeric zinc finger proteins mediate their phenotypic effect by binding to an RNA or protein target. Some naturally-occurring zinc finger proteins in fact bind to these macromolecules.

Additional Features for Chimeric Transcription Factors

With respect to a library encoding chimeric nucleic acid binding domains, the encoded polypeptides can also include one or more of the following features. These features may be constant among all members of the library or may also vary. In one example, some nucleic acids encode polypeptides that include an activation domain, whereas others include a repression domain, or no transcriptional regulatory domain.

Activation domains. Transcriptional activation domains that may be used in the present invention include but are not limited to the Gal4 activation domain from yeast and the VP16 domain from herpes simplex virus. The ability of a domain to activate transcription can be validated by fusing the domain to a known DNA binding domain and then determining if a reporter gene operably linked to sites recognized by the known DNA-binding domain is activated by the fusion protein.

An exemplary activation domain is the following domain from p65:

```
YLPDTDDRHRIEEKRKRTYETFKSIMKKSPFSGPTDPRPPPRRIAVPSRSSASVPKPAP    (SEQ ID NO: 131)
QPYPFTSSLSTINYDEFPTMVFPSGQISQASALAPAPPQVLPQAPAPAPAPAMVSALA
QAPAPVPVLAPGPPQAVAPPAPKPTQAGEGTLSEALLQLQFDDEDLGALLGNSTDPA
VFTDLASVDNSEFQQLLNQGIPVAPHTTEPMLMEYPEAITRLVTAQRPPDPAPAPLGA
PGLPNGLLSGDEDFSSIADMDFSALLSQ
```

The sequence of an exemplary Gal4 activation domain is as follows:

```
NFNQSGNIADSSLSFTFTNSSNGPNLITTQTNSQALSQPIASSNVHDNFMNNEITASKI    (SEQ ID NO: 132)
DDGNNSKPLSPGWTDQTAYNAFGITTGMFNTTTMDDVYNYLFDDEDTPPNPKKEIS
MAYPYDVPDYAS
```

In bacteria, activation domain function can be emulated by a domain that recruits a wild-type RNA polymerase alpha subunit C-terminal domain or a mutant alpha subunit C-terminal domain, e.g., a C-terminal domain fused to a protein interaction domain.

Repression domains. If desired, a repression domain instead of an activation domain can be fused to the DNA binding domain. Examples of eukaryotic repression domains include repression domains from Kid, UME6, ORANGE, groucho, and WRPW (see, e.g., Dawson et al., (1995) *Mol. Cell Biol.* 15:6923-31). The ability of a domain to repress transcription can be validated by fusing the domain to a known DNA binding domain and then determining if a reporter gene operably linked to sites recognized by the known DNA-binding domain is repressed by the fusion protein.

An exemplary repression domain is the following domain from UME6 protein:

```
NSASSSTKLDDDLGTAAAVLSNMRSSPYRTHDKPISNVNDMNNTNALGVPASRPHSS    (SEQ ID NO: 133)
SFPSKGVLRPILLRIHNSEQQPIFESNNSTACI
```

Another exemplary repression domain is from the Kid protein:

```
VSVTFEDVAVLFTRDEWKKLDLSQRSLYREVMLENYSNLASMAGFLFTKPKVISLL    (SEQ ID NO: 134)
QQGEDPW
```

Still other chimeric transcription factors include neither an activation or repression domain. Rather, such transcription factors may alter transcription by displacing or otherwise competing with a bound endogenous transcription factor (e.g., an activator or repressor).

Peptide Linkers. DNA binding domains can be connected by a variety of linkers. The utility and design of linkers are well known in the art. A particularly useful linker is a peptide linker that is encoded by nucleic acid. Thus, one can construct a synthetic gene that encodes a first DNA binding domain, the peptide linker, and a second DNA binding domain. This design can be repeated in order to construct large, synthetic, multi-domain DNA binding proteins. PCT WO 99/45132 and Kim and Pabo ((1998) *Proc. Natl. Acad. Sci. USA* 95:2812-7) describe the design of peptide linkers suitable for joining zinc finger domains.

Additional peptide linkers are available that form random coil, α-helical or α-pleated tertiary structures. Polypeptides that form suitable flexible linkers are well known in the art (see, e.g., Robinson and Sauer (1998) *Proc Natl Acad Sci USA*. 95:5929-34). Flexible linkers typically include glycine, because this amino acid, which lacks a side chain, is unique in its rotational freedom. Serine or threonine can be interspersed in the linker to increase hydrophilicity. In additional, amino acids capable of interacting with the phosphate backbone of DNA can be utilized in order to increase binding affinity. Judicious use of such amino acids allows for balancing increases in affinity with loss of sequence specificity. If a rigid extension is desirable as a linker, α-helical linkers, such as the helical linker described in Pantoliano et al. (1991) *Biochem*. 30:10117-10125, can be used. Linkers can also be designed by computer modeling (see, e.g., U.S. Pat. No. 4,946,778). Software for molecular modeling is commercially available (e.g., from Molecular Simulations, Inc., San Diego, Calif.). The linker is optionally optimized, e.g., to reduce antigenicity and/or to increase stability, using standard mutagenesis techniques and appropriate biophysical tests as practiced in the art of protein engineering, and functional assays as described herein.

For implementations utilizing zinc finger domains, the peptide that occurs naturally between zinc fingers can be used as a linker to join zinc fingers together. An example of a naturally occurring linker is: Thr-Gly-(Glu or Gln)-(Lys or Arg)-Pro-(Tyr or Phe) (SEQ ID NO:74) (Agata et al., supra). Generally, linkers can be selected or based on the sequences that join zinc fingers in naturally occurring proteins.

Dimerization Domains. An alternative method of linking DNA binding domains is the use of dimerization domains, especially heterodimerization domains (see, e.g., Pomerantz et al (1998) *Biochemistry* 37:965-970). In this implementation, DNA binding domains are present in separate polypeptide chains. For example, a first polypeptide encodes DNA binding domain A, linker, and domain B, while a second polypeptide encodes domain C, linker, and domain D. An artisan can select a dimerization domain from the many well-characterized dimerization domains. Domains that favor heterodimerization can be used if homodimers are not desired. A particularly adaptable dimerization domain is the coiled-coil motif, e.g., a dimeric parallel or anti-parallel coiled-coil. Coiled-coil sequences that preferentially form heterodimers are also available (Lumb and Kim, (1995) *Biochemistry* 34:8642-8648). Another species of dimerization domain is one in which dimerization is triggered by a small molecule or by a signaling event. For example, a dimeric form of FK506 can be used to dimerize two FK506 binding protein (FKBP) domains. Such dimerization domains can be utilized to provide additional levels of regulation.

Chimeric Proteins for Non-DNA Applications

It is also possible to modify the examples herein to make libraries of nucleic acids that encode chimeric proteins that include different combinations of non-DNA binding domains, e.g., intracellular signal transduction domains (e.g., SH2, SH3, PDZ, Che domains, or kinase domains). The chimeric proteins encoded by the library can be expressed in cells, and cells having an altered phenotypic trait are identified. For example, chimeric proteins formed of different combinations of signaling domains can be identified that decrease or increase the rate of cell proliferation.

Expression of Zinc Finger Proteins

Method described herein can include use of routine techniques in the field of molecular biology, biochemistry, classical genetics, and recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

In addition to other methods described herein, nucleic acids encoding zinc proteins can be constructed using synthetic oligonucleotides as linkers to construct a synthetic gene. In another example, synthetic oligonucleotides are used and/or primers to amplify sequences encoding one or more zinc finger domains, e.g., from an RNA or DNA template, artificial or synthetic. See U.S. Pat. Nos. 4,683,195 and 4,683, 202; *PCR Protocols: A Guide to Methods and Applications* (Innis et al., eds, 1990)). Methods such as polymerase chain reaction (PCR) can be used to amplify nucleic acid sequences directly from mRNA, from cDNA, from genomic, cDNA, or zinc finger protein libraries. Degenerate oligonucleotides can be designed to amplify homologs using the sequences provided herein. Restriction endonuclease sites can be incorporated into the primers.

Gene expression of zinc finger proteins can also be analyzed by techniques known in the art, e.g., reverse transcription and amplification of mRNA, isolation of total RNA or polyA$^+$ RNA, northern blotting, dot blotting, in situ hybridization, RNase protection, nucleic acid array technology, e.g., and the like.

The polynucleotide encoding an artificial zinc finger protein can be cloned into vectors before transformation into prokaryotic or eukaryotic cells for replication and/or expression. These vectors are typically prokaryote vectors, e.g., plasmids, phage or shuttle vectors, or eukaryotic vectors.

Protein Expression. To obtain recombinant expression (e.g., high level) expression of a polynucleotide encoding an artificial zinc finger protein, one can subclone the relevant coding nucleic acids into an expression vector that contains a strong promoter to direct transcription, a transcription/translation terminator, and a ribosome binding site for translational initiation. Suitable bacterial promoters are well known in the art and described, e.g., in Sambrook et al., and Ausubel et al, supra. Bacterial expression systems for expression are available in, e.g., *E. coli, Bacillus sp.,* and *Salmonella* (Palva et al., (1983) *Gene* 22:229-235; Mosbach et al., (1983) *Nature* 302:543-545. Kits for such expression systems are commercially available. Eukaryotic expression systems for mammalian cells, yeast (e.g., *S. cerevisiae, S. pombe, Pichia,* and *Hanseula*), and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for expression in host cells. A typical expression cassette thus contains a promoter operably linked to the coding nucleic acid sequence and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc-, or a hexa-histidine tag.

Expression vectors can contain regulatory elements from eukaryotic viruses, e.g., SV40 vectors, papilloma virus vectors, and vectors derived from Epstein-Barr virus. Other exemplary eukaryotic vectors include pMSC; pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal. Inducible expression vectors are often chosen if expression of the protein of interest is detrimental to eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with mitochondrial respiratory chain protein encoding sequences and glycolysis protein encoding sequence under the direction of the polyhedrin promoter or other strong baculovirus promoters The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The prokaryotic sequences can be chosen such that they do not interfere with the replication of the DNA in eukaryotic cells.

Standard transfection methods are used to produce bacterial, mammalian, yeast or insect cell lines that express large quantities of zinc finger proteins, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell.

After the expression vector is introduced into the cells, the transfected cells are cultured under conditions favoring expression or activating expression. The protein can then be isolated from a cell extract, cell membrane component or vesicle, or media.

Expression vectors with appropriate regulatory sequences can also be used to express a heterologous gene encoding an artificial zinc finger in a model organism, e.g., a Drosophila, nematode, zebrafish, Xenopus, or mouse. See, e.g., Riddle et al., eds., *C. elegans II*. Plainview (NY): Cold Spring Harbor Laboratory Press; 1997.

Protein Purification. Zinc finger protein can be purified from materials generated by any suitable expression system, e.g., those described above.

Zinc finger proteins may be purified to substantial purity by standard techniques, including selective precipitation with such substances as ammonium sulfate; column chromatography, affinity purification, immunopurification methods, and others (see, e.g., Scopes, *Protein Purification: Principles and Practice* (1982); U.S. Pat. No. 4,673,641; Ausubel et al., supra; and Sambrook et al., supra). For example, zinc finger proteins can include an affinity tag that can be used for purification, e.g., in combination with other steps.

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein. Proteins expressed in bacteria may form insoluble aggregates ("inclusion bodies"). Several protocols are suitable for purifying proteins from inclusion bodies. See, e.g., Sambrook et al., supra; Ausubel et al., supra). If the proteins are soluble or exported to the periplasm, they can be obtained from cell lysates or periplasmic preparations.

Differential Precipitation. Salting-in or out can be used to selectively precipitate a zinc finger protein or a contaminating protein. An exemplary salt is ammonium sulfate. Ammonium sulfate precipitates proteins on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration precipitates many of the more hydrophobic proteins. The precipitate is analyzed to determine if the protein of interest is precipitated or in the supernatant. Ammonium sulfate is added to the supernatant to a concentration known to precipitate the protein of interest. The precipitate is then solubilized in buffer and the excess salt removed if necessary, either through dialysis or diafiltration.

Column chromatography. A zinc finger protein can be separated from other proteins on the basis of its size, net surface charge, hydrophobicity, and affinity for ligands. In addition, antibodies raised against proteins can be conjugated to column matrices and the proteins immunopurified. All of these methods are well known in the art. Chromatographic techniques can be performed at any scale and using equipment from many different manufacturers (e.g., Pharmacia Biotech). See, generally, Scopes, *Protein Purification: Principles and Practice* (1982).

Similarly general protein purification procedures can be used to recover a protein whose production is altered (e.g., enhanced) by expression of an artificial zinc finger protein in a producing cell.

The invention also provides compositions, e.g., pharmaceutically acceptable compositions, which include an artificial transcription factor, e.g., as described herein, or a nucleic acid encoding such a factor formulated together with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The compositions may be in a variety of forms. These include, for example, liquid, semi-solid and solid dosage forms, such as liquid solutions (e.g., injectable and infusible solutions), dispersions or suspensions, tablets, pills, powders, and liposomes.

The compositions can be administered by a variety of methods known in the art, although for many applications, the route/mode of administration is intravenous injection or infusion. For example, the composition can be administered by intravenous infusion at a rate of less than 30, 20, 10, 5, or 1 mg/min to reach a dose of about 1 to 100 mg/m$^2$ or 7 to 25 mg/m$^2$. The route and/or mode of administration will vary depending upon the desired results. Many methods for the preparation of such formulations are patented or generally known. See, e.g., *Sustained and Controlled Release Drug Delivery Systems*, J. R. Robinson, ed., Marcel Dekker, Inc., New York, 1978.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of the protein or nucleic acid is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Gene and Cell-based Therapeutics

One aspect of the invention, described above, provides for isolated DNA molecules which encode an artificial zinc finger protein. These isolated DNA molecules can be inserted into a variety of DNA constructs and vectors for the purposes of gene therapy. As used herein, a "vector" is a nucleic acid molecule competent to transport another nucleic acid molecule to which it has been covalently linked. Vectors include plasmids, cosmids, artificial chromosomes, and viral elements. The vector can be competent to replicate in a host cell or to integrate into a host DNA. Viral vectors include, e.g., replication defective retroviruses, adenoviruses and adeno-associated viruses. A gene therapy vector is a vector designed for administration to a subject, e.g., a mammal, such that a cell of the subject is able to express a therapeutic gene contained in the vector.

The gene therapy vector can contain regulatory elements, e.g., a 5' regulatory element, an enhancer, a promoter, a 5' untranslated region, a signal sequence, a 3' untranslated region, a polyadenylation site, and a 3' regulatory region. For example, the 5' regulatory element, enhancer or promoter can regulate transcription of the DNA encoding the therapeutic polypeptide. The regulation can be tissue specific. For example, the regulation can restrict transcription of the desired gene to brain cells, e.g., cortical neurons or glial cells; hematopoietic cells; or endothelial cells. Alternatively, regulatory elements can be included that respond to an exogenous drug, e.g., a steroid, tetracycline, or the like. Thus, the level and timing of expression of the therapeutic zinc finger polypeptide (e.g., a polypeptide that regulates VEGF) can be controlled.

Gene therapy vectors can be prepared for delivery as naked nucleic acid, as a component of a virus, or of an inactivated virus, or as the contents of a liposome or other delivery vehicle. Alternatively, where the gene delivery agent, e.g., a viral vector, can be produced from recombinant cells which produce the gene delivery system. Appropriate viral vectors include retroviruses, e.g., Moloney retrovirus, adenoviruses, adeno-associated viruses, and lentiviruses, e.g., Herpes simplex viruses (HSV). HSV is potentially useful for infecting nervous system cells.

A gene therapy vector can be administered to a subject, for example, by intravenous injection, by local administration (see U.S. Pat. No. 5,328,470) or by stereotactic injection (see e.g., Chen et al. (1994) *Proc. Natl. Acad. Sci. USA* 91:3054-3057). The gene therapy agent can be further formulated, for example, to delay or prolong the release of the agent by means of a slow release matrix. One method of providing a recombinant therapeutic tri-domain polypeptide, is by inserting a gene therapy vector into bone marrow cells harvested from a subject. The cells are infected, for example, with a retroviral gene therapy vector, and grown in culture. Meanwhile, the subject is irradiated to deplete the subject of bone marrow cells. The bone marrow of the subject is then replenished with the infected culture cells. The subject is monitored for recovery and for production of the therapeutic polypeptide.

Cell based-therapeutic methods include introducing a nucleic acid that encoding the artificial zinc finger protein operably linked to a promoter into a cell in culture. The artificial zinc finger protein can be selected to regulate an endogenous gene in the culture cell or to produce a desired phenotype in the cultured cell. Further, it is also possible to modify cells, e.g., stem cells, using nucleic acid recombination, e.g., to insert a transgene, e.g., a transgene encoding an artificial zinc finger protein that regulates an endogenous gene. The modified stem cell can be administered to a subject. Methods for cultivating stem cells in vitro are described, e.g., in US Application 2002-0081724. In some examples, the stem cells can be induced to differentiate in the subject and express the transgene. For example, the stem cells can be differentiated into liver, adipose, or skeletal muscle cells. The stem cells can be derived from a lineage that produces cells of the desired tissue type, e.g., liver, adipose, or skeletal muscle cells.

In another embodiment, recombinant cells that express or can express an artificial zinc finger protein, e.g., as described herein, can be used for replacement therapy in a subject. For example, a nucleic acid encoding the artificial zinc finger protein operably linked to a promoter (e.g., an inducible promoter, e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) Nat. Biotechnol. 14:1107; Joki et al. (2001) Nat. Biotechnol. 19:35; and U.S. Pat. No. 5,876,742. In implementations where the artificial zinc finger protein regulates an endogenous gene that encodes a secreted protein, production of the secreted polypeptide can be regulated in the subject by administering an agent (e.g., a steroid hormone) to the subject.

In still another embodiment, the recombinant cells that express or can express an artificial zinc finger protein are cultivated in vitro. A protein produced by the recombinant cells can be recovered (e.g., purified) from the cells or from media surrounding the cells.

Target for Altered Protein Production

In one embodiment, a nucleic acid library is screened to identify an artificial zinc finger protein that alters production, synthesis or activity of one or more particular target proteins. The alteration can increase or decrease activity or abundance of the target protein. The phenotype screened for can be associated with altered production or activity of one or more target proteins or can be the level of production or activity itself. For example, it is possible to screen a nucleic acid library for artificial transcription factors that activate or suppress expression of a reporter gene (such as those encoding luciferase, LacZ, or GFP) under the control of a regulatory sequence (e.g., the promoter) of an endogenous target gene.

Some exemplary target proteins include: cell surface proteins (e.g., glycosylated surface proteins), cancer-associated proteins, cytokines, chemokines, peptide hormones, neurotransmitters, cell surface receptors (e.g., cell surface receptor kinases, seven transmembrane receptors, virus receptors and co-receptors, extracellular matrix binding proteins, cell-binding proteins, antigens of pathogens (e.g., bacterial antigens, malarial antigens, and so forth). Additional protein targets include enzymes such as enolases, cytochrome P450s, acyltransferases, methylases, TIM barrel enzymes, isomerases, acyl transferases, and so forth.

More specific examples include: integrins, cell attachment molecules or "CAMs" such as cadherins, selections, N-CAM, E-CAM, U-CAM, I-CAM and so forth); proteases (e.g., subtilisin, trypsin, chymotrypsin; a plasminogen activator, such as urokinase or human tissue-type plasminogen activator); bombesin; factor IX, thrombin; CD-4; platelet-derived growth factor; insulin-like growth factor-I and -II; nerve growth factor; fibroblast growth factor (e.g., aFGF and bFGF); epidermal growth factor (EGF); VEGFa; transforming growth factor (TGF, e.g., TGF-$\alpha$ and TGF-$\beta$; insulin-like growth factor binding proteins; erythropoietin; thrombopoietin; mucins; human serum albumin; growth hormone (e.g., human growth hormone); proinsulin, insulin A-chain insulin B-chain; parathyroid hormone; thyroid stimulating hormone; thyroxine; follicle stimulating hormone; calcitonin; atrial natriuretic peptides A, B or C; leutinizing hormone; glucagon; factor VIII; hemopoietic growth factor; tumor necrosis factor (e.g., TNF-$\alpha$: and TNF-$\beta$); enkephalinase; Mullerian-inhibiting substance; gonadotropin-associated peptide; tissue factor protein; inhibin; activin; vascular endothelial growth factor; receptors for hormones or growth factors; rheumatoid factors; osteoinductive factors; an interferon, e.g., interferon-$\alpha,\beta,\gamma$; colony stimulating factors (CSFs), e.g., M-CSF, GM-CSF, and G-CSF; interleukins (ILs), e.g., IL-1, IL-2, IL-3, IL-4, etc.; decay accelerating factor; and immunoglobulins. In some embodiments, the target is associated with a disease, e.g., cancer.

The present invention will be described in more detail through the following examples. However, it should be noted that these examples are not intended to limit the scope of the present invention.

EXAMPLE 1

Construction Of ZFP Libraries

In one example, various phenotypes of *Saccharomyces cerevisiae* are altered by regulating gene expression using zinc finger protein (ZFP) expression libraries. The zinc finger proteins in these exemplary libraries consist of three or four zinc finger domains (ZFDs) and recognize 9- to 12-bp DNA sequences respectively. The chimeric zinc finger protein is identified without a priori knowledge of the target genes. Three different class of transcription factors are produced from the ZFPs in the libraries: isolated ZFPs themselves function as efficient transcriptional repressors when they bind to a site near the promoter region; ZFPs are also expressed as fusion proteins to a transcriptional activation domain or to a repression domain to yield transcriptional activators or repressors, respectively.

We used 40 different zinc finger domains as modular building blocks to construct 3-finger or 4-finger zinc finger protein.

(3) Construction of Plasmid pYCT-Lib

We used pYCT-Lib as the parental vector for conditional expression of zinc finger proteins in yeast. pYCT-Lib is a yeast shuttle vector that includes the inducible GAL1 promoter (FIG. 1). Other features can include (i) a sequence encoding a nuclear localization signal (NLS) and a hemagglutinin tag (HA) and (ii) a sequence including the TRP1 gene for selection of plasmid containing cells on synthetic minimal media lacking tryptophan.

The polylinker from the T7 primer site to the SphI site region can include:

```
TAATACGACTCACTATAGGGAATATTAAGCTAAGCTCACCATGGGTAAGCCTATC   (SEQ ID NO: 135)

CCTAACCCTCTCCTCGGTCTCGATTCTACACAAGCTATGGGTGCTCCTCCAAAAA

AGAAGAGAAAGGTAGCTGGATCCACTAGTAACGGCCGCCAGTGTGCTGGAATTC

TGCAGATATCCATCACACTGGCGGCGCTCGAGGCATGCATCTA
```

At their upper limits, a 3-finger ZFP library consists of 64,000 (=$40^3$) sequences and a 4-finger library consists of 2.6 million (=$40^4$) sequences.

These libraries of ZFP expression plasmids were then transformed into yeast cells. In each transformed cell, a different ZFP transcription factor would be expressed and regulate unspecified target genes in the genome. This alteration of gene expression pattern can lead to phenotypic changes. By screening a large number of transformed cells, one can isolate clones with desired phenotypes. In addition, the regulated target genes can be identified by genome-wide analyses of gene expression profile (e.g., via DNA microarray analysis) or in silico prediction of target DNA sequences after identifying zinc finger proteins introduced to the transformants.

(1) Yeast Strains

The *S. cerevisiae* strain used for this experiment was YPH499a (MATa, ade2-101, ura3-52, lys2-801, trpl-Δ 63, his3-Δ 200, leu2-Δ 1, GAL+). Transformation of yeast cells was carried out by using the lithium acetate transformation method (see, e.g., Gietz et al., (1992) *Nucl. Acids Res* 20:1245).

(2) Construction of Plasmid p3

The parental vector that we used to construct libraries of zinc finger proteins is the plasmid p3. p3 was constructed by modifying the pcDNA3 vector (Invitrogen, San Diego Calif.) as follows. The pcDNA3 vector was digested with HindIII and XhoI. A synthetic oligonucleotide duplex with compatible overhangs was ligated into the digested pcDNA3. The duplex contains nucleic acid that encodes the hemagglutinin (HA) tag and a nuclear localization signal. The duplex also includes: restriction sites for BamHI, EcoRI, NotI, and BglII; and a stop codon. The XmaI site in SV40 origin of the vector was destroyed by digestion with XmaI, filling in the overhanging ends of the digested XmaI restriction site, and religation of the ends.

p-YCT-Lib was constructed as follows. The yeast expression plasmid pYESTrp2 (Invitrogen, San Diego Calif.) was digested with NgoM4 and then was partially digested with PstI to remove the 2μ ori fragment from the vector. The 5.0 kb DNA fragment from the NgoM4-PstI digested vector was purified after gel electrophoresis and ligated with a CEN-ARS fragment that was amplified from pRS313 (forward primer: 5'-CGATCT-GCAGGG TCCTTTTCATCACGTGCT-3' (SEQ ID NO:136), reverse primer: 5'-CGATCGATGCCG GCG-GACGGATCGCTTGCCT (SEQ ID NO:137)).

The DNA segment that encodes the B42 activation domain was removed by digestion with NcoI and BamHI and replaced with a DNA fragment encoding the V5 epitope tag and the nuclear localization signal. The latter DNA fragment was PCR-amplified from pYESTrp2 (forward primer: 5'-AATTCCATGGGTAAGCCTATCCCTAACC-3' (SEQ ID NO:138), reverse primer: 5'-AATTGGATCCAGCTAC-CTTTCTCTTCTT-3 '(SEQ ID NO:139)) and ligated into the NcoI and BamHI sites. The resulting plasmid was named as pYTC-Lib (FIG. 1).

(4) Construction of plasmid pYCT-Lib-Gal4

To generate pYCT-Lib-Gal4, the Gal4 activation domain was PCR-amplified from yeast genomic DNA (forward primer: 5'-AAGGAAGGAAGGAAGCGGC CGCAGC-CAATTTTAATCAAAGTGG-3' (SEQ ID NO:140), reverse primer: 5'-ACATACATGCATGCGCCGTTACTAGTG-GATCC-3' sequence (SEQ ID NO:141)) and inserted between the NotI and SphI recognition sites of pYTC-Lib to generate pYTC-Lib-Gal4. An exemplary sequence encoding the Gal4 activation domain and linking sequences includes:

```
GGCCGCCAGTGTGCTGGAATTCTGCAGATATCCATCACACTGGCGGCCGCAGCC    (SEQ ID NO: 142)

AATTTTAATCAAAGTGGGAATATTGCTGATAGCTCATTGTCCTTCACTTTCACTA

ACAGTAGCAACGGTCCGAACCTCATAACAACTCAAACAAATTCTCAAGCGCTTT

CACAACCAATTGCCTCCTCTAACGTTCATGATAACTTCATGAATAATGAAATCAC

GGCTAGTAAAATTGATGATGGTAATAATTCAAAACCACTGTCACCTGGTTGGAC

GGACCAAACTGCGTATAACGCGTTTGGAATCACTACAGGGATGTTTAATACCACT

ACAATGGATGATGTATATAACTATCTATTCGATGATGAAGATACCCCACCAAACC

CAAAAAAAGAGATCTCTATGGCTTACCCATACGATGTTCCAGATTACGCTAGCTA

AGGATCCACTAGTAACGGCGCATGCATCTAGAGGGCC
```

(5) Construction of Plasmid pYCT-Lib-Ume6

To generate pYCT-Lib-Ume6, a DNA fragment encoding amino acids 508 to 594 of *S. cerevisiae* Ume6 was amplified from yeast genomic DNA (forward primer: 5'-AAGGAAG-GAAGGAAGCGGCCGCAAATTCTGCATCT-TCATCTACC-3' (SEQ ID NO:143), reverse primer: 5'-ACATACATGCATGCTGTAGAATTGTTGCTTTCG-3' (SEQ ID NO:144)) and inserted between the NotI and SphI recognition sites of pYTC-Lib. This 87-amino acid region functions as a transcriptional repression domain (Kadosh and Struhl (1997) *Cell* 89:365-371). An exemplary sequence encoding the Ume6 repression domain and linking sequences includes:

```
GGCCGCCAGTGTGCTGGAATTCTGCAGATATCCATCACACTGGCGGCCGCAAATT     (SEQ ID NO: 145)

CTGCATCTTCATCTACCAAACTAGACGACGACTTGGGTACAGCAGCAGCAGTGCT

ATCAAACATGAGATCATCCCCATATAGAACTCATGATAAACCCATTTCCAATGTC

AATGACATGAATAACACAAATGCGCTCGGTGTGCCGGCTAGTAGGCCTCATTCG

TCATCTTTTCCATCAAAGGGTGTCTTAAGACCAATTCTGTTACGTATCCATAATTC

CGAACAACAACCCATTTTCGAAAGCAACAATTCTACAGCATGCATCTAGAGGGC

C
```

(6) Library Construction

A three-fingered protein library (the "3-F library"), encoding zinc finger proteins that have an array of three ZFDs, was constructed from nucleic acids encoding 40 different ZFDs or "fingers." A four-fingered protein library (the "4-F library") was constructed from nucleic acids encoding 27 different ZFDs (Table 2, below).

TABLE 2

Zinc finger domains for construction of 3-finger or 4-finger ZFP libraries.

| Domain Name | Source | Target Sites | Amino acid sequences | SEQ ID NO: | Library |
|---|---|---|---|---|---|
| DSAR3m | Mutated[1] | GTC | FMCTWSYCGKRFTDRSALARHKRTH | 146 | 3F |
| DSHRm | Mutated[1] | GGC | HICHIQGCGKVYGDRSHLTRHLRWH | 147 | 3F |
| DSKRm | Mutated[1] | GGT | FACPECPKRFMDSSKLSRHIKTH | 148 | 3F |
| DSNRm | Mutated[2] | GAC | YACPVESCDRRFSDSSNLTRHIRIH | 149 | 3F |
| DSSRm | Mutated[3] | GCC | HICHIQGCGKVYGDRSSLTRHLRWH | 150 | 3F |
| HSNK | Human | GAC | YKCKECGKAFNHSSNFNKHHRIH | 151 | 3F |
| HSSR | Human | GTT | FKCPVCGKAFRHSSSLVRHQRTH | 152 | 3F |
| ISNR | Human | GAA > GAT > GAC | YRCKYCDRSFSISSNLQRHVRNIH | 153 | 3F |

TABLE 2-continued

Zinc finger domains for construction of 3-finger or 4-finger ZFP libraries.

| Domain Name | Source | Target Sites | Amino acid sequences | SEQ ID NO: | Library |
|---|---|---|---|---|---|
| KSNR | Human | GAG | YGCHLCGKAFSKSSNLRRHEMIH | 154 | 3F |
| QAHR | Human | GGA | YKCKECGQAFRQRAHLIRHHKLH | 155 | 3F |
| QFNR | Human | GAG | YKCHQCGKAFIQSFNLRRHERTH | 156 | 3F |
| QGNR | Human | GAA | FQCNQCGASFTQKGNLLRHIKLH | 157 | 3F |
| QNTQ | Drosophila[4] | ATA | YTCSYCGKSFTQSNTLKQHTRIH | 158 | 3F |
| QSHR5 | Human | GGA > AGA > GAA > CGA | YVCRECGRGFRQHSHLVRHKRTH | 159 | 3F- |
| QSHV | Human | CGA > AGA > TGA | YECDHCGKSFSQSSHLNVHKRTH | 160 | 3F |
| QSNI | Human | AAA, CAA | YMCSECGRGFSQKSNLIIHQRTH | 161 | 3F |
| QSNK | Human | GAA > TAA > AAA | YKCEECGKAFTQSSNLTKHKKIH | 162 | 3F |
| QSTR | Human | GTA > GCA | YKCEECGKAFNQSSTLTRHKIVH | 163 | 3F |
| QTHR1 | Human | GGA > AGA, GAA > TGA, CGA | YECHDCGKSFRQSTHLTRHRRIH | 164 | 3F |
| RDHR1 | Human | GAG, GGG | FLCQYCAQRFGRKDHLTRHMKKSH | 165 | 3F |
| RDKR | Human | GGG > AGG | YVCDVEGCTWKFARSDKLNRHKKRH | 166 | 3F |
| RDNQm | Mutated[6] | AAG | FACPECPKRFMRSDNLTQHIKTH | 167 | 3F |
| SADRm | Mutated[3] | AGA | FQCRICMRNFSSPADLTRHIRTH | 168 | 3F |
| SSNR | Human | GAG > GAC | YECKECGKAFSSGSNFTRHQRIH | 169 | 3F |
| TIDRm | Mutated[5] | ACT | FQCRICMRNFSTHIDLIRHIRTH | 170 | 3F |
| VSNV | Human | AAT > CAT > TAT | YECDHCGKAFSVSSNLNVHRRIH | 171 | 3F |
| VSTR | Human | GCT > GCG | YECNYCGKTFSVSSTLIRHQRIH | 172 | 3F |
| CSNR1 | Human | GAA > GAC > GAG | YKCKQCGKAFGCPSNLRRHGRTH | 173 | 3F-, 4F- |
| DGNVm | Mutated[5] | AAC | FQCRICMRNFSDSGNLRVHIRTH | 174 | 3F-, 4F- |
| QSHR3 | Human | GGA > GAA | YACHLCGKAFTQCSHLRRHEKTH | 175 | 3F- |
| QSHT | Human | AGA, CGA > TGA > GGA | YKCEECGKAFRQSSHLTTHKIIH | 176 | 3F-, 4F- |
| QSNR1 | Human | GAA | FECKDCGKAFIQKSNLRHQRTH | 177 | 3F-, 4F- |
| QSNV2 | Human | AAA, CAA | YVCSKCGKAFTQSSNLTVHQKIH | 178 | 3F-, 4F- |
| QSSR1 | Human | GTA > GCA | YKCPDCGKSFSQSSSLIRHQRTH | 179 | 3F-, 4F- |
| QTHQ | Human | CGA > TGA, AGA | YECHDCGKSFRQSTHLTQHRRIH | 180 | 3F-, 4F- |
| RDER1 | Human | GCG > GTG, GAG | YVCDVEGCTWKFARSDELNRHKKRH | 181 | 3F-, 4F- |
| RDHT | Human | TGG, AGG, CGG, GGG | FQCKTCQRKFSRSDHLKTHTRTH | 182 | 3F-, 4F- |
| RSHR | Human | GGG | YKCMECGKAFNRRSHLTRHQRIH | 183 | 3F-, 4F- |
| RSNR | Human | GAG > GTG | YICRKCGRGFSRKSNLIRHQRTH | 184 | 3F-, 4F- |
| VDYK | Drosophila[7] | TAT, GAT | FHCGYCEKSFSVKDYLTKIRTH | 185 | 3F-, 4F- |
| VSSR | Human | GTT > GCT > GTG > GTA | YTCKQCGKAFSVSSSLRRHETTH | 186 | 3F-, 4F- |
| DGARm | Mutated[3] | GTC | FQCRICMRNFSDPGALVRHIRTH | 187 | 4F- |
| DGHRm | Mutated[3] | GGC | FQCRICMRNFSDPGHLVRHIRTH | 188 | 4F- |
| DGNRm | Mutated[3] | GAC | FQCRICMRNFSDPGNLKRHIRTH | 189 | 4F- |
| DRDRm | Mutated[3] | GCC | FQCRICMRNFSDCRDLARHIRTH | 190 | 4F- |

TABLE 2-continued

Zinc finger domains for construction of 3-finger or 4-finger ZFP libraries.

| Domain Name | Source | Target Sites | Amino acid sequences | SEQ ID NO: | Library |
|---|---|---|---|---|---|
| MMHEm | Mutated[8] | TGT | YACPVESCDRRFSMSHHLKEHIRTH | 191 | 4F- |
| QASAm | Mutated[8] | ATA | FQCRICMRNFSQQASLNAHIRTH | 192 | 4F- |
| QGDRm | Mutated[3] | GCA, GCC | FQCRICMRNFSQSGDLRRHIRTH | 193 | 4F- |
| QSDRm | Mutated[9] | GCT | FQCRICMRNFSQSSDLVRHIRTH | 194 | 4F- |
| QGTRm | Mutated[8] | ACA | FQCRICMRNFSQRGTLTRHIRTH | 195 | 4F- |
| RDTNm | Mutated[5] | AAG | FQCRICMRNFSRSDTLSNHIRTH | 196 | 4F- |
| TDKRm | Mutated[3] | GGG, GGT | FQCRICMRNFSTADKLSRHIRTH | 197 | 4F- |
| TGNRm | Mutated[3] | GAT > GAA | FQCRICMRNFSTSGNLVRHIRTH | 198 | 4F- |
| TIDRm | Mutated[5] | ACT | FQCRICMRNFSTHIDLIRHIRTH | 199 | 4F- |

Superscripts in column 2 of Table 2 refer to
[1]Zhang et al, (2000) J. Biol. Chem. 275: 33850-33860;
[2]Rebar and Pabo (1994) Science 263: 671-673;
[3]Segal (1999) Proc. Natl. Acad. Sci. USA 96: 2758;
[4]Gogus et al., (1996) Proc. Natl. Acad. Sci. USA. 93: 2159-2164;
[5]Drier et al., (2001) J Biol. Chem. 276: 29466-29478;
[6]Liu et al. (2001) J. Biol. Chem. 276(14): 11323-11334;
[7]Hsu et al., (1992) Science 257: 1946-50.
The small letter m after the name of certain zinc finger domains indicates that the domain obtained by mutation of a parental domain.

Figure 7:
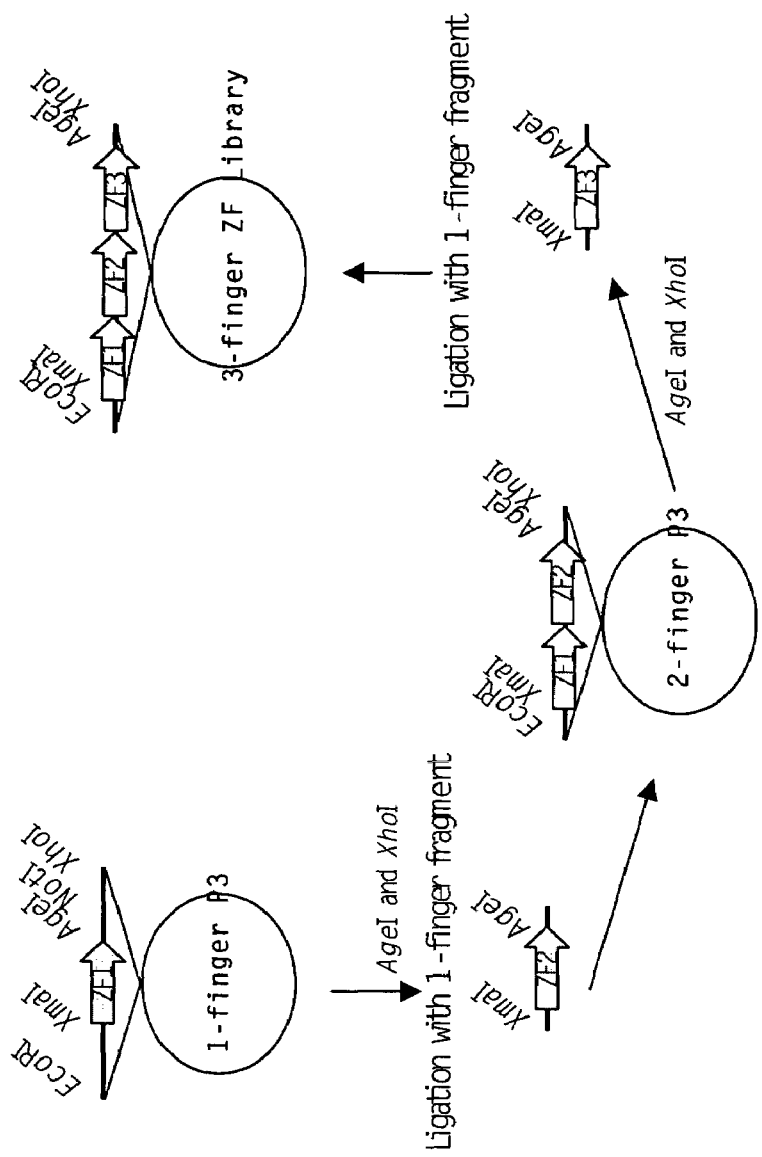
FIG. 7 depicts one method of constructing a diverse three finger library.

FIG. 7 depicts a method of constructing a diverse three finger library. Nucleic acid fragments encoding each ZFD were individually cloned into the p3 vector to form "single fingered" vectors. Equal amounts of each "single fingered" vector were combined to form a pool. One aliquot of the pool was digested with AgeI and XhoI to obtain digested vector fragments. These vector fragments were treated with phosphatase for 30 minutes. Another aliquot of the pool was digested with XmaI and XhoI to obtain segments encoding single fingers. The digested vector nucleic acids from the AgeI and XhoI digested pool were ligated to the nucleic acid segments released from the vector by the XmaI and XhoI digestion. The ligation generated vectors that each encode two zinc finger domains. After transformation into E. coli, approximately 1.4×10[4] independent transformants were obtained, thereby forming a two-fingered library. The size of the insert region of the two-fingered library was verified by PCR analysis of 40 colonies. The correct size insert was present in 95% of the library members.

To prepare a three-fingered library, DNA segments encoding one finger were inserted into plasmids encoding two fingers. The 2-fingered library was digested with AgeI and XhoI. The digested plasmids, which retain nucleic acid sequences encoding two zinc finger domains, were ligated to the pool of nucleic acid segments encoding a single finger (prepared as described above by digestion with XmaI and XhoI). The products of this ligation were transformed into E. coli to obtain about 2.4×10[5] independent transformants. Verification of the insert region confirmed that library members predominantly included sequences encoding three zinc finger domains.

To prepare a four-fingered library, DNA segments encoding two fingers were inserted into plasmids encoding two fingers. The two-fingered library was digested with XmaI and XhoI to obtain nucleic acid segments that encode two zinc finger domains. The two-fingered library was also digested with AgeI and XhoI to obtain a pool of digested plasmids. The digested plasmids, which retain nucleic acid sequences encoding two zinc finger domains, were ligated to the nucleic acid segments encoding two zinc finger domains to produce a population of plasmids encoding different combination of four fingered proteins. The products of this ligation were transformed into E. coli and yielded about 7×10[6] Independent transformants.

(7) Construction of Libraries for Expression in Yeast

The three-fingered (3-F) and four-fingered (4-F) libraries were subcloned into the EcoRI and NotI sites of pYTC-Lib, pYTC-Gal4, and pYTC-Ume6. These subcloning procedures produced six different libraries encoding three and four fingered ZFPs with and without transcriptional regulatory domains. After amplification in E. coli, each library was transformed into the yeast strain YPH499a using lithium acetate. The transformation yielded approximately 1.5×10[7] colonies. The size of the insert region of the library was verified by PCR analysis of 50 colonies. 95% of the library members included the correct insert size. The transformants were resuspended in TE buffer and stored in glycerol at −80° C.

EXAMPLE 2

Growth-Defective Transformants on Galactose Media

The 3-F libraries were screened to identify chimeric zinc finger proteins that impair the growth of yeast cells. This screen uses the GAL promoter to conditionally express chimeric zinc finger proteins. Previous studies have used the GAL promoter to yeast cDNA and genomic DNA sequences to identify genes whose overexpression is lethal (Liu et al., (1992) *Genetics* 132:665-673; Ramer et al. (1992) *Proc. Natl. Acad. Sci. USA* 89:11589-11593; Espinet et al., (1995) *Yeast* 11:25-32; Akada et al., (1997) *Mol. Gen. Genet* 254:267-274; Stevenson et al., (2001) *Proc. Natl. Acad. Sci. USA.* 98:3946-3951).

Yeast strain YPH499a was transformed with nucleic acid from the 3-F libraries. Transformants were grown for two days at 30° C. on plates containing synthetic minimal medium that lack tryptophan and that include glucose. Each of these glucose plates was replica-plated onto a galactose plate and a second glucose plate. The replica plates were grown overnight at 30° C. Then, each galactose plate was compared to its corresponding glucose replica plate. Colonies were identified that did not grow on galactose, but grew on glucose. These colonies were recovered from the glucose plate and retested by streaking selected colonies on galactose media. Library plasmids were rescued from each colony that retested. The plasmids were retransformed into YPH499a to confirm that the growth defect is caused by expression of the zinc finger protein. The vector plasmids pYTC and pYTC-Gal4, both of which do not encode any zinc finger domains, were analyzed as controls.

As shown in Table 3, 0.7% to 2.8% of transformants from the 3-F and 4-F libraries were unable to grow on galactose media. These percentages are significantly greater than the similar values obtained with the pYTC-Lib vector control (0.1%) and pYTC-Lib-Gal4 vector control (0.2%).

TABLE 3

Ratio of growth-defective transformants on galactose media

| Library | No. of colonies on glucose media (A) | No. of growth-defective colonies on galactose media (B) | Ratio of growth-defective mutants (B/A × 100) |
|---|---|---|---|
| 3-finger | 5,820 | 42 | 0.7 |
| 3-finger + Gal4AD | 7,428 | 206 | 2.8 |
| 3-finger + Ume6RD | 8,400 | 78 | 0.93 |
| pYTC-Lib vector | 2,690 | 3 | 0.1 |
| pYTC-Lib-Gal4 vector | 2,750 | 6 | 0.2 |

Plasmids were recovered from ten colonies that were growth-defective on galactose. The plasmids (L1 to L10) were retransformed into yeast cells. All ten plasmids retested. Cells transformed with the recovered plasmids were unable to grow on galactose media but were able to grow on glucose media. The zinc finger proteins encoded by these ten plasmids were characterized by DNA sequencing (Table 4). The potential target DNA binding sites for these proteins were inferred from information about the binding specificities of the component zinc finger domains.

TABLE 4

ZFPs encoded in plasmids isolated from growth-defective transformants

| No | Name of ZFD (N to C) | | | Potential target sequence |
|---|---|---|---|---|
| | 1 | 2 | 3 | |
| L1 | RSHR | CSNR1 | RDHT | 5'-NGG GAV GGG-3' (SEQ ID NO: 200) |
| L2 | RSNR | RDHT | TDKR | 5'-GGK NGG GAG-3' (SEQ ID NO: 201) |

TABLE 4-continued

ZFPs encoded in plasmids isolated from growth-defective transformants

| No | Name of ZFD (N to C) | | | Potential target sequence |
|---|---|---|---|---|
| | 1 | 2 | 3 | |
| L3 | RDHT | QSHR3 | RDHT | 5'-NGG GRA NTT-3' (SEQ ID NO: 202) |
| L4 | QSDR | RDHT | RSNR | 5'-GAANGG GCT-3' (SEQ ID NO: 203) |
| L5 | CSNR1 | RDTN | VSSR | 5'-GTD AAG GAV-3' (SEQ ID NO: 204) |
| L6 | RDHT | RDHT | RDER1 | 5'-GHG NGG KGG-3' (SEQ ID NO: 205) |
| L7 | QSNR1 | RDTN | QTHQ | 5'-HGA AAG GAA-3' (SEQ ID NO: 206) |
| L8 | TGNR | RDER1 | RDHT | 5'-NGG GHG GAW-3' (SEQ ID NO: 207) |
| L9 | QSSR1 | RDHT | QTHQ | 5'-HGA NGG GYA-3' (SEQ ID NO: 208) |
| L10 | QSSR1 | RDHT | QSNR1 | 5'-GAA NGG GYA-3' (SEQ ID NO: 209) |

EXAMPLE 3

Anti-Fungal Drug Resistance

Ketoconazole is an orally absorbed antimycotic imidazole drug. It can be administered for the treatment of certain mucoses. Ketoconazole blocks the biosynthesis of ergosterol in yeasts and other fungi (Burden et al., (1989) *Phytochemistry* 28:1791-1804) and has additional effects on cellular metabolism (Kelly et al., (1992) In Fernandes, P. B. (Ed.) *New Approaches for Antifungal Drug*, Birkhäuser, Boston, pp.155-187).

To check the fungistatic response of the tester strain YPH499a to ketoconazole, $10^7$ cells of the YPH499a strain were plated onto synthetic media containing different concentrations of the drug. We found that 35 µM ketoconazole inhibited growth of YPH499a cells and used this concentration to screen for ketoconazole-resistant yeast colonies.

$1 \times 10^7$ yeast cells containing plasmids from the 3-finger and 4-finger libraries were cultivated in synthetic liquid medium with 2% galactose for 3 hours at 30° C. to induce zinc finger protein expression and then were plated onto synthetic galactose agar plates containing 35 µM ketoconazole (ICN Biomedicals). After fours days of incubation at 30° C., about 120 clones formed colonies on galactose media containing 35 µM ketoconazole. These ketoconazole resistant yeast colonies were picked and streaked on fresh synthetic galactose agar plates containing 35 µM ketoconazole. 23 clones were randomly selected from the 120 resistant clones. For each of these 23 clones, the resistant phenotype was verified by plasmid rescue. The plasmids were isolated, transformed into *E. coli* for amplification, and retransformed into yeast strain YPH499a (Ausubel, et al. (Eds) (1995) *Current Protocols in Molecular Biology* John Wiley and Sons Ltd, New York). Equal numbers of retransformants were spotted onto synthetic galactose agar plates with or without 35 µM ketoconazole. The retransformants were also spotted onto synthetic glucose agar plates with or without ketoconazole to verify that the drug resistance was induced by galactose-inducible expression of zinc finger protein.

In one experiment, $5 \times 10^4$ cells from each transformant were serially diluted ($10^{-1}$, $10^{-2}$, and $10^{-3}$ fold) and spotted on galactose or glucose media supplemented without or with 35 μM ketoconazole. Growth of the cells was monitored after four days at 30° C. and compared to controls on the same plate. Controls included a plasmid encoding a zinc finger protein that does not confer ketoconazole resistance and the pYTC-Lib plasmid without an insert encoding a zinc finger protein. In all 23 cases, recovered plasmids retested. In addition, ketoconazole resistance was observed only when the cells were plated on galactose media, confirming that expression of the zinc finger protein confers ketoconazole resistance.

The plasmids isolated from ketoconazole resistant transformants were sequenced and their expected target sequences in yeast genome were predicted (Table 5). Eleven unique clones were identified (Table 5).

-continued

HQCGKAFIQSFNLRRHERTHTGEKPYKCMECGKA

FNRRSHLTRHQRIHAAAANSASSSTKLDDDLGTA

AAVLSNMRSSPYRTHDKPISNVNDMNNTNALGVP

ASRPHSSSFPSKGVLRPILLRIHNSEQQPIFESN

NSTACI

K2: RSNR-RSNR-QSSR1-QSHT-Ume6 includes the following amino acid sequence:

MGKPIPNPLLGLNSTQAMGAPPKKKRKVGIRIPG (SEQ ID NO: 222)

EKPYICRKCGRGFSRKSNLIRHQRTHTGEKPYIC

RKCGRGFSRKSNLIRHQRTHTGEKPYKCPDCGKS

TABLE 5

ZFPs that confer ketoconazole resistance

| No. | Name of ZFD (N to C) #1 | #2 | #3 | #4 | Functional domain | Potential target sequence | Number of isolates[1] |
|---|---|---|---|---|---|---|---|
| K1 | QSHV | QFNR | RSHR | — | UME6 | 5'-GGG GAG HGA-3' (SEQ ID NO: 210) | 3 |
| K2 | RSNR | RSNR | QSSR1 | QSHT | UME6 | 5'-HGA GYA GAG GAG-3' (SEQ ID NO: 211) | 1 |
| K3 | RSNR | RSNR | QGTR | QSHR5 | UME6 | 5'-GRA ACA GAG GAG-3' (SEQ ID NO: 212) | 2 |
| K4 | RSNR | RSNR | QGTR | QTHQ | UME6 | 5'-HGA ACA GAG GAG-3' (SEQ ID NO: 213) | 1 |
| K5 | VSSR | DGNV | VSSR | VDYK | GAL4 | 5'-KAT GTD AAC GTD-3' (SEQ ID NO: 214) | 2 |
| K6 | MHHE | QSNR1 | VSSR | QGDR | GAL4 | 5'-GCA GTD GAA TGT-3' (SEQ ID NO: 215) | 3 |
| K7 | DGNV | QSHT | QSSR1 | DGHR | GAL4 | 5'-GGC GYA HGA AAC-3' (SEQ ID NO: 216) | 3 |
| K8 | DGAR | RDTN | QTHQ | RDTN | — | 5'-AAG HGA AAG GTG-3' (SEQ ID NO: 217) | 1 |
| K9 | RDHT | QTHQ | QSHT | DGNV | — | 5'-AAC HGA HGA NGG-3' (SEQ ID NO: 218) | 1 |
| K10 | RDHT | QTHQ | QSHT | — | — | 5'-HGA HGA NGG-3'5 (SEQ ID NO: 219) | |
| K11 | RDHT | QSHV | QSHV | — | — | 5'-HGA HGA NGG-3' (SEQ ID NO: 220) | 1 |

[1] The number of isolates of the ZFP among the 23 isolated ketoconazole-resistant transformants.

The amino acid sequences of these proteins are listed below (zinc finger domains are underscored and transcriptional regulatory domains are bolded). K1:QSHV-QFNR-RSHR-Ume6 includes the following amino acid sequence:

MGKPIPNPLLGLNSTQAMGAPPKKKRKVGIRIPG (SEQ ID NO: 221)

EKPYECDHCGKSFSQSSHLNVHKRTHTGEKPYKC

-continued

FSQSSSLIRHQRTHTGEKPYKCEECGKAFRQSSH

LTTHKIIHAAAANSASSSTKLDDDLGTAAAVLSN

MRSSPYRTHDKPISNVNDMNNTNALGVPASRPHS

SSFPSKGVLRPILLRIHNSEQQPIFESNNSTACI

K3: RSNR-RSNR-QGTR-QSHR5-Ume6 includes the following amino acid sequence:

MGKPIPNPLLGLNSTQAMGAPPKKKRKVGIRIPG (SEQ ID NO: 223)
EKP*YICRKCGRGFSRKSNLIRHQRTH*TGEKP*YIC
RKCGRGFSRKSNLIRHQRTH*TGEKP*FQCRICMRN
FSQRGTLTRHIRTH*TGEKP*YVCRECGRGFRQHSH
LVRHKRTH*AAAA**NSASSSTKLDDDLGTAAAVLSN
MRSSPYRTHDKPISNVNDMNNTNALGVPASRPHS
SSFPSKGVLRPILLRIHNSEQQPIFESNNSTACI**

K4: RSNR-RSNR-QGTR-QTHQ-Ume6 includes the following amino acid sequence:

MGKPIPNPLLGLNSTQAMGAPPKKKRKVGIRIPG (SEQ ID NO: 224)
EKP*YICRKCGRGFSRKSNLIRHQRTH*TGEKP*YIC
RKCGRGFSRKSNLIRHQRTH*TGEKP*FQCRICMRN
FSQRGTLTRHIRTH*TGEKP*YECHDCGKSFRQSTH
LTQHRRIH*AAAA**NSASSSTKLDDDLGTAAAVLSN
MRSSPYRTHDKPISNVNDMNNTNALGVPASRPHS
SSFPSKGVLRPILLRIHNSEQQPIFESNNSTACI**

K5: VSSR-DGNV-VSSR-VDYK-Gal4 includes the following amino acid sequence:

MGKPIPNPLLGLNSTQAMGAPPKKKRKVGIRIPG (SEQ ID NO: 225)
EKP*YTCKQCGKAFSVSSSLRRHETTH*TGEKP*FQC
RICMRNFSDSGNLRVHIRTH*TGEKP*YTCKQCGKA
FSVSSSLRRHETTH*TGEKP*FHCGYCEKSFSVKDY
LTKIRTH*AAAA**NFQSGNIADSSLSFTFTNSSNG
PNLITTQTNSQALSQPIASSNVHDNFMNNEITAS
KIDDGNNSKPLSPGWTDQTAYNAFGITTGMFNTT
TMDDVYNYLFDDEDTPPNPKKEISMAYPYDVPDY
AS**

K6: MHHE-QSNR1-VSSR-QGDR-Gal4 includes the following amino acid sequence:

MGKPIPNPLLGLNSTQAMGAPPKKKRKVGIRIPG (SEQ ID NO: 226)
EKP*YACPVESCDRRFSMSHHLKEHIRTH*TGEKP*F
ECKDCGKAFIQKSNLIRHQRTH*TGEKP*YTCKQCG
KAFSVSSSLRRHETTH*TGEKP*FQCRICMRNFSQS
GDLRRHIRTH*AAAA**NFQSGNIADSSLSFTFTNS
SNGPNLITTQTNSQALSQPIASSNVHDNFMNNEI
TASKIDDGNNSKPLSPGWTDQTAYNAFGITTGMF
NTTTMDDVYNYLFDDEDTPPNPKKEISMAYPYDV
PDYAS**

K7: DGNV-QSHT-QSSR1-DGHR-Gal4 includes the following amino acid sequence:

MGKPIPNPLLGLNSTQAMGAPPKKKRKVGIRIPG (SEQ ID NO: 227)
EKP*FQCRICMRNFSDSGNLRVHIRTH*TGEKP*YKC
EECGKAFRQSSHLTTHKIIH*TGEKP*YKCPDCGKS
FSQSSSLIRHQRTH*TGEKP*FQCRICMRNFSDPGH
LVRHIRTH*AAAA**NFQSGNIADSSLSFTFTNSSN
GPNLITTQTNSQALSQPIASSNVHDNFMNNEITA
SKIDDGNNSKPLSPGWTDQTAYNAFGITTGMFNT
TTMDDVYNYLFDDEDTPPNPKKEISMAYPYDVPD
YAS**

K8: DGAR-RDTN-QTHQ-RDTN includes the following amino acid sequence:

MGKPIPNPLLGLNSTQAMGAPPKKKRKVGIRIPG (SEQ ID NO: 228)
EKP*FQCRICMRNFSDPGALVRHIRTH*TGEKP*FQC
RICMRNFSRSDTLSNHIRTH*TGEKP*YECHDCGKS
FRQSTHLTQHRRIH*TGEKP*FQCRICMRNFSRSDT
LSNHIRTH*AAAARGMHLEGRIM

K9: RDHT-QTHQ-QSHT-DGNV includes the following amino acid sequence:

MGKPIPNPLLGLNSTQAMGAPPKKKRKVGIRIPG (SEQ ID NO: 229)
EKP*FQCKTCQRKFSRSDHLKTHTRTH*TGEKP*YEC
HDCGKSFRQSTHLTQHRRIH*TGEKP*YKCEECGKA
FRQSSHLTTHKIIH*TGEKP*FQCRICMRNFSDSGN
LRVHIRTH*AAAARGMHLEGRIM

K10: RDHT-QTHQ-QSHT includes the following amino acid sequence:

MGKPIPNPLLGLNSTQAMGAPPKKKRKVGIRIPG (SEQ ID NO: 230)
EKP*FQCKTCQRKFSRSDHLKTHTRTH*TGEKP*YEC
HDCGKSFRQSTHLTQHRRIH*TGEKP*YKCEECGKA
FRQSSHLTTHKIIH*AAAARGMHLEGRIM

K11: RDHT-QSHV-QSHV includes the following amino acid sequence:

MGKPIPNPLLGLNSTQAMGAPPKKKRKVGIRIPG (SEQ ID NO: 231)
EKP*FQCKTCQRKFSRSDHLKTHTRTH*TGEKP*YEC
DHCGKSFSQSSHLNVHKRTH*TGEKP*YECDHCGKS
FSQSSHLNVHKRTH*AAAARGMHLEGRIM

Other zinc finger proteins that include two, three, or more zinc finger domains that have the same general motifs (i.e., set of four DNA contacting residues) and that are arranged in the same consecutive order as any of the proteins described above may also confer drug resistance to a fungal cell.

Some of clones had included a similar configuration of zinc finger domains. The first and second fingers of K2, K3, and K4 are identical to one another. In these clones, three out of four fingers are identical to those in corresponding positions in the other proteins. It is extremely unlikely that these ZFPs are related only by chance (P<1.6×10-5). Accordingly, the K2, K3, and K4 ZFPs may bind to the same target site in vivo and regulate the same target genes.

In addition, the zinc finger protein encoded by the K10 clone is closely related to those encoded in the K9 and K11 clones. The QTHQ, QSHT, and QSHV fingers found in K9, K10, and K11 can recognize the same 3-bp DNA site: 5'-HGA-3'. Given their structural similarity, the K9, K10, and K11 ZFPs may bind to the same target site in vivo and regulate the same target genes. Within each of the two groups of related clones (i.e., K2, K3, and K4; and K9, K10, and K11), all the ZFPs include the same type of regulatory features. The K2, K3, and K4 clones each include the Ume6 repression domain. The K9, K10, and K11 clones each function without a dedicated transcriptional regulatory domain.

Synergistic or additive effects may result when two or more ZFPs are cotransformed into cells. For example, when the K4 and K5 ZFPs were co-expressed, yeast cells became completely resistant to ketoconazole. The combination produced an approximately 1,000-fold enhancement of the phenotype.

ZFP mutants were constructed that alter a DNA contacting residue or that remove or replace a regulatory domain. In one mutant (VSSR-DGAV-VSSR-VDYK-GAL4AD), the asparagine DNA contacting residue of the second zinc finger of K5 was mutated to alanine. Gel shift assays demonstrated that this mutated ZFP had at least 10-fold decrease in DNA-binding affinity for its expected DNA site. This mutant K5 protein does not confer drug resistance to yeast cells. In another mutant, the Gal4 activation domain of the K5 zinc finger protein was deleted by inserting a stop codon in front of the DNA sequence encoding the activation domain. This protein also does not confer resistance to ketoconazole. Similar results were obtained for the other ketoconazole resistance ZFPs.

When the activation domain fused to the K5 ZFP was replaced with the Ume6 repression domain, expression of the Ume6-form of the protein reversed the ketoconazole resistance phenotype. The cells that express the Ume6-form were more sensitive to ketoconazole relative to control cells. This result indicates that transcription factors can be selected by selecting for transcription factors that exacerbate a phenotype and then altering the attached regulatory domain (e.g., by switching the directionality of its function) to produce a transcription factor that has the desired phenotypic effect. Screening for opposite phenotype opposite to the desired phenotype can be more amenable than screening for the desired phenotype itself. Examples of replacements that switch functional directionality include replacing one type of regulatory domain with another type or regulatory domain and removing a regulatory domain. In the case of the K5 ZFP, a protein that increases drug sensitivity was obtained by screening for a protein that increased drug resistance and replacing its transcriptional activation domain with a transcriptional repression domain.

TABLE 6

| Ketoconazole conc. (uM) | control | | K5 | | YLL053C | |
|---|---|---|---|---|---|---|
| | average | stdev | average | stdev | average | stdev |
| 0 | 100 | 0 | 100 | 0 | 100 | 0 |
| 5 | 82.7 | 4.1569 | 89.9 | 15.544 | 84.167 | 16.003 |
| 10 | 0.031 | 0.0044 | 90.6 | 5.8207 | 28.433 | 7.0002 |
| 15 | 0.0123 | 0.0021 | 82.467 | 7.7106 | 15.7 | 11.95 |
| 20 | 0.001 | 0 | 50.367 | 4.7014 | 2.4 | 0.1 |
| 25 | | | 4.2 | 3.1193 | 0.0233 | 0.0058 |
| 30 | | | 0.0433 | 0.0058 | 0.0033 | 0.0006 |
| 35 | | | 0.0167 | 0.0058 | 0.0013 | 0.0006 |

DNA microarray analysis was used to identify genes associated with the drug resistance phenotype. We reasoned that different ZFPs conferring the identical phenotype may regulate identical gene sets whose differential expression is directly or indirectly associate with the phenotype. Three ZFPs—K5, K6, and K7—were chosen for expression profiling analyses. All three transcription factors contain the Gal4 activation domain. Out of 6,400 yeast open reading frames, ten were activated over 2 fold by at least two different ZFP transcription factors, and four open reading frames were activated by all three tested ZFP transcription factors. The four activated open reading frames are: YLL053C, YJR147W, YLL052C and YPL091 W.

Table 7 lists the number of genes that are regulated by more than one chimeric ZFP.

TABLE 7

Coordinately Regulated Genes

| K5 | K6 | K7 | Number of Commonly Regulated Genes |
|---|---|---|---|
| + | − | − | 39 |
| + | + | − | 1 |
| + | − | + | 2 |
| + | + | + | 4 |
| − | + | − | 95 |
| − | + | + | 3 |
| − | − | + | 126 |

PDR5, a gene known to pump out ketoconazole, was activated by two ZFPs, K6 and K7, but not by K5. This result suggests that K5 confers ketoconazole resistance by a PDR5-independent mechanism and that at least two different pathways can confer ketoconazole resistance in yeast. One pathway depends on activation of PDR, and the other is independent of PDR5.

To identify new genes associated with the drug resistant phenotype, we evaluated the drug resistance phenotype of cells overexpressing one of the four genes activated by all three tested ZFP transcription factors. We found that one of the genes—YLL053C—induced ketoconazole resistance when overexpressed on its own. See Table 6, above. YLL053C is homologous to plasma membrane and water channel proteins from *Candida albicans*. The amino acid sequence of YLL053C is as follows:

MWFPQIIAGMAAGGAASAMTPGKVLFTNALGLGC (SEQ ID NO: 232)

SRSRGLFLEMFGTAVLCLTVLMTAVEKRETNFMA

ALPIGISLFMAHMALTGYTGTGVNPARSLGAAVA

-continued
ARYFPHYHWIYWISPLLGAFLAWSVWQLLQILDY

TTYVNAEKAAGQKKED

The amino acid sequence of an exemplary homologous channel protein (AQY1) from *Candida albicans* is as follows:

MVAESSSIDNTPNDVEAQRPVYEPKYDDSVNVSP (SEQ ID NO: 233)

LKNHMIAFLGEFFGTFIFLWVAFVIAQIANQDPT

IPDKGSDPMQLIMISFGFGFGVMMGVFMFFRVSG

GNLNPAVTLTLVLAQAVPPIRGLFMMVAQMIAGM

AAAGAASAMTPGPIAFTNGLGGGASKARGVFLEA

FGTCILCLTVLMMAVEKSRATFMAPFVIGISLFL

GHLICVYYTGAGLNPARSFGPCVAARSFPVYHWI

YWVGPILGSVIAFAIWKIFKILKYETCNPGQDSD

A

The YLL053C gene product may confer resistance by pumping out ketoconazole as does the PDR5 gene product. These data demonstrate that genes associated with phenotypic changes can be identified by the analysis of gene expression profiles of cells. Gene identification is further assisted by the use of different chimeric ZFPs that cause the same phenotype (in this example, ketoconazole resistance).

EXAMPLE 4

Thermotolerant Transformants Screening

We screened libraries encoding chimeric zinc fingers for nucleic acids that encode proteins that confer thermotolerance to yeast cells.

$1 \times 10^7$ yeast cells containing nucleic acids from the 3-fingered libraries were cultivated on SD synthetic liquid medium with 2% galactose for 3 hrs at 30° C. and then incubated at 52° C. (air temperature) with slow gyration for 2 hrs. After heat treatment, the culture were plated on galactose media and incubated for 5 days at 30° C. Growing yeast colonies were suspended in galactose liquid media and incubated at 52° C. for 2 hrs to confirm the thermotolerant phenotype. Plasmids were isolated from these cells and retransformed into yeast as describe above. The retransformants were cultivated in galactose liquid media for 3 hrs at 30° C. and incubated at 52° C. for 2 hrs. The incubated retransformants were spotted in four dilution onto SD galactose agar plates. To verify that the thermotolerance is induced by the expression of zinc finger protein in the mutants, retransformants were cultivated in SD glucose liquid media with the same condition described above and then spotted onto SD glucose agar plates. The transformants with pYTC vector and plasmid encoding randomly-picked 3-fingered proteins were used as controls for the procedure.

Thermotolerant yeast cells were identified from the cells transformed with zinc finger protein expression plasmids. Wild-type cells carrying the pYTC-Lib plasmid or plasmid encoding a randomly-selected zinc finger protein were used as negative controls. A total of $10^7$ cells were grown in galactose liquid media. Galactose induces zinc finger protein expression. Cells were heat treated at 52° C. for 2 hrs and then plated on galactose minimal agar plates. After five days of incubation at 30° C., 26 colonies grew on the plates. We rescued plasmids from these colonies and retransformed them into YPH499a. We isolated nine clones that induced varying degrees of thermotolerance. Typically, expression of the zinc finger proteins from these clones caused up to 10% of the cells to survive heat treatment, when cultured in galactose media but not in glucose media. Only about 0.3% of cells transformed with control plasmid survived under the same conditions. Freshly-growing retransformed cells survive better under the experimental conditions than frozen cell stocks. These results demonstrate that the expression of particular zinc finger proteins can induce thermotolerance in yeast cells. ZFPs were characterized by DNA sequencing of the recovered library plasmids (Table 8).

TABLE 8

ZFPs encoded in plasmids isolated from thermotolerant transformants

| No. | Name of ZFD Motif (N to C) 1 | 2 | 3 | Functional domain | Potential target sequence |
|---|---|---|---|---|---|
| H1 | ISNR | QSNI | RDNQ | UME6 | 5'-AAG MAA GAH-3' |
| H2 | QNTQ | QNTQ | HSNK | UME6 | 5'-GAC ATA ATA-3' |
| H3 | QSHR5 | DSHR | DSKR | GAL4 | 5'-GGT GGC GRA-3' |
| H4 | RDKR | QSTR | QSHR5 | GAL4 | 5'-GRA GYA RGG-3' |
| H5 | RDHR1 | QSSR1 | QSHR5 | UME6 | 5'-GRA GYA GRG-3' |
| H6 | QAHR | RSHR | RSHR | UME6 | 5'-GGG GGG GGA-3' |
| H7 | DSNR | RDHT | QNTQ | — | 5'-ATA NGG GAC-3' |
| H8 | ISNR | RSNR | RSNR | — | 5'-GAG GAG GAH-3' |
| H9 | RDHT | QSNK | QSTR | — | 5'-GYA DAA NGG-3' |

EXAMPLE 5

Neurite Formation

We screened our nucleic acid libraries for nucleic acids encoding zinc finger proteins that induce neuritogenesis in the mouse neuroblastoma cell line Neuro2A, a cell line capable of differentiating into a neuronal cell type. We identified a novel chimeric ZFP that induces neuronal differentiation, as evidenced by alterations in cell morphology and the expression of neuronal marker genes.

Materials and Methods

Library Construction

See Example 1, above. As described, a three-finger and four-finger ZFP-Tf libraries were constructed using 40 and 25 zinc finger domains, respectively. The three-finger and four-finger libraries recognize approximately 9- and 12-bp DNA binding sites, respectively. ZFPs were expressed as fusion proteins to the p65 transcriptional activation domain and to the KRAB repression domain.

Cell Culture And Neuronal Differentiation of Neuro2A Cells

Mouse neuroblastoma Neuro2a cells were maintained in MEM-a media with 10% FBS and antibiotics at 37° C., in a humidified atmosphere containing 95% air and 5% $CO_2$. Cells were seeded at $8.0 \cdot 10^3$ cells per 96-well culture plate and then were transfected using LIPOFECTAMINE PLUS™ reagent (Invitrogen,CA) according to the manufacturer's protocol, with 50 ng of ZFP, together with 20 ng of LacZ reporter plasmid. In vitro differentiation was carried out with or without retinoic acid (RA) (10 µM) respectively, and G418 (1 mg/ml) was treated 24 hours after transfection to reduce the number of untransfected cells. Cells were then cultured for 96 hours and then fixed, stained for β-galactosidase activity, and photographed. Among β-galactosidase-positive cells, cells were regarded as differentiated if the length of neurite extension was at least two times the diameter of the cell body.

Result and Discussion

Screening ZFP-TFs inducing neuritogenesis

To screen for ZFP-TFs that can induce neuronal differentiation, Neuro2A cells were transiently transfected with library plasmids and a reporter plasmid that includes the LacZ gene. LacZ expression was used to visualize the morphology of transfected cells. Because the differentiating cells grow slower than non-differentiating cells and the latter will dominate the cell population, we treated the cell culture with G418 24 hr after transfection to reduce the number of untransfected cells. After five days, cells were fixed and LacZ-stained. We then characterized the cells by their morphological characteristics. In particular, we identified cells with increased neurite length and thickness.

We identified several ZFP-TFs that alter neuritogenesis. These ZFP-TFs affect neuritogenesis to varying degrees. The ZFP-TF, named Neuro1-p65, had the most prominent effect on differentiation, as measured by the length and thickness of neurites that it produced. A marked acceleration of neuritogenesis in the Neuro1-p65-transfected Neuro2A cell was also observed when cells were treated with 10 µM RA (retinoic acid).

The nucleic acid sequence encoding Neuro1-p65 and its amino acid sequence is shown in FIG. 14. The Neuro1-p65 nucleic acid encodes a chimeric ZFP that includes the zinc finger domains QSNR1-QSNK-CSNR1. Other ZFPs with the same motifs and/or ZFPs that binding to a site that at least partially overlaps the Neuro1-p65 binding site are also expected to modulate differentiation. Based on the zinc finger-DNA binding site directory (see Table 6), the predicted binding site for Neuro1 is 5'-GACGAAGAA-3'.

Figure 8:
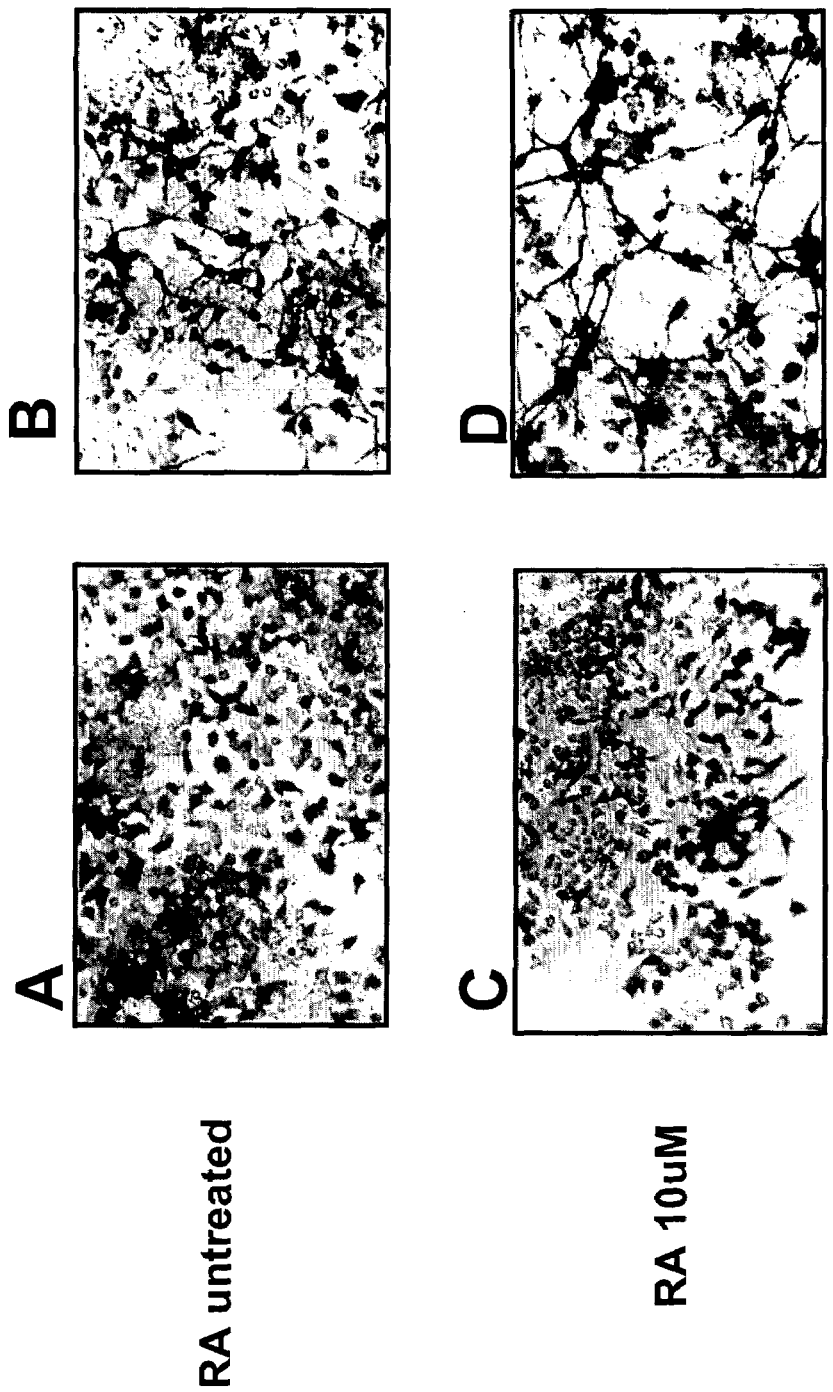
FIG. 8 is a photograph of control and ZFP-expressing cells in which neurite formation is induced.

Neuro1-p65 requires the p65 activation domain to induce neurite formation. The same zinc finger domains fused to the KRAB transcriptional repression domain or without any effector domain do not drive neuritogenesis. See FIG. 8 and Table 9. Also the DNA binding ability of Neuro1-p65 is critical, since mutations that are predicted to disable its DNA binding ability of the zinc finger domains of Neuro 1-p65 (Neuro1-p65mut) abolished its ability to support neuritogenesis.

Real-time PCR is used to characterize the expression level of neuronal marker genes during the course of Neuro1-p65 expression in cells. Similarly, nucleic acid microarrays are used to compare the pattern of gene expression between RA-treated cells and ZFP-TF treated cells at various time points during differentiation. Neuro1-p65 may activate a pathway that is required for neuroblastoma cell differentiation at least in vitro.

TABLE 9

Percentage of neurite bearing cells

| Construct | No RA | RA 10 uM |
|---|---|---|
| pCDNA3 (vector) | 5.77 ± 1.99 | 14.93 ± 7.69 |
| 08_D1-p65 | 42.39 ± 5.56 | 41.59 ± 6.46 |
| 08_D1mut-p65 | 5.25 ± 0.71 | NA |

TABLE 9-continued

Percentage of neurite bearing cells

| Construct | No RA | RA 10 uM |
|---|---|---|
| 08_D1 alone | 5.85 ± 4.44 | NA |
| 08_D1-KRAB | 4.46 ± 0.57 | NA |

EXAMPLE 6

Osteogenesis

The C2C12 cell line is derived from the myoblast lineage, but can differentiate into osteoblasts upon the addition of bone morphogenic protein-2 (BMP-2) (Katagiri, T. et al., (1994) *J. Cell. Biol.* 127, 1755). Several naturally-occurring transcription factors have been identified as candidates for controlling this process (Lee, K.-S. et al., (2000) *Mol. Cell. Biol.* 20:8783; Nakashima, K. et al., (2002) *Cell* 108:17).

We screened for chimeric zinc finger proteins that induce transdifferentiation of C2C12 myoblasts to osteoblasts in the absence of BMP-2. We transiently transfected a nucleic acid library encoding chimeric zinc finger proteins into C2C12 cells and screened for cells that undergo transdifferentiation in the absence of BMP-2. Seven days after transfection, the transformed cells were stained for alkaline phosphatase (ALP), a marker for osteoblasts (Katagiri, T. et al., (1994) *J. Cell. Biol.* 127:1755).

From a screen of about 2,000 ZFP-TFs, we identified one activator, Osteo1-p65, that induced strong ALP staining in about 30% of cells. The percentage of cells stained with ALP was similar to the percentage of transfected cells detected by LacZ staining. From these results, we conclude that the Osteo 1-p65 transcription factor can trigger the transdifferentiation of C2C12 myoblasts to osteoblasts in the absence of BMP-2.

As a positive control, cells were treated with 1 µg/ml of BMP-2. Nearly 100% of the positive control cells strongly stained for ALP upon BMP-2 treatment. Without BMP-2 treatment, negative control cells that were transfected with a control vector had only background staining. Osteo1-p65 is a four-finger protein composed of the RDKR-QTHR1-VSTR-RDKR zinc finger domains (from N- to C-terminus). See FIG. 15. This protein is predicted to recognize the DNA element 5'-GGGGCWRGAGGG-3' (SEQ ID NO:234).

For these experiments, the mouse myoblast cell line, C2C12, was maintained in Dulbecco's Modified Eagle's Medium (DMEM) with 4.5 g/L glucose, 10% FBS, and antibiotics, at 37° C., in a humidified atmosphere containing 95% air and 5% $CO_2$. Cells were seeded at $1.0 \cdot 10^4$ cells per 96-well culture plates. The cells were transfected with 50 ng of library nucleic acid using LIPOFECTAMINE PLUS™ (Invitrogen) according to the manufacturer's protocol. Twenty-four hours after transfection, the growth medium was replaced with DMEM containing 2% FBS, and the cells were cultured for an additional six days.

To examine the differentiation of C2C12 cells to osteoblasts, ALP staining was performed as described in Katagiri, T. et al., (1994) *J. Cell. Biol.* 127:1755.

In summary (referring to Examples 5 and 6), we have screened artificial transcription factor libraries for proteins that can induce two different cell differentiation processes, neurogenesis and oosteogenesis. Again, the method does not require prior knowledge of the biology of particular stem cells.

EXAMPLE 7

Insulin Regulation

Figure 4:
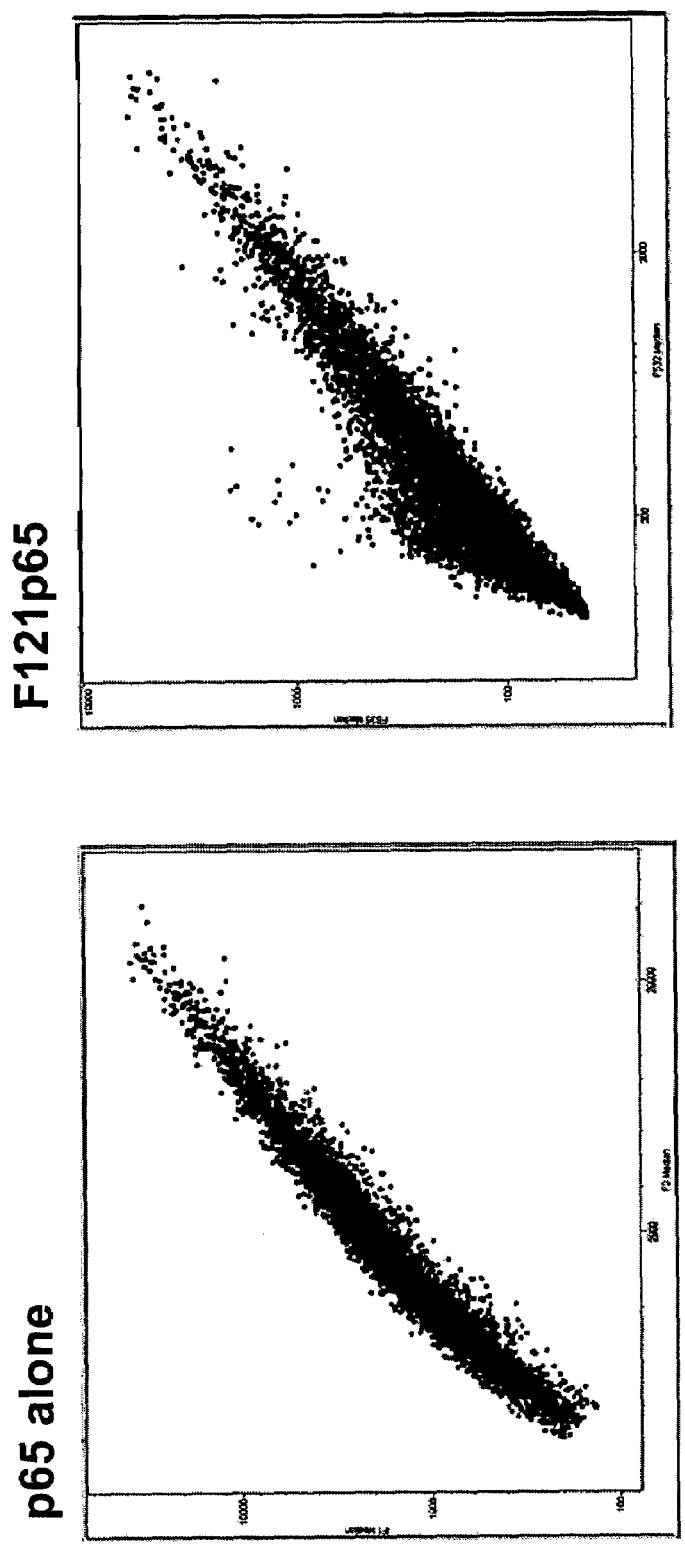
FIG. 4 depicts an expression profile of transiently transfected ZFPs. In the left panel, a cell expressing p65 activation domain alone is compared to a control. In the right panel, a cell expressing the zinc finger protein F121_p65 is compared to a control. Each dot displaced from the diagonal represents a gene whose expression is substantially altered.
Figure 5:
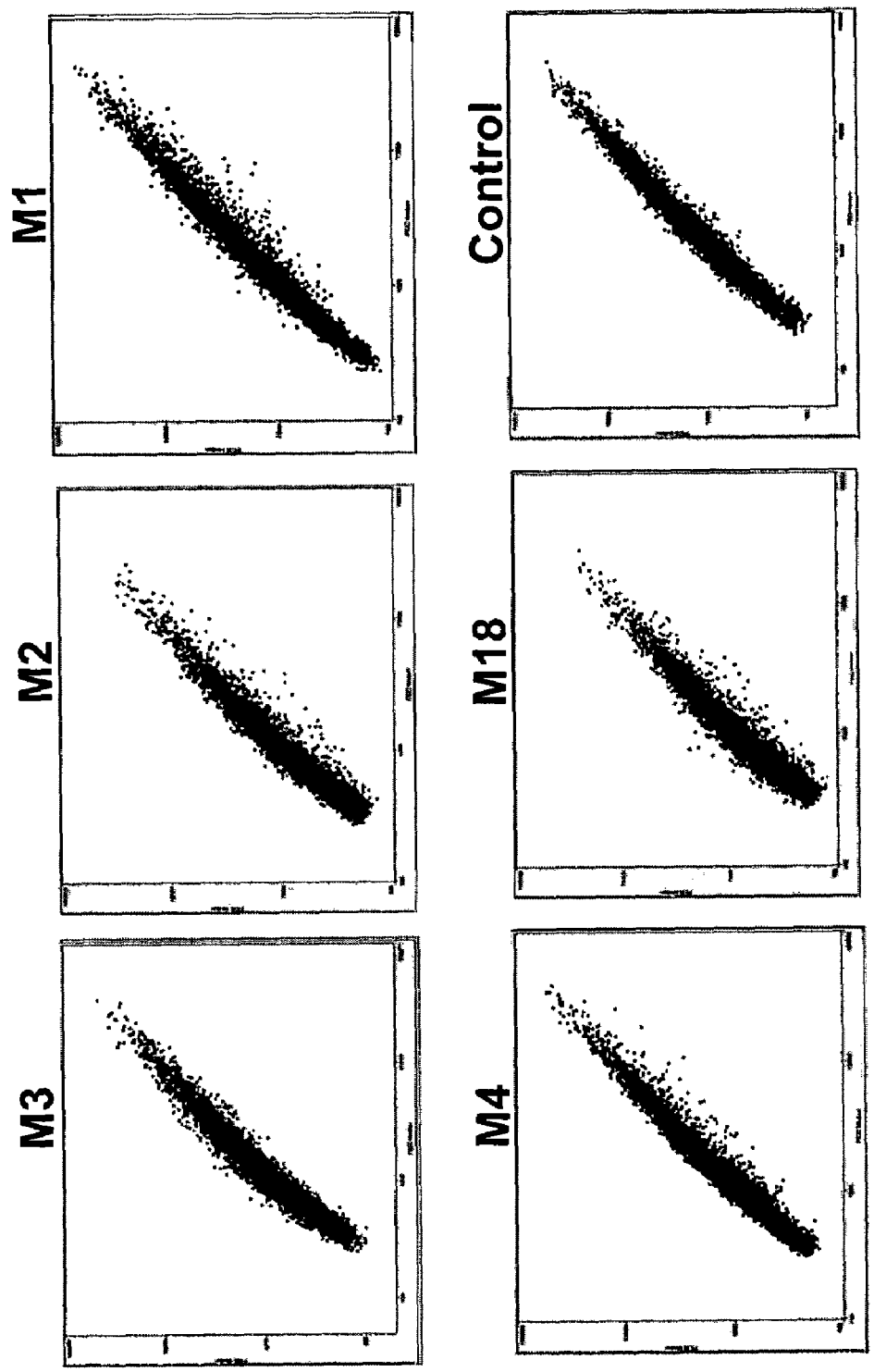
FIG. 5 depicts expression profiles of stably transfected ZFPs.
Figure 6:
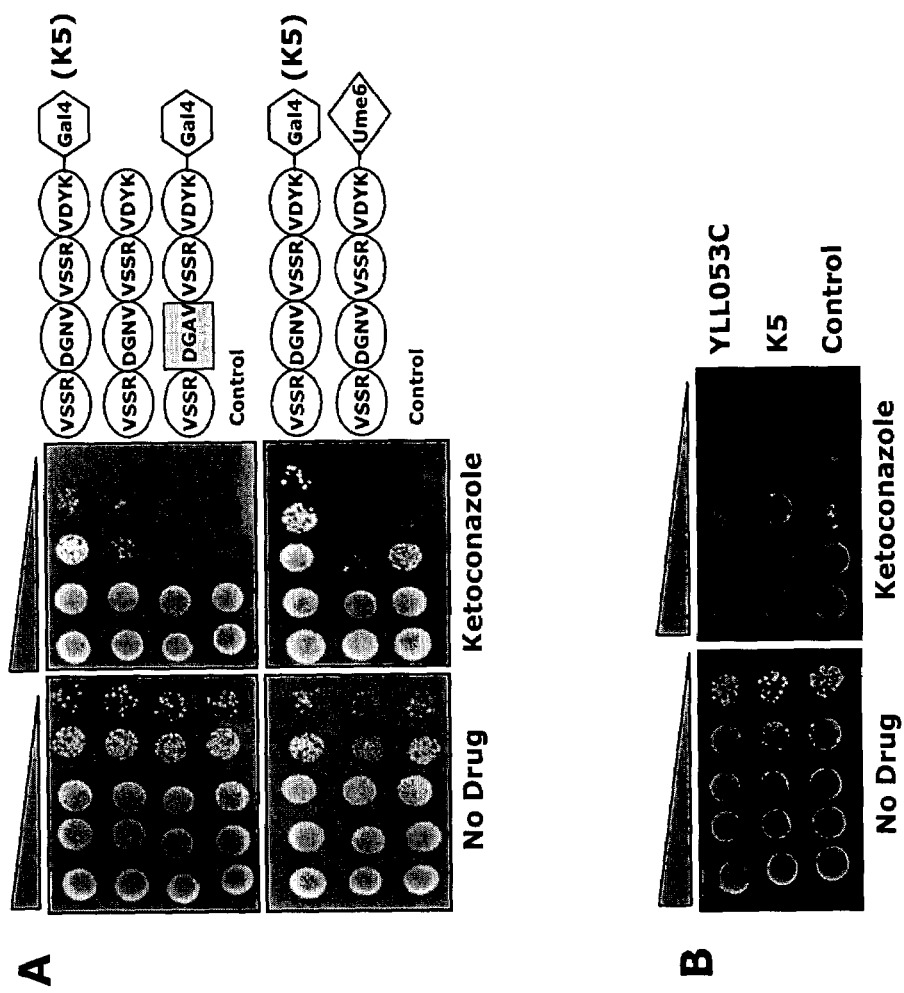
FIG. 6A depicts the effects of DNA-binding domain mutants and effector domain alterations to the K5 ZFP on drug resistance.
FIG. 6B depicts the effects of K5 and YLL053C overexpression.
Figure 9:
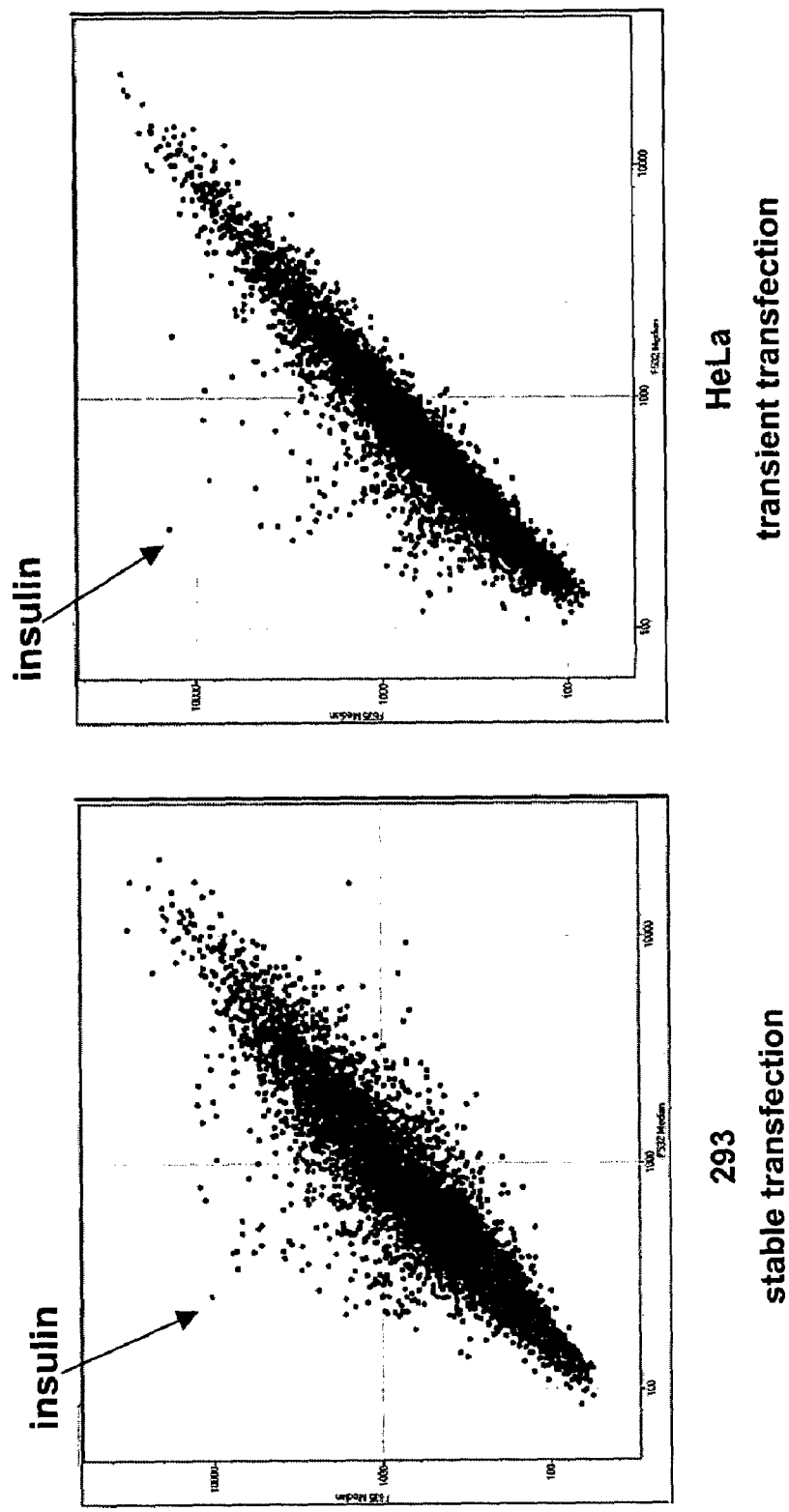
FIG. 9 depicts comparative microarray data for cells in which the insulin gene is over-expressed. The chimeric ZFP is 08_D04-p65. The sequence of which is listed in FIG. 16.

We stably transfected nucleic acids encoding chimeric zinc finger proteins in human 293 cell lines, and analyzed transformed cells using DNA microarray experiments to characterize genes regulated by each chimeric zinc finger protein (see FIGS. 4, 5, and 9). We have identified a chimeric zinc finger protein (08_D04-p65) that increases the expression of human insulin gene more than 60 fold.

To test whether 08_D04-p65 can induce insulin gene expression in different human cell lines, we transiently transfected a nucleic acid encoding 08_D04-p65 into HeLa cells. Expression of the nucleic acid in HeLa cells caused a 80 fold increase in expression of the insulin gene.

Accordingly, 08_D04-p65, its derivatives, and similarly functional zinc finger proteins can be used as therapeutics for diabetes. DNA encoding 08-D04-p65 or a similarly functional zinc finger protein can be delivered into diabetic patients by viral delivery or in encapsulated form (e.g., a liposome). Once DNA is delivered into cells, the zinc finger protein can be expressed to induce the production of insulin. In some implementations, the nucleic acid encoding the zinc finger protein can be operably linked to an inducible promoter, e.g., a Tet-inducible promoter. The use of doxycycline as an inducer enables the level of insulin production to be regulated by a small chemical. Because insulin-inducing zinc finger proteins, such as 08-D04-p65, can function in different human cell lines, it may work in both pancreatic cells (e.g., beta cells and non-beta cells) and non-pancreatic cells.

It is also possible to identify an artificial transcription factor that induces expression of insulin processing enzymes. Cells can be engineered to express such a transcription factor and a transcription factor that induces the insulin gene, e.g., 08_D04-p65. In addition, insulin-inducing zinc finger proteins can be also used for ex vivo cell therapy. In one example, cells from a patient are modified in vitro by the introduction of a nucleic acid encoding an insulin-inducing zinc finger protein. The modified cells are then transplanted back into patients or into another subject.

Materials and Methods

DNA Microarray Analysis of Cell Lines Expressing ZFP-TFs

Nucleic acids encoding zinc finger proteins were stably introduced into FlpTRex-293 cell lines (Invitrogen) essentially as described in the manufacturer's protocols. Briefly, the HindIII-XhoI fragment from the pLFD-p65 or pLFD-Kid vectors was subcloned into pcDNA5/FRT/TO (Invitrogen Calif.). This fragment includes a sequence encoding the zinc finger proteins. Resulting plasmids were cotransfected into FlpTRex-293 cells with pOG44 (Invitrogen). Stable integrants that express ZFP-TFs upon doxycycline induction were obtained.

DNA microarrays containing 7458 human EST clones were obtained from Genomictree (Korea). FlpTRex-293 cells stably expressing ZFP-TFs were grown with (+Dox) or without Dox) 1 µg/ml Doxycycline for 48 hours. Total RNA was prepared from each sample. RNA from the −Dox sample was used as a reference (Cy3), and +Dox as the experimental sample (Cy5). Microarray analysis was performed according to the manufacturer's protocols. Spots with sum of median less than 500 were colored red and not analyzed.

Nucleic acids encoding certain zinc finger proteins were also expressed in HeLa cells. pLFD-p65 containing 08-D04 ZFP was transiently transfected into HeLa cells using LIPOFECTAMINE™ 2000 (Invitrogen). The pLFD-p65 vector, which does not encode a zinc finger protein, was also transfected into cells in parallel as a control.

EXAMPLE 8

We screened libraries encoding chimeric zinc fingers to identify nucleic acids that encode proteins that alter reporter gene expression in a mammalian cell.

Construction of Libraries

Two ZFP libraries were constructed as four finger proteins and three finger proteins in P3, a modified pcDNA3 vector. Construction of these libraries is described above.

Transfection of ZFP Plasmids

Human embryonic kidney 293 cells were cultured with 100 µl of DMEM with 10% of FBS in a humidified atmosphere containing 95% air and 5% $CO_2$ and seeded in wells of a 96 well plates 1 day ahead of transfection. The plasmids were isolated from individual colonies of each library separately and transfected into 293 cells LIPOFECTAMINE PLUS™ (Invitrogen) as recommended by the manufacturer. For MTT assay, 50 ng of plasmids containing zinc finger protein gene fused to the functional domains were transfected into cells cultured at $5 \cdot 10^3$ cells/well. For the SEAP assay, 10 ng of pSEAP2-control (Clontech) plasmid was co-transfected with 50 ng of plasmids containing zinc finger protein gene fused to the functional domains into cells cultured at $1 \cdot 10^4$ cells/well. The transfected cells were incubated at 37° C. for three days before assays.

SEAP Assay

Three days after transfection, medium was transferred to the new tubes and heated for 30 minutes at 65° C. to inactivate the endogenous alkaline phosphatase. 25 µl of medium was mixed with the same volume of 2×SEAP assay buffer (2 M Diethanolamine (pH 9.8) 10 ml, 1 M $MgCl_2$ 10 µl, 1 M homoarginine 200 µl, pNitro phenyl phosphate 44.52 mg). Absorbance at 405 nm was measured after the indicated incubation times at 37° C.

Luciferase Assay

For the luciferase assay, 5 ng of both CMV-luciferase and pRL-SV40 plasmid were co-transfected with 50 ng of ZFP coding plasmids to 293 cells seeded in wells of a 96 well plate. After 3 days of incubation, cells were harvested and the luciferase assay was done by a Dual Luciferase reporter assay system (Promega) as recommended by the manufacturer.

MTT assay

MTT assay is used to measure cell growth. Tetrazolium MTT reduced by metabolically active cells changes to a yellow color. Measurement of light absorbance by the yellow color indicates the number of viable cells. MTT assay was done using a MTT assay kit (Trevigen). The MTT assay was done at three days after transfection. Briefly, 10 µl of MTT solution was added directly to the culture medium and incubated for two hours in a $CO_2$ incubator. Then, 100 µl of detergent solution from the MTT assay kit was added and incubated in the dark for two hours before measurement of absorbance at 570 nm was measured using a Power-Wave 340× (Bio-Tek Instrument).

To count cell numbers, 293 cells were seeded at $1.5 \cdot 10^4$ cells/well in a 24 well plate one day before transfection. Three days after transfection with 200 ng of ZFP-coding nucleic acid or control vector plasmids, cells were washed with PBS once and suspended in 30 ul of TE (10 mM Tris 1 mM EDTA, pH 8.0) buffer and counted by hematocytometery.

Results

Change of Protein Productivity

We tested whether library nucleic acids could alter expression of a heterologous nucleic acid. SEAP (secretory alkaline phosphatase) was used as a reporter protein to test whether a ZFP can affect amount of foreign protein produced intracellularly. Table 10 shows representative results obtained from 81 wells, each well containing cells transfected with a nucleic acid encoding a random chimeric ZFP from the library and three wells containing reference cells transfected with a control vector. Several wells exhibited increased absorbance relative to other wells that contain cells transfected with nucleic acid encoding other random ZFPs and relative to the wells that contain cells transfected with a control vector.

TABLE 10

Reporter activity in the presence of 81 random ZFPs.

| ZFP | Absorbance (405 nm) |
|---|---|
| A01 | 0.29 |
| A02 | 0.14 |
| A03 | 0.14 |
| A04 | 0.13 |
| A05 | 0.19 |
| A06 | 0.13 |
| A07 | 0.12 |
| A08 | 0.13 |
| A09 | 0.11 |
| A10 | 0.15 |
| A11 | 0.15 |
| A12 | 0.12 |
| B01 | 0.15 |
| B02 | 0.78 |
| B03 | 0.15 |
| B04 | 0.19 |
| B05 | 0.13 |
| B06 | 0.15 |
| B07 | 0.14 |
| B08 | 2.40 |
| B09 | 0.11 |
| B10 | 0.12 |
| B11 | 0.13 |
| B12 | 0.11 |
| C01 | 0.20 |
| C02 | 0.14 |
| C03 | 0.31 |
| C04 | 0.13 |
| C05 | 0.13 |
| C06 | 0.13 |
| C07 | 0.12 |
| C08 | 0.16 |
| C09 | 0.18 |
| C10 | 0.17 |
| C11 | 0.18 |
| C12 | 0.15 |
| D01 | 0.17 |
| D02 | 0.15 |
| D03 | 0.14 |
| D04 | 0.14 |
| D05 | 0.12 |
| D06 | 0.13 |
| D07 | 0.21 |
| D08 | 0.12 |
| D09 | 0.14 |
| D10 | 0.15 |
| D11 | 0.20 |
| D12 | 0.12 |
| E01 | 0.16 |
| E02 | 0.13 |
| E03 | 0.12 |
| E04 | 0.41 |

TABLE 10-continued

Reporter activity in the presence of 81 random ZFPs.

| ZFP | Absorbance (405 nm) |
|---|---|
| E05 | 0.12 |
| E06 | 0.15 |
| E07 | 0.12 |
| E08 | 0.12 |
| E09 | 0.13 |
| E10 | 0.34 |
| E11 | 0.22 |
| E12 | 0.11 |
| F01 | 0.15 |
| F02 | 0.13 |
| F03 | 0.13 |
| F04 | 0.12 |
| F05 | 0.13 |
| F06 | 0.12 |
| F07 | 0.12 |
| F08 | 0.14 |
| F09 | 0.19 |
| F10 | 0.12 |
| F11 | 0.20 |
| F12 | 0.12 |
| G01 | 0.15 |
| G02 | 0.16 |
| G03 | 0.14 |
| G04 | 0.49 |
| G05 | 0.26 |
| G06 | 0.15 |
| G07 | 0.22 |
| G08 | 0.65 |
| G09 | 0.18 |
| vector | 0.37 |
| vector | 0.39 |
| vector | 0.34 |

The P_B08, a zinc finger protein fused to the p65 domain showing the highest SEAP activity. This ZFP was retested by transfection with the SEAP plasmid in three separate transfections. Table 11 illustrates one such retesting. The P value for P_B08 in this assay is 0.008. P_B08 exhibited approximately 16-fold increase of SEAP activity compared to that of the parental plasmid.

TABLE 11

SV40-SEAP reporter in 293 cells.

| Expression Plasmid | average | st. dev. |
|---|---|---|
| P_B08 | 16.51 | 0.54 |
| Vector (HANLS) | 1 | 0.17 |

Since the SEAP assay was used to assay the production of foreign proteins, reasons for the observed increased SEAP activity could be various, for example, the direct or indirect activation of a SV40 promoter used for the SEAP gene expression in pSEAP2-Control plasmid. Other reasons include: increased activity of proteins functioning in secretion pathway or activation of the general machinery for the protein production. The mechanism of enhanced activity of SEAP can be elucidated by determining the effect of P_B08 on the production of other proteins, e.g., using other reporter proteins (e.g., unsecreted reporters) and reporters linked to other promoters.

To investigate this point, an extensive screening had been carried out using the SEAP reporter under the control of CMV promoter (CMV-SEAP) in 293F cells. Two ZFPs, K44_11_D01 and K44_11_G12, that increase activity of the SEAP protein were isolated. These two ZFPs were further tested using two other reporter plasmids, SV40-SEAP and the luciferase reporter under the control of CMV promoter (CMV-Luc). Table 12 lists some of the results. K44__11_D01 and K44__11_G12 exhibited approximately 3-fold increase of SEAP activity compared to that of the parental plasmid (vector). K44__11_D01 showed activation of SV40-SEAP but not the CMV-Luciferase, suggesting that the activation may be related to mechanisms specific to SEAP such as secretion. In contrast, K44__11_G12 showed approximately 2-3 fold activation for both CMV-luciferase and SV40-SEAP, suggesting that the mechanism is specific to neither promoter nor reporter. Thus, K44__11_G12 may be used increase the production of proteins generally in cells, e.g., eukaryotic cells.

TABLE 12

CMV-SEAP, CMV-Luc and SV40-SEAP reporter in 293F cells.

| Expression plasmid | average | | | st.dev. | | |
|---|---|---|---|---|---|---|
| | CMV-SEAP | CMV-Luc | SV40-SEAP | CMV-SEAP | CMV-Luc | SV40-SEAP |
| K44__11_D01 | 3.49 | 0.87 | 3.66 | 0.46 | 0.26 | 0.28 |
| K44__11_G12 | 2.82 | 2.75 | 2.14 | 0.50 | 0.38 | 0.15 |
| Vector (HANLS) | 1 | 1 | 1 | 0.22 | 0.19 | 0.17 |

Zinc finger proteins K44-16-E12 (FIG. 25) and K12_A111 (FIG. 24) may also alter protein production, e.g., as indicated by CMV-SEAP and SMV-Luc expression.

As an analogous example, the overexpression of cyclin D1 has been reported to cause to increase production of some proteins (U.S. Pat. No. 6,210,924 B1). A zinc finger protein that can directly or indirectly activate the cyclin D1 expression may up-regulate protein production, although the effects of a zinc finger protein may be different, far more broad ranging, or more potent. Other zinc finger proteins resulting in a physiological effect similar to cyclin D1 overexpression can be isolated by this assay. Such zinc finger proteins can be used to enhance production of the protein of interest.

Change of Cellular Growth Rate

Two ZFPs fused to the kid domain, K_D10 and K-F02, were selected as representatives of the ZFPs regulating cell growth since they exhibited the maximum variations compared to the controls based on the MTT assay results. To confirm the MTT assay, the cell numbers were counted after transfection of K_D10 and K_F02 in 293 cells. The result was compared to the cell number of the well transfected with the parental vector, converted to relative percentages and shown in Table 13. Compared to the parental vector, K_D10 exhibited approximately 3-fold inhibition and K_F02 showed 2.7-fold activation of cell growth compared to the control. The P values for K_D10 and K_F02 are 0.001 and 0.01, respectively. For sequence information, see FIGS. 18 and 19.

TABLE 13

MTT assay results for two ZFPs.

| | relative cell number | |
|---|---|---|
| | average | st. dev. |
| K_F02 | 279.3 | 6.9 |
| K_D10 | 27.4 | 4.3 |
| vector | 99.99 | 3.4 |

Change of Cellular Growth Rate

We have identified zinc finger proteins that can alter the rate of cell growth and proliferation. These important phenotypes are linked to diseases such as cancer and viral infection and to developmental processes. The ability to use zinc finger protein to control cell growth and proliferation can include, for example, controlling apoptosis, cell differentiation, host cell defenses (e.g., against viral infection), and p53-mediated signaling A zinc finger protein that produces one or more of these phenotypes may directly or indirectly regulate a gene that regulates cell growth or signaling. The specific zinc finger proteins describe here produce detectable effects to cellular growth as detected by the MTT assay. For example, two zinc finger proteins showed at least a two-fold difference of cell growth compared to the controls. Considering that this assay was based on observations of transiently transfected cells three days after transfection, the two-fold difference is significant. In addition, the change in the cell number confirms that that the difference detected using the MTT assay is not particular to the assay.

Since cell growth is such an important parameter of cell physiology, this experiment can be extended to a large screening to isolate sufficient numbers of zinc finger proteins regulating cellular growth. The cDNA microarrays can be used profile the gene expression patterns of cells that expressing each of these zinc finger proteins. The profiles can identify novel genes and pathways that participate in cell proliferation or apoptosis.

These experiments indicate that the zinc finger proteins are able to induce various phenotypes in mammalian cells, e.g., in this case altering cell proliferation.

EXAMPLE 9

Solvent Tolerant Bacterial Cells

We screened for bacterial cells that express artificial chimeric zinc finger proteins for cells that were resistant to an organic solvent as a result of the artificial chimeric zinc finger protein. Three different zinc finger proteins were identified for their ability to confer hexane tolerance to E. coli cells (Table 17). Hexane tolerance was evaluated by comparing the survival rate of transformants expressing one of the zinc finger proteins—HT-1, HT-2, and HT-3—to the survival rate control cells. The control cells either included an empty vector (C1) or ZFP-1. The ZFP-1 construct encodes a zinc finger protein that does not confer hexane resistance and that includes the fingers RDER-QSSR-DSKR. Bacterial cells that express hexane resistance-conferring zinc finger proteins exhibited as much as a 200-fold increase in hexane tolerance.

TABLE 17

Hexane Resistant Zinc Finger Proteins.

| Expression Construct | Name | Survival Rate |
|---|---|---|
| Control | C1 | 0.14% |
| Control | ZFP-1 | 0.05% |
| Hexane resistance ZFP | HT-1 | 21.4% |
| Hexane resistance ZFP | HT-2 | 1.85% |
| Hexane resistance ZFP | HT-3 | 28.6 |

The expression plasmids for these zinc finger proteins include an IPTG-inducible promoter. Transformants that express each of the hexane resistance inducing ZFPs were characterized in the presence and absence of IPTG. Transformants expressing HT-2 showed higher hexane tolerance in the presence of IPTG, whereas HT-1 or HT-3 expressing cells were hexane tolerant even in the absence of IPTG.

TABLE 14

Zinc finger proteins that confer hexane tolerance in E. coli

| Name | F1 | F2 | F3 | F4 | putative DNA target | No. of occurrences (##) |
|------|------|------|-------|------|---------------------|-------------------------|
| HT-1 | RSHR | HSSR | ISNR |      | GAH GTT GGG         | 5 |
| HT-2 | ISNR | RDHT | QTHR1 | VSTR | GCT GRA NGG GAH (SEQ ID NO: 235) | 3 |
| HT-3 | QNTQ | CSNR | ISNR |      | GAH GAV ATA         | 1 |

(##) Occurrence of the ZFP in nine colonies that could grow after third round of hexane tolerant screening Construction of a nucleic acid library that encodes ZFPs for E.coli expression. To express zinc finger proteins conditionally in E. coli, we subcloned the zinc finger proteins cloned in pYTC-Lib yeast vector into a pZL1. pZL1 was constructed by the modification of pBT-LGF2 (Clontech, Palo Alto, Calif.). Plac-UV5 was amplified from pBT-LGF2 by PCR (forward primer: 5'-GACA ACC GGT CAT CGA TAA GCT AAT TCT CAC-3' (SEQ ID NO:236); reverse primer: 5'-TTG TCC ATG GAC GCT GTT TCC TG GTG AAA-3' (SEQ ID NO:237)). The PCR product was cloned into the pYTC Lib vector between AgeI and NcoI site. The vector was named as pYTC-lac. pYTC-lac was digested with ClaI and NotI to subclone the DNA fragment containing the following elements: Plac promoter-V5 epitope-MCS. The digested DNA fragment was purified after gel-electrophoresis and subcloned into the ClaI and NotI sites of pBT-LGF2. The resulting vector was named as pZL1. The 3F- or 4F-ZFP library constructed in pYTC-Lib was digested with EcoRI and NotI. The digested DNA fragments were gel-purified and subcloned into EcoRI and NotI site of pZL1, thus providing a library for E. coli expression.

Screening for Solvent Tolerance. The E. coli strain DH5α was transformed with the 3-finger or 4-finger ZFP nucleic acid library formatted for prokaryotic expression. Transformants were cultured overnight in LB with chloramphenicol (34 µg/ml). The overnight-culture was diluted to 1:500 in 1 ml fresh LB media with 1 mM IPTG and chloramphenicol to induce ZFP expression. After a three hour incubation at 30° C., hexane was added to 1.5% and rapidly vortexed to make emulsion of hexane and E. coli culture. The mixture was incubated for three hours with shaking (250 rpm) at 37° C. and plated on LB plates with chloramphenicol µg/ml (34 µg/ml). Plasmids were purified from the pool of growing colonies and transformed into DH5α. The transformants were treated with hexane as described above. Selection for hexane tolerance was repeated two additional times. Plasmids were recovered from 20 individual colonies that could grow on LB plates with chloramphenicol (34 µg/ml) after the third round of selection. These plasmids were retransformed into DH5α. Each transformant was retested for hexane-tolerance as described above. Plasmids that induce hexane tolerance were sequenced to characterize the encoded zinc finger protein.

EXAMPLE 10

Thermo-Tolerant Bacterial Cells

We screened for zinc finger proteins that conferred heat resistance to cells. The nucleic acid library encoding different zinc finger proteins was transformed into E. coli cells. The cells were exposed to heat, and heat-resistant cells were recovered. Plasmids were purified from ~23 individual colonies that were selected after the third round of phenotypic screening. Ten different zinc finger proteins were identified (Table 15) and the improvement of thermo-tolerance was analyzed by comparing survival rate of ZFP transformants and control cells, C1 or ZFP-2 upon heat treatment. C1 or ZFP-2 represent the transformants of empty vector or a control ZFP that has no effect on thermotolerance (QTHQ-RSHR-QTHR1), respectively. More than 99.99% of wild type cells died upon heat treatment at 50° C. for 2 hours. In contrast, about 6% of cells transformed with certain ZFP-TFs survived under these extreme conditions, a 700 fold increase in the thermotolerance phenotype—that is, the percentage of cells expressing ZFP-TFs that survive under stress conditions (6.3%) divided by the percentage of C1 that survived under the same conditions (0.0085%). Since the expression of ZFP is induced by IPTG, transformants of ZFPs that induce thermo-tolerance were analyzed for their phenotype in the presence or absence of IPTG. Transformants of T-1 or T-10 showed higher thermo-tolerance in the presence of IPTG.

TABLE 15

ZFPs that confer thermotolerance.

| Name | F1 | F2 | F3 | F4 | putative DNA target | occurrences |
|------|------|------|-------|-------|---------------------|-------------|
| T-1  | QSHV | VSNV | QSNK  | QSNK  | 5' DAA DAA AAT HGA 3' (SEQ ID NO: 238) | 6 |
| T-2  | RDHT | QSHV | QTHR1 | QSSR1 | 5' GYA GRA HGA NGG K 3' (SEQ ID NO: 239) | 3 |

TABLE 15-continued

ZFPs that confer thermotolerance.

| Name | F1 | F2 | F3 | F4 | putative DNA target | occurrences |
|---|---|---|---|---|---|---|
| T-3 | WSNR | QSHV | VSNV | QSHV | 5' HGA AAT HGA GGT 3'<br>(SEQ ID NO: 240) | 1 |
| T-4 | QTHR1 | RSHR | QTHR1 | QTHR1 | 5' GRA GRA GGG GRA 3'<br>(SEQ ID NO: 241) | 1 |
| T-5 | DSAR | RDHT | QSHV | QTHR1 | 5' GRA HGA NGG GTC 3'<br>(SEQ ID NO: 242) | 2 |
| T-6 | QTHQ | RSHR | QTHR1 | QTHR1 | 5' GRA GRA GGG HGA 3'<br>(SEQ ID NO: 243) | 1 |
| T-7 | QSHV | VSNV | QSNR1 | CSNR1 | 5' GAV GAA AAT HGA 3'<br>(SEQ ID NO: 244) | 3 |
| T-8 | VSNV | QTHR1 | QSSR1 | RDHT | 5' NGG GYA GRA AAT 3'<br>(SEQ ID NO: 245) | 2 |
| T-9 | RDHT | QSHV | QTHR1 | QSNR1 | 5' GAA GRA HGA NGG K 3'<br>(SEQ ID NO: 246) | 2 |
| T-10 | DSAR | RDHT | QSNK | QTHR1 | 5' GRA DAA NGG GTC 3'<br>(SEQ ID NO: 247) | 2 |

Screening for thermotolerance. Libraries for prokaryotic expression were prepared as described in Example 9. *E. coli* strain DH5αa was transformed with 3-finger or 4-finger ZFP library and cultured overnight in LB with chloramphenicol (34 µg/ml). The overnight-culture was diluted to 1:500 in 1 ml fresh LB media with 1 µM IPTG and chloramphenicol (341 g/ml) to induce ZFP expression. After a 3 hour incubation at 30° C., 100 ul culture was transferred to micro-centrifuge tube and incubated in water bath at 50° C. for 2 hrs. The culture was plated on LB plate with chloramphenicol (34 µg/ml). Plasmids were purified from the pool of growing colonies and transformed into DH5α. Selection for thermotolerance was repeated with retransformants. Plasmid was purified from 30 individual colonies that could grow on LB+chloramphenicol plate (34 µg/ml) after third round of selection and retransformed into DH5α. Each transformant was analyzed for thermo-tolerance as described above. Plasmids that could induce thermo-tolerance were sequenced to identify ZFP.

EXAMPLE 11

Genes Regulated By ZFP F121_p65

The zinc finger protein F121_p65 was expressed in human embryonic kidney 293 cells. Transcripts from the cells were profiled and compared transcripts profiled from a corresponding control cell that does not express F121_p65. Examples of transcripts up-regulated by F121_p65 are listed in Table 16. F121_p65 increases transcription of insulin-like growth factor 2, among other genes.

TABLE 16

Genes up-regulated by F121_p65

| Name | ID | Norm ratio of medians (ROM) |
|---|---|---|
| insulin-like growth factor 2 | H59614 | 17.71 |
| insulin-like growth factor 2 | H59614 | 16.88 |
| protein tyrosine phosphatase, receptor | R45941 | 16.45 |
| insulin-like growth factor 2 | N54596 | 14.40 |
| putative gene product | H09111 | 12.35 |
| jun B proto-oncogene | N94468 | 11.61 |
| cellular retinoic acid-binding protein 2 | AA598508 | 10.30 |
| protein phosphatase 2, regulatory subunit | R59165 | 9.89 |
| nuclear factor of activated T-cells | AA679278 | 9.64 |
| FK506-binding protein 8 (38 kD) | N95418 | 8.66 |
| protein phosphatase 2, regulatory subunit | R59165 | 8.60 |
| cadherin 13, H-cadherin (heart) | R41787 | 7.34 |
| cysteine-rich protein 2 | AA485427 | 6.71 |
| zinc finger protein homologous to Zfp-36 | R38383 | 6.46 |
| tumor necrosis factor (ligand) superfamily | AI347622 | 6.15 |
| cadherin 13, H-cadherin (heart) | R41787 | 5.90 |
| brain-specific protein p25 alpha | AA133959 | 5.71 |
| growth arrest and DNA-damage-inducible, | AA404666 | 5.55 |
| lymphocyte antigen 6 complex, locus H | AI929550 | 5.50 |
| ketohexokinase (fructokinase) | T61256 | 5.28 |
| cyclin D1 (PRAD1: parathyroid adenomatosis | AA487486 | 5.27 |
| — | AA045731 | 5.27 |
| Fn14 for type I transmenmbrane protein | AI221536 | 5.06 |

EXAMPLE 12

Change Of Foreign Protein Solubility in *E. coli*

We screened for zinc finger proteins that conferred enhanced solubility of the recombinant protein, Akt1 expressed in *E. coli*. The mammalian Akt1 gene was cloned in pET21b vector and GFP was ligated to the C-terminal of the Akt1 ORF. The nucleic acid library encoding different zinc finger proteins was transformed into *E. coli* cells. The Akt1:GFP construct was introduced into ZFP transformants. Increased solubility of Akt1 was analyzed by FACS sorting, since soluble Akt1 expressing cells produce more fluorescent GFP. After the eighth round of phenotypic screening, individual colonies were selected and the improvement of solubility was analyzed by comparing the amount of Akt1 in soluble fraction between ZFP expressed and C1 expressed cell by western blot analysis. The western blot result was quantified by image analysis software, QUANTITY ONE™ (Bio-Rad, Hercules, Calif.). C1 represent the transformants of empty vector, pZL1. Two different zinc finger proteins were identified that increase the solubility to a recombinant Akt1 protein expressed in *E. coli*.

The ratio of the amount of Akt1 protein between soluble and insoluble fraction in C1 was 32.5:67.5. In contrast, cells transformed with certain zinc finger proteins showed a 2 fold increase of the ratio of Akt1 in soluble fraction—that is, the percentage of the amount of Akt1 protein in soluble fraction of cells expressing ZFP-TFs (66.1%) divided by the amount in C1 (32.5%).

TABLE 18

ZFPs that improve solubility of Akt1 protein in *E. coli*.

| Expression Construct | Name | Ratio of the amount of Akt1 protein (%) | |
|---|---|---|---|
| | | Soluble fraction | Insoluble fraction |
| Control | C1 | 32.5 | 67.5 |
| Solubility increasing ZFP | S-1 | 66.1 | 33.9 |
| Solubility increasing ZFP | S-2 | 45.7 | 54.3 |

TABLE 19

ZFPs that confer increased solubility to Akt1 protein in *E. coli*.

| Name | F1 | F2 | F3 | F4 | putative DNA target |
|---|---|---|---|---|---|
| S-1 | QSTR | DSAR | RDHT | WSNR | GGT NGG GTC GYA (SEQ ID NO: 248) |
| S-2 | VSTR | DGNV | QSNR | QSNK | DAA GAA AAC GCT (SEQ ID NO: 249) |

Screening For Enhanced Solubility of Recombinant Proteins

Libraries for prokaryotic expression were prepared as described in Example 9. *E. coli* strain DH5α was co-transformed with ZFP library and Akt1 expression vector and cultured overnight in LB with chloramphenicol (34 µg/ml) and ampicillin (50 µg/ml). The overnight-culture was diluted to 1:500 in 1 ml fresh LB media with 1 mM IPTG and chloramphenicol (34 µg/ml) and ampicillin (50 µg/ml) to induce ZFP expression. After a three hour incubation at 30° C., $10^6$ cells were analyzed with FACS on a FACS VANTAGE™ flow cytometer and sorted for 5 to 10% of cells that expressed higher fluorescence. The GFP expressing or pET21b empty vector transformed cells were used as a positive or negative control to set the background fluorescence.

Sorted cell were overnight cultured in LB media with chloramphenicol (34 µg/ml) and ampicillin (50 µg/ml). Plasmids were purified from the culture and transformed into DH5α. Screening for enhanced solubility of recombinant protein was repeated with retransformants. Plasmid was purified from individual colonies that could grow on LB+chloramphenicol (34 µg/ml)+ampicillin (50 µg/ml) plate after eighth round of selection and retransformed into DH5α. Each transformant was analyzed for enhanced solubility of Akt1 with western blot analysis. Plasmids that could increase solubility of Akt1 were sequenced to identify ZFP.

A number of embodiments of the invention have been described. Nevertheless, it will be understood that various modifications may be made without departing from the spirit and scope of the invention. Accordingly, other embodiments are within the scope of the following claims.

What is claimed is:

1. An isolated transcription factor that comprises a first, second and third zinc finger domain in this order, wherein presence of the transcription factor in a vertebrate cell can alter the differentiation state of the cell, the transcription factor further comprises an activation domain, and the DNA contacting residues of the first, second, and third domains are as shown in reference sequence SEQ ID NO: 2 as follows:
   (i) glutamine at position −1 of the first zinc finger domain; serine at position 2 of the first zinc finger domain; asparagine at position 3 of the first zinc finger domain; and arginine at position 6 of the first zinc finger domain;
   (ii) glutamine at position −1 of the second zinc finger domain; serine at position 2 of the second zinc finger domain; asparagine at position 3 of the second zinc finger domain; and lysine at position 6 of the second zinc finger domain; and
   (iii) cysteine at position −1 of the third zinc finger domain; serine at position 2 of the third zinc finger domain; asparagine at position 3 of the third zinc finger domain; and arginine at position 6 of the third zinc finger domain.

2. The transcription factor of claim 1 wherein the cell is a vertebrate cell, and presence of the transcription factor in the cell can induce a neuronal phenotype in the cell.

3. The transcription factor of claim 2 wherein the zinc finger domains are domains from different naturally occurring human protein sequences.

4. An isolated recombinant cell that contains the transcription factor of claim 2.

5. The transcription factor of claim 1 wherein the cell is a vertebrate cell, and presence of the transcription factor in the cell can induce neurite extension in the cell.

6. The transcription factor of claim 5 wherein the cell is a mouse neuroblastoma cell.

7. An isolated recombinant cell that contains the transcription factor of claim 5.

8. The transcription factor of claim 1 wherein
   (i) the first zinc finger domain comprises SEQ ID NO: 177, or an amino acid sequence that differs by no more than three substitutions, wherein glutamine is at position −1, serine is at position 2, asparagine is at position 3, and arginine is at position 6 of the first zinc finger domain;
   (ii) the second zinc finger domain comprises SEQ ID NO: 162, or an amino acid sequence that differs by no more than three substitutions, wherein glutamine is at position −1, serine is at position 2, asparagine is at position 3, and lysine is at position 6 of the second zinc finger domain; and
   (iii) the third zinc finger domain comprises SEQ ID NO: 173, or an amino acid sequence that differs by no more than three substitutions, wherein cysteine is at position −1, serine is at position 2, asparagine is at position 3, and arginine is at position 6 of the third zinc finger domain.

9. The transcription factor of claim 8 wherein
   (i) the first zinc finger domain comprises SEQ ID NO: 177, or an amino acid sequence that differs by no more than two substitutions, wherein glutamine is at position −1, serine is at position 2, asparagine is at position 3, and arginine is at position 6 of the first zinc finger domain;
   (ii) the second zinc finger domain comprises SEQ ID NO: 162, or an amino acid sequence that differs by no more than two substitutions, wherein glutamine is at position −1, serine is at position 2, asparagine is at position 3, and lysine is at position 6 of the second zinc finger domain; and
   (iii) the third zinc finger domain comprises SEQ ID NO: 173, or an amino acid sequence that differs by no more than two sub substitutions, wherein cysteine is at position −1, serine is at position 2, asparagine is at position 3, and arginine is at position 6 of the third zinc finger domain.

10. The transcription factor of claim 9 wherein
    (i) the first zinc finger domain comprises SEQ ID NO: 177;
    (ii) the second zinc finger domain comprises SEQ ID NO: 162; and
    (iii) the third zinc finger domain comprises SEQ ID NO: 173.

11. The transcription factor of claim 1 that comprises an amino acid sequence at least 90% identical to amino acids 31 to 109 of SEQ ID NO: 2, wherein the first, second, and third zinc finger domains comprise the following DNA contacting residues:
    (i) glutamine at position −1 of the first zinc finger domain; serine at position 2 of the first zinc finger domain; asparagine at position 3 of the first zinc finger domain; and arginine at position 6 of the first zinc finger domain;
    (ii) glutamine at position −1 of the second zinc finger domain; serine at position 2 of the second zinc finger domain; asparagine at position 3 of the second zinc finger domain; and lysine at position 6 of the second zinc finger domain; and
    (iii) cysteine at position −1 of the third zinc finger domain; serine at position 2 of the third zinc finger domain; asparagine at position 3 of the third zinc finger domain; and arginine at position 6 of the third zinc finger domain.

12. The transcription factor of claim 1 that comprises an amino acid sequence at least 95% identical to amino acids 31 to 109 of SEQ ID NO: 2, wherein the first, second, and third zinc finger domains comprise the following DNA contacting residues:
    (i) glutamine at position −1 of the first zinc finger domain; serine at position 2 of the first zinc finger domain; asparagine at position 3 of the first zinc finger domain; and arginine at position 6 of the first zinc finger domain;
    (ii) glutamine at position −1 of the second zinc finger domain; serine at position 2 of the second zinc finger domain; asparagine at position 3 of the second zinc finger domain; and lysine at position 6 of the second zinc finger domain; and
    (iii) cysteine at position −1 of the third zinc finger domain; serine at position 2 of the third zinc finger domain; asparagine at position 3 of the third zinc finger domain; and arginine at position 6 of the third zinc finger domain.

13. The transcription factor of claim 1 that comprises an amino acid sequence at least 97% identical to amino acids 31 to 109 of SEQ ID NO: 2, wherein the first, second, and third zinc finger domains comprise the following DNA contacting residues;
    (i) glutamine at position −1 of the first zinc finger domain; serine at position 2 of the first zinc finger domain; asparagine at position 3 of the first zinc finger domain; and arginine at position 6 of the first zinc finger domain;
    (ii) glutamine at position −1 of the second zinc finger domain; serine at position 2 of the second zinc finger domain; asparagine at position 3 of the second zinc finger domain; and lysine at position 6 of the second zinc finger domain; and (iii) cysteine at position −1 of the third zinc finger domain; serine at position 2 of the third zinc finger domain; asparagine at position 3 of the third zinc finger domain; and arginine at position 6 of the third zinc finger domain.

14. An isolated transcription factor that comprises amino acids 31 to 109 of SEQ ID NO:2.

15. An isolated recombinant cell that contains the transcription factor of claim 14.

* * * * *

SEQUENCE LISTING

```
<160> NUMBER OF SEQ ID NOS: 261

<210> SEQ ID NO 1
<211> LENGTH: 1137
<212> TYPE: DNA
<213> ORGANISM: Artificial Sequence
<220> FEATURE:
<223> OTHER INFORMATION: plasmid sequence
<220> FEATURE:
<221> NAME/KEY: CDS
<222> LOCATION: (1)...(1134)

<400> SEQUENCE: 1 atg gtg tac ccc tac gac gtg ccc gac tac gcc gaa ttg cct cca aaa      48
Met Val Tyr Pro Tyr Asp Val Pro Asp Tyr Ala Glu Leu Pro Pro Lys
 1               5                  10                  15 aag aag aga aag gta ggg atc cga att ccc ggg gaa aaa ccg ttt gag      96
Lys Lys Arg Lys Val Gly Ile Arg Ile Pro Gly Glu Lys Pro Phe Glu
             20                  25                  30
```

```
tgt aaa gat tgc ggg aaa gct ttc att cag aag tca aac ctc atc aga      144
Cys Lys Asp Cys Gly Lys Ala Phe Ile Gln Lys Ser Asn Leu Ile Arg
         35                  40                  45 cac cag aga act cac acc ggg gaa aaa ccg tac aag tgt gaa gaa tgt      192
His Gln Arg Thr His Thr Gly Glu Lys Pro Tyr Lys Cys Glu Glu Cys
 50                  55                  60 ggc aaa gct ttt acc caa tcc tca aac ctt act aaa cat aag aaa att      240
Gly Lys Ala Phe Thr Gln Ser Ser Asn Leu Thr Lys His Lys Lys Ile
 65                  70                  75                  80 cat acc ggg gaa aaa ccg tat aaa tgt aag caa tgt ggg aaa gct ttt      288
His Thr Gly Glu Lys Pro Tyr Lys Cys Lys Gln Cys Gly Lys Ala Phe
                 85                  90                  95 gga tgt ccc tca aac ctt cga agg cat gga agg act cac acc ggt gaa      336
Gly Cys Pro Ser Asn Leu Arg Arg His Gly Arg Thr His Thr Gly Glu
            100                 105                 110 aaa gcg gcc gct aaa ttc tac ctg cca gat aca gac gat cgt cac cgg      384
Lys Ala Ala Ala Lys Phe Tyr Leu Pro Asp Thr Asp Asp Arg His Arg
        115                 120                 125 att gag gag aaa cgt aaa agg aca tat gag acc ttc aag agc atc atg      432
Ile Glu Glu Lys Arg Lys Arg Thr Tyr Glu Thr Phe Lys Ser Ile Met
130                 135                 140 aag aag agt cct ttc agc gga ccc acc gac ccc cgg cct cca cct cga      480
Lys Lys Ser Pro Phe Ser Gly Pro Thr Asp Pro Arg Pro Pro Pro Arg
145                 150                 155                 160 cgc att gct gtg cct tcc cgc agc tca gct tct gtc ccc aag cca gca      528
Arg Ile Ala Val Pro Ser Arg Ser Ser Ala Ser Val Pro Lys Pro Ala
                165                 170                 175 ccc cag ccc tat ccc ttt acg tca tcc ctg agc acc atc aac tat gat      576
Pro Gln Pro Tyr Pro Phe Thr Ser Ser Leu Ser Thr Ile Asn Tyr Asp
            180                 185                 190 gag ttt ccc acc atg gtg ttt cct tct ggg cag atc agc cag gcc tcg      624
Glu Phe Pro Thr Met Val Phe Pro Ser Gly Gln Ile Ser Gln Ala Ser
        195                 200                 205 gcc ttg gcc ccg gcc cct ccc caa gtc ctg ccc cag gct cca gcc cct      672
Ala Leu Ala Pro Ala Pro Pro Gln Val Leu Pro Gln Ala Pro Ala Pro
210                 215                 220 gcc cct gct cca gcc atg gta tca gct ctg gcc cag gcc cca gcc cct      720
Ala Pro Ala Pro Ala Met Val Ser Ala Leu Ala Gln Ala Pro Ala Pro
225                 230                 235                 240 gtc cca gtc cta gcc cca ggc cct cct cag gct gtg gcc cca cct gcc      768
Val Pro Val Leu Ala Pro Gly Pro Pro Gln Ala Val Ala Pro Pro Ala
                245                 250                 255 ccc aag ccc acc cag gct ggg gaa gga acg ctg tca gag gcc ctg ctg      816
Pro Lys Pro Thr Gln Ala Gly Glu Gly Thr Leu Ser Glu Ala Leu Leu
            260                 265                 270 cag ctg cag ttt gat gat gaa gac ctg ggg gcc ttg ctt ggc aac agc      864
Gln Leu Gln Phe Asp Asp Glu Asp Leu Gly Ala Leu Leu Gly Asn Ser
        275                 280                 285 aca gac cca gct gtg ttc aca gac ctg gca tcc gtc gac aac tcc gag      912
Thr Asp Pro Ala Val Phe Thr Asp Leu Ala Ser Val Asp Asn Ser Glu
290                 295                 300 ttt cag cag ctg ctg aac cag ggc ata cct gtg gcc ccc cac aca act      960
Phe Gln Gln Leu Leu Asn Gln Gly Ile Pro Val Ala Pro His Thr Thr
305                 310                 315                 320 gag ccc atg ctg atg gag tac cct gag gct ata act cgc cta gtg aca     1008
Glu Pro Met Leu Met Glu Tyr Pro Glu Ala Ile Thr Arg Leu Val Thr
                325                 330                 335 gcc cag agg ccc ccc gac cca gct cct gct cca ctg ggg gcc ccg ggg     1056
Ala Gln Arg Pro Pro Asp Pro Ala Pro Ala Pro Leu Gly Ala Pro Gly
            340                 345                 350
```

```
ctc ccc aat ggc ctc ctt tca gga gat gaa gac ttc tcc tcc att gcg    1104
Leu Pro Asn Gly Leu Leu Ser Gly Asp Glu Asp Phe Ser Ser Ile Ala
        355                 360                 365 gac atg gac ttc tca gcc ctg ctg agt cag taa                        1137
Asp Met Asp Phe Ser Ala Leu Leu Ser Gln
    370                 375
```

<210> SEQ ID NO 2
<211> LENGTH: 378
<212> TYPE: PRT
<213> ORGANISM: Artificial Sequence
<220> FEATURE:
<223> OTHER INFORMATION: plasmid sequence

<400> SEQUENCE: 2

```
Met Val Tyr Pro Tyr Asp Val Pro Asp Tyr Ala Glu Leu Pro Pro Lys
 1               5                  10                  15

Lys Lys Arg Lys Val Gly Ile Arg Ile Pro Gly Glu Lys Pro Phe Glu
            20                  25                  30

Cys Lys Asp Cys Gly Lys Ala Phe Ile Gln Lys Ser Asn Leu Ile Arg
        35                  40                  45

His Gln Arg Thr His Thr Gly Glu Lys Pro Tyr Lys Cys Glu Glu Cys
    50                  55                  60

Gly Lys Ala Phe Thr Gln Ser Ser Asn Leu Thr Lys His Lys Lys Ile
65                  70                  75                  80

His Thr Gly Glu Lys Pro Tyr Lys Cys Lys Gln Cys Gly Lys Ala Phe
                85                  90                  95

Gly Cys Pro Ser Asn Leu Arg Arg His Gly Arg Thr His Thr Gly Glu
            100                 105                 110

Lys Ala Ala Ala Lys Phe Tyr Leu Pro Asp Thr Asp Arg His Arg
        115                 120                 125

Ile Glu Glu Lys Arg Lys Arg Thr Tyr Glu Thr Phe Lys Ser Ile Met
    130                 135                 140

Lys Lys Ser Pro Phe Ser Gly Pro Thr Asp Pro Arg Pro Pro Arg
145                 150                 155                 160

Arg Ile Ala Val Pro Ser Arg Ser Ser Ala Ser Val Pro Lys Pro Ala
                165                 170                 175

Pro Gln Pro Tyr Pro Phe Thr Ser Ser Leu Ser Thr Ile Asn Tyr Asp
            180                 185                 190

Glu Phe Pro Thr Met Val Phe Pro Ser Gly Gln Ile Ser Gln Ala Ser
        195                 200                 205

Ala Leu Ala Pro Ala Pro Pro Gln Val Leu Pro Gln Ala Pro Ala Pro
    210                 215                 220

Ala Pro Ala Pro Ala Met Val Ser Ala Leu Ala Gln Ala Pro Ala Pro
225                 230                 235                 240

Val Pro Val Leu Ala Pro Gly Pro Pro Gln Ala Val Ala Pro Pro Ala
                245                 250                 255

Pro Lys Pro Thr Gln Ala Gly Glu Gly Thr Leu Ser Glu Ala Leu Leu
            260                 265                 270

Gln Leu Gln Phe Asp Asp Glu Asp Leu Gly Ala Leu Leu Gly Asn Ser
        275                 280                 285

Thr Asp Pro Ala Val Phe Thr Asp Leu Ala Ser Val Asp Asn Ser Glu
    290                 295                 300

Phe Gln Gln Leu Leu Asn Gln Gly Ile Pro Val Ala Pro His Thr Thr
305                 310                 315                 320
```

-continued

```
Glu Pro Met Leu Met Glu Tyr Pro Glu Ala Ile Thr Arg Leu Val Thr
            325                 330                 335

Ala Gln Arg Pro Pro Asp Pro Ala Pro Leu Gly Ala Pro Gly
        340                 345                 350

Leu Pro Asn Gly Leu Leu Ser Gly Asp Glu Asp Phe Ser Ser Ile Ala
            355                 360                 365

Asp Met Asp Phe Ser Ala Leu Leu Ser Gln
        370                 375

<210> SEQ ID NO 3
<211> LENGTH: 1233
<212> TYPE: DNA
<213> ORGANISM: Artificial Sequence
<220> FEATURE:
<223> OTHER INFORMATION: plasmid sequence
<220> FEATURE:
<221> NAME/KEY: CDS
<222> LOCATION: (1)...(1230)

<400> SEQUENCE: 3 atg gtg tac ccc tac gac gtg ccc gac tac gcc gaa ttg cct cca aaa      48
Met Val Tyr Pro Tyr Asp Val Pro Asp Tyr Ala Glu Leu Pro Pro Lys
  1               5                  10                  15 aag aag aga aag gta ggg atc cga att ccc ggg gaa aaa ccg tat gta      96
Lys Lys Arg Lys Val Gly Ile Arg Ile Pro Gly Glu Lys Pro Tyr Val
                 20                  25                  30 tgc gat gta gag gga tgt acg tgg aaa ttt gcc cgc tca gat aag ctc     144
Cys Asp Val Glu Gly Cys Thr Trp Lys Phe Ala Arg Ser Asp Lys Leu
             35                  40                  45 aac aga cac aag aaa agg cac acc ggg gaa aaa ccg tat gag tgt cac     192
Asn Arg His Lys Lys Arg His Thr Gly Glu Lys Pro Tyr Glu Cys His
         50                  55                  60 gat tgc gga aag tcc ttt agg cag agc acc cac ctc act cgg cac cgg     240
Asp Cys Gly Lys Ser Phe Arg Gln Ser Thr His Leu Thr Arg His Arg
 65                  70                  75                  80 agg atc cac acc ggg gaa aaa ccg tat gag tgt aat tac tgt gga aaa     288
Arg Ile His Thr Gly Glu Lys Pro Tyr Glu Cys Asn Tyr Cys Gly Lys
                 85                  90                  95 acc ttt agt gtg agc tca acc ctt att aga cat cag aga atc cac acc     336
Thr Phe Ser Val Ser Ser Thr Leu Ile Arg His Gln Arg Ile His Thr
                100                 105                 110 ggg gaa aaa ccg tat gta tgc gat gta gag gga tgt acg tgg aaa ttt     384
Gly Glu Lys Pro Tyr Val Cys Asp Val Glu Gly Cys Thr Trp Lys Phe
            115                 120                 125 gcc cgc tca gat aag ctc aac aga cac aag aaa agg cac acc ggt gaa     432
Ala Arg Ser Asp Lys Leu Asn Arg His Lys Lys Arg His Thr Gly Glu
        130                 135                 140 aaa gcg gcc gct aaa ttc tac ctg cca gat aca gac gat cgt cac cgg     480
Lys Ala Ala Ala Lys Phe Tyr Leu Pro Asp Thr Asp Asp Arg His Arg
145                 150                 155                 160 att gag gag aaa cgt aaa agg aca tat gag acc ttc aag agc atc atg     528
Ile Glu Glu Lys Arg Lys Arg Thr Tyr Glu Thr Phe Lys Ser Ile Met
                165                 170                 175 aag aag agt cct ttc agc gga ccc acc gac ccc cgg cct cca cct cga     576
Lys Lys Ser Pro Phe Ser Gly Pro Thr Asp Pro Arg Pro Pro Pro Arg
            180                 185                 190 cgc att gct gtg cct tcc cgc agc tca gct tct gtc ccc aag cca gca     624
Arg Ile Ala Val Pro Ser Arg Ser Ser Ala Ser Val Pro Lys Pro Ala
        195                 200                 205 ccc cag ccc tat ccc ttt acg tca tcc ctg agc acc atc aac tat gat     672
Pro Gln Pro Tyr Pro Phe Thr Ser Ser Leu Ser Thr Ile Asn Tyr Asp
```

```
                210                 215                 220
gag ttt ccc acc atg gtg ttt cct tct ggg cag atc agc cag gcc tcg        720
Glu Phe Pro Thr Met Val Phe Pro Ser Gly Gln Ile Ser Gln Ala Ser
225                 230                 235                 240 gcc ttg gcc ccg gcc cct ccc caa gtc ctg ccc cag gct cca gcc cct        768
Ala Leu Ala Pro Ala Pro Pro Gln Val Leu Pro Gln Ala Pro Ala Pro
                245                 250                 255 gcc cct gct cca gcc atg gta tca gct ctg gcc cag gcc cca gcc cct        816
Ala Pro Ala Pro Ala Met Val Ser Ala Leu Ala Gln Ala Pro Ala Pro
            260                 265                 270 gtc cca gtc cta gcc cca ggc cct cct cag gct gtg gcc cca cct gcc        864
Val Pro Val Leu Ala Pro Gly Pro Pro Gln Ala Val Ala Pro Pro Ala
        275                 280                 285 ccc aag ccc acc cag gct ggg gaa gga acg ctg tca gag gcc ctg ctg        912
Pro Lys Pro Thr Gln Ala Gly Glu Gly Thr Leu Ser Glu Ala Leu Leu
    290                 295                 300 cag ctg cag ttt gat gat gaa gac ctg ggg gcc ttg ctt ggc aac agc        960
Gln Leu Gln Phe Asp Asp Glu Asp Leu Gly Ala Leu Leu Gly Asn Ser
305                 310                 315                 320 aca gac cca gct gtg ttc aca gac ctg gca tcc gtc gac aac tcc gag       1008
Thr Asp Pro Ala Val Phe Thr Asp Leu Ala Ser Val Asp Asn Ser Glu
                325                 330                 335 ttt cag cag ctg ctg aac cag ggc ata cct gtg gcc ccc cac aca act       1056
Phe Gln Gln Leu Leu Asn Gln Gly Ile Pro Val Ala Pro His Thr Thr
            340                 345                 350 gag ccc atg ctg atg gag tac cct gag gct ata act cgc cta gtg aca       1104
Glu Pro Met Leu Met Glu Tyr Pro Glu Ala Ile Thr Arg Leu Val Thr
        355                 360                 365 gcc cag agg ccc ccc gac cca gct cct gct cca ctg ggg gcc ccg ggg       1152
Ala Gln Arg Pro Pro Asp Pro Ala Pro Ala Pro Leu Gly Ala Pro Gly
    370                 375                 380 ctc ccc aat ggc ctc ctt tca gga gat gaa gac ttc tcc tcc att gcg       1200
Leu Pro Asn Gly Leu Leu Ser Gly Asp Glu Asp Phe Ser Ser Ile Ala
385                 390                 395                 400 gac atg gac ttc tca gcc ctg ctg agt cag taa                           1233
Asp Met Asp Phe Ser Ala Leu Leu Ser Gln
                405                 410

<210> SEQ ID NO 4
<211> LENGTH: 410
<212> TYPE: PRT
<213> ORGANISM: Artificial Sequence
<220> FEATURE:
<223> OTHER INFORMATION: plasmid sequence

<400> SEQUENCE: 4

Met Val Tyr Pro Tyr Asp Val Pro Asp Tyr Ala Glu Leu Pro Pro Lys
 1               5                  10                  15

Lys Lys Arg Lys Val Gly Ile Arg Ile Pro Gly Glu Lys Pro Tyr Val
                20                  25                  30

Cys Asp Val Glu Gly Cys Thr Trp Lys Phe Ala Arg Ser Asp Lys Leu
            35                  40                  45

Asn Arg His Lys Lys Arg His Thr Gly Glu Lys Pro Tyr Glu Cys His
        50                  55                  60

Asp Cys Gly Lys Ser Phe Arg Gln Ser Thr His Leu Thr Arg His Arg
65                  70                  75                  80

Arg Ile His Thr Gly Glu Lys Pro Tyr Glu Cys Asn Tyr Cys Gly Lys
                85                  90                  95

Thr Phe Ser Val Ser Ser Thr Leu Ile Arg His Gln Arg Ile His Thr
```

```
                        100                     105                     110
Gly Glu Lys Pro Tyr Val Cys Asp Val Glu Gly Cys Thr Trp Lys Phe
        115                     120                     125

Ala Arg Ser Asp Lys Leu Asn Arg His Lys Arg His Thr Gly Glu
130                     135                     140

Lys Ala Ala Lys Phe Tyr Leu Pro Asp Thr Asp Arg His Arg
145                     150                     155                     160

Ile Glu Glu Lys Arg Lys Arg Thr Tyr Glu Thr Phe Lys Ser Ile Met
                        165                     170                     175

Lys Lys Ser Pro Phe Ser Gly Pro Thr Asp Pro Arg Pro Pro Arg
        180                     185                     190

Arg Ile Ala Val Pro Ser Arg Ser Ala Ser Val Pro Lys Pro Ala
        195                     200                     205

Pro Gln Pro Tyr Pro Phe Thr Ser Ser Leu Ser Thr Ile Asn Tyr Asp
        210                     215                     220

Glu Phe Pro Thr Met Val Phe Pro Ser Gly Gln Ile Ser Gln Ala Ser
225                     230                     235                     240

Ala Leu Ala Pro Ala Pro Gln Val Leu Pro Gln Ala Pro Ala Pro
                245                     250                     255

Ala Pro Ala Pro Ala Met Val Ser Ala Leu Ala Gln Ala Pro Ala Pro
                260                     265                     270

Val Pro Val Leu Ala Pro Gly Pro Pro Gln Ala Val Ala Pro Pro Ala
        275                     280                     285

Pro Lys Pro Thr Gln Ala Gly Glu Gly Thr Leu Ser Glu Ala Leu Leu
        290                     295                     300

Gln Leu Gln Phe Asp Asp Glu Asp Leu Gly Ala Leu Leu Gly Asn Ser
305                     310                     315                     320

Thr Asp Pro Ala Val Phe Thr Asp Leu Ala Ser Val Asp Asn Ser Glu
                325                     330                     335

Phe Gln Gln Leu Leu Asn Gln Gly Ile Pro Val Ala Pro His Thr Thr
                340                     345                     350

Glu Pro Met Leu Met Glu Tyr Pro Glu Ala Ile Thr Arg Leu Val Thr
        355                     360                     365

Ala Gln Arg Pro Pro Asp Pro Ala Pro Ala Pro Leu Gly Ala Pro Gly
        370                     375                     380

Leu Pro Asn Gly Leu Leu Ser Gly Asp Glu Asp Phe Ser Ser Ile Ala
385                     390                     395                     400

Asp Met Asp Phe Ser Ala Leu Leu Ser Gln
                405                     410

<210> SEQ ID NO 5
<211> LENGTH: 1137
<212> TYPE: DNA
<213> ORGANISM: Artificial Sequence
<220> FEATURE:
<223> OTHER INFORMATION: plasmid sequence
<220> FEATURE:
<221> NAME/KEY: CDS
<222> LOCATION: (1)...(1134)

<400> SEQUENCE: 5 atg gtg tac ccc tac gac gtg ccc gac tac gcc gaa ttg cct cca aaa       48
Met Val Tyr Pro Tyr Asp Val Pro Asp Tyr Ala Glu Leu Pro Pro Lys
 1               5                  10                  15 aag aag aga aag gta ggg atc cga att ccc ggg gaa aaa ccg tat aag       96
Lys Lys Arg Lys Val Gly Ile Arg Ile Pro Gly Glu Lys Pro Tyr Lys
             20                  25                  30
```

```
tgc atg gag tgt ggg aag gct ttt aac cgc agg tca cac ctc aca cgg         144
Cys Met Glu Cys Gly Lys Ala Phe Asn Arg Arg Ser His Leu Thr Arg
        35                  40                  45 cac cag cgg att cac acc ggg gaa aaa ccg ttc cag tgt aaa act tgt         192
His Gln Arg Ile His Thr Gly Glu Lys Pro Phe Gln Cys Lys Thr Cys
    50                  55                  60 cag cga aag ttc tcc cgg tcc gac cac ctg aag acc cac acc agg act         240
Gln Arg Lys Phe Ser Arg Ser Asp His Leu Lys Thr His Thr Arg Thr
65                  70                  75                  80 cat acc ggg gaa aaa ccg tat aca tgt aaa cag tgt ggg aaa gcc ttc         288
His Thr Gly Glu Lys Pro Tyr Thr Cys Lys Gln Cys Gly Lys Ala Phe
                85                  90                  95 agt gtt tcc agt tcc ctt cga aga cat gaa acc act cac acc ggt gaa         336
Ser Val Ser Ser Ser Leu Arg Arg His Glu Thr Thr His Thr Gly Glu
            100                 105                 110 aaa gcg gcc gct aaa ttc tac ctg cca gat aca gac gat cgt cac cgg         384
Lys Ala Ala Ala Lys Phe Tyr Leu Pro Asp Thr Asp Asp Arg His Arg
        115                 120                 125 att gag gag aaa cgt aaa agg aca tat gag acc ttc aag agc atc atg         432
Ile Glu Glu Lys Arg Lys Arg Thr Tyr Glu Thr Phe Lys Ser Ile Met
130                 135                 140 aag aag agt cct ttc agc gga ccc acc gac ccc cgg cct cca cct cga         480
Lys Lys Ser Pro Phe Ser Gly Pro Thr Asp Pro Arg Pro Pro Pro Arg
145                 150                 155                 160 cgc att gct gtg cct tcc cgc agc tca gct tct gtc ccc aag cca gca         528
Arg Ile Ala Val Pro Ser Arg Ser Ser Ala Ser Val Pro Lys Pro Ala
                165                 170                 175 ccc cag ccc tat ccc ttt acg tca tcc ctg agc acc atc aac tat gat         576
Pro Gln Pro Tyr Pro Phe Thr Ser Ser Leu Ser Thr Ile Asn Tyr Asp
            180                 185                 190 gag ttt ccc acc atg gtg ttt cct tct ggg cag atc agc cag gcc tcg         624
Glu Phe Pro Thr Met Val Phe Pro Ser Gly Gln Ile Ser Gln Ala Ser
        195                 200                 205 gcc ttg gcc ccg gcc cct ccc caa gtc ctg ccc cag gct cca gcc cct         672
Ala Leu Ala Pro Ala Pro Pro Gln Val Leu Pro Gln Ala Pro Ala Pro
210                 215                 220 gcc cct gct cca gcc atg gta tca gct ctg gcc cag gcc cca gcc cct         720
Ala Pro Ala Pro Ala Met Val Ser Ala Leu Ala Gln Ala Pro Ala Pro
225                 230                 235                 240 gtc cca gtc cta gcc cca ggc cct cct cag gct gtg gcc cca cct gcc         768
Val Pro Val Leu Ala Pro Gly Pro Pro Gln Ala Val Ala Pro Pro Ala
                245                 250                 255 ccc aag ccc acc cag gct ggg gaa gga acg ctg tca gag gcc ctg ctg         816
Pro Lys Pro Thr Gln Ala Gly Glu Gly Thr Leu Ser Glu Ala Leu Leu
            260                 265                 270 cag ctg cag ttt gat gat gaa gac ctg ggg gcc ttg ctt ggc aac agc         864
Gln Leu Gln Phe Asp Asp Glu Asp Leu Gly Ala Leu Leu Gly Asn Ser
        275                 280                 285 aca gac cca gct gtg ttc aca gac ctg gca tcc gtc gac aac tcc gag         912
Thr Asp Pro Ala Val Phe Thr Asp Leu Ala Ser Val Asp Asn Ser Glu
290                 295                 300 ttt cag cag ctg ctg aac cag ggc ata cct gtg gcc ccc cac aca act         960
Phe Gln Gln Leu Leu Asn Gln Gly Ile Pro Val Ala Pro His Thr Thr
305                 310                 315                 320 gag ccc atg ctg atg gag tac cct gag gct ata act cgc tta gtg aca        1008
Glu Pro Met Leu Met Glu Tyr Pro Glu Ala Ile Thr Arg Leu Val Thr
                325                 330                 335 gcc cag agg ccc ccc gac cca gct cct gct cca ctg ggg gcc ccg ggg        1056
Ala Gln Arg Pro Pro Asp Pro Ala Pro Ala Pro Leu Gly Ala Pro Gly
```

```
                    340                 345                 350
ctc ccc aat ggc ctc ctt tca gga gat gaa gac ttc tcc tcc att gcg    1104
Leu Pro Asn Gly Leu Leu Ser Gly Asp Glu Asp Phe Ser Ser Ile Ala
        355                 360                 365 gac atg gac ttc tca gcc ctg ctg agt cag taa                        1137
Asp Met Asp Phe Ser Ala Leu Leu Ser Gln
    370                 375
```

<210> SEQ ID NO 6
<211> LENGTH: 378
<212> TYPE: PRT
<213> ORGANISM: Artificial Sequence
<220> FEATURE:
<223> OTHER INFORMATION: plasmid sequence

<400> SEQUENCE: 6

```
Met Val Tyr Pro Tyr Asp Val Pro Asp Tyr Ala Glu Leu Pro Pro Lys
 1               5                  10                  15

Lys Lys Arg Lys Val Gly Ile Arg Ile Pro Gly Glu Lys Pro Tyr Lys
            20                  25                  30

Cys Met Glu Cys Gly Lys Ala Phe Asn Arg Arg Ser His Leu Thr Arg
        35                  40                  45

His Gln Arg Ile His Thr Gly Glu Lys Pro Phe Gln Cys Lys Thr Cys
    50                  55                  60

Gln Arg Lys Phe Ser Arg Ser Asp His Leu Lys Thr His Thr Arg Thr
65                  70                  75                  80

His Thr Gly Glu Lys Pro Tyr Thr Cys Lys Gln Cys Gly Lys Ala Phe
                85                  90                  95

Ser Val Ser Ser Ser Leu Arg Arg His Glu Thr Thr His Thr Gly Glu
            100                 105                 110

Lys Ala Ala Ala Lys Phe Tyr Leu Pro Asp Thr Asp Asp Arg His Arg
        115                 120                 125

Ile Glu Glu Lys Arg Lys Arg Thr Tyr Glu Thr Phe Lys Ser Ile Met
    130                 135                 140

Lys Lys Ser Pro Phe Ser Gly Pro Thr Asp Pro Arg Pro Pro Pro Arg
145                 150                 155                 160

Arg Ile Ala Val Pro Ser Arg Ser Ser Ala Ser Val Pro Lys Pro Ala
                165                 170                 175

Pro Gln Pro Tyr Pro Phe Thr Ser Ser Leu Ser Thr Ile Asn Tyr Asp
            180                 185                 190

Glu Phe Pro Thr Met Val Phe Pro Ser Gly Gln Ile Ser Gln Ala Ser
        195                 200                 205

Ala Leu Ala Pro Ala Pro Pro Gln Val Leu Pro Gln Ala Pro Ala Pro
    210                 215                 220

Ala Pro Ala Pro Ala Met Val Ser Ala Leu Ala Gln Ala Pro Ala Pro
225                 230                 235                 240

Val Pro Val Leu Ala Pro Gly Pro Pro Gln Ala Val Ala Pro Pro Ala
                245                 250                 255

Pro Lys Pro Thr Gln Ala Gly Glu Gly Thr Leu Ser Glu Ala Leu Leu
            260                 265                 270

Gln Leu Gln Phe Asp Asp Glu Asp Leu Gly Ala Leu Leu Gly Asn Ser
        275                 280                 285

Thr Asp Pro Ala Val Phe Thr Asp Leu Ala Ser Val Asp Asn Ser Glu
    290                 295                 300

Phe Gln Gln Leu Leu Asn Gln Gly Ile Pro Val Ala Pro His Thr Thr
305                 310                 315                 320
```

```
Glu Pro Met Leu Met Glu Tyr Pro Glu Ala Ile Thr Arg Leu Val Thr
            325                 330                 335

Ala Gln Arg Pro Pro Asp Pro Ala Pro Leu Gly Ala Pro Gly
        340                 345                 350

Leu Pro Asn Gly Leu Leu Ser Gly Asp Glu Asp Phe Ser Ser Ile Ala
            355                 360                 365

Asp Met Asp Phe Ser Ala Leu Leu Ser Gln
        370                 375

<210> SEQ ID NO 7
<211> LENGTH: 1149
<212> TYPE: DNA
<213> ORGANISM: Artificial Sequence
<220> FEATURE:
<223> OTHER INFORMATION: plasmid sequence
<220> FEATURE:
<221> NAME/KEY: CDS
<222> LOCATION: (1)...(1146)

<400> SEQUENCE: 7
```

| | | | | | | | | | | | | | | | | |
|---|---|---|---|---|---|---|---|---|---|---|---|---|---|---|---|---|
| atg | gtg | tac | ccc | tac | gac | gtg | ccc | gac | tac | gcc | gaa | ttg | cct | cca | aaa | 48 |
| Met | Val | Tyr | Pro | Tyr | Asp | Val | Pro | Asp | Tyr | Ala | Glu | Leu | Pro | Pro | Lys | |
| 1 | | | | 5 | | | | | 10 | | | | | 15 | | |

```
aag aag aga aag gta ggg atc cga att ccc ggg gaa aaa ccg ttt gag     96
Lys Lys Arg Lys Val Gly Ile Arg Ile Pro Gly Glu Lys Pro Phe Glu
             20                  25                  30 tgt aaa gat tgc ggg aaa gct ttc att cag aag tca aac ctc atc aga    144
Cys Lys Asp Cys Gly Lys Ala Phe Ile Gln Lys Ser Asn Leu Ile Arg
         35                  40                  45 cac cag aga act cac acc ggg gaa aaa ccg tat gct tgc cct gtc gag    192
His Gln Arg Thr His Thr Gly Glu Lys Pro Tyr Ala Cys Pro Val Glu
     50                  55                  60 tcc tgc gat cgc cgc ttt tct gat tcg tcg aac ctt acc cgc cat atc    240
Ser Cys Asp Arg Arg Phe Ser Asp Ser Ser Asn Leu Thr Arg His Ile
 65                  70                  75                  80 cgc atc cac acc ggg gaa aaa ccg tat gct tgc cct gtc gag tcc tgc    288
Arg Ile His Thr Gly Glu Lys Pro Tyr Ala Cys Pro Val Glu Ser Cys
                 85                  90                  95 gat cgc cgc ttt tct gat tcg tcg aac ctt acc cgc cat atc cgc atc    336
Asp Arg Arg Phe Ser Asp Ser Ser Asn Leu Thr Arg His Ile Arg Ile
            100                 105                 110 cac acc ggt gaa aaa gcg gcc gct aaa ttc tac ctg cca gat aca gac    384
His Thr Gly Glu Lys Ala Ala Ala Lys Phe Tyr Leu Pro Asp Thr Asp
        115                 120                 125 gat cgt cac cgg att gag gag aaa cgt aaa agg aca tat gag acc ttc    432
Asp Arg His Arg Ile Glu Glu Lys Arg Lys Arg Thr Tyr Glu Thr Phe
    130                 135                 140 aag agc atc atg aag aag agt cct ttc agc gga ccc acc gac ccc cgg    480
Lys Ser Ile Met Lys Lys Ser Pro Phe Ser Gly Pro Thr Asp Pro Arg
145                 150                 155                 160 cct cca cct cga cgc att gct gtg cct tcc cgc agc tca gct tct gtc    528
Pro Pro Pro Arg Arg Ile Ala Val Pro Ser Arg Ser Ser Ala Ser Val
                165                 170                 175 ccc aag cca gca ccc cag ccc tat ccc ttt acg tca tcc ctg agc acc    576
Pro Lys Pro Ala Pro Gln Pro Tyr Pro Phe Thr Ser Ser Leu Ser Thr
            180                 185                 190 atc aac tat gat gag ttt ccc acc atg gtg ttt cct tct ggg cag atc    624
Ile Asn Tyr Asp Glu Phe Pro Thr Met Val Phe Pro Ser Gly Gln Ile
        195                 200                 205 agc cag gcc tcg gcc ttg gcc ccg gcc cct ccc caa gtc ctg ccc cag    672
Ser Gln Ala Ser Ala Leu Ala Pro Ala Pro Pro Gln Val Leu Pro Gln
```

```
Ser Gln Ala Ser Ala Leu Ala Pro Ala Pro Pro Gln Val Leu Pro Gln
    210                 215                 220 gct cca gcc cct gcc cct gct cca gcc atg gta tca gct ctg gcc cag        720
Ala Pro Ala Pro Ala Pro Ala Pro Ala Met Val Ser Ala Leu Ala Gln
225                 230                 235                 240 gcc cca gcc cct gtc cca gtc cta gcc cca ggc cct cct cag gct gtg        768
Ala Pro Ala Pro Val Pro Val Leu Ala Pro Gly Pro Pro Gln Ala Val
                    245                 250                 255 gcc cca cct gcc ccc aag ccc acc cag gct ggg gaa gga acg ctg tca        816
Ala Pro Pro Ala Pro Lys Pro Thr Gln Ala Gly Glu Gly Thr Leu Ser
                260                 265                 270 gag gcc ctg ctg cag ctg cag ttt gat gat gaa gac ctg ggg gcc ttg        864
Glu Ala Leu Leu Gln Leu Gln Phe Asp Asp Glu Asp Leu Gly Ala Leu
            275                 280                 285 ctt ggc aac agc aca gac cca gct gtg ttc aca gac ctg gca tcc gtc        912
Leu Gly Asn Ser Thr Asp Pro Ala Val Phe Thr Asp Leu Ala Ser Val
        290                 295                 300 gac aac tcc gag ttt cag cag ctg ctg aac cag ggc ata cct gtg gcc        960
Asp Asn Ser Glu Phe Gln Gln Leu Leu Asn Gln Gly Ile Pro Val Ala
305                 310                 315                 320 ccc cac aca act gag ccc atg ctg atg gag tac cct gag gct ata act       1008
Pro His Thr Thr Glu Pro Met Leu Met Glu Tyr Pro Glu Ala Ile Thr
                325                 330                 335 cgc cta gtg aca gcc cag agg ccc ccc gac cca gct cct gct cca ctg       1056
Arg Leu Val Thr Ala Gln Arg Pro Pro Asp Pro Ala Pro Ala Pro Leu
                    340                 345                 350 ggg gcc ccg ggg ctc ccc aat ggc ctc ctt tca gga gat gaa gac ttc       1104
Gly Ala Pro Gly Leu Pro Asn Gly Leu Leu Ser Gly Asp Glu Asp Phe
                355                 360                 365 tcc tcc att gcg gac atg gac ttc tca gcc ctg ctg agt cag                1146
Ser Ser Ile Ala Asp Met Asp Phe Ser Ala Leu Leu Ser Gln
            370                 375                 380 taa                                                                    1149

<210> SEQ ID NO 8
<211> LENGTH: 382
<212> TYPE: PRT
<213> ORGANISM: Artificial Sequence
<220> FEATURE:
<223> OTHER INFORMATION: plasmid sequence

<400> SEQUENCE: 8

Met Val Tyr Pro Tyr Asp Val Pro Asp Tyr Ala Glu Leu Pro Pro Lys
1               5                   10                  15

Lys Lys Arg Lys Val Gly Ile Arg Ile Pro Gly Glu Lys Pro Phe Glu
            20                  25                  30

Cys Lys Asp Cys Gly Lys Ala Phe Ile Gln Lys Ser Asn Leu Ile Arg
        35                  40                  45

His Gln Arg Thr His Thr Gly Glu Lys Pro Tyr Ala Cys Pro Val Glu
    50                  55                  60

Ser Cys Asp Arg Arg Phe Ser Asp Ser Ser Asn Leu Thr Arg His Ile
65                  70                  75                  80

Arg Ile His Thr Gly Glu Lys Pro Tyr Ala Cys Pro Val Glu Ser Cys
                85                  90                  95

Asp Arg Arg Phe Ser Asp Ser Ser Asn Leu Thr Arg His Ile Arg Ile
            100                 105                 110

His Thr Gly Glu Lys Ala Ala Ala Lys Phe Tyr Leu Pro Asp Thr Asp
        115                 120                 125
```

```
Asp Arg His Arg Ile Glu Glu Lys Arg Lys Arg Thr Tyr Glu Thr Phe
        130                 135                 140

Lys Ser Ile Met Lys Lys Ser Pro Phe Ser Gly Pro Thr Asp Pro Arg
145                 150                 155                 160

Pro Pro Pro Arg Arg Ile Ala Val Pro Ser Arg Ser Ser Ala Ser Val
                165                 170                 175

Pro Lys Pro Ala Pro Gln Pro Tyr Pro Phe Thr Ser Ser Leu Ser Thr
                180                 185                 190

Ile Asn Tyr Asp Glu Phe Pro Thr Met Val Phe Pro Ser Gly Gln Ile
                195                 200                 205

Ser Gln Ala Ser Ala Leu Ala Pro Ala Pro Pro Gln Val Leu Pro Gln
        210                 215                 220

Ala Pro Ala Pro Ala Pro Ala Pro Ala Met Val Ser Ala Leu Ala Gln
225                 230                 235                 240

Ala Pro Ala Pro Val Pro Val Leu Ala Pro Gly Pro Pro Gln Ala Val
                245                 250                 255

Ala Pro Pro Ala Pro Lys Pro Thr Gln Ala Gly Glu Gly Thr Leu Ser
                260                 265                 270

Glu Ala Leu Leu Gln Leu Gln Phe Asp Asp Glu Asp Leu Gly Ala Leu
        275                 280                 285

Leu Gly Asn Ser Thr Asp Pro Ala Val Phe Thr Asp Leu Ala Ser Val
290                 295                 300

Asp Asn Ser Glu Phe Gln Gln Leu Leu Asn Gln Gly Ile Pro Val Ala
305                 310                 315                 320

Pro His Thr Thr Glu Pro Met Leu Met Glu Tyr Pro Glu Ala Ile Thr
                325                 330                 335

Arg Leu Val Thr Ala Gln Arg Pro Pro Asp Pro Ala Pro Ala Pro Leu
                340                 345                 350

Gly Ala Pro Gly Leu Pro Asn Gly Leu Leu Ser Gly Asp Glu Asp Phe
                355                 360                 365

Ser Ser Ile Ala Asp Met Asp Phe Ser Ala Leu Leu Ser Gln
        370                 375                 380

<210> SEQ ID NO 9
<211> LENGTH: 630
<212> TYPE: DNA
<213> ORGANISM: Artificial Sequence
<220> FEATURE:
<223> OTHER INFORMATION: plasmid sequence
<220> FEATURE:
<221> NAME/KEY: CDS
<222> LOCATION: (1)...(627)

<400> SEQUENCE: 9 atg gtg tac ccc tac gac gtg ccc gac tac gcc gaa ttg cct cca aaa      48
Met Val Tyr Pro Tyr Asp Val Pro Asp Tyr Ala Glu Leu Pro Pro Lys
  1               5                  10                  15 aag aag aga aag gta ggg atc cga att ccc ggg gaa aaa ccg tat gag      96
Lys Lys Arg Lys Val Gly Ile Arg Ile Pro Gly Glu Lys Pro Tyr Glu
             20                  25                  30 tgt gat cac tgt gga aaa tcc ttt agc cag agc tct cat ctg aat gtg     144
Cys Asp His Cys Gly Lys Ser Phe Ser Gln Ser Ser His Leu Asn Val
         35                  40                  45 cac aaa aga act cac acc ggg gaa aaa ccg tac aga tgt gag gaa tgt     192
His Lys Arg Thr His Thr Gly Glu Lys Pro Tyr Arg Cys Glu Glu Cys
     50                  55                  60 ggc aaa gcc ttt agg tgg ccc tca aac ctt act aga cat aag aga att     240
Gly Lys Ala Phe Arg Trp Pro Ser Asn Leu Thr Arg His Lys Arg Ile
 65                  70                  75                  80
```

```
                65                  70                  75                  80
cac acc ggg gaa aaa ccg tac aga tgt gag gaa tgt ggc aaa gcc ttt         288
His Thr Gly Glu Lys Pro Tyr Arg Cys Glu Glu Cys Gly Lys Ala Phe
                    85                  90                  95 agg tgg ccc tca aac ctt act aga cat aag aga att cac acc ggg gaa         336
Arg Trp Pro Ser Asn Leu Thr Arg His Lys Arg Ile His Thr Gly Glu
                100                 105                 110 aaa ccg ttt gcc tgc cct gag tgt cct aag cgc ttc atg aga tcc gac         384
Lys Pro Phe Ala Cys Pro Glu Cys Pro Lys Arg Phe Met Arg Ser Asp
            115                 120                 125 aac ctg acc cag cat atc aag acc cac acc ggt gaa aaa gcg gcc gct         432
Asn Leu Thr Gln His Ile Lys Thr His Thr Gly Glu Lys Ala Ala Ala
        130                 135                 140 aaa ttc gtg tca gtg aca ttt gaa gat gtg gct gtg ctc ttt act cgg         480
Lys Phe Val Ser Val Thr Phe Glu Asp Val Ala Val Leu Phe Thr Arg
145                 150                 155                 160 gac gag tgg aag aag ctg gat ctg tct cag aga agc ctg tac cgt gag         528
Asp Glu Trp Lys Lys Leu Asp Leu Ser Gln Arg Ser Leu Tyr Arg Glu
                165                 170                 175 gtg atg ctg gag aat tac agc aac ctg gcc tcc atg gca gga ttc ctg         576
Val Met Leu Glu Asn Tyr Ser Asn Leu Ala Ser Met Ala Gly Phe Leu
            180                 185                 190 ttt acc aaa cca aag gtg atc tcc ctg ttg cag caa gga gag gat ccc         624
Phe Thr Lys Pro Lys Val Ile Ser Leu Leu Gln Gln Gly Glu Asp Pro
        195                 200                 205 tgg taa                                                                 630
Trp

<210> SEQ ID NO 10
<211> LENGTH: 209
<212> TYPE: PRT
<213> ORGANISM: Artificial Sequence
<220> FEATURE:
<223> OTHER INFORMATION: plasmid sequence

<400> SEQUENCE: 10

Met Val Tyr Pro Tyr Asp Val Pro Asp Tyr Ala Glu Leu Pro Pro Lys
1               5                   10                  15

Lys Lys Arg Lys Val Gly Ile Arg Ile Pro Gly Glu Lys Pro Tyr Glu
            20                  25                  30

Cys Asp His Cys Gly Lys Ser Phe Ser Gln Ser Ser His Leu Asn Val
        35                  40                  45

His Lys Arg Thr His Thr Gly Glu Lys Pro Tyr Arg Cys Glu Glu Cys
    50                  55                  60

Gly Lys Ala Phe Arg Trp Pro Ser Asn Leu Thr Arg His Lys Arg Ile
65                  70                  75                  80

His Thr Gly Glu Lys Pro Tyr Arg Cys Glu Glu Cys Gly Lys Ala Phe
                85                  90                  95

Arg Trp Pro Ser Asn Leu Thr Arg His Lys Arg Ile His Thr Gly Glu
            100                 105                 110

Lys Pro Phe Ala Cys Pro Glu Cys Pro Lys Arg Phe Met Arg Ser Asp
        115                 120                 125

Asn Leu Thr Gln His Ile Lys Thr His Thr Gly Glu Lys Ala Ala Ala
    130                 135                 140

Lys Phe Val Ser Val Thr Phe Glu Asp Val Ala Val Leu Phe Thr Arg
145                 150                 155                 160

Asp Glu Trp Lys Lys Leu Asp Leu Ser Gln Arg Ser Leu Tyr Arg Glu
                165                 170                 175
```

```
Val Met Leu Glu Asn Tyr Ser Asn Leu Ala Ser Met Ala Gly Phe Leu
            180                 185                 190

Phe Thr Lys Pro Lys Val Ile Ser Leu Leu Gln Gln Gly Glu Asp Pro
        195                 200                 205

Trp

<210> SEQ ID NO 11
<211> LENGTH: 642
<212> TYPE: DNA
<213> ORGANISM: Artificial Sequence
<220> FEATURE:
<223> OTHER INFORMATION: plasmid sequence
<220> FEATURE:
<221> NAME/KEY: CDS
<222> LOCATION: (1)...(639)

<400> SEQUENCE: 11 atg gtg tac ccc tac gac gtg ccc gac tac gcc gaa ttg cct cca aaa      48
Met Val Tyr Pro Tyr Asp Val Pro Asp Tyr Ala Glu Leu Pro Pro Lys
  1               5                  10                  15 aag aag aga aag gta ggg atc cga att ccc ggg gaa aaa ccg tac tcc      96
Lys Lys Arg Lys Val Gly Ile Arg Ile Pro Gly Glu Lys Pro Tyr Ser
             20                  25                  30 tgt ggc att tgt ggc aaa tcc ttc tct gac tcc agt gcc aaa agg aga     144
Cys Gly Ile Cys Gly Lys Ser Phe Ser Asp Ser Ser Ala Lys Arg Arg
         35                  40                  45 cac tgc att cta cac acc ggg gaa aaa ccg tat gta tgc gat gta gag     192
His Cys Ile Leu His Thr Gly Glu Lys Pro Tyr Val Cys Asp Val Glu
     50                  55                  60 gga tgt acg tgg aaa ttt gcc cgc tca gat aag ctc aac aga cac aag     240
Gly Cys Thr Trp Lys Phe Ala Arg Ser Asp Lys Leu Asn Arg His Lys
 65                  70                  75                  80 aaa agg cac acc ggg gaa aaa ccg tat gta tgc gat gta gag gga tgt     288
Lys Arg His Thr Gly Glu Lys Pro Tyr Val Cys Asp Val Glu Gly Cys
                 85                  90                  95 acg tgg aaa ttt gcc cgc tca gat gag ctc aac aga cac aag aaa agg     336
Thr Trp Lys Phe Ala Arg Ser Asp Glu Leu Asn Arg His Lys Lys Arg
            100                 105                 110 cac acc ggg gaa aaa ccg tat gag tgt cac gat tgc gga aag tcc ttt     384
His Thr Gly Glu Lys Pro Tyr Glu Cys His Asp Cys Gly Lys Ser Phe
        115                 120                 125 agg cag agc acc cac ctc act cgg cac cgg agg atc cac acc ggt gaa     432
Arg Gln Ser Thr His Leu Thr Arg His Arg Arg Ile His Thr Gly Glu
    130                 135                 140 aaa gcg gcc gct aaa ttc gtg tca gtg aca ttt gaa gat gtg gct gtg     480
Lys Ala Ala Ala Lys Phe Val Ser Val Thr Phe Glu Asp Val Ala Val
145                 150                 155                 160 ctc ttt act cgg gac gag tgg aag aag ctg gat ctg tct cag aga agc     528
Leu Phe Thr Arg Asp Glu Trp Lys Lys Leu Asp Leu Ser Gln Arg Ser
                165                 170                 175 ctg tac cgt gag gtg atg ctg gag aat tac agc aac ctg gcc tcc atg     576
Leu Tyr Arg Glu Val Met Leu Glu Asn Tyr Ser Asn Leu Ala Ser Met
            180                 185                 190 gca gga ttc ctg ttt acc aaa cca aag gtg atc tcc ctg ttg cag caa     624
Ala Gly Phe Leu Phe Thr Lys Pro Lys Val Ile Ser Leu Leu Gln Gln
        195                 200                 205 gga gag gat ccc tgg taa                                             642
Gly Glu Asp Pro Trp
    210
```

<210> SEQ ID NO 12
<211> LENGTH: 213
<212> TYPE: PRT
<213> ORGANISM: Artificial Sequence
<220> FEATURE:
<223> OTHER INFORMATION: plasmid sequence

<400> SEQUENCE: 12

```
Met Val Tyr Pro Tyr Asp Val Pro Asp Tyr Ala Glu Leu Pro Pro Lys
 1               5                  10                  15

Lys Lys Arg Lys Val Gly Ile Arg Ile Pro Gly Glu Lys Pro Tyr Ser
            20                  25                  30

Cys Gly Ile Cys Gly Lys Ser Phe Ser Asp Ser Ser Ala Lys Arg Arg
        35                  40                  45

His Cys Ile Leu His Thr Gly Glu Lys Pro Tyr Val Cys Asp Val Glu
    50                  55                  60

Gly Cys Thr Trp Lys Phe Ala Arg Ser Asp Lys Leu Asn Arg His Lys
65                  70                  75                  80

Lys Arg His Thr Gly Glu Lys Pro Tyr Val Cys Asp Val Glu Gly Cys
                85                  90                  95

Thr Trp Lys Phe Ala Arg Ser Asp Glu Leu Asn Arg His Lys Lys Arg
            100                 105                 110

His Thr Gly Glu Lys Pro Tyr Glu Cys His Asp Cys Gly Lys Ser Phe
        115                 120                 125

Arg Gln Ser Thr His Leu Thr Arg His Arg Ile His Thr Gly Glu
    130                 135                 140

Lys Ala Ala Ala Lys Phe Val Ser Val Thr Phe Glu Asp Val Ala Val
145                 150                 155                 160

Leu Phe Thr Arg Asp Glu Trp Lys Lys Leu Asp Leu Ser Gln Arg Ser
                165                 170                 175

Leu Tyr Arg Glu Val Met Leu Glu Asn Tyr Ser Asn Leu Ala Ser Met
            180                 185                 190

Ala Gly Phe Leu Phe Thr Lys Pro Lys Val Ile Ser Leu Leu Gln Gln
        195                 200                 205

Gly Glu Asp Pro Trp
    210
```

<210> SEQ ID NO 13
<211> LENGTH: 630
<212> TYPE: DNA
<213> ORGANISM: Artificial Sequence
<220> FEATURE:
<223> OTHER INFORMATION: plasmid sequence
<220> FEATURE:
<221> NAME/KEY: CDS
<222> LOCATION: (1)...(627)

<400> SEQUENCE: 13

```
atg gtg tac ccc tac gac gtg ccc gac tac gcc gaa ttg cct cca aaa    48
Met Val Tyr Pro Tyr Asp Val Pro Asp Tyr Ala Glu Leu Pro Pro Lys
 1               5                  10                  15 aag aag aga aag gta ggg atc cga att ccc ggg gaa aaa ccg tat gag    96
Lys Lys Arg Lys Val Gly Ile Arg Ile Pro Gly Glu Lys Pro Tyr Glu
            20                  25                  30 tgt gat cac tgt gga aaa tcc ttt agc cag agc tct cat ctg aat gtg   144
Cys Asp His Cys Gly Lys Ser Phe Ser Gln Ser Ser His Leu Asn Val
        35                  40                  45 cac aaa aga act cac acc ggg gaa aaa ccg tac atg tgc agt gag tgt   192
His Lys Arg Thr His Thr Gly Glu Lys Pro Tyr Met Cys Ser Glu Cys
    50                  55                  60
```

```
ggg cga ggc ttc agc cag aag tca aac ctc atc ata cac cag agg aca      240
Gly Arg Gly Phe Ser Gln Lys Ser Asn Leu Ile Ile His Gln Arg Thr
         65                  70                  75                  80 cac acc ggg gaa aaa ccg tat gag tgt cac gat tgc gga aag tcc ttt      288
His Thr Gly Glu Lys Pro Tyr Glu Cys His Asp Cys Gly Lys Ser Phe
                 85                  90                  95 agg cag agc acc cac ctc act cgg cac cgg agg atc cac acc ggg gaa      336
Arg Gln Ser Thr His Leu Thr Arg His Arg Arg Ile His Thr Gly Glu
            100                 105                 110 aaa ccg tat aaa tgt aag caa tgt ggg aaa gct ttt gga tgt ccc tca      384
Lys Pro Tyr Lys Cys Lys Gln Cys Gly Lys Ala Phe Gly Cys Pro Ser
        115                 120                 125 aac ctt cga agg cat gga agg act cac acc ggt gaa aaa gcg gcc gct      432
Asn Leu Arg Arg His Gly Arg Thr His Thr Gly Glu Lys Ala Ala Ala
    130                 135                 140 aaa ttc gtg tca gtg aca ttt gaa gat gtg gct gtg ctc ttt act cgg      480
Lys Phe Val Ser Val Thr Phe Glu Asp Val Ala Val Leu Phe Thr Arg
145                 150                 155                 160 gac gag tgg aag aag ctg gat ctg tct cag aga agc ctg tac cgt gag      528
Asp Glu Trp Lys Lys Leu Asp Leu Ser Gln Arg Ser Leu Tyr Arg Glu
                165                 170                 175 gtg atg ctg gag aat tac agc aac ctg gcc tcc atg gca gga ttc ctg      576
Val Met Leu Glu Asn Tyr Ser Asn Leu Ala Ser Met Ala Gly Phe Leu
            180                 185                 190 ttt acc aaa cca aag gtg atc tcc ctg ttg cag caa gga gag gat ccc      624
Phe Thr Lys Pro Lys Val Ile Ser Leu Leu Gln Gln Gly Glu Asp Pro
        195                 200                 205 tgg taa                                                              630
Trp

<210> SEQ ID NO 14
<211> LENGTH: 209
<212> TYPE: PRT
<213> ORGANISM: Artificial Sequence
<220> FEATURE:
<223> OTHER INFORMATION: plasmid sequence

<400> SEQUENCE: 14

Met Val Tyr Pro Tyr Asp Val Pro Asp Tyr Ala Glu Leu Pro Pro Lys
 1               5                  10                  15

Lys Lys Arg Lys Val Gly Ile Arg Ile Pro Gly Glu Lys Pro Tyr Glu
            20                  25                  30

Cys Asp His Cys Gly Lys Ser Phe Ser Gln Ser Ser His Leu Asn Val
        35                  40                  45

His Lys Arg Thr His Thr Gly Glu Lys Pro Tyr Met Cys Ser Glu Cys
    50                  55                  60

Gly Arg Gly Phe Ser Gln Lys Ser Asn Leu Ile Ile His Gln Arg Thr
65                  70                  75                  80

His Thr Gly Glu Lys Pro Tyr Glu Cys His Asp Cys Gly Lys Ser Phe
                85                  90                  95

Arg Gln Ser Thr His Leu Thr Arg His Arg Arg Ile His Thr Gly Glu
            100                 105                 110

Lys Pro Tyr Lys Cys Lys Gln Cys Gly Lys Ala Phe Gly Cys Pro Ser
        115                 120                 125

Asn Leu Arg Arg His Gly Arg Thr His Thr Gly Glu Lys Ala Ala Ala
    130                 135                 140

Lys Phe Val Ser Val Thr Phe Glu Asp Val Ala Val Leu Phe Thr Arg
145                 150                 155                 160
```

```
Asp Glu Trp Lys Lys Leu Asp Leu Ser Gln Arg Ser Leu Tyr Arg Glu
            165                 170                 175

Val Met Leu Glu Asn Tyr Ser Asn Leu Ala Ser Met Ala Gly Phe Leu
        180                 185                 190

Phe Thr Lys Pro Lys Val Ile Ser Leu Leu Gln Gln Gly Glu Asp Pro
        195                 200                 205

Trp

<210> SEQ ID NO 15
<211> LENGTH: 630
<212> TYPE: DNA
<213> ORGANISM: Artificial Sequence
<220> FEATURE:
<223> OTHER INFORMATION: plasmid sequence
<220> FEATURE:
<221> NAME/KEY: CDS
<222> LOCATION: (1)...(627)

<400> SEQUENCE: 15 atg gtg tac ccc tac gac gtg ccc gac tac gcc gaa ttg cct cca aaa        48
Met Val Tyr Pro Tyr Asp Val Pro Asp Tyr Ala Glu Leu Pro Pro Lys
 1               5                  10                  15 aag aag aga aag gta ggg atc cga att ccc ggg gaa aaa ccg tat gag        96
Lys Lys Arg Lys Val Gly Ile Arg Ile Pro Gly Glu Lys Pro Tyr Glu
                20                  25                  30 tgt gat cac tgt gga aaa tcc ttt agc cag agc tct cat ctg aat gtg       144
Cys Asp His Cys Gly Lys Ser Phe Ser Gln Ser Ser His Leu Asn Val
            35                  40                  45 cac aaa aga act cac acc ggg gaa aaa ccg tat gag tgt aat tac tgt       192
His Lys Arg Thr His Thr Gly Glu Lys Pro Tyr Glu Cys Asn Tyr Cys
        50                  55                  60 gga aaa acc ttt agt gtg agc tca acc ctt att aga cat cag aga atc       240
Gly Lys Thr Phe Ser Val Ser Ser Thr Leu Ile Arg His Gln Arg Ile
65                  70                  75                  80 cac acc ggg gaa aaa ccg ttt gcc tgc cct gag tgt cct aag cgc ttc       288
His Thr Gly Glu Lys Pro Phe Ala Cys Pro Glu Cys Pro Lys Arg Phe
                85                  90                  95 atg aga tcc gac aac ctg acc cag cat atc aag acc cac acc ggg gaa       336
Met Arg Ser Asp Asn Leu Thr Gln His Ile Lys Thr His Thr Gly Glu
                100                 105                 110 aaa ccg tat gag tgt cac gat tgc gga aag tcc ttt agg cag agc acc       384
Lys Pro Tyr Glu Cys His Asp Cys Gly Lys Ser Phe Arg Gln Ser Thr
            115                 120                 125 cac ctc act cgg cac cgg agg atc cac acc ggt gaa aaa gcg gcc gct       432
His Leu Thr Arg His Arg Arg Ile His Thr Gly Glu Lys Ala Ala Ala
        130                 135                 140 aaa ttc gtg tca gtg aca ttt gaa gat gtg gct gtg ctc ttt act cgg       480
Lys Phe Val Ser Val Thr Phe Glu Asp Val Ala Val Leu Phe Thr Arg
145                 150                 155                 160 gac gag tgg aag aag ctg gat ctg tct cag aga agc ctg tac cgt gag       528
Asp Glu Trp Lys Lys Leu Asp Leu Ser Gln Arg Ser Leu Tyr Arg Glu
                165                 170                 175 gtg atg ctg gag aat tac agc aac ctg gcc tcc atg gca gga ttc ctg       576
Val Met Leu Glu Asn Tyr Ser Asn Leu Ala Ser Met Ala Gly Phe Leu
                180                 185                 190 ttt acc aaa cca aag gtg atc tcc ctg ttg cag caa gga gag gat ccc       624
Phe Thr Lys Pro Lys Val Ile Ser Leu Leu Gln Gln Gly Glu Asp Pro
            195                 200                 205 tgg taa                                                               630
Trp
```

<210> SEQ ID NO 16
<211> LENGTH: 209
<212> TYPE: PRT
<213> ORGANISM: Artificial Sequence
<220> FEATURE:
<223> OTHER INFORMATION: plasmid sequence

<400> SEQUENCE: 16

```
Met Val Tyr Pro Tyr Asp Val Pro Asp Tyr Ala Glu Leu Pro Pro Lys
 1               5                  10                  15

Lys Lys Arg Lys Val Gly Ile Arg Ile Pro Gly Glu Lys Pro Tyr Glu
            20                  25                  30

Cys Asp His Cys Gly Lys Ser Phe Ser Gln Ser Ser His Leu Asn Val
        35                  40                  45

His Lys Arg Thr His Thr Gly Glu Lys Pro Tyr Glu Cys Asn Tyr Cys
    50                  55                  60

Gly Lys Thr Phe Ser Val Ser Ser Thr Leu Ile Arg His Gln Arg Ile
65                  70                  75                  80

His Thr Gly Glu Lys Pro Phe Ala Cys Pro Glu Cys Pro Lys Arg Phe
                85                  90                  95

Met Arg Ser Asp Asn Leu Thr Gln His Ile Lys Thr His Thr Gly Glu
            100                 105                 110

Lys Pro Tyr Glu Cys His Asp Cys Gly Lys Ser Phe Arg Gln Ser Thr
        115                 120                 125

His Leu Thr Arg His Arg Ile His Thr Gly Glu Lys Ala Ala Ala
    130                 135                 140

Lys Phe Val Ser Val Thr Phe Glu Asp Val Ala Val Leu Phe Thr Arg
145                 150                 155                 160

Asp Glu Trp Lys Lys Leu Asp Leu Ser Gln Arg Ser Leu Tyr Arg Glu
                165                 170                 175

Val Met Leu Glu Asn Tyr Ser Asn Leu Ala Ser Met Ala Gly Phe Leu
            180                 185                 190

Phe Thr Lys Pro Lys Val Ile Ser Leu Leu Gln Gln Gly Glu Asp Pro
        195                 200                 205

Trp
```

<210> SEQ ID NO 17
<211> LENGTH: 1137
<212> TYPE: DNA
<213> ORGANISM: Artificial Sequence
<220> FEATURE:
<223> OTHER INFORMATION: plasmid sequence
<220> FEATURE:
<221> NAME/KEY: CDS
<222> LOCATION: (1)...(1134)

<400> SEQUENCE: 17

```
atg gtg tac ccc tac gac gtg ccc gac tac gcc gaa ttg cct cca aaa       48
Met Val Tyr Pro Tyr Asp Val Pro Asp Tyr Ala Glu Leu Pro Pro Lys
 1               5                  10                  15 aag aag aga aag gta ggg atc cga att ccc ggg gaa aaa ccg ttc cag       96
Lys Lys Arg Lys Val Gly Ile Arg Ile Pro Gly Glu Lys Pro Phe Gln
            20                  25                  30 tgt aaa act tgt cag cga aag ttc tcc cgg tcc gac cac ctg aag acc      144
Cys Lys Thr Cys Gln Arg Lys Phe Ser Arg Ser Asp His Leu Lys Thr
        35                  40                  45 cac acc agg act cat acc ggg gaa aaa ccg tat aag tgc atg gag tgt      192
His Thr Arg Thr His Thr Gly Glu Lys Pro Tyr Lys Cys Met Glu Cys
```

```
                50                      55                      60
ggg aag gct ttt aac cgc agg tca cac ctc aca cgg cac cag cgg att      240
Gly Lys Ala Phe Asn Arg Arg Ser His Leu Thr Arg His Gln Arg Ile
 65                  70                  75                  80 cac acc ggg gaa aaa ccg tat aaa tgc ggc cag tgt ggg aag ttc tac      288
His Thr Gly Glu Lys Pro Tyr Lys Cys Gly Gln Cys Gly Lys Phe Tyr
                 85                  90                  95 tcg cag gtc tcc cac ctc acc cgc cac cag aaa atc cac acc ggt gaa      336
Ser Gln Val Ser His Leu Thr Arg His Gln Lys Ile His Thr Gly Glu
                100                 105                 110 aaa gcg gcc gct aaa ttc tac ctg cca gat aca gac gat cgt cac cgg      384
Lys Ala Ala Ala Lys Phe Tyr Leu Pro Asp Thr Asp Asp Arg His Arg
            115                 120                 125 att gag gag aaa cgt aaa agg aca tat gag acc ttc aag agc atc atg      432
Ile Glu Glu Lys Arg Lys Arg Thr Tyr Glu Thr Phe Lys Ser Ile Met
        130                 135                 140 aag aag agt cct ttc agc gga ccc acc gac ccc cgg cct cca cct cga      480
Lys Lys Ser Pro Phe Ser Gly Pro Thr Asp Pro Arg Pro Pro Pro Arg
145                 150                 155                 160 cgc att gct gtg cct tcc cgc agc tca gct tct gtc ccc aag cca gca      528
Arg Ile Ala Val Pro Ser Arg Ser Ser Ala Ser Val Pro Lys Pro Ala
                165                 170                 175 ccc cag ccc tat ccc ttt acg tca tcc ctg agc acc atc aac tat gat      576
Pro Gln Pro Tyr Pro Phe Thr Ser Ser Leu Ser Thr Ile Asn Tyr Asp
                180                 185                 190 gag ttt ccc acc atg gtg ttt cct tct ggg cag atc agc cag gcc tcg      624
Glu Phe Pro Thr Met Val Phe Pro Ser Gly Gln Ile Ser Gln Ala Ser
            195                 200                 205 gcc ttg gcc ccg gcc cct ccc caa gtc ctg ccc cag gct cca gcc cct      672
Ala Leu Ala Pro Ala Pro Pro Gln Val Leu Pro Gln Ala Pro Ala Pro
        210                 215                 220 gcc cct gct cca gcc atg gta tca gct ctg gcc cag gcc cca gcc cct      720
Ala Pro Ala Pro Ala Met Val Ser Ala Leu Ala Gln Ala Pro Ala Pro
225                 230                 235                 240 gtc cca gtc cta gcc cca ggc cct cct cag gct gtg gcc cca cct gcc      768
Val Pro Val Leu Ala Pro Gly Pro Pro Gln Ala Val Ala Pro Pro Ala
                245                 250                 255 ccc aag ccc acc cag gct ggg gaa gga acg ctg tca gag gcc ctg ctg      816
Pro Lys Pro Thr Gln Ala Gly Glu Gly Thr Leu Ser Glu Ala Leu Leu
                260                 265                 270 cag ctg cag ttt gat gat gaa gac ctg ggg gcc ttg ctt ggc aac agc      864
Gln Leu Gln Phe Asp Asp Glu Asp Leu Gly Ala Leu Leu Gly Asn Ser
            275                 280                 285 aca gac cca gct gtg ttc aca gac ctg gca tcc gtc gac aac tcc gag      912
Thr Asp Pro Ala Val Phe Thr Asp Leu Ala Ser Val Asp Asn Ser Glu
        290                 295                 300 ttt cag cag ctg ctg aac cag ggc ata cct gtg gcc ccc cac aca act      960
Phe Gln Gln Leu Leu Asn Gln Gly Ile Pro Val Ala Pro His Thr Thr
305                 310                 315                 320 gag ccc atg ctg atg gag tac cct gag gct ata act cgc cta gtg aca     1008
Glu Pro Met Leu Met Glu Tyr Pro Glu Ala Ile Thr Arg Leu Val Thr
                325                 330                 335 gcc cag agg ccc ccc gac cca gct cct gct cca ctg ggg gcc ccg ggg     1056
Ala Gln Arg Pro Pro Asp Pro Ala Pro Ala Pro Leu Gly Ala Pro Gly
                340                 345                 350 ctc ccc aat ggc ctc ctt tca gga gat gaa gac ttc tcc tcc att gcg     1104
Leu Pro Asn Gly Leu Leu Ser Gly Asp Glu Asp Phe Ser Ser Ile Ala
            355                 360                 365 gac atg gac ttc tca gcc ctg ctg agt cag taa                         1137
Asp Met Asp Phe Ser Ala Leu Leu Ser Gln
```

```
Asp Met Asp Phe Ser Ala Leu Leu Ser Gln
    370                 375
```

<210> SEQ ID NO 18
<211> LENGTH: 378
<212> TYPE: PRT
<213> ORGANISM: Artificial Sequence
<220> FEATURE:
<223> OTHER INFORMATION: plasmid sequence

<400> SEQUENCE: 18

```
Met Val Tyr Pro Tyr Asp Val Pro Asp Tyr Ala Glu Leu Pro Pro Lys
1               5                   10                  15

Lys Lys Arg Lys Val Gly Ile Arg Ile Pro Gly Glu Lys Pro Phe Gln
            20                  25                  30

Cys Lys Thr Cys Gln Arg Lys Phe Ser Arg Ser Asp His Leu Lys Thr
        35                  40                  45

His Thr Arg Thr His Thr Gly Glu Lys Pro Tyr Lys Cys Met Glu Cys
    50                  55                  60

Gly Lys Ala Phe Asn Arg Arg Ser His Leu Thr Arg His Gln Arg Ile
65                  70                  75                  80

His Thr Gly Glu Lys Pro Tyr Lys Cys Gly Gln Cys Gly Lys Phe Tyr
                85                  90                  95

Ser Gln Val Ser His Leu Thr Arg His Gln Lys Ile His Thr Gly Glu
            100                 105                 110

Lys Ala Ala Lys Phe Tyr Leu Pro Asp Thr Asp Asp Arg His Arg
        115                 120                 125

Ile Glu Glu Lys Arg Lys Arg Thr Tyr Glu Thr Phe Lys Ser Ile Met
    130                 135                 140

Lys Lys Ser Pro Phe Ser Gly Pro Thr Asp Pro Arg Pro Pro Pro Arg
145                 150                 155                 160

Arg Ile Ala Val Pro Ser Arg Ser Ser Ala Ser Val Pro Lys Pro Ala
                165                 170                 175

Pro Gln Pro Tyr Pro Phe Thr Ser Ser Leu Ser Thr Ile Asn Tyr Asp
            180                 185                 190

Glu Phe Pro Thr Met Val Phe Pro Ser Gly Gln Ile Ser Gln Ala Ser
        195                 200                 205

Ala Leu Ala Pro Ala Pro Pro Gln Val Leu Pro Gln Ala Pro Ala Pro
    210                 215                 220

Ala Pro Ala Pro Ala Met Val Ser Ala Leu Ala Gln Ala Pro Ala Pro
225                 230                 235                 240

Val Pro Val Leu Ala Pro Gly Pro Pro Gln Ala Val Ala Pro Ala
                245                 250                 255

Pro Lys Pro Thr Gln Ala Gly Glu Gly Thr Leu Ser Glu Ala Leu Leu
            260                 265                 270

Gln Leu Gln Phe Asp Asp Glu Asp Leu Gly Ala Leu Leu Gly Asn Ser
        275                 280                 285

Thr Asp Pro Ala Val Phe Thr Asp Leu Ala Ser Val Asp Asn Ser Glu
    290                 295                 300

Phe Gln Gln Leu Leu Asn Gln Gly Ile Pro Val Ala Pro His Thr Thr
305                 310                 315                 320

Glu Pro Met Leu Met Glu Tyr Pro Glu Ala Ile Thr Arg Leu Val Thr
                325                 330                 335

Ala Gln Arg Pro Pro Asp Pro Ala Pro Ala Pro Leu Gly Ala Pro Gly
            340                 345                 350
```

```
Leu Pro Asn Gly Leu Leu Ser Gly Asp Glu Asp Phe Ser Ser Ile Ala
            355                 360                 365
Asp Met Asp Phe Ser Ala Leu Leu Ser Gln
    370                 375

<210> SEQ ID NO 19
<211> LENGTH: 1137
<212> TYPE: DNA
<213> ORGANISM: Artificial Sequence
<220> FEATURE:
<223> OTHER INFORMATION: plasmid sequence
<220> FEATURE:
<221> NAME/KEY: CDS
<222> LOCATION: (1)...(1134)

<400> SEQUENCE: 19 atg gtg tac ccc tac gac gtg ccc gac tac gcc gaa ttg cct cca aaa      48
Met Val Tyr Pro Tyr Asp Val Pro Asp Tyr Ala Glu Leu Pro Pro Lys
  1               5                  10                  15 aag aag aga aag gta ggg atc cga att ccc ggg gaa aaa ccg tac aaa      96
Lys Lys Arg Lys Val Gly Ile Arg Ile Pro Gly Glu Lys Pro Tyr Lys
             20                  25                  30 tgt gaa gaa tgt ggc aaa gcc ttt agg cag tcc tca cac ctt act aca     144
Cys Glu Glu Cys Gly Lys Ala Phe Arg Gln Ser Ser His Leu Thr Thr
         35                  40                  45 cat aag ata att cat acc ggg gaa aaa ccg tat aag tgc atg gag tgt     192
His Lys Ile Ile His Thr Gly Glu Lys Pro Tyr Lys Cys Met Glu Cys
     50                  55                  60 ggg aag gct ttt aac cgc agg tca cac ctc aca cgg cac cag cgg att     240
Gly Lys Ala Phe Asn Arg Arg Ser His Leu Thr Arg His Gln Arg Ile
 65                  70                  75                  80 cac acc ggg gaa aaa ccg ttc cag tgt aaa act tgt cag cga aag ttc     288
His Thr Gly Glu Lys Pro Phe Gln Cys Lys Thr Cys Gln Arg Lys Phe
                 85                  90                  95 tcc cgg tcc gac cac ctg aag acc cac acc agg act cat acc ggt gaa     336
Ser Arg Ser Asp His Leu Lys Thr His Thr Arg Thr His Thr Gly Glu
            100                 105                 110 aaa gcg gcc gct aaa ttc tac ctg cca gat aca gac gat cgt cac cgg     384
Lys Ala Ala Ala Lys Phe Tyr Leu Pro Asp Thr Asp Asp Arg His Arg
        115                 120                 125 att gag gag aaa cgt aaa agg aca tat gag acc ttc aag agc atc atg     432
Ile Glu Glu Lys Arg Lys Arg Thr Tyr Glu Thr Phe Lys Ser Ile Met
    130                 135                 140 aag aag agt cct ttc agc gga ccc acc gac ccc cgg cct cca cct cga     480
Lys Lys Ser Pro Phe Ser Gly Pro Thr Asp Pro Arg Pro Pro Pro Arg
145                 150                 155                 160 cgc att gct gtg cct tcc cgc agc tca gct tct gtc ccc aag cca gca     528
Arg Ile Ala Val Pro Ser Arg Ser Ser Ala Ser Val Pro Lys Pro Ala
                165                 170                 175 ccc cag ccc tat ccc ttt acg tca tcc ctg agc acc atc aac tat gat     576
Pro Gln Pro Tyr Pro Phe Thr Ser Ser Leu Ser Thr Ile Asn Tyr Asp
            180                 185                 190 gag ttt ccc acc atg gtg ttt cct tct ggg cag atc agc cag gcc tcg     624
Glu Phe Pro Thr Met Val Phe Pro Ser Gly Gln Ile Ser Gln Ala Ser
        195                 200                 205 gcc ttg gcc ccg gcc cct ccc caa gtc ctg ccc cag gct cca gcc cct     672
Ala Leu Ala Pro Ala Pro Pro Gln Val Leu Pro Gln Ala Pro Ala Pro
    210                 215                 220 gcc cct gct cca gcc atg gta tca gct ctg gcc cag gcc cca gcc cct     720
Ala Pro Ala Pro Ala Met Val Ser Ala Leu Ala Gln Ala Pro Ala Pro
225                 230                 235                 240
```

```
gtc cca gtc cta gcc cca ggc cct cct cag gct gtg gcc cca cct gcc      768
Val Pro Val Leu Ala Pro Gly Pro Pro Gln Ala Val Ala Pro Pro Ala
            245                 250                 255 ccc aag ccc acc cag gct ggg gaa gga acg ctg tca gag gcc ctg ctg      816
Pro Lys Pro Thr Gln Ala Gly Glu Gly Thr Leu Ser Glu Ala Leu Leu
            260                 265                 270 cag ctg cag ttt gat gat gaa gac ctg ggg gcc ttg ctt ggc aac agc      864
Gln Leu Gln Phe Asp Asp Glu Asp Leu Gly Ala Leu Leu Gly Asn Ser
            275                 280                 285 aca gac cca gct gtg ttc aca gac ctg gca tcc gtc gac aac tcc gag      912
Thr Asp Pro Ala Val Phe Thr Asp Leu Ala Ser Val Asp Asn Ser Glu
            290                 295                 300 ttt cag cag ctg ctg aac cag ggc ata cct gtg gcc ccc cac aca act      960
Phe Gln Gln Leu Leu Asn Gln Gly Ile Pro Val Ala Pro His Thr Thr
305                 310                 315                 320 gag ccc atg ctg atg gag tac cct gag gct ata act cgc cta gtg aca     1008
Glu Pro Met Leu Met Glu Tyr Pro Glu Ala Ile Thr Arg Leu Val Thr
            325                 330                 335 gcc cag agg ccc ccc gac cca gct cct gct cca ctg ggg gcc ccg ggg     1056
Ala Gln Arg Pro Pro Asp Pro Ala Pro Ala Pro Leu Gly Ala Pro Gly
            340                 345                 350 ctc ccc aat ggc ctc ctt tca gga gat gaa gac ttc tcc tcc att gcg     1104
Leu Pro Asn Gly Leu Leu Ser Gly Asp Glu Asp Phe Ser Ser Ile Ala
            355                 360                 365 gac atg gac ttc tca gcc ctg ctg agt cag taa                         1137
Asp Met Asp Phe Ser Ala Leu Leu Ser Gln
            370                 375

<210> SEQ ID NO 20
<211> LENGTH: 378
<212> TYPE: PRT
<213> ORGANISM: Artificial Sequence
<220> FEATURE:
<223> OTHER INFORMATION: plasmid sequence

<400> SEQUENCE: 20

Met Val Tyr Pro Tyr Asp Val Pro Asp Tyr Ala Glu Leu Pro Pro Lys
1               5                   10                  15

Lys Lys Arg Lys Val Gly Ile Arg Ile Pro Gly Glu Lys Pro Tyr Lys
            20                  25                  30

Cys Glu Glu Cys Gly Lys Ala Phe Arg Gln Ser Ser His Leu Thr Thr
        35                  40                  45

His Lys Ile Ile His Thr Gly Glu Lys Pro Tyr Lys Cys Met Glu Cys
    50                  55                  60

Gly Lys Ala Phe Asn Arg Arg Ser His Leu Thr Arg His Gln Arg Ile
65                  70                  75                  80

His Thr Gly Glu Lys Pro Phe Gln Cys Lys Thr Cys Gln Arg Lys Phe
                85                  90                  95

Ser Arg Ser Asp His Leu Lys Thr His Thr Arg Thr His Thr Gly Glu
            100                 105                 110

Lys Ala Ala Ala Lys Phe Tyr Leu Pro Asp Thr Asp Asp Arg His Arg
        115                 120                 125

Ile Glu Glu Lys Arg Lys Arg Thr Tyr Glu Thr Phe Lys Ser Ile Met
    130                 135                 140

Lys Lys Ser Pro Phe Ser Gly Pro Thr Asp Pro Arg Pro Pro Pro Arg
145                 150                 155                 160

Arg Ile Ala Val Pro Ser Arg Ser Ser Ala Ser Val Pro Lys Pro Ala
                165                 170                 175
```

```
Pro Gln Pro Tyr Pro Phe Thr Ser Ser Leu Ser Thr Ile Asn Tyr Asp
            180                 185                 190

Glu Phe Pro Thr Met Val Phe Pro Ser Gly Gln Ile Ser Gln Ala Ser
        195                 200                 205

Ala Leu Ala Pro Ala Pro Gln Val Leu Pro Gln Ala Pro Ala Pro
    210                 215                 220

Ala Pro Ala Pro Ala Met Val Ser Ala Leu Ala Gln Ala Pro Ala Pro
225                 230                 235                 240

Val Pro Val Leu Ala Pro Gly Pro Pro Gln Ala Val Ala Pro Ala
                245                 250                 255

Pro Lys Pro Thr Gln Ala Gly Glu Gly Thr Leu Ser Glu Ala Leu Leu
            260                 265                 270

Gln Leu Gln Phe Asp Asp Glu Asp Leu Gly Ala Leu Leu Gly Asn Ser
        275                 280                 285

Thr Asp Pro Ala Val Phe Thr Asp Leu Ala Ser Val Asp Asn Ser Glu
    290                 295                 300

Phe Gln Gln Leu Leu Asn Gln Gly Ile Pro Val Ala Pro His Thr Thr
305                 310                 315                 320

Glu Pro Met Leu Met Glu Tyr Pro Glu Ala Ile Thr Arg Leu Val Thr
                325                 330                 335

Ala Gln Arg Pro Pro Asp Pro Ala Pro Ala Pro Leu Gly Ala Pro Gly
            340                 345                 350

Leu Pro Asn Gly Leu Leu Ser Gly Asp Glu Asp Phe Ser Ser Ile Ala
        355                 360                 365

Asp Met Asp Phe Ser Ala Leu Leu Ser Gln
    370                 375

<210> SEQ ID NO 21
<211> LENGTH: 83
<212> TYPE: PRT
<213> ORGANISM: Artificial Sequence
<220> FEATURE:
<223> OTHER INFORMATION: plasmid sequence

<400> SEQUENCE: 21

Phe Glu Cys Lys Asp Cys Gly Lys Ala Phe Ile Gln Lys Ser Asn Leu
1               5                   10                  15

Ile Arg His Gln Arg Thr His Thr Gly Glu Lys Pro Tyr Ala Cys Pro
            20                  25                  30

Val Glu Ser Cys Asp Arg Arg Phe Ser Asp Ser Ser Asn Leu Thr Arg
        35                  40                  45

His Ile Arg Ile His Thr Gly Glu Lys Pro Tyr Ala Cys Pro Val Glu
    50                  55                  60

Ser Cys Asp Arg Arg Phe Ser Asp Ser Ser Asn Leu Thr Arg His Ile
65                  70                  75                  80

Arg Ile His

<210> SEQ ID NO 22
<211> LENGTH: 110
<212> TYPE: PRT
<213> ORGANISM: Artificial Sequence
<220> FEATURE:
<223> OTHER INFORMATION: plasmid sequence

<400> SEQUENCE: 22

Ser Cys Gly Ile Cys Gly Lys Ser Phe Ser Asp Ser Ser Ala Lys Arg
1               5                   10                  15
```

```
Arg His Cys Ile Leu His Thr Gly Glu Lys Pro Tyr Val Cys Asp Val
            20                  25                  30

Glu Gly Cys Thr Trp Lys Phe Ala Arg Ser Asp Lys Leu Asn Arg His
            35                  40                  45

Lys Lys Arg His Thr Gly Glu Lys Pro Tyr Val Cys Asp Val Glu Gly
 50                  55                  60

Cys Thr Trp Lys Phe Ala Arg Ser Asp Glu Leu Asn Arg His Lys Lys
 65                  70                  75                  80

Arg His Thr Gly Glu Lys Pro Tyr Glu Cys His Asp Cys Gly Lys Ser
             85                  90                  95

Phe Arg Gln Ser Thr His Leu Thr Arg His Arg Arg Ile His
            100                 105                 110

<210> SEQ ID NO 23
<211> LENGTH: 107
<212> TYPE: PRT
<213> ORGANISM: Artificial Sequence
<220> FEATURE:
<223> OTHER INFORMATION: plasmid sequence

<400> SEQUENCE: 23

Tyr Glu Cys Asp His Cys Gly Lys Ser Phe Ser Gln Ser Ser His Leu
 1               5                  10                  15

Asn Val His Lys Arg Thr His Thr Gly Glu Lys Pro Tyr Arg Cys Glu
             20                  25                  30

Glu Cys Gly Lys Ala Phe Arg Trp Pro Ser Asn Leu Thr Arg His Lys
             35                  40                  45

Arg Ile His Thr Gly Glu Lys Pro Tyr Arg Cys Glu Glu Cys Gly Lys
 50                  55                  60

Ala Phe Arg Trp Pro Ser Asn Leu Thr Arg His Lys Arg Ile His Thr
 65                  70                  75                  80

Gly Glu Lys Pro Phe Ala Cys Pro Glu Cys Pro Lys Arg Phe Met Arg
             85                  90                  95

Ser Asp Asn Leu Thr Gln His Ile Lys Thr His
            100                 105

<210> SEQ ID NO 24
<211> LENGTH: 26
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(26)
<223> OTHER INFORMATION: Xaa = any amino acid

<400> SEQUENCE: 24

Cys Xaa Xaa Xaa Xaa Cys Xaa Xaa Xaa Xaa Xaa Gln Xaa Ser Asn
 1               5                  10                  15

Xaa Xaa Arg His Xaa Xaa Xaa Xaa Xaa His
             20                  25

<210> SEQ ID NO 25
<211> LENGTH: 26
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(26)
```

<223> OTHER INFORMATION: Xaa = any amino acid

<400> SEQUENCE: 25

Cys Xaa Xaa Xaa Xaa Xaa Cys Xaa Xaa Xaa Xaa Xaa Asp Xaa Ser Asn
 1               5                  10                  15

Xaa Xaa Arg His Xaa Xaa Xaa Xaa Xaa His
            20                  25

<210> SEQ ID NO 26
<211> LENGTH: 26
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(26)
<223> OTHER INFORMATION: Xaa = any amino acid

<400> SEQUENCE: 26

Cys Xaa Xaa Xaa Xaa Xaa Cys Xaa Xaa Xaa Xaa Xaa Asp Xaa Ser Asn
 1               5                  10                  15

Xaa Xaa Arg His Xaa Xaa Xaa Xaa Xaa His
            20                  25

<210> SEQ ID NO 27
<211> LENGTH: 26
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(26)
<223> OTHER INFORMATION: Xaa = any amino acid

<400> SEQUENCE: 27

Cys Xaa Xaa Xaa Xaa Xaa Cys Xaa Xaa Xaa Xaa Xaa Asp Xaa Ser Ala
 1               5                  10                  15

Xaa Xaa Arg His Xaa Xaa Xaa Xaa Xaa His
            20                  25

<210> SEQ ID NO 28
<211> LENGTH: 26
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(26)
<223> OTHER INFORMATION: Xaa = any amino acid

<400> SEQUENCE: 28

Cys Xaa Xaa Xaa Xaa Xaa Cys Xaa Xaa Xaa Xaa Arg Xaa Asp Lys
 1               5                  10                  15

Xaa Xaa Arg His Xaa Xaa Xaa Xaa Xaa His
            20                  25

<210> SEQ ID NO 29
<211> LENGTH: 26
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT

```
<222> LOCATION: (1)...(26)
<223> OTHER INFORMATION: Xaa = any amino acid

<400> SEQUENCE: 29

Cys Xaa Xaa Xaa Xaa Xaa Cys Xaa Xaa Xaa Xaa Xaa Arg Xaa Asp Glu
 1               5                  10                  15

Xaa Xaa Arg His Xaa Xaa Xaa Xaa Xaa His
            20                  25

<210> SEQ ID NO 30
<211> LENGTH: 26
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(26)
<223> OTHER INFORMATION: Xaa = any amino acid

<400> SEQUENCE: 30

Cys Xaa Xaa Xaa Xaa Xaa Cys Xaa Xaa Xaa Xaa Xaa Gln Xaa Thr His
 1               5                  10                  15

Xaa Xaa Arg His Xaa Xaa Xaa Xaa Xaa His
            20                  25

<210> SEQ ID NO 31
<211> LENGTH: 26
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(26)
<223> OTHER INFORMATION: Xaa = any amino acid

<400> SEQUENCE: 31

Cys Xaa Xaa Xaa Xaa Xaa Cys Xaa Xaa Xaa Xaa Xaa Gln Xaa Ser His
 1               5                  10                  15

Xaa Xaa Val His Xaa Xaa Xaa Xaa Xaa His
            20                  25

<210> SEQ ID NO 32
<211> LENGTH: 26
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(26)
<223> OTHER INFORMATION: Xaa = any amino acid

<400> SEQUENCE: 32

Cys Xaa Xaa Xaa Xaa Xaa Cys Xaa Xaa Xaa Xaa Trp Xaa Ser Asn
 1               5                  10                  15

Xaa Xaa Arg His Xaa Xaa Xaa Xaa Xaa His
            20                  25

<210> SEQ ID NO 33
<211> LENGTH: 26
<212> TYPE: PRT
<213> ORGANISM: Artificial Sequence
<220> FEATURE:
<223> OTHER INFORMATION: purified polypeptide
<220> FEATURE:
```

```
<221> NAME/KEY: VARIANT
<222> LOCATION: (1)...(26)
<223> OTHER INFORMATION: Xaa = any amino acid

<400> SEQUENCE: 33

Cys Xaa Xaa Xaa Xaa Xaa Cys Xaa Xaa Xaa Xaa Xaa Trp Xaa Ser Asn
  1               5                  10                  15

Xaa Xaa Arg His Xaa Xaa Xaa Xaa Xaa His
            20                  25

<210> SEQ ID NO 34
<211> LENGTH: 26
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(26)
<223> OTHER INFORMATION: Xaa = any amino acid

<400> SEQUENCE: 34

Cys Xaa Xaa Xaa Xaa Xaa Cys Xaa Xaa Xaa Xaa Xaa Arg Xaa Asp Asn
  1               5                  10                  15

Xaa Xaa Lys His Xaa Xaa Xaa Xaa Xaa His
            20                  25

<210> SEQ ID NO 35
<211> LENGTH: 96
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(96)
<223> OTHER INFORMATION: Xaa = any amino acid

<400> SEQUENCE: 35

Xaa Xaa Cys Xaa Xaa Xaa Xaa Xaa Cys Xaa Xaa Xaa Xaa Xaa Xaa Xaa
  1               5                  10                  15

Xaa Xaa Xaa Xaa Arg His Xaa Xaa Xaa Xaa Xaa His Xaa Xaa Xaa Xaa
            20                  25                  30

Xaa Xaa Xaa Xaa Cys Xaa Xaa Xaa Xaa Xaa Cys Xaa Xaa Xaa Xaa Xaa
            35                  40                  45

Xaa Xaa Xaa Xaa Xaa Xaa Arg His Xaa Xaa Xaa Xaa Xaa His Xaa Xaa
 50                  55                  60

Xaa Xaa Xaa Xaa Xaa Cys Xaa Xaa Xaa Xaa Cys Xaa Xaa Xaa
 65                  70                  75                  80

Xaa Xaa Xaa Xaa Xaa Xaa Xaa Xaa Arg His Xaa Xaa Xaa Xaa Xaa His
            85                  90                  95

<210> SEQ ID NO 36
<211> LENGTH: 94
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(94)
<223> OTHER INFORMATION: Xaa = any amino acid

<400> SEQUENCE: 36

Cys Xaa Xaa Xaa Xaa Xaa Cys Xaa Xaa Xaa Xaa Xaa Gln Xaa Ser Asn
  1               5                  10                  15
```

```
                1               5                   10                  15
Xaa Xaa Arg His Xaa Xaa Xaa Xaa His Xaa Xaa Xaa Xaa Xaa
                20                  25                  30

Xaa Xaa Cys Xaa Xaa Xaa Xaa Cys Xaa Xaa Xaa Xaa Gln Xaa
                35                  40                  45

Ser Asn Xaa Xaa Lys His Xaa Xaa Xaa Xaa His Xaa Xaa Xaa Xaa
        50                  55                  60

Xaa Xaa Xaa Xaa Cys Xaa Xaa Xaa Xaa Cys Xaa Xaa Xaa Xaa
65                  70                  75                  80

Cys Xaa Ser Asn Xaa Xaa Arg His Xaa Xaa Xaa Xaa His
                85                  90
```

<210> SEQ ID NO 37
<211> LENGTH: 60
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(60)
<223> OTHER INFORMATION: Xaa = any amino acid

<400> SEQUENCE: 37

```
Cys Xaa Xaa Xaa Xaa Xaa Cys Xaa Xaa Xaa Xaa Gln Xaa Ser Asn
1               5                   10                  15

Xaa Xaa Arg His Xaa Xaa Xaa Xaa His Xaa Xaa Xaa Xaa Xaa
                20                  25                  30

Xaa Xaa Cys Xaa Xaa Xaa Xaa Cys Xaa Xaa Xaa Xaa Gln Xaa
                35                  40                  45

Ser Asn Xaa Xaa Lys His Xaa Xaa Xaa Xaa His
        50                  55                  60
```

<210> SEQ ID NO 38
<211> LENGTH: 60
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(60)
<223> OTHER INFORMATION: Xaa = any amino acid

<400> SEQUENCE: 38

```
Cys Xaa Xaa Xaa Xaa Xaa Cys Xaa Xaa Xaa Xaa Gln Xaa Ser Asn
1               5                   10                  15

Xaa Xaa Lys His Xaa Xaa Xaa Xaa His Xaa Xaa Xaa Xaa Xaa
                20                  25                  30

Xaa Xaa Cys Xaa Xaa Xaa Xaa Cys Xaa Xaa Xaa Xaa Cys Xaa
                35                  40                  45

Ser Asn Xaa Xaa Arg His Xaa Xaa Xaa Xaa His
        50                  55                  60
```

<210> SEQ ID NO 39
<211> LENGTH: 128
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(128)

<223> OTHER INFORMATION: Xaa = any amino acid

<400> SEQUENCE: 39

```
Cys Xaa Xaa Xaa Xaa Cys Xaa Xaa Xaa Xaa Xaa Arg Xaa Asp Lys
 1               5                  10                  15

Xaa Xaa Arg His Xaa Xaa Xaa Xaa Xaa His Xaa Xaa Xaa Xaa Xaa
             20                  25                  30

Xaa Xaa Cys Xaa Xaa Xaa Xaa Cys Xaa Xaa Xaa Xaa Gln Xaa
         35                  40                  45

Thr His Xaa Xaa Arg His Xaa Xaa Xaa Xaa Xaa His Xaa Xaa Xaa Xaa
         50                  55                  60

Xaa Xaa Xaa Xaa Cys Xaa Xaa Xaa Xaa Xaa Cys Xaa Xaa Xaa Xaa
 65                  70                  75                  80

Val Xaa Ser Thr Xaa Xaa Arg His Xaa Xaa Xaa Xaa Xaa His Xaa Xaa
                 85                  90                  95

Xaa Xaa Xaa Xaa Xaa Xaa Cys Xaa Xaa Xaa Xaa Cys Xaa Xaa Xaa
                 100                 105                 110

Xaa Xaa Arg Xaa Asp Lys Xaa Xaa Arg His Xaa Xaa Xaa Xaa Xaa His
         115                 120                 125
```

<210> SEQ ID NO 40
<211> LENGTH: 94
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(94)
<223> OTHER INFORMATION: Xaa = any amino acid

<400> SEQUENCE: 40

```
Cys Xaa Xaa Xaa Xaa Cys Xaa Xaa Xaa Xaa Xaa Arg Xaa Asp Lys
 1               5                  10                  15

Xaa Xaa Arg His Xaa Xaa Xaa Xaa Xaa His Xaa Xaa Xaa Xaa Xaa
             20                  25                  30

Xaa Xaa Cys Xaa Xaa Xaa Xaa Cys Xaa Xaa Xaa Xaa Gln Xaa
         35                  40                  45

Thr His Xaa Xaa Arg His Xaa Xaa Xaa Xaa Xaa His Xaa Xaa Xaa Xaa
         50                  55                  60

Xaa Xaa Xaa Xaa Cys Xaa Xaa Xaa Xaa Xaa Cys Xaa Xaa Xaa Xaa
 65                  70                  75                  80

Val Xaa Ser Thr Xaa Xaa Arg His Xaa Xaa Xaa Xaa Xaa His
                 85                  90
```

<210> SEQ ID NO 41
<211> LENGTH: 94
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(94)
<223> OTHER INFORMATION: Xaa = any amino acid

<400> SEQUENCE: 41

```
Cys Xaa Xaa Xaa Xaa Cys Xaa Xaa Xaa Xaa Xaa Gln Xaa Thr His
 1               5                  10                  15

Xaa Xaa Arg His Xaa Xaa Xaa Xaa Xaa His Xaa Xaa Xaa Xaa Xaa
             20                  25                  30
```

Xaa Xaa Cys Xaa Xaa Xaa Xaa Cys Xaa Xaa Xaa Xaa Val Xaa
            35                  40                  45

Ser Thr Xaa Xaa Arg His Xaa Xaa Xaa Xaa His Xaa Xaa Xaa Xaa
        50                  55                  60

Xaa Xaa Xaa Xaa Cys Xaa Xaa Xaa Xaa Cys Xaa Xaa Xaa Xaa
65              70                  75                  80

Arg Xaa Asp Lys Xaa Xaa Arg His Xaa Xaa Xaa Xaa Xaa His
            85                  90

<210> SEQ ID NO 42
<211> LENGTH: 60
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(60)
<223> OTHER INFORMATION: Xaa = any amino acid

<400> SEQUENCE: 42

Cys Xaa Xaa Xaa Xaa Xaa Cys Xaa Xaa Xaa Xaa Arg Xaa Asp Lys
1               5                   10                  15

Xaa Xaa Arg His Xaa Xaa Xaa Xaa His Xaa Xaa Xaa Xaa Xaa
            20                  25                  30

Xaa Xaa Cys Xaa Xaa Xaa Xaa Cys Xaa Xaa Xaa Xaa Gln Xaa
            35                  40                  45

Thr His Xaa Xaa Arg His Xaa Xaa Xaa Xaa Xaa His
    50                  55                  60

<210> SEQ ID NO 43
<211> LENGTH: 60
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(60)
<223> OTHER INFORMATION: Xaa = any amino acid

<400> SEQUENCE: 43

Cys Xaa Xaa Xaa Xaa Xaa Cys Xaa Xaa Xaa Xaa Val Xaa Ser Thr
1               5                   10                  15

Xaa Xaa Arg His Xaa Xaa Xaa Xaa His Xaa Xaa Xaa Xaa Xaa
            20                  25                  30

Xaa Xaa Cys Xaa Xaa Xaa Xaa Cys Xaa Xaa Xaa Xaa Arg Xaa
            35                  40                  45

Asp Lys Xaa Xaa Arg His Xaa Xaa Xaa Xaa Xaa His
    50                  55                  60

<210> SEQ ID NO 44
<211> LENGTH: 94
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(94)
<223> OTHER INFORMATION: Xaa = any amino acid

<400> SEQUENCE: 44

```
Cys Xaa Xaa Xaa Xaa Cys Xaa Xaa Xaa Xaa Arg Xaa Ser His
 1               5                  10                  15

Xaa Xaa Arg His Xaa Xaa Xaa Xaa His Xaa Xaa Xaa Xaa Xaa
             20                  25                  30

Xaa Xaa Cys Xaa Xaa Xaa Xaa Cys Xaa Xaa Xaa Xaa Arg Xaa
         35                  40                  45

Asp His Xaa Xaa Thr His Xaa Xaa Xaa Xaa His Xaa Xaa Xaa
     50                  55                  60

Xaa Xaa Xaa Xaa Cys Xaa Xaa Xaa Xaa Cys Xaa Xaa Xaa Xaa
 65              70                  75                  80

Val Xaa Ser Ser Xaa Xaa Arg His Xaa Xaa Xaa Xaa Xaa His
             85                  90
```

<210> SEQ ID NO 45
<211> LENGTH: 60
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(60)
<223> OTHER INFORMATION: Xaa = any amino acid

<400> SEQUENCE: 45

```
Cys Xaa Xaa Xaa Xaa Cys Xaa Xaa Xaa Xaa Xaa Arg Xaa Ser His
 1               5                  10                  15

Xaa Arg His Xaa Xaa Xaa Xaa Xaa His Xaa Xaa Xaa Xaa Xaa
             20                  25                  30

Xaa Xaa Cys Xaa Xaa Xaa Xaa Cys Xaa Xaa Xaa Xaa Arg Xaa
         35                  40                  45

Asp His Xaa Xaa Thr His Xaa Xaa Xaa Xaa Xaa His
     50                  55                  60
```

<210> SEQ ID NO 46
<211> LENGTH: 60
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(60)
<223> OTHER INFORMATION: Xaa = any amino acid

<400> SEQUENCE: 46

```
Cys Xaa Xaa Xaa Xaa Cys Xaa Xaa Xaa Xaa Xaa Arg Xaa Asp His
 1               5                  10                  15

Xaa Xaa Thr His Xaa Xaa Xaa Xaa His Xaa Xaa Xaa Xaa Xaa
             20                  25                  30

Xaa Xaa Cys Xaa Xaa Xaa Xaa Cys Xaa Xaa Xaa Xaa Val Xaa
         35                  40                  45

Ser Ser Xaa Xaa Arg His Xaa Xaa Xaa Xaa Xaa His
     50                  55                  60
```

<210> SEQ ID NO 47
<211> LENGTH: 94
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(94)
<223> OTHER INFORMATION: Xaa = any amino acid

<400> SEQUENCE: 47

Cys Xaa Xaa Xaa Xaa Xaa Cys Xaa Xaa Xaa Xaa Xaa Gln Xaa Ser Asn
1               5                   10                  15

Xaa Xaa Arg His Xaa Xaa Xaa Xaa Xaa His Xaa Xaa Xaa Xaa Xaa Xaa
            20                  25                  30

Xaa Xaa Cys Xaa Xaa Xaa Xaa Xaa Cys Xaa Xaa Xaa Xaa Xaa Asp Xaa
        35                  40                  45

Ser Asn Xaa Xaa Arg His Xaa Xaa Xaa Xaa Xaa His Xaa Xaa Xaa Xaa
50                  55                  60

Xaa Xaa Xaa Xaa Cys Xaa Xaa Xaa Xaa Xaa Cys Xaa Xaa Xaa Xaa Xaa
65                  70                  75                  80

Asp Xaa Ser Asn Xaa Xaa Arg His Xaa Xaa Xaa Xaa Xaa His
                85                  90

<210> SEQ ID NO 48
<211> LENGTH: 60
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(60)
<223> OTHER INFORMATION: Xaa = any amino acid

<400> SEQUENCE: 48

Cys Xaa Xaa Xaa Xaa Xaa Cys Xaa Xaa Xaa Xaa Xaa Gln Xaa Ser Asn
1               5                   10                  15

Xaa Xaa Arg His Xaa Xaa Xaa Xaa Xaa His Xaa Xaa Xaa Xaa Xaa Xaa
            20                  25                  30

Xaa Xaa Cys Xaa Xaa Xaa Xaa Xaa Cys Xaa Xaa Xaa Xaa Xaa Asp Xaa
        35                  40                  45

Ser Asn Xaa Xaa Arg His Xaa Xaa Xaa Xaa Xaa His
50                  55                  60

<210> SEQ ID NO 49
<211> LENGTH: 60
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(60)
<223> OTHER INFORMATION: Xaa = any amino acid

<400> SEQUENCE: 49

Cys Xaa Xaa Xaa Xaa Xaa Cys Xaa Xaa Xaa Xaa Xaa Asp Xaa Ser Asn
1               5                   10                  15

Xaa Xaa Arg His Xaa Xaa Xaa Xaa Xaa His Xaa Xaa Xaa Xaa Xaa Xaa
            20                  25                  30

Xaa Xaa Cys Xaa Xaa Xaa Xaa Xaa Cys Xaa Xaa Xaa Xaa Xaa Asp Xaa
        35                  40                  45

Ser Asn Xaa Xaa Arg His Xaa Xaa Xaa Xaa Xaa His
50                  55                  60

<210> SEQ ID NO 50
<211> LENGTH: 128
<212> TYPE: PRT

<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(128)
<223> OTHER INFORMATION: Xaa = any amino acid

<400> SEQUENCE: 50

```
Cys Xaa Xaa Xaa Xaa Cys Xaa Xaa Xaa Xaa Gln Xaa Ser His
 1               5                  10                 15

Xaa Xaa Val His Xaa Xaa Xaa Xaa Xaa His Xaa Xaa Xaa Xaa Xaa
            20                  25                  30

Xaa Xaa Cys Xaa Xaa Xaa Xaa Cys Xaa Xaa Xaa Xaa Trp Xaa
        35                  40                  45

Ser Asn Xaa Xaa Arg His Xaa Xaa Xaa Xaa Xaa His Xaa Xaa Xaa Xaa
 50                  55                  60

Xaa Xaa Xaa Xaa Cys Xaa Xaa Xaa Xaa Cys Xaa Xaa Xaa Xaa
 65              70                  75                  80

Trp Xaa Ser Asn Xaa Xaa Arg His Xaa Xaa Xaa Xaa Xaa His Xaa Xaa
             85                  90                  95

Xaa Xaa Xaa Xaa Xaa Cys Xaa Xaa Xaa Xaa Cys Xaa Xaa Xaa
            100                 105                 110

Xaa Xaa Arg Xaa Asp Asn Xaa Xaa Gln His Xaa Xaa Xaa Xaa Xaa His
        115                 120                 125
```

<210> SEQ ID NO 51
<211> LENGTH: 94
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(94)
<223> OTHER INFORMATION: Xaa = any amino acid

<400> SEQUENCE: 51

```
Cys Xaa Xaa Xaa Xaa Cys Xaa Xaa Xaa Xaa Trp Xaa Ser Asn
 1               5                  10                 15

Xaa Xaa Arg His Xaa Xaa Xaa Xaa Xaa His Xaa Xaa Xaa Xaa Xaa
            20                  25                  30

Xaa Xaa Cys Xaa Xaa Xaa Xaa Cys Xaa Xaa Xaa Xaa Trp Xaa
        35                  40                  45

Ser Asn Xaa Xaa Arg His Xaa Xaa Xaa Xaa Xaa His Xaa Xaa Xaa Xaa
 50                  55                  60

Xaa Xaa Xaa Xaa Cys Xaa Xaa Xaa Xaa Cys Xaa Xaa Xaa Xaa
 65              70                  75                  80

Arg Xaa Asp Asn Xaa Xaa Gln His Xaa Xaa Xaa Xaa Xaa His
             85                  90
```

<210> SEQ ID NO 52
<211> LENGTH: 94
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(94)
<223> OTHER INFORMATION: Xaa = any amino acid

<400> SEQUENCE: 52

```
Cys Xaa Xaa Xaa Xaa Cys Xaa Xaa Xaa Xaa Gln Xaa Ser His
1               5                   10                  15

Xaa Xaa Val His Xaa Xaa Xaa Xaa Xaa His Xaa Xaa Xaa Xaa Xaa
            20                  25                  30

Xaa Xaa Cys Xaa Xaa Xaa Xaa Cys Xaa Xaa Xaa Xaa Trp Xaa
            35                  40                  45

Ser Asn Xaa Xaa Arg His Xaa Xaa Xaa Xaa Xaa His Xaa Xaa Xaa Xaa
        50                  55                  60

Xaa Xaa Xaa Xaa Cys Xaa Xaa Xaa Xaa Cys Xaa Xaa Xaa Xaa
65              70                  75                  80

Trp Xaa Ser Asn Xaa Xaa Arg His Xaa Xaa Xaa Xaa Xaa His
            85                  90

<210> SEQ ID NO 53
<211> LENGTH: 128
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(128)
<223> OTHER INFORMATION: Xaa = any amino acid

<400> SEQUENCE: 53

Cys Xaa Xaa Xaa Xaa Cys Xaa Xaa Xaa Xaa Xaa Asp Xaa Ser Ala
1               5                   10                  15

Xaa Xaa Arg His Xaa Xaa Xaa Xaa Xaa His Xaa Xaa Xaa Xaa Xaa
            20                  25                  30

Xaa Xaa Cys Xaa Xaa Xaa Xaa Cys Xaa Xaa Xaa Xaa Arg Xaa
            35                  40                  45

Asp Lys Xaa Xaa Arg His Xaa Xaa Xaa Xaa Xaa His Xaa Xaa Xaa Xaa
        50                  55                  60

Xaa Xaa Xaa Xaa Cys Xaa Xaa Xaa Xaa Cys Xaa Xaa Xaa Xaa
65              70                  75                  80

Arg Xaa Asp Glu Xaa Xaa Arg His Xaa Xaa Xaa Xaa Xaa His Xaa Xaa
            85                  90                  95

Xaa Xaa Xaa Xaa Xaa Xaa Cys Xaa Xaa Xaa Xaa Cys Xaa Xaa Xaa
                100                 105                 110

Xaa Xaa Gln Xaa Thr His Xaa Xaa Arg His Xaa Xaa Xaa Xaa Xaa His
        115                 120                 125

<210> SEQ ID NO 54
<211> LENGTH: 93
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(93)
<223> OTHER INFORMATION: Xaa = any amino acid

<400> SEQUENCE: 54

Cys Xaa Xaa Xaa Xaa Cys Xaa Xaa Xaa Xaa Arg Xaa Asp Lys
1               5                   10                  15

Xaa Xaa Arg His Xaa Xaa Xaa Xaa Xaa His Xaa Xaa Xaa Xaa Xaa
            20                  25                  30

Xaa Xaa Cys Xaa Xaa Xaa Xaa Cys Xaa Xaa Xaa Xaa Arg Xaa
            35                  40                  45
```

Asp Glu Xaa Xaa Arg His Xaa Xaa Xaa Xaa His Xaa Xaa Xaa Xaa
         50                  55                  60

Xaa Xaa Xaa Xaa Cys Xaa Xaa Xaa Xaa Cys Xaa Xaa Xaa Xaa
 65                  70                  75                  80

Gln Xaa Thr His Xaa Xaa Arg His Xaa Xaa Xaa Xaa Xaa
             85                  90

<210> SEQ ID NO 55
<211> LENGTH: 94
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(94)
<223> OTHER INFORMATION: Xaa = any amino acid

<400> SEQUENCE: 55

Cys Xaa Xaa Xaa Xaa Xaa Cys Xaa Xaa Xaa Xaa Xaa Asp Xaa Ser Ala
 1               5                  10                  15

Xaa Xaa Arg His Xaa Xaa Xaa Xaa Xaa His Xaa Xaa Xaa Xaa Xaa
             20                  25                  30

Xaa Xaa Cys Xaa Xaa Xaa Xaa Cys Xaa Xaa Xaa Xaa Xaa Arg Xaa
         35                  40                  45

Asp Lys Xaa Xaa Arg His Xaa Xaa Xaa Xaa Xaa His Xaa Xaa Xaa Xaa
 50                  55                  60

Xaa Xaa Xaa Xaa Cys Xaa Xaa Xaa Xaa Cys Xaa Xaa Xaa Xaa Xaa
 65                  70                  75                  80

Arg Xaa Asp Glu Xaa Xaa Arg His Xaa Xaa Xaa Xaa Xaa His
             85                  90

<210> SEQ ID NO 56
<211> LENGTH: 128
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(128)
<223> OTHER INFORMATION: Xaa = any amino acid

<400> SEQUENCE: 56

Cys Xaa Xaa Xaa Xaa Xaa Cys Xaa Xaa Xaa Xaa Arg Xaa Asp His
 1               5                  10                  15

Xaa Xaa Thr His Xaa Xaa Xaa Xaa Xaa His Xaa Xaa Xaa Xaa Xaa
             20                  25                  30

Xaa Xaa Cys Xaa Xaa Xaa Xaa Cys Xaa Xaa Xaa Xaa Gln Xaa
         35                  40                  45

Ser Asn Xaa Xaa Val His Xaa Xaa Xaa Xaa His Xaa Xaa Xaa Xaa
 50                  55                  60

Xaa Xaa Xaa Xaa Cys Xaa Xaa Xaa Xaa Cys Xaa Xaa Xaa Xaa Xaa
 65                  70                  75                  80

Gln Xaa Thr His Xaa Xaa Arg His Xaa Xaa Xaa Xaa His Xaa Xaa
             85                  90                  95

Xaa Xaa Xaa Xaa Xaa Cys Xaa Xaa Xaa Xaa Xaa Cys Xaa Xaa
             100                 105                 110

Xaa Xaa Gln Xaa Phe Asn Xaa Xaa Arg His Xaa Xaa Xaa Xaa Xaa His
         115                 120                 125

<210> SEQ ID NO 57
<211> LENGTH: 94
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(94)
<223> OTHER INFORMATION: Xaa = any amino acid

<400> SEQUENCE: 57

Cys Xaa Xaa Xaa Xaa Cys Xaa Xaa Xaa Xaa Arg Xaa Asp His
 1               5                  10                  15

Xaa Xaa Thr His Xaa Xaa Xaa Xaa Xaa His Xaa Xaa Xaa Xaa Xaa
            20                  25                  30

Xaa Xaa Cys Xaa Xaa Xaa Xaa Xaa Cys Xaa Xaa Xaa Xaa Gln Xaa
        35                  40                  45

Ser Asn Xaa Xaa Val His Xaa Xaa Xaa Xaa Xaa His Xaa Xaa Xaa Xaa
    50                  55                  60

Xaa Xaa Xaa Xaa Cys Xaa Xaa Xaa Xaa Cys Xaa Xaa Xaa Xaa Xaa
65                  70                  75                  80

Gln Xaa Thr His Xaa Xaa Arg His Xaa Xaa Xaa Xaa Xaa His
            85                  90

<210> SEQ ID NO 58
<211> LENGTH: 94
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(94)
<223> OTHER INFORMATION: Xaa = any amino acid

<400> SEQUENCE: 58

Cys Xaa Xaa Xaa Xaa Xaa Cys Xaa Xaa Xaa Xaa Gln Xaa Ser Asn
 1               5                  10                  15

Xaa Xaa Val His Xaa Xaa Xaa Xaa Xaa His Xaa Xaa Xaa Xaa Xaa
            20                  25                  30

Xaa Xaa Cys Xaa Xaa Xaa Xaa Xaa Cys Xaa Xaa Xaa Xaa Gln Xaa
        35                  40                  45

Thr His Xaa Xaa Arg His Xaa Xaa Xaa Xaa Xaa His Xaa Xaa Xaa Xaa
    50                  55                  60

Xaa Xaa Xaa Xaa Cys Xaa Xaa Xaa Xaa Cys Xaa Xaa Xaa Xaa Xaa
65                  70                  75                  80

Gln Xaa Phe Asn Xaa Xaa Arg His Xaa Xaa Xaa Xaa Xaa His
            85                  90

<210> SEQ ID NO 59
<211> LENGTH: 94
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(94)
<223> OTHER INFORMATION: Xaa = any amino acid

<400> SEQUENCE: 59

```
Cys Xaa Xaa Xaa Xaa Cys Xaa Xaa Xaa Xaa Gln Xaa Ser His
1               5                   10                  15

Xaa Xaa Val His Xaa Xaa Xaa Xaa His Xaa Xaa Xaa Xaa Xaa
            20                  25                  30

Xaa Xaa Cys Xaa Xaa Xaa Xaa Cys Xaa Xaa Xaa Xaa Gln Xaa
        35                  40                  45

Ser Ser Xaa Xaa Arg His Xaa Xaa Xaa Xaa His Xaa Xaa Xaa Xaa
50                  55                  60

Xaa Xaa Xaa Xaa Cys Xaa Xaa Xaa Xaa Cys Xaa Xaa Xaa Xaa
65              70                  75                  80

Gln Xaa Thr His Xaa Xaa Arg His Xaa Xaa Xaa Xaa Xaa His
            85                  90
```

<210> SEQ ID NO 60
<211> LENGTH: 60
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(60)
<223> OTHER INFORMATION: Xaa = any amino acid

<400> SEQUENCE: 60

```
Cys Xaa Xaa Xaa Xaa Cys Xaa Xaa Xaa Xaa Gln Xaa Ser Ser
1               5                   10                  15

Xaa Xaa Arg His Xaa Xaa Xaa Xaa His Xaa Xaa Xaa Xaa Xaa
            20                  25                  30

Xaa Xaa Cys Xaa Xaa Xaa Xaa Cys Xaa Xaa Xaa Xaa Gln Xaa
        35                  40                  45

Thr His Xaa Xaa Arg His Xaa Xaa Xaa Xaa Xaa His
50                  55                  60
```

<210> SEQ ID NO 61
<211> LENGTH: 60
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(60)
<223> OTHER INFORMATION: Xaa = any amino acid

<400> SEQUENCE: 61

```
Cys Xaa Xaa Xaa Xaa Cys Xaa Xaa Xaa Xaa Gln Xaa Ser His
1               5                   10                  15

Xaa Xaa Val His Xaa Xaa Xaa Xaa His Xaa Xaa Xaa Xaa Xaa
            20                  25                  30

Xaa Xaa Cys Xaa Xaa Xaa Xaa Cys Xaa Xaa Xaa Xaa Gln Xaa
        35                  40                  45

Ser Ser Xaa Xaa Arg His Xaa Xaa Xaa Xaa Xaa His
50                  55                  60
```

<210> SEQ ID NO 62
<211> LENGTH: 128
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT

```
<222> LOCATION: (1)...(128)
<223> OTHER INFORMATION: Xaa = any amino acid

<400> SEQUENCE: 62

Cys Xaa Xaa Xaa Xaa Cys Xaa Xaa Xaa Xaa Xaa Gln Xaa Ser His
1               5                   10                  15

Xaa Xaa Val His Xaa Xaa Xaa Xaa His Xaa Xaa Xaa Xaa Xaa
            20                  25                  30

Xaa Xaa Cys Xaa Xaa Xaa Xaa Cys Xaa Xaa Xaa Xaa Gln Xaa
        35                  40                  45

Ser Asn Xaa Xaa Ile His Xaa Xaa Xaa Xaa His Xaa Xaa Xaa Xaa
    50                  55                  60

Xaa Xaa Xaa Xaa Cys Xaa Xaa Xaa Xaa Cys Xaa Xaa Xaa Xaa
65              70                  75                  80

Gln Xaa Thr His Xaa Xaa Arg His Xaa Xaa Xaa Xaa His Xaa Xaa
            85                  90                  95

Xaa Xaa Xaa Xaa Xaa Cys Xaa Xaa Xaa Xaa Cys Xaa Xaa Xaa
            100                 105                 110

Xaa Xaa Cys Xaa Ser Asn Xaa Xaa Arg His Xaa Xaa Xaa Xaa His
    115                 120                 125

<210> SEQ ID NO 63
<211> LENGTH: 128
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(128)
<223> OTHER INFORMATION: Xaa = any amino acid

<400> SEQUENCE: 63

Cys Xaa Xaa Xaa Xaa Cys Xaa Xaa Xaa Xaa Xaa Gln Xaa Ser His
1               5                   10                  15

Xaa Xaa Val His Xaa Xaa Xaa Xaa His Xaa Xaa Xaa Xaa Xaa
            20                  25                  30

Xaa Xaa Cys Xaa Xaa Xaa Xaa Cys Xaa Xaa Xaa Xaa Val Xaa
        35                  40                  45

Ser Thr Xaa Xaa Arg His Xaa Xaa Xaa Xaa His Xaa Xaa Xaa Xaa
    50                  55                  60

Xaa Xaa Xaa Xaa Cys Xaa Xaa Xaa Xaa Cys Xaa Xaa Xaa Xaa
65              70                  75                  80

Arg Xaa Asp Asn Xaa Xaa Gln His Xaa Xaa Xaa Xaa His Xaa Xaa
            85                  90                  95

Xaa Xaa Xaa Xaa Xaa Cys Xaa Xaa Xaa Xaa Cys Xaa Xaa Xaa
            100                 105                 110

Xaa Xaa Gln Xaa Thr His Xaa Xaa Arg His Xaa Xaa Xaa Xaa His
        115                 120                 125

<210> SEQ ID NO 64
<211> LENGTH: 181
<212> TYPE: PRT
<213> ORGANISM: Artificial Sequence
<220> FEATURE:
<223> OTHER INFORMATION: plasmid sequence

<400> SEQUENCE: 64

Met Val Tyr Pro Tyr Asp Val Pro Asp Tyr Ala Glu Leu Pro Pro Lys
1               5                   10                  15
```

Lys Lys Arg Lys Val Gly Ile Arg Ile Pro Gly Glu Lys Pro Tyr Glu
            20                  25                  30

Cys Asp His Cys Gly Lys Ser Phe Ser Gln Ser Ser His Leu Asn Val
            35                  40                  45

His Lys Arg Thr His Thr Gly Glu Lys Pro Tyr Lys Cys Pro Asp Cys
        50                  55                  60

Gly Lys Ser Phe Ser Gln Ser Ser Ser Leu Ile Arg His Gln Arg Thr
65                  70                  75                  80

His Thr Gly Glu Lys Pro Tyr Glu Cys His Asp Cys Gly Lys Ser Phe
                85                  90                  95

Arg Gln Ser Thr His Leu Thr Arg His Arg Ile His Thr Gly Glu
            100                 105                 110

Lys Ala Ala Ala Lys Phe Val Ser Val Thr Phe Glu Asp Val Ala Val
            115                 120                 125

Leu Phe Thr Arg Asp Glu Trp Lys Lys Leu Asp Leu Ser Gln Arg Ser
            130                 135                 140

Leu Tyr Arg Glu Val Met Leu Glu Asn Tyr Ser Asn Leu Ala Ser Met
145                 150                 155                 160

Ala Gly Phe Leu Phe Thr Lys Pro Lys Val Ile Ser Leu Leu Gln Gln
                165                 170                 175

Gly Glu Asp Pro Trp
            180

<210> SEQ ID NO 65
<211> LENGTH: 94
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(94)
<223> OTHER INFORMATION: Xaa = any amino acid

<400> SEQUENCE: 65

Cys Xaa Xaa Xaa Xaa Xaa Cys Xaa Xaa Xaa Xaa Xaa Arg Xaa Asp His
1               5                   10                  15

Xaa Xaa Thr His Xaa Xaa Xaa Xaa Xaa His Xaa Xaa Xaa Xaa Xaa
            20                  25                  30

Xaa Xaa Cys Xaa Xaa Xaa Xaa Xaa Cys Xaa Xaa Xaa Xaa Xaa Arg Xaa
            35                  40                  45

Ser His Xaa Xaa Arg His Xaa Xaa Xaa Xaa Xaa His Xaa Xaa Xaa Xaa
        50                  55                  60

Xaa Xaa Xaa Xaa Cys Xaa Xaa Xaa Xaa Xaa Cys Xaa Xaa Xaa Xaa Xaa
65                  70                  75                  80

Gln Xaa Ser His Xaa Xaa Arg His Xaa Xaa Xaa Xaa Xaa His
                85                  90

<210> SEQ ID NO 66
<211> LENGTH: 60
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(60)
<223> OTHER INFORMATION: Xaa = any amino acid

<400> SEQUENCE: 66

```
Cys Xaa Xaa Xaa Xaa Cys Xaa Xaa Xaa Xaa Arg Xaa Ser His
 1               5                  10                  15

Xaa Xaa Arg His Xaa Xaa Xaa Xaa His Xaa Xaa Xaa Xaa Xaa
            20                  25                  30

Xaa Xaa Cys Xaa Xaa Xaa Xaa Cys Xaa Xaa Xaa Xaa Gln Xaa
        35                  40                  45

Ser His Xaa Xaa Arg His Xaa Xaa Xaa Xaa His
 50                  55                  60

<210> SEQ ID NO 67
<211> LENGTH: 60
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(60)
<223> OTHER INFORMATION: Xaa = any amino acid

<400> SEQUENCE: 67

Cys Xaa Xaa Xaa Xaa Cys Xaa Xaa Xaa Xaa Arg Xaa Asp His
 1               5                  10                  15

Xaa Xaa Thr His Xaa Xaa Xaa Xaa His Xaa Xaa Xaa Xaa Xaa
            20                  25                  30

Xaa Xaa Cys Xaa Xaa Xaa Xaa Cys Xaa Xaa Xaa Xaa Arg Xaa
        35                  40                  45

Ser His Xaa Xaa Arg His Xaa Xaa Xaa Xaa His
 50                  55                  60

<210> SEQ ID NO 68
<211> LENGTH: 94
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(94)
<223> OTHER INFORMATION: Xaa = any amino acid

<400> SEQUENCE: 68

Cys Xaa Xaa Xaa Xaa Cys Xaa Xaa Xaa Xaa Gln Xaa Ser His
 1               5                  10                  15

Xaa Xaa Thr His Xaa Xaa Xaa Xaa His Xaa Xaa Xaa Xaa Xaa
            20                  25                  30

Xaa Xaa Cys Xaa Xaa Xaa Xaa Cys Xaa Xaa Xaa Xaa Arg Xaa
        35                  40                  45

Ser His Xaa Xaa Arg His Xaa Xaa Xaa Xaa His Xaa Xaa Xaa Xaa
 50                  55                  60

Xaa Xaa Xaa Xaa Cys Xaa Xaa Xaa Xaa Cys Xaa Xaa Xaa Xaa Xaa
 65                  70                  75                  80

Arg Xaa Asp His Xaa Xaa Thr His Xaa Xaa Xaa Xaa Xaa His
                85                  90

<210> SEQ ID NO 69
<211> LENGTH: 60
<212> TYPE: PRT
<213> ORGANISM: Artificial Sequence
<220> FEATURE:
<223> OTHER INFORMATION: purified polypeptide
<220> FEATURE:
```

```
<221> NAME/KEY: VARIANT
<222> LOCATION: (1)...(60)
<223> OTHER INFORMATION: Xaa = any amino acid

<400> SEQUENCE: 69

Cys Xaa Xaa Xaa Xaa Cys Xaa Xaa Xaa Xaa Arg Xaa Ser His
 1               5                  10                  15

Xaa Xaa Arg His Xaa Xaa Xaa Xaa His Xaa Xaa Xaa Xaa Xaa
             20                  25              30

Xaa Xaa Cys Xaa Xaa Xaa Xaa Cys Xaa Xaa Xaa Xaa Arg Xaa
         35              40                  45

Asp His Xaa Xaa Thr His Xaa Xaa Xaa Xaa His
 50                  55              60

<210> SEQ ID NO 70
<211> LENGTH: 60
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: (1)...(60)
<223> OTHER INFORMATION: Xaa = any amino acid

<400> SEQUENCE: 70

Cys Xaa Xaa Xaa Xaa Cys Xaa Xaa Xaa Xaa Xaa Gln Xaa Ser His
 1               5                  10                  15

Xaa Xaa Thr His Xaa Xaa Xaa Xaa His Xaa Xaa Xaa Xaa Xaa
             20                  25              30

Xaa Xaa Cys Xaa Xaa Xaa Xaa Cys Xaa Xaa Xaa Xaa Arg Xaa
         35              40                  45

Ser His Xaa Xaa Arg His Xaa Xaa Xaa Xaa Xaa His
 50                  55              60

<210> SEQ ID NO 71
<211> LENGTH: 89
<212> TYPE: PRT
<213> ORGANISM: Artificial Sequence
<220> FEATURE:
<223> OTHER INFORMATION: plasmid sequence

<400> SEQUENCE: 71

Glu Arg Pro Tyr Ala Cys Pro Val Glu Ser Cys Asp Arg Arg Phe Ser
 1               5                  10                  15

Arg Ser Asp Glu Leu Thr Arg His Ile Arg Ile His Thr Gly Gln Lys
             20                  25                  30

Pro Phe Gln Cys Arg Ile Cys Met Arg Asn Phe Ser Arg Ser Asp His
         35                  40              45

Leu Thr Thr His Ile Arg Thr His Thr Gly Glu Lys Pro Phe Ala Cys
 50                  55              60

Asp Ile Cys Gly Arg Lys Phe Ala Arg Ser Asp Glu Arg Lys Arg His
65                  70                  75                  80

Thr Lys Ile His Leu Arg Gln Lys Asp
                 85

<210> SEQ ID NO 72
<211> LENGTH: 28
<212> TYPE: PRT
<213> ORGANISM: Artificial Sequence
<220> FEATURE:
<223> OTHER INFORMATION: coordinating residue
```

```
<220> FEATURE:
<221> NAME/KEY: VARIANT
<222> LOCATION: 1, 13
<223> OTHER INFORMATION: Xaa = Phe or Tyr
<220> FEATURE:
<221> NAME/KEY: VARIANT
<222> LOCATION: 19
<223> OTHER INFORMATION: Xaa = hydrophobic residue
<220> FEATURE:
<221> NAME/KEY: VARIANT
<222> LOCATION: 2, 4-8, 10-12, 14-18, 20-21, 23-27
<223> OTHER INFORMATION: Xaa = any amino acid

<400> SEQUENCE: 72

Xaa Xaa Cys Xaa Xaa Xaa Xaa Xaa Cys Xaa Xaa Xaa Xaa Xaa Xaa
 1               5                  10                  15

Xaa Xaa Xaa Xaa Xaa His Xaa Xaa Xaa Xaa Xaa His
            20                  25

<210> SEQ ID NO 73
<211> LENGTH: 28
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: 1, 13
<223> OTHER INFORMATION: Xaa = Phe or Tyr
<220> FEATURE:
<221> NAME/KEY: VARIANT
<222> LOCATION: 19
<223> OTHER INFORMATION: Xaa = hydrophobic residue
<220> FEATURE:
<221> NAME/KEY: VARIANT
<222> LOCATION: 2, 4-8, 10-12, 14, 16, 20, 23-27
<223> OTHER INFORMATION: Xaa = any amino acid

<400> SEQUENCE: 73

Xaa Xaa Cys Xaa Xaa Xaa Xaa Xaa Cys Xaa Xaa Xaa Xaa Xaa Cys Xaa
 1               5                  10                  15

Ser Asn Xaa Xaa Arg His Xaa Xaa Xaa Xaa Xaa His
            20                  25

<210> SEQ ID NO 74
<211> LENGTH: 6
<212> TYPE: PRT
<213> ORGANISM: Eukaryote
<220> FEATURE:
<221> NAME/KEY: VARIANT
<222> LOCATION: 3
<223> OTHER INFORMATION: Xaa = Glu or Gln
<220> FEATURE:
<221> NAME/KEY: VARIANT
<222> LOCATION: 4
<223> OTHER INFORMATION: Xaa = Lys or Arg
<220> FEATURE:
<221> NAME/KEY: VARIANT
<222> LOCATION: 6
<223> OTHER INFORMATION: Xaa = Tyr or Phe

<400> SEQUENCE: 74

Thr Gly Xaa Xaa Pro Xaa
 1               5

<210> SEQ ID NO 75
<211> LENGTH: 23
<212> TYPE: PRT
<213> ORGANISM: Homo sapiens

<400> SEQUENCE: 75
```

```
Tyr Lys Cys Lys Gln Cys Gly Lys Ala Phe Gly Cys Pro Ser Asn Leu
1               5                   10                  15

Arg Arg His Gly Arg Thr His
            20

<210> SEQ ID NO 76
<211> LENGTH: 23
<212> TYPE: PRT
<213> ORGANISM: Homo sapiens

<400> SEQUENCE: 76

Tyr Gln Cys Asn Ile Cys Gly Lys Cys Phe Ser Cys Asn Ser Asn Leu
1               5                   10                  15

His Arg His Gln Arg Thr His
            20

<210> SEQ ID NO 77
<211> LENGTH: 23
<212> TYPE: PRT
<213> ORGANISM: Homo sapiens

<400> SEQUENCE: 77

Tyr Ser Cys Gly Ile Cys Gly Lys Ser Phe Ser Asp Ser Ser Ala Lys
1               5                   10                  15

Arg Arg His Cys Ile Leu His
            20

<210> SEQ ID NO 78
<211> LENGTH: 23
<212> TYPE: PRT
<213> ORGANISM: Homo sapiens

<400> SEQUENCE: 78

Tyr Thr Cys Ser Asp Cys Gly Lys Ala Phe Arg Asp Lys Ser Cys Leu
1               5                   10                  15

Asn Arg His Arg Arg Thr His
            20

<210> SEQ ID NO 79
<211> LENGTH: 23
<212> TYPE: PRT
<213> ORGANISM: Homo sapiens

<400> SEQUENCE: 79

Tyr Lys Cys Lys Glu Cys Gly Lys Ala Phe Asn His Ser Ser Asn Phe
1               5                   10                  15

Asn Lys His His Arg Ile His
            20

<210> SEQ ID NO 80
<211> LENGTH: 23
<212> TYPE: PRT
<213> ORGANISM: Homo sapiens

<400> SEQUENCE: 80

Phe Lys Cys Pro Val Cys Gly Lys Ala Phe Arg His Ser Ser Ser Leu
1               5                   10                  15

Val Arg His Gln Arg Thr His
            20

<210> SEQ ID NO 81
```

```
<211> LENGTH: 24
<212> TYPE: PRT
<213> ORGANISM: Homo sapiens

<400> SEQUENCE: 81

Tyr Arg Cys Lys Tyr Cys Asp Arg Ser Phe Ser Ile Ser Ser Asn Leu
 1               5                  10                  15

Gln Arg His Val Arg Asn Ile His
            20

<210> SEQ ID NO 82
<211> LENGTH: 23
<212> TYPE: PRT
<213> ORGANISM: Homo sapiens

<400> SEQUENCE: 82

Tyr Glu Cys Asp His Cys Gly Lys Ala Phe Ser Ile Gly Ser Asn Leu
 1               5                  10                  15

Asn Val His Arg Arg Ile His
            20

<210> SEQ ID NO 83
<211> LENGTH: 23
<212> TYPE: PRT
<213> ORGANISM: Homo sapiens

<400> SEQUENCE: 83

Tyr Gly Cys His Leu Cys Gly Lys Ala Phe Ser Lys Ser Ser Asn Leu
 1               5                  10                  15

Arg Arg His Glu Met Ile His
            20

<210> SEQ ID NO 84
<211> LENGTH: 23
<212> TYPE: PRT
<213> ORGANISM: Homo sapiens

<400> SEQUENCE: 84

Tyr Lys Cys Lys Glu Cys Gly Gln Ala Phe Arg Gln Arg Ala His Leu
 1               5                  10                  15

Ile Arg His His Lys Leu His
            20

<210> SEQ ID NO 85
<211> LENGTH: 23
<212> TYPE: PRT
<213> ORGANISM: Homo sapiens

<400> SEQUENCE: 85

Tyr Lys Cys His Gln Cys Gly Lys Ala Phe Ile Gln Ser Phe Asn Leu
 1               5                  10                  15

Arg Arg His Glu Arg Thr His
            20

<210> SEQ ID NO 86
<211> LENGTH: 23
<212> TYPE: PRT
<213> ORGANISM: Homo sapiens

<400> SEQUENCE: 86

Phe Gln Cys Asn Gln Cys Gly Ala Ser Phe Thr Gln Lys Gly Asn Leu
 1               5                  10                  15
```

Leu Arg His Ile Lys Leu His
            20

<210> SEQ ID NO 87
<211> LENGTH: 23
<212> TYPE: PRT
<213> ORGANISM: Homo sapiens

<400> SEQUENCE: 87

Tyr Ala Cys His Leu Cys Gly Lys Ala Phe Thr Gln Ser Ser His Leu
1               5                   10                  15

Arg Arg His Glu Lys Thr His
            20

<210> SEQ ID NO 88
<211> LENGTH: 23
<212> TYPE: PRT
<213> ORGANISM: Homo sapiens

<400> SEQUENCE: 88

Tyr Lys Cys Gly Gln Cys Gly Lys Phe Tyr Ser Gln Val Ser His Leu
1               5                   10                  15

Thr Arg His Gln Lys Ile His
            20

<210> SEQ ID NO 89
<211> LENGTH: 23
<212> TYPE: PRT
<213> ORGANISM: Homo sapiens

<400> SEQUENCE: 89

Tyr Ala Cys His Leu Cys Gly Lys Ala Phe Thr Gln Cys Ser His Leu
1               5                   10                  15

Arg Arg His Glu Lys Thr His
            20

<210> SEQ ID NO 90
<211> LENGTH: 23
<212> TYPE: PRT
<213> ORGANISM: Homo sapiens

<400> SEQUENCE: 90

Tyr Ala Cys His Leu Cys Ala Lys Ala Phe Ile Gln Cys Ser His Leu
1               5                   10                  15

Arg Arg His Glu Lys Thr His
            20

<210> SEQ ID NO 91
<211> LENGTH: 23
<212> TYPE: PRT
<213> ORGANISM: Homo sapiens

<400> SEQUENCE: 91

Tyr Val Cys Arg Glu Cys Gly Arg Gly Phe Arg Gln His Ser His Leu
1               5                   10                  15

Val Arg His Lys Arg Thr His
            20

<210> SEQ ID NO 92
<211> LENGTH: 23
<212> TYPE: PRT
<213> ORGANISM: Homo sapiens

```
<400> SEQUENCE: 92

Tyr Lys Cys Glu Glu Cys Gly Lys Ala Phe Arg Gln Ser Ser His Leu
1               5                   10                  15

Thr Thr His Lys Ile Ile His
            20

<210> SEQ ID NO 93
<211> LENGTH: 23
<212> TYPE: PRT
<213> ORGANISM: Homo sapiens

<400> SEQUENCE: 93

Tyr Glu Cys Asp His Cys Gly Lys Ser Phe Ser Gln Ser Ser His Leu
1               5                   10                  15

Asn Val His Lys Arg Thr His
            20

<210> SEQ ID NO 94
<211> LENGTH: 23
<212> TYPE: PRT
<213> ORGANISM: Homo sapiens

<400> SEQUENCE: 94

Tyr Met Cys Ser Glu Cys Gly Arg Gly Phe Ser Gln Lys Ser Asn Leu
1               5                   10                  15

Ile Ile His Gln Arg Thr His
            20

<210> SEQ ID NO 95
<211> LENGTH: 23
<212> TYPE: PRT
<213> ORGANISM: Homo sapiens

<400> SEQUENCE: 95

Tyr Lys Cys Glu Glu Cys Gly Lys Ala Phe Thr Gln Ser Ser Asn Leu
1               5                   10                  15

Thr Lys His Lys Lys Ile His
            20

<210> SEQ ID NO 96
<211> LENGTH: 23
<212> TYPE: PRT
<213> ORGANISM: Homo sapiens

<400> SEQUENCE: 96

Phe Glu Cys Lys Asp Cys Gly Lys Ala Phe Ile Gln Lys Ser Asn Leu
1               5                   10                  15

Ile Arg His Gln Arg Thr His
            20

<210> SEQ ID NO 97
<211> LENGTH: 23
<212> TYPE: PRT
<213> ORGANISM: Homo sapiens

<400> SEQUENCE: 97

Tyr Val Cys Arg Glu Cys Arg Arg Gly Phe Ser Gln Lys Ser Asn Leu
1               5                   10                  15

Ile Arg His Gln Arg Thr His
            20
```

```
<210> SEQ ID NO 98
<211> LENGTH: 23
<212> TYPE: PRT
<213> ORGANISM: Homo sapiens

<400> SEQUENCE: 98

Tyr Glu Cys Glu Lys Cys Gly Lys Ala Phe Asn Gln Ser Ser Asn Leu
1               5                   10                  15

Thr Arg His Lys Lys Ser His
            20

<210> SEQ ID NO 99
<211> LENGTH: 23
<212> TYPE: PRT
<213> ORGANISM: Homo sapiens

<400> SEQUENCE: 99

Tyr Glu Cys Asn Thr Cys Arg Lys Thr Phe Ser Gln Lys Ser Asn Leu
1               5                   10                  15

Ile Val His Gln Arg Thr His
            20

<210> SEQ ID NO 100
<211> LENGTH: 23
<212> TYPE: PRT
<213> ORGANISM: Homo sapiens

<400> SEQUENCE: 100

Tyr Val Cys Ser Lys Cys Gly Lys Ala Phe Thr Gln Ser Ser Asn Leu
1               5                   10                  15

Thr Val His Gln Lys Ile His
            20

<210> SEQ ID NO 101
<211> LENGTH: 23
<212> TYPE: PRT
<213> ORGANISM: Homo sapiens

<400> SEQUENCE: 101

Tyr Lys Cys Asp Glu Cys Gly Lys Asn Phe Thr Gln Ser Ser Asn Leu
1               5                   10                  15

Ile Val His Lys Arg Ile His
            20

<210> SEQ ID NO 102
<211> LENGTH: 23
<212> TYPE: PRT
<213> ORGANISM: Homo sapiens

<400> SEQUENCE: 102

Tyr Glu Cys Asp Val Cys Gly Lys Thr Phe Thr Gln Lys Ser Asn Leu
1               5                   10                  15

Gly Val His Gln Arg Thr His
            20

<210> SEQ ID NO 103
<211> LENGTH: 23
<212> TYPE: PRT
<213> ORGANISM: Homo sapiens

<400> SEQUENCE: 103

Tyr Glu Cys Val Gln Cys Gly Lys Gly Phe Thr Gln Ser Ser Asn Leu
1               5                   10                  15
```

Ile Thr His Gln Arg Val His
            20

<210> SEQ ID NO 104
<211> LENGTH: 23
<212> TYPE: PRT
<213> ORGANISM: Homo sapiens

<400> SEQUENCE: 104

Tyr Lys Cys Pro Asp Cys Gly Lys Ser Phe Ser Gln Ser Ser Ser Leu
1               5                   10                  15

Ile Arg His Gln Arg Thr His
            20

<210> SEQ ID NO 105
<211> LENGTH: 23
<212> TYPE: PRT
<213> ORGANISM: Homo sapiens

<400> SEQUENCE: 105

Tyr Glu Cys Gln Asp Cys Gly Arg Ala Phe Asn Gln Asn Ser Ser Leu
1               5                   10                  15

Gly Arg His Lys Arg Thr His
            20

<210> SEQ ID NO 106
<211> LENGTH: 23
<212> TYPE: PRT
<213> ORGANISM: Homo sapiens

<400> SEQUENCE: 106

Tyr Glu Cys Asn Glu Cys Gly Lys Phe Phe Ser Gln Ser Ser Ser Leu
1               5                   10                  15

Ile Arg His Arg Arg Ser His
            20

<210> SEQ ID NO 107
<211> LENGTH: 23
<212> TYPE: PRT
<213> ORGANISM: Homo sapiens

<400> SEQUENCE: 107

Tyr Lys Cys Glu Glu Cys Gly Lys Ala Phe Asn Gln Ser Ser Thr Leu
1               5                   10                  15

Thr Arg His Lys Ile Val His
            20

<210> SEQ ID NO 108
<211> LENGTH: 23
<212> TYPE: PRT
<213> ORGANISM: Homo sapiens

<400> SEQUENCE: 108

Tyr Glu Cys Asn Glu Cys Gly Lys Ala Phe Ala Gln Asn Ser Thr Leu
1               5                   10                  15

Arg Val His Gln Arg Ile His
            20

<210> SEQ ID NO 109
<211> LENGTH: 23
<212> TYPE: PRT
<213> ORGANISM: Homo sapiens

```
<400> SEQUENCE: 109

Tyr Glu Cys His Asp Cys Gly Lys Ser Phe Arg Gln Ser Thr His Leu
1               5                   10                  15

Thr Gln His Arg Arg Ile His
            20

<210> SEQ ID NO 110
<211> LENGTH: 23
<212> TYPE: PRT
<213> ORGANISM: Homo sapiens

<400> SEQUENCE: 110

Tyr Glu Cys His Asp Cys Gly Lys Ser Phe Arg Gln Ser Thr His Leu
1               5                   10                  15

Thr Arg His Arg Arg Ile His
            20

<210> SEQ ID NO 111
<211> LENGTH: 22
<212> TYPE: PRT
<213> ORGANISM: Homo sapiens

<400> SEQUENCE: 111

His Lys Cys Leu Glu Cys Gly Lys Cys Phe Ser Gln Asn Thr His Leu
1               5                   10                  15

Thr Arg His Gln Arg Thr
            20

<210> SEQ ID NO 112
<211> LENGTH: 25
<212> TYPE: PRT
<213> ORGANISM: Homo sapiens

<400> SEQUENCE: 112

Tyr Val Cys Asp Val Glu Gly Cys Thr Trp Lys Phe Ala Arg Ser Asp
1               5                   10                  15

Glu Leu Asn Arg His Lys Lys Arg His
            20                  25

<210> SEQ ID NO 113
<211> LENGTH: 25
<212> TYPE: PRT
<213> ORGANISM: Homo sapiens

<400> SEQUENCE: 113

Tyr His Cys Asp Trp Asp Gly Cys Gly Trp Lys Phe Ala Arg Ser Asp
1               5                   10                  15

Glu Leu Thr Arg His Tyr Arg Lys His
            20                  25

<210> SEQ ID NO 114
<211> LENGTH: 25
<212> TYPE: PRT
<213> ORGANISM: Homo sapiens

<400> SEQUENCE: 114

Tyr Arg Cys Ser Trp Glu Gly Cys Glu Trp Arg Phe Ala Arg Ser Asp
1               5                   10                  15

Glu Leu Thr Arg His Phe Arg Lys His
            20                  25
```

```
<210> SEQ ID NO 115
<211> LENGTH: 25
<212> TYPE: PRT
<213> ORGANISM: Homo sapiens

<400> SEQUENCE: 115

Phe Ser Cys Ser Trp Lys Gly Cys Glu Arg Arg Phe Ala Arg Ser Asp
1               5                   10                  15

Glu Leu Ser Arg His Arg Arg Thr His
            20                  25

<210> SEQ ID NO 116
<211> LENGTH: 25
<212> TYPE: PRT
<213> ORGANISM: Homo sapiens

<400> SEQUENCE: 116

Phe Ala Cys Ser Trp Gln Asp Cys Asn Lys Lys Phe Ala Arg Ser Asp
1               5                   10                  15

Glu Leu Ala Arg His Tyr Arg Thr His
            20                  25

<210> SEQ ID NO 117
<211> LENGTH: 25
<212> TYPE: PRT
<213> ORGANISM: Homo sapiens

<400> SEQUENCE: 117

Tyr His Cys Asn Trp Asp Gly Cys Gly Trp Lys Phe Ala Arg Ser Asp
1               5                   10                  15

Glu Leu Thr Arg His Tyr Arg Lys His
            20                  25

<210> SEQ ID NO 118
<211> LENGTH: 24
<212> TYPE: PRT
<213> ORGANISM: Homo sapiens

<400> SEQUENCE: 118

Phe Leu Cys Gln Tyr Cys Ala Gln Arg Phe Gly Arg Lys Asp His Leu
1               5                   10                  15

Thr Arg His Met Lys Lys Ser His
            20

<210> SEQ ID NO 119
<211> LENGTH: 23
<212> TYPE: PRT
<213> ORGANISM: Homo sapiens

<400> SEQUENCE: 119

Phe Gln Cys Lys Thr Cys Gln Arg Lys Phe Ser Arg Ser Asp His Leu
1               5                   10                  15

Lys Thr His Thr Arg Thr His
            20

<210> SEQ ID NO 120
<211> LENGTH: 23
<212> TYPE: PRT
<213> ORGANISM: Homo sapiens

<400> SEQUENCE: 120

Phe Ala Cys Glu Val Cys Gly Val Arg Phe Thr Arg Asn Asp Lys Leu
```

```
                1               5                  10                 15
Lys Ile His Met Arg Lys His
            20

<210> SEQ ID NO 121
<211> LENGTH: 25
<212> TYPE: PRT
<213> ORGANISM: Homo sapiens

<400> SEQUENCE: 121

Tyr Val Cys Asp Val Glu Gly Cys Thr Trp Lys Phe Ala Arg Ser Asp
 1               5                  10                 15

Lys Leu Asn Arg His Lys Lys Arg His
            20                  25

<210> SEQ ID NO 122
<211> LENGTH: 23
<212> TYPE: PRT
<213> ORGANISM: Homo sapiens

<400> SEQUENCE: 122

Tyr Lys Cys Met Glu Cys Gly Lys Ala Phe Asn Arg Arg Ser His Leu
 1               5                  10                 15

Thr Arg His Gln Arg Ile His
            20

<210> SEQ ID NO 123
<211> LENGTH: 23
<212> TYPE: PRT
<213> ORGANISM: Homo sapiens

<400> SEQUENCE: 123

Tyr Ile Cys Arg Lys Cys Gly Arg Gly Phe Ser Arg Lys Ser Asn Leu
 1               5                  10                 15

Ile Arg His Gln Arg Thr His
            20

<210> SEQ ID NO 124
<211> LENGTH: 23
<212> TYPE: PRT
<213> ORGANISM: Homo sapiens

<400> SEQUENCE: 124

Tyr Leu Cys Ser Glu Cys Asp Lys Cys Phe Ser Arg Ser Thr Asn Leu
 1               5                  10                 15

Ile Arg His Arg Arg Thr His
            20

<210> SEQ ID NO 125
<211> LENGTH: 23
<212> TYPE: PRT
<213> ORGANISM: Homo sapiens

<400> SEQUENCE: 125

Tyr Glu Cys Lys Glu Cys Gly Lys Ala Phe Ser Ser Gly Ser Asn Phe
 1               5                  10                 15

Thr Arg His Gln Arg Ile His
            20

<210> SEQ ID NO 126
<211> LENGTH: 23
<212> TYPE: PRT
```

<213> ORGANISM: Homo sapiens

<400> SEQUENCE: 126

Tyr Glu Cys Asp His Cys Gly Lys Ala Phe Ser Val Ser Ser Asn Leu
1               5                   10                  15

Asn Val His Arg Arg Ile His
            20

<210> SEQ ID NO 127
<211> LENGTH: 23
<212> TYPE: PRT
<213> ORGANISM: Homo sapiens

<400> SEQUENCE: 127

Tyr Thr Cys Lys Gln Cys Gly Lys Ala Phe Ser Val Ser Ser Ser Leu
1               5                   10                  15

Arg Arg His Glu Thr Thr His
            20

<210> SEQ ID NO 128
<211> LENGTH: 23
<212> TYPE: PRT
<213> ORGANISM: Homo sapiens

<400> SEQUENCE: 128

Tyr Glu Cys Asn Tyr Cys Gly Lys Thr Phe Ser Val Ser Ser Thr Leu
1               5                   10                  15

Ile Arg His Gln Arg Ile His
            20

<210> SEQ ID NO 129
<211> LENGTH: 23
<212> TYPE: PRT
<213> ORGANISM: Homo sapiens

<400> SEQUENCE: 129

Tyr Arg Cys Glu Glu Cys Gly Lys Ala Phe Arg Trp Pro Ser Asn Leu
1               5                   10                  15

Thr Arg His Lys Arg Ile His
            20

<210> SEQ ID NO 130
<211> LENGTH: 10
<212> TYPE: DNA
<213> ORGANISM: Artificial Sequence
<220> FEATURE:
<223> OTHER INFORMATION: target site

<400> SEQUENCE: 130
gaagaggacc                                                          10

<210> SEQ ID NO 131
<211> LENGTH: 260
<212> TYPE: PRT
<213> ORGANISM: Homo sapiens

<400> SEQUENCE: 131

Tyr Leu Pro Asp Thr Asp Asp Arg His Arg Ile Glu Glu Lys Arg Lys
1               5                   10                  15

Arg Thr Tyr Glu Thr Phe Lys Ser Ile Met Lys Lys Ser Pro Phe Ser
            20                  25                  30

Gly Pro Thr Asp Pro Arg Pro Pro Pro Arg Arg Ile Ala Val Pro Ser

```
                35                  40                  45
Arg Ser Ser Ala Ser Val Pro Lys Pro Ala Pro Gln Pro Tyr Pro Phe
 50                  55                  60

Thr Ser Ser Leu Ser Thr Ile Asn Tyr Asp Glu Phe Pro Thr Met Val
 65                  70                  75                  80

Phe Pro Ser Gly Gln Ile Ser Gln Ala Ser Ala Leu Ala Pro Ala Pro
                 85                  90                  95

Pro Gln Val Leu Pro Gln Ala Pro Ala Pro Ala Pro Ala Pro Ala Met
                100                 105                 110

Val Ser Ala Leu Ala Gln Ala Pro Ala Pro Val Pro Val Leu Ala Pro
                115                 120                 125

Gly Pro Pro Gln Ala Val Ala Pro Pro Ala Pro Lys Pro Thr Gln Ala
                130                 135                 140

Gly Glu Gly Thr Leu Ser Glu Ala Leu Leu Gln Leu Gln Phe Asp Asp
145                 150                 155                 160

Glu Asp Leu Gly Ala Leu Leu Gly Asn Ser Thr Asp Pro Ala Val Phe
                165                 170                 175

Thr Asp Leu Ala Ser Val Asp Asn Ser Glu Phe Gln Gln Leu Leu Asn
                180                 185                 190

Gln Gly Ile Pro Val Ala Pro His Thr Thr Glu Pro Met Leu Met Glu
                195                 200                 205

Tyr Pro Glu Ala Ile Thr Arg Leu Val Thr Ala Gln Arg Pro Pro Asp
                210                 215                 220

Pro Ala Pro Ala Pro Leu Gly Ala Pro Gly Leu Pro Asn Gly Leu Leu
225                 230                 235                 240

Ser Gly Asp Glu Asp Phe Ser Ser Ile Ala Asp Met Asp Phe Ser Ala
                245                 250                 255

Leu Leu Ser Gln
                260

<210> SEQ ID NO 132
<211> LENGTH: 127
<212> TYPE: PRT
<213> ORGANISM: Saccharomyces cerevisiae

<400> SEQUENCE: 132

Asn Phe Asn Gln Ser Gly Asn Ile Ala Asp Ser Ser Leu Ser Phe Thr
  1               5                  10                  15

Phe Thr Asn Ser Ser Asn Gly Pro Asn Leu Ile Thr Thr Gln Thr Asn
                 20                  25                  30

Ser Gln Ala Leu Ser Gln Pro Ile Ala Ser Ser Asn Val His Asp Asn
                 35                  40                  45

Phe Met Asn Asn Glu Ile Thr Ala Ser Lys Ile Asp Asp Gly Asn Asn
 50                  55                  60

Ser Lys Pro Leu Ser Pro Gly Trp Thr Asp Gln Thr Ala Tyr Asn Ala
 65                  70                  75                  80

Phe Gly Ile Thr Thr Gly Met Phe Asn Thr Thr Thr Met Asp Asp Val
                 85                  90                  95

Tyr Asn Tyr Leu Phe Asp Asp Glu Asp Thr Pro Pro Asn Pro Lys Lys
                100                 105                 110

Glu Ile Ser Met Ala Tyr Pro Tyr Asp Val Pro Asp Tyr Ala Ser
                115                 120                 125

<210> SEQ ID NO 133
<211> LENGTH: 90
```

<212> TYPE: PRT
<213> ORGANISM: Saccharomyces cerevisiae

<400> SEQUENCE: 133

```
Asn Ser Ala Ser Ser Thr Lys Leu Asp Asp Leu Gly Thr Ala
 1               5                  10                  15
Ala Ala Val Leu Ser Asn Met Arg Ser Ser Pro Tyr Arg Thr His Asp
            20                  25                  30
Lys Pro Ile Ser Asn Val Asn Asp Met Asn Asn Thr Asn Ala Leu Gly
            35                  40                  45
Val Pro Ala Ser Arg Pro His Ser Ser Phe Pro Ser Lys Gly Val
50                  55                  60
Leu Arg Pro Ile Leu Leu Arg Ile His Asn Ser Glu Gln Gln Pro Ile
65                  70                  75                  80
Phe Glu Ser Asn Asn Ser Thr Ala Cys Ile
                85                  90
```

<210> SEQ ID NO 134
<211> LENGTH: 63
<212> TYPE: PRT
<213> ORGANISM: Homo sapiens

<400> SEQUENCE: 134

```
Val Ser Val Thr Phe Glu Asp Val Ala Val Leu Phe Thr Arg Asp Glu
 1               5                  10                  15
Trp Lys Lys Leu Asp Leu Ser Gln Arg Ser Leu Tyr Arg Glu Val Met
            20                  25                  30
Leu Glu Asn Tyr Ser Asn Leu Ala Ser Met Ala Gly Phe Leu Phe Thr
            35                  40                  45
Lys Pro Lys Val Ile Ser Leu Leu Gln Gln Gly Glu Asp Pro Trp
       50                  55                  60
```

<210> SEQ ID NO 135
<211> LENGTH: 207
<212> TYPE: DNA
<213> ORGANISM: Artificial Sequence
<220> FEATURE:
<223> OTHER INFORMATION: plasmid sequence

<400> SEQUENCE: 135

```
taatacgact cactataggg aatattaagc taagctcacc atgggtaagc ctatccctaa    60
ccctctcctc ggtctcgatt ctacacaagc tatgggtgct cctccaaaaa agaagagaaa   120
ggtagctgga tccactagta acggccgcca gtgtgctgga attctgcaga tatccatcac   180
actggcggcg ctcgaggcat gcatcta                                       207
```

<210> SEQ ID NO 136
<211> LENGTH: 30
<212> TYPE: DNA
<213> ORGANISM: Artificial Sequence
<220> FEATURE:
<223> OTHER INFORMATION: primer

<400> SEQUENCE: 136

```
cgatctgcag ggtccttttc atcacgtgct                                     30
```

<210> SEQ ID NO 137
<211> LENGTH: 31
<212> TYPE: DNA
<213> ORGANISM: Artificial Sequence
<220> FEATURE:

```
<223> OTHER INFORMATION: primer

<400> SEQUENCE: 137
cgatcgatgc cggcggacgg atcgcttgcc t                                    31

<210> SEQ ID NO 138
<211> LENGTH: 28
<212> TYPE: DNA
<213> ORGANISM: Artificial Sequence
<220> FEATURE:
<223> OTHER INFORMATION: primer

<400> SEQUENCE: 138
aattccatgg gtaagcctat ccctaacc                                        28

<210> SEQ ID NO 139
<211> LENGTH: 28
<212> TYPE: DNA
<213> ORGANISM: Artificial Sequence
<220> FEATURE:
<223> OTHER INFORMATION: primer

<400> SEQUENCE: 139
aattggatcc agctaccttt ctcttctt                                        28

<210> SEQ ID NO 140
<211> LENGTH: 43
<212> TYPE: DNA
<213> ORGANISM: Artificial Sequence
<220> FEATURE:
<223> OTHER INFORMATION: primer

<400> SEQUENCE: 140
aaggaaggaa ggaagcggcc gcagccaatt ttaatcaaag tgg                       43

<210> SEQ ID NO 141
<211> LENGTH: 32
<212> TYPE: DNA
<213> ORGANISM: Artificial Sequence
<220> FEATURE:
<223> OTHER INFORMATION: primer

<400> SEQUENCE: 141
acatacatgc atgcgccgtt actagtggat cc                                   32

<210> SEQ ID NO 142
<211> LENGTH: 474
<212> TYPE: DNA
<213> ORGANISM: Artificial Sequence
<220> FEATURE:
<223> OTHER INFORMATION: plasmid sequence

<400> SEQUENCE: 142
ggccgccagt gtgctggaat tctgcagata tccatcacac tggcggccgc agccaattt      60 aatcaaagtg gaatattgc tgatagctca ttgtccttca ctttcactaa cagtagcaac     120
ggtccgaacc tcataacaac tcaaacaat tctcaagcgc tttcacaacc aattgcctcc     180
tctaacgttc atgataactt catgaataat gaaatcacgg ctagtaaaat tgatgatggt    240
aataattcaa aaccactgtc acctggttgg acgaccaaa ctgcgtataa cgcgtttgga    300
atcactacag ggatgtttaa taccactaca atggatgatg tatataacta tctattcgat   360
gatgaagata ccccaccaaa cccaaaaaaa gagatctcta tggcttaccc atacgatgtt    420
ccagattacg ctagctaagg atccactagt aacggcgcat gcatctagag ggcc          474
```

<210> SEQ ID NO 143
<211> LENGTH: 44
<212> TYPE: DNA
<213> ORGANISM: Artificial Sequence
<220> FEATURE:
<223> OTHER INFORMATION: primer

<400> SEQUENCE: 143
aaggaaggaa ggaagcggcc gcaaattctg catcttcatc tacc         44

<210> SEQ ID NO 144
<211> LENGTH: 33
<212> TYPE: DNA
<213> ORGANISM: Artificial Sequence
<220> FEATURE:
<223> OTHER INFORMATION: primer

<400> SEQUENCE: 144
acatacatgc atgctgtaga attgttgctt tcg                     33

<210> SEQ ID NO 145
<211> LENGTH: 330
<212> TYPE: DNA
<213> ORGANISM: Artificial Sequence
<220> FEATURE:
<223> OTHER INFORMATION: plasmid sequence

<400> SEQUENCE: 145
ggccgccagt gtgctggaat tctgcagata tccatcacac tggcggccgc aaattctgca    60
tcttcatcta ccaaactaga cgacgacttg ggtacagcag cagcagtgct atcaaacatg   120
agatcatccc catatagaac tcatgataaa cccatttcca atgtcaatga catgaataac   180
acaaatgcgc tcggtgtgcc ggctagtagg cctcattcgt catcttttcc atcaaagggt   240
gtcttaagac caattctgtt acgtatccat aattccgaac aacaacccat tttcgaaagc   300
aacaattcta cagcatgcat ctagagggcc                                    330

<210> SEQ ID NO 146
<211> LENGTH: 25
<212> TYPE: PRT
<213> ORGANISM: Homo sapiens

<400> SEQUENCE: 146

Phe Met Cys Thr Trp Ser Tyr Cys Gly Lys Arg Phe Thr Asp Arg Ser
 1               5                  10                  15

Ala Leu Ala Arg His Lys Arg Thr His
            20                  25

<210> SEQ ID NO 147
<211> LENGTH: 25
<212> TYPE: PRT
<213> ORGANISM: Homo sapiens

<400> SEQUENCE: 147

His Ile Cys His Ile Gln Gly Cys Gly Lys Val Tyr Gly Asp Arg Ser
 1               5                  10                  15

His Leu Thr Arg His Leu Arg Trp His
            20                  25

<210> SEQ ID NO 148
<211> LENGTH: 23
<212> TYPE: PRT

<213> ORGANISM: Homo sapiens

<400> SEQUENCE: 148

Phe Ala Cys Pro Glu Cys Pro Lys Arg Phe Met Asp Ser Ser Lys Leu
1               5                   10                  15

Ser Arg His Ile Lys Thr His
            20

<210> SEQ ID NO 149
<211> LENGTH: 25
<212> TYPE: PRT
<213> ORGANISM: Homo sapiens

<400> SEQUENCE: 149

Tyr Ala Cys Pro Val Glu Ser Cys Asp Arg Arg Phe Ser Asp Ser Ser
1               5                   10                  15

Asn Leu Thr Arg His Ile Arg Ile His
            20                  25

<210> SEQ ID NO 150
<211> LENGTH: 25
<212> TYPE: PRT
<213> ORGANISM: Homo sapiens

<400> SEQUENCE: 150

His Ile Cys His Ile Gln Gly Cys Gly Lys Val Tyr Gly Asp Arg Ser
1               5                   10                  15

Ser Leu Thr Arg His Leu Arg Trp His
            20                  25

<210> SEQ ID NO 151
<211> LENGTH: 23
<212> TYPE: PRT
<213> ORGANISM: Homo sapiens

<400> SEQUENCE: 151

Tyr Lys Cys Lys Glu Cys Gly Lys Ala Phe Asn His Ser Ser Asn Phe
1               5                   10                  15

Asn Lys His His Arg Ile His
            20

<210> SEQ ID NO 152
<211> LENGTH: 23
<212> TYPE: PRT
<213> ORGANISM: Homo sapiens

<400> SEQUENCE: 152

Phe Lys Cys Pro Val Cys Gly Lys Ala Phe Arg His Ser Ser Ser Leu
1               5                   10                  15

Val Arg His Gln Arg Thr His
            20

<210> SEQ ID NO 153
<211> LENGTH: 24
<212> TYPE: PRT
<213> ORGANISM: Homo sapiens

<400> SEQUENCE: 153

Tyr Arg Cys Lys Tyr Cys Asp Arg Ser Phe Ser Ile Ser Ser Asn Leu
1               5                   10                  15

Gln Arg His Val Arg Asn Ile His
            20

<210> SEQ ID NO 154
<211> LENGTH: 23
<212> TYPE: PRT
<213> ORGANISM: Homo sapiens

<400> SEQUENCE: 154

Tyr Gly Cys His Leu Cys Gly Lys Ala Phe Ser Lys Ser Ser Asn Leu
 1               5                  10                  15

Arg Arg His Glu Met Ile His
            20

<210> SEQ ID NO 155
<211> LENGTH: 23
<212> TYPE: PRT
<213> ORGANISM: Homo sapiens

<400> SEQUENCE: 155

Tyr Lys Cys Lys Glu Cys Gly Gln Ala Phe Arg Gln Arg Ala His Leu
 1               5                  10                  15

Ile Arg His His Lys Leu His
            20

<210> SEQ ID NO 156
<211> LENGTH: 23
<212> TYPE: PRT
<213> ORGANISM: Homo sapiens

<400> SEQUENCE: 156

Tyr Lys Cys His Gln Cys Gly Lys Ala Phe Ile Gln Ser Phe Asn Leu
 1               5                  10                  15

Arg Arg His Glu Arg Thr His
            20

<210> SEQ ID NO 157
<211> LENGTH: 23
<212> TYPE: PRT
<213> ORGANISM: Homo sapiens

<400> SEQUENCE: 157

Phe Gln Cys Asn Gln Cys Gly Ala Ser Phe Thr Gln Lys Gly Asn Leu
 1               5                  10                  15

Leu Arg His Ile Lys Leu His
            20

<210> SEQ ID NO 158
<211> LENGTH: 23
<212> TYPE: PRT
<213> ORGANISM: Drosophila melanogaster

<400> SEQUENCE: 158

Tyr Thr Cys Ser Tyr Cys Gly Lys Ser Phe Thr Gln Ser Asn Thr Leu
 1               5                  10                  15

Lys Gln His Thr Arg Ile His
            20

<210> SEQ ID NO 159
<211> LENGTH: 23
<212> TYPE: PRT
<213> ORGANISM: Homo sapiens

<400> SEQUENCE: 159

Tyr Val Cys Arg Glu Cys Gly Arg Gly Phe Arg Gln His Ser His Leu
1               5                   10                  15

Val Arg His Lys Arg Thr His
            20

<210> SEQ ID NO 160
<211> LENGTH: 23
<212> TYPE: PRT
<213> ORGANISM: Homo sapiens

<400> SEQUENCE: 160

Tyr Glu Cys Asp His Cys Gly Lys Ser Phe Ser Gln Ser His Leu
1               5                   10                  15

Asn Val His Lys Arg Thr His
            20

<210> SEQ ID NO 161
<211> LENGTH: 23
<212> TYPE: PRT
<213> ORGANISM: Homo sapiens

<400> SEQUENCE: 161

Tyr Met Cys Ser Glu Cys Gly Arg Gly Phe Ser Gln Lys Ser Asn Leu
1               5                   10                  15

Ile Ile His Gln Arg Thr His
            20

<210> SEQ ID NO 162
<211> LENGTH: 23
<212> TYPE: PRT
<213> ORGANISM: Homo sapiens

<400> SEQUENCE: 162

Tyr Lys Cys Glu Glu Cys Gly Lys Ala Phe Thr Gln Ser Ser Asn Leu
1               5                   10                  15

Thr Lys His Lys Lys Ile His
            20

<210> SEQ ID NO 163
<211> LENGTH: 23
<212> TYPE: PRT
<213> ORGANISM: Homo sapiens

<400> SEQUENCE: 163

Tyr Lys Cys Glu Glu Cys Gly Lys Ala Phe Asn Gln Ser Ser Thr Leu
1               5                   10                  15

Thr Arg His Lys Ile Val His
            20

<210> SEQ ID NO 164
<211> LENGTH: 23
<212> TYPE: PRT
<213> ORGANISM: Homo sapiens

<400> SEQUENCE: 164

Tyr Glu Cys His Asp Cys Gly Lys Ser Phe Arg Gln Ser Thr His Leu
1               5                   10                  15

Thr Arg His Arg Arg Ile His
            20

<210> SEQ ID NO 165
<211> LENGTH: 24

```
<212> TYPE: PRT
<213> ORGANISM: Homo sapiens

<400> SEQUENCE: 165

Phe Leu Cys Gln Tyr Cys Ala Gln Arg Phe Gly Arg Lys Asp His Leu
 1               5                  10                  15

Thr Arg His Met Lys Lys Ser His
            20

<210> SEQ ID NO 166
<211> LENGTH: 25
<212> TYPE: PRT
<213> ORGANISM: Homo sapiens

<400> SEQUENCE: 166

Tyr Val Cys Asp Val Glu Gly Cys Thr Trp Lys Phe Ala Arg Ser Asp
 1               5                  10                  15

Lys Leu Asn Arg His Lys Lys Arg His
            20                  25

<210> SEQ ID NO 167
<211> LENGTH: 23
<212> TYPE: PRT
<213> ORGANISM: Homo sapiens

<400> SEQUENCE: 167

Phe Ala Cys Pro Glu Cys Pro Lys Arg Phe Met Arg Ser Asp Asn Leu
 1               5                  10                  15

Thr Gln His Ile Lys Thr His
            20

<210> SEQ ID NO 168
<211> LENGTH: 23
<212> TYPE: PRT
<213> ORGANISM: Homo sapiens

<400> SEQUENCE: 168

Phe Gln Cys Arg Ile Cys Met Arg Asn Phe Ser Ser Pro Ala Asp Leu
 1               5                  10                  15

Thr Arg His Ile Arg Thr His
            20

<210> SEQ ID NO 169
<211> LENGTH: 23
<212> TYPE: PRT
<213> ORGANISM: Homo sapiens

<400> SEQUENCE: 169

Tyr Glu Cys Lys Glu Cys Gly Lys Ala Phe Ser Ser Gly Ser Asn Phe
 1               5                  10                  15

Thr Arg His Gln Arg Ile His
            20

<210> SEQ ID NO 170
<211> LENGTH: 23
<212> TYPE: PRT
<213> ORGANISM: Homo sapiens

<400> SEQUENCE: 170

Phe Gln Cys Arg Ile Cys Met Arg Asn Phe Ser Thr His Ile Asp Leu
 1               5                  10                  15

Ile Arg His Ile Arg Thr His
```

-continued

```
<210> SEQ ID NO 171
<211> LENGTH: 23
<212> TYPE: PRT
<213> ORGANISM: Homo sapiens

<400> SEQUENCE: 171

Tyr Glu Cys Asp His Cys Gly Lys Ala Phe Ser Val Ser Ser Asn Leu
 1               5                  10                  15

Asn Val His Arg Arg Ile His
            20

<210> SEQ ID NO 172
<211> LENGTH: 23
<212> TYPE: PRT
<213> ORGANISM: Homo sapiens

<400> SEQUENCE: 172

Tyr Glu Cys Asn Tyr Cys Gly Lys Thr Phe Ser Val Ser Ser Thr Leu
 1               5                  10                  15

Ile Arg His Gln Arg Ile His
            20

<210> SEQ ID NO 173
<211> LENGTH: 23
<212> TYPE: PRT
<213> ORGANISM: Homo sapiens

<400> SEQUENCE: 173

Tyr Lys Cys Lys Gln Cys Gly Lys Ala Phe Gly Cys Pro Ser Asn Leu
 1               5                  10                  15

Arg Arg His Gly Arg Thr His
            20

<210> SEQ ID NO 174
<211> LENGTH: 23
<212> TYPE: PRT
<213> ORGANISM: Homo sapiens

<400> SEQUENCE: 174

Phe Gln Cys Arg Ile Cys Met Arg Asn Phe Ser Asp Ser Gly Asn Leu
 1               5                  10                  15

Arg Val His Ile Arg Thr His
            20

<210> SEQ ID NO 175
<211> LENGTH: 23
<212> TYPE: PRT
<213> ORGANISM: Homo sapiens

<400> SEQUENCE: 175

Tyr Ala Cys His Leu Cys Gly Lys Ala Phe Thr Gln Cys Ser His Leu
 1               5                  10                  15

Arg Arg His Glu Lys Thr His
            20

<210> SEQ ID NO 176
<211> LENGTH: 23
<212> TYPE: PRT
<213> ORGANISM: Homo sapiens

<400> SEQUENCE: 176
```

```
Tyr Lys Cys Glu Glu Cys Gly Lys Ala Phe Arg Gln Ser Ser His Leu
1               5                   10                  15

Thr Thr His Lys Ile Ile His
            20
```

<210> SEQ ID NO 177
<211> LENGTH: 23
<212> TYPE: PRT
<213> ORGANISM: Homo sapiens

<400> SEQUENCE: 177

```
Phe Glu Cys Lys Asp Cys Gly Lys Ala Phe Ile Gln Lys Ser Asn Leu
1               5                   10                  15

Ile Arg His Gln Arg Thr His
            20
```

<210> SEQ ID NO 178
<211> LENGTH: 23
<212> TYPE: PRT
<213> ORGANISM: Homo sapiens

<400> SEQUENCE: 178

```
Tyr Val Cys Ser Lys Cys Gly Lys Ala Phe Thr Gln Ser Ser Asn Leu
1               5                   10                  15

Thr Val His Gln Lys Ile His
            20
```

<210> SEQ ID NO 179
<211> LENGTH: 23
<212> TYPE: PRT
<213> ORGANISM: Homo sapiens

<400> SEQUENCE: 179

```
Tyr Lys Cys Pro Asp Cys Gly Lys Ser Phe Ser Gln Ser Ser Ser Leu
1               5                   10                  15

Ile Arg His Gln Arg Thr His
            20
```

<210> SEQ ID NO 180
<211> LENGTH: 23
<212> TYPE: PRT
<213> ORGANISM: Homo sapiens

<400> SEQUENCE: 180

```
Tyr Glu Cys His Asp Cys Gly Lys Ser Phe Arg Gln Ser Thr His Leu
1               5                   10                  15

Thr Gln His Arg Arg Ile His
            20
```

<210> SEQ ID NO 181
<211> LENGTH: 25
<212> TYPE: PRT
<213> ORGANISM: Homo sapiens

<400> SEQUENCE: 181

```
Tyr Val Cys Asp Val Glu Gly Cys Thr Trp Lys Phe Ala Arg Ser Asp
1               5                   10                  15

Glu Leu Asn Arg His Lys Lys Arg His
            20                  25
```

<210> SEQ ID NO 182

```
<211> LENGTH: 23
<212> TYPE: PRT
<213> ORGANISM: Homo sapiens

<400> SEQUENCE: 182

Phe Gln Cys Lys Thr Cys Gln Arg Lys Phe Ser Arg Ser Asp His Leu
1               5                   10                  15

Lys Thr His Thr Arg Thr His
            20

<210> SEQ ID NO 183
<211> LENGTH: 23
<212> TYPE: PRT
<213> ORGANISM: Homo sapiens

<400> SEQUENCE: 183

Tyr Lys Cys Met Glu Cys Gly Lys Ala Phe Asn Arg Arg Ser His Leu
1               5                   10                  15

Thr Arg His Gln Arg Ile His
            20

<210> SEQ ID NO 184
<211> LENGTH: 23
<212> TYPE: PRT
<213> ORGANISM: Homo sapiens

<400> SEQUENCE: 184

Tyr Ile Cys Arg Lys Cys Gly Arg Gly Phe Ser Arg Lys Ser Asn Leu
1               5                   10                  15

Ile Arg His Gln Arg Thr His
            20

<210> SEQ ID NO 185
<211> LENGTH: 22
<212> TYPE: PRT
<213> ORGANISM: Drosophila melanogaster

<400> SEQUENCE: 185

Phe His Cys Gly Tyr Cys Glu Lys Ser Phe Ser Val Lys Asp Tyr Leu
1               5                   10                  15

Thr Lys Ile Arg Thr His
            20

<210> SEQ ID NO 186
<211> LENGTH: 23
<212> TYPE: PRT
<213> ORGANISM: Homo sapiens

<400> SEQUENCE: 186

Tyr Thr Cys Lys Gln Cys Gly Lys Ala Phe Ser Val Ser Ser Ser Leu
1               5                   10                  15

Arg Arg His Glu Thr Thr His
            20

<210> SEQ ID NO 187
<211> LENGTH: 23
<212> TYPE: PRT
<213> ORGANISM: Homo sapiens

<400> SEQUENCE: 187

Phe Gln Cys Arg Ile Cys Met Arg Asn Phe Ser Asp Pro Gly Ala Leu
1               5                   10                  15
```

Val Arg His Ile Arg Thr His
            20

<210> SEQ ID NO 188
<211> LENGTH: 23
<212> TYPE: PRT
<213> ORGANISM: Homo sapiens

<400> SEQUENCE: 188

Phe Gln Cys Arg Ile Cys Met Arg Asn Phe Ser Asp Pro Gly His Leu
1               5                   10                  15

Val Arg His Ile Arg Thr His
            20

<210> SEQ ID NO 189
<211> LENGTH: 23
<212> TYPE: PRT
<213> ORGANISM: Homo sapiens

<400> SEQUENCE: 189

Phe Gln Cys Arg Ile Cys Met Arg Asn Phe Ser Asp Pro Gly Asn Leu
1               5                   10                  15

Lys Arg His Ile Arg Thr His
            20

<210> SEQ ID NO 190
<211> LENGTH: 23
<212> TYPE: PRT
<213> ORGANISM: Homo sapiens

<400> SEQUENCE: 190

Phe Gln Cys Arg Ile Cys Met Arg Asn Phe Ser Asp Cys Arg Asp Leu
1               5                   10                  15

Ala Arg His Ile Arg Thr His
            20

<210> SEQ ID NO 191
<211> LENGTH: 25
<212> TYPE: PRT
<213> ORGANISM: Homo sapiens

<400> SEQUENCE: 191

Tyr Ala Cys Pro Val Glu Ser Cys Asp Arg Arg Phe Ser Met Ser His
1               5                   10                  15

His Leu Lys Glu His Ile Arg Thr His
            20                  25

<210> SEQ ID NO 192
<211> LENGTH: 23
<212> TYPE: PRT
<213> ORGANISM: Homo sapiens

<400> SEQUENCE: 192

Phe Gln Cys Arg Ile Cys Met Arg Asn Phe Ser Gln Gln Ala Ser Leu
1               5                   10                  15

Asn Ala His Ile Arg Thr His
            20

<210> SEQ ID NO 193
<211> LENGTH: 23
<212> TYPE: PRT
<213> ORGANISM: Homo sapiens

```
<400> SEQUENCE: 193

Phe Gln Cys Arg Ile Cys Met Arg Asn Phe Ser Gln Ser Gly Asp Leu
 1               5                  10                  15

Arg Arg His Ile Arg Thr His
            20

<210> SEQ ID NO 194
<211> LENGTH: 23
<212> TYPE: PRT
<213> ORGANISM: Homo sapiens

<400> SEQUENCE: 194

Phe Gln Cys Arg Ile Cys Met Arg Asn Phe Ser Gln Ser Ser Asp Leu
 1               5                  10                  15

Val Arg His Ile Arg Thr His
            20

<210> SEQ ID NO 195
<211> LENGTH: 23
<212> TYPE: PRT
<213> ORGANISM: Homo sapiens

<400> SEQUENCE: 195

Phe Gln Cys Arg Ile Cys Met Arg Asn Phe Ser Gln Arg Gly Thr Leu
 1               5                  10                  15

Thr Arg His Ile Arg Thr His
            20

<210> SEQ ID NO 196
<211> LENGTH: 23
<212> TYPE: PRT
<213> ORGANISM: Homo sapiens

<400> SEQUENCE: 196

Phe Gln Cys Arg Ile Cys Met Arg Asn Phe Ser Arg Ser Asp Thr Leu
 1               5                  10                  15

Ser Asn His Ile Arg Thr His
            20

<210> SEQ ID NO 197
<211> LENGTH: 23
<212> TYPE: PRT
<213> ORGANISM: Homo sapiens

<400> SEQUENCE: 197

Phe Gln Cys Arg Ile Cys Met Arg Asn Phe Ser Thr Ala Asp Lys Leu
 1               5                  10                  15

Ser Arg His Ile Arg Thr His
            20

<210> SEQ ID NO 198
<211> LENGTH: 23
<212> TYPE: PRT
<213> ORGANISM: Homo sapiens

<400> SEQUENCE: 198

Phe Gln Cys Arg Ile Cys Met Arg Asn Phe Ser Thr Ser Gly Asn Leu
 1               5                  10                  15

Val Arg His Ile Arg Thr His
            20
```

```
<210> SEQ ID NO 199
<211> LENGTH: 23
<212> TYPE: PRT
<213> ORGANISM: Homo sapiens

<400> SEQUENCE: 199

Phe Gln Cys Arg Ile Cys Met Arg Asn Phe Ser Thr His Ile Asp Leu
1               5                   10                  15

Ile Arg His Ile Arg Thr His
            20

<210> SEQ ID NO 200
<211> LENGTH: 9
<212> TYPE: DNA
<213> ORGANISM: Artificial Sequence
<220> FEATURE:
<223> OTHER INFORMATION: target sequence
<220> FEATURE:
<221> NAME/KEY: misc_feature
<222> LOCATION: (1)...(9)
<223> OTHER INFORMATION: n = A,T,C or G

<400> SEQUENCE: 200 ngggavggg                                                         9

<210> SEQ ID NO 201
<211> LENGTH: 9
<212> TYPE: DNA
<213> ORGANISM: Artificial Sequence
<220> FEATURE:
<223> OTHER INFORMATION: target sequence
<220> FEATURE:
<221> NAME/KEY: misc_feature
<222> LOCATION: (1)...(9)
<223> OTHER INFORMATION: n = A,T,C or G

<400> SEQUENCE: 201 ggkngggag                                                         9

<210> SEQ ID NO 202
<211> LENGTH: 9
<212> TYPE: DNA
<213> ORGANISM: Artificial Sequence
<220> FEATURE:
<223> OTHER INFORMATION: target sequence
<220> FEATURE:
<221> NAME/KEY: misc_feature
<222> LOCATION: (1)...(9)
<223> OTHER INFORMATION: n = A,T,C or G

<400> SEQUENCE: 202 ngggrantt                                                         9

<210> SEQ ID NO 203
<211> LENGTH: 9
<212> TYPE: DNA
<213> ORGANISM: Artificial Sequence
<220> FEATURE:
<223> OTHER INFORMATION: target sequence
<220> FEATURE:
<221> NAME/KEY: misc_feature
<222> LOCATION: (1)...(9)
<223> OTHER INFORMATION: n = A,T,C or G

<400> SEQUENCE: 203 gaangggct                                                         9

<210> SEQ ID NO 204
```

```
<211> LENGTH: 9
<212> TYPE: DNA
<213> ORGANISM: Artificial Sequence
<220> FEATURE:
<223> OTHER INFORMATION: target sequence

<400> SEQUENCE: 204 gtdaaggav                                                                 9

<210> SEQ ID NO 205
<211> LENGTH: 9
<212> TYPE: DNA
<213> ORGANISM: Artificial Sequence
<220> FEATURE:
<223> OTHER INFORMATION: target sequence
<220> FEATURE:
<221> NAME/KEY: misc_feature
<222> LOCATION: (1)...(9)
<223> OTHER INFORMATION: n = A,T,C or G

<400> SEQUENCE: 205 ghgnggkgg                                                                 9

<210> SEQ ID NO 206
<211> LENGTH: 9
<212> TYPE: DNA
<213> ORGANISM: Artificial Sequence
<220> FEATURE:
<223> OTHER INFORMATION: target sequence

<400> SEQUENCE: 206 hgaaaggaa                                                                 9

<210> SEQ ID NO 207
<211> LENGTH: 9
<212> TYPE: DNA
<213> ORGANISM: Artificial Sequence
<220> FEATURE:
<223> OTHER INFORMATION: target sequence
<220> FEATURE:
<221> NAME/KEY: misc_feature
<222> LOCATION: (1)...(9)
<223> OTHER INFORMATION: n = A,T,C or G

<400> SEQUENCE: 207 ngghhggaw                                                                 9

<210> SEQ ID NO 208
<211> LENGTH: 9
<212> TYPE: DNA
<213> ORGANISM: Artificial Sequence
<220> FEATURE:
<223> OTHER INFORMATION: target sequence
<220> FEATURE:
<221> NAME/KEY: misc_feature
<222> LOCATION: (1)...(9)
<223> OTHER INFORMATION: n = A,T,C or G

<400> SEQUENCE: 208 hgangggya                                                                 9

<210> SEQ ID NO 209
<211> LENGTH: 9
<212> TYPE: DNA
<213> ORGANISM: Artificial Sequence
<220> FEATURE:
<223> OTHER INFORMATION: target sequence
<220> FEATURE:
<221> NAME/KEY: misc_feature
```

```
<222> LOCATION: (1)...(9)
<223> OTHER INFORMATION: n = A,T,C or G

<400> SEQUENCE: 209 gaangggya                                                                  9

<210> SEQ ID NO 210
<211> LENGTH: 9
<212> TYPE: DNA
<213> ORGANISM: Artificial Sequence
<220> FEATURE:
<223> OTHER INFORMATION: target sequence

<400> SEQUENCE: 210 ggggaghga                                                                  9

<210> SEQ ID NO 211
<211> LENGTH: 12
<212> TYPE: DNA
<213> ORGANISM: Artificial Sequence
<220> FEATURE:
<223> OTHER INFORMATION: target sequence

<400> SEQUENCE: 211
hgagyagagg ag                                                             12

<210> SEQ ID NO 212
<211> LENGTH: 12
<212> TYPE: DNA
<213> ORGANISM: Artificial Sequence
<220> FEATURE:
<223> OTHER INFORMATION: target sequence

<400> SEQUENCE: 212
graacagagg ag                                                             12

<210> SEQ ID NO 213
<211> LENGTH: 12
<212> TYPE: DNA
<213> ORGANISM: Artificial Sequence
<220> FEATURE:
<223> OTHER INFORMATION: target sequence

<400> SEQUENCE: 213
hgaacagagg ag                                                             12

<210> SEQ ID NO 214
<211> LENGTH: 12
<212> TYPE: DNA
<213> ORGANISM: Artificial Sequence
<220> FEATURE:
<223> OTHER INFORMATION: target sequence

<400> SEQUENCE: 214
katgtdaacg td                                                             12

<210> SEQ ID NO 215
<211> LENGTH: 12
<212> TYPE: DNA
<213> ORGANISM: Artificial Sequence
<220> FEATURE:
<223> OTHER INFORMATION: target sequence

<400> SEQUENCE: 215
gcagtdgaat gt                                                             12
```

```
<210> SEQ ID NO 216
<211> LENGTH: 12
<212> TYPE: DNA
<213> ORGANISM: Artificial Sequence
<220> FEATURE:
<223> OTHER INFORMATION: target sequence

<400> SEQUENCE: 216
ggcgyahgaa ac                                                              12

<210> SEQ ID NO 217
<211> LENGTH: 12
<212> TYPE: DNA
<213> ORGANISM: Artificial Sequence
<220> FEATURE:
<223> OTHER INFORMATION: target sequence

<400> SEQUENCE: 217
aaghgaaagg tg                                                              12

<210> SEQ ID NO 218
<211> LENGTH: 12
<212> TYPE: DNA
<213> ORGANISM: Artificial Sequence
<220> FEATURE:
<223> OTHER INFORMATION: target sequence
<220> FEATURE:
<221> NAME/KEY: misc_feature
<222> LOCATION: (1)...(12)
<223> OTHER INFORMATION: n = A,T,C or G

<400> SEQUENCE: 218
aachgahgan gg                                                              12

<210> SEQ ID NO 219
<211> LENGTH: 9
<212> TYPE: DNA
<213> ORGANISM: Artificial Sequence
<220> FEATURE:
<223> OTHER INFORMATION: target sequence
<220> FEATURE:
<221> NAME/KEY: misc_feature
<222> LOCATION: (1)...(9)
<223> OTHER INFORMATION: n = A,T,C or G

<400> SEQUENCE: 219 hgahgangg                                                                   9

<210> SEQ ID NO 220
<211> LENGTH: 9
<212> TYPE: DNA
<213> ORGANISM: Artificial Sequence
<220> FEATURE:
<223> OTHER INFORMATION: target sequence
<220> FEATURE:
<221> NAME/KEY: misc_feature
<222> LOCATION: (1)...(9)
<223> OTHER INFORMATION: n = A,T,C or G

<400> SEQUENCE: 220 hgahgangg                                                                   9

<210> SEQ ID NO 221
<211> LENGTH: 210
<212> TYPE: PRT
<213> ORGANISM: Artificial Sequence
<220> FEATURE:
<223> OTHER INFORMATION: plasmid sequence
```

<400> SEQUENCE: 221

```
Met Gly Lys Pro Ile Pro Asn Pro Leu Leu Gly Leu Asn Ser Thr Gln
  1               5                  10                  15
Ala Met Gly Ala Pro Pro Lys Lys Arg Lys Val Gly Ile Arg Ile
             20                  25                  30
Pro Gly Glu Lys Pro Tyr Glu Cys Asp His Cys Gly Lys Ser Phe Ser
             35                  40                  45
Gln Ser Ser His Leu Asn Val His Lys Arg Thr His Thr Gly Glu Lys
 50                  55                  60
Pro Tyr Lys Cys His Gln Cys Gly Lys Ala Phe Ile Gln Ser Phe Asn
 65                  70                  75                  80
Leu Arg Arg His Glu Arg Thr His Thr Gly Glu Lys Pro Tyr Lys Cys
                 85                  90                  95
Met Glu Cys Gly Lys Ala Phe Asn Arg Arg Ser His Leu Thr Arg His
                100                 105                 110
Gln Arg Ile His Ala Ala Ala Ala Asn Ser Ala Ser Ser Ser Thr Lys
                115                 120                 125
Leu Asp Asp Asp Leu Gly Thr Ala Ala Ala Val Leu Ser Asn Met Arg
130                 135                 140
Ser Ser Pro Tyr Arg Thr His Asp Lys Pro Ile Ser Asn Val Asn Asp
145                 150                 155                 160
Met Asn Asn Thr Asn Ala Leu Gly Val Pro Ala Ser Arg Pro His Ser
                165                 170                 175
Ser Ser Phe Pro Ser Lys Gly Val Leu Arg Pro Ile Leu Leu Arg Ile
                180                 185                 190
His Asn Ser Glu Gln Gln Pro Ile Phe Glu Ser Asn Asn Ser Thr Ala
                195                 200                 205
Cys Ile
    210

<210> SEQ ID NO 222
<211> LENGTH: 238
<212> TYPE: PRT
<213> ORGANISM: Artificial Sequence
<220> FEATURE:
<223> OTHER INFORMATION: plasmid sequence

<400> SEQUENCE: 222

Met Gly Lys Pro Ile Pro Asn Pro Leu Leu Gly Leu Asn Ser Thr Gln
  1               5                  10                  15
Ala Met Gly Ala Pro Pro Lys Lys Arg Lys Val Gly Ile Arg Ile
             20                  25                  30
Pro Gly Glu Lys Pro Tyr Ile Cys Arg Lys Cys Gly Arg Gly Phe Ser
             35                  40                  45
Arg Lys Ser Asn Leu Ile Arg His Gln Arg Thr His Thr Gly Glu Lys
 50                  55                  60
Pro Tyr Ile Cys Arg Lys Cys Gly Arg Gly Phe Ser Arg Lys Ser Asn
 65                  70                  75                  80
Leu Ile Arg His Gln Arg Thr His Thr Gly Glu Lys Pro Tyr Lys Cys
                 85                  90                  95
Pro Asp Cys Gly Lys Ser Phe Ser Gln Ser Ser Ser Leu Ile Arg His
                100                 105                 110
Gln Arg Thr His Thr Gly Glu Lys Pro Tyr Lys Cys Glu Glu Cys Gly
                115                 120                 125
```

```
Lys Ala Phe Arg Gln Ser Ser His Leu Thr Thr His Lys Ile Ile His
    130                 135                 140

Ala Ala Ala Ala Asn Ser Ala Ser Ser Ser Thr Lys Leu Asp Asp Asp
145                 150                 155                 160

Leu Gly Thr Ala Ala Val Leu Ser Asn Met Arg Ser Ser Pro Tyr
                165                 170                 175

Arg Thr His Asp Lys Pro Ile Ser Asn Val Asn Asp Met Asn Asn Thr
                180                 185                 190

Asn Ala Leu Gly Val Pro Ala Ser Arg Pro His Ser Ser Ser Phe Pro
                195                 200                 205

Ser Lys Gly Val Leu Arg Pro Ile Leu Leu Arg Ile His Asn Ser Glu
        210                 215                 220

Gln Gln Pro Ile Phe Glu Ser Asn Asn Ser Thr Ala Cys Ile
225                 230                 235

<210> SEQ ID NO 223
<211> LENGTH: 238
<212> TYPE: PRT
<213> ORGANISM: Artificial Sequence
<220> FEATURE:
<223> OTHER INFORMATION: plasmid sequence

<400> SEQUENCE: 223

Met Gly Lys Pro Ile Pro Asn Pro Leu Leu Gly Leu Asn Ser Thr Gln
  1               5                  10                  15

Ala Met Gly Ala Pro Pro Lys Lys Lys Arg Lys Val Gly Ile Arg Ile
                20                  25                  30

Pro Gly Glu Lys Pro Tyr Ile Cys Arg Lys Cys Gly Arg Gly Phe Ser
                35                  40                  45

Arg Lys Ser Asn Leu Ile Arg His Gln Arg Thr His Thr Gly Glu Lys
    50                  55                  60

Pro Tyr Ile Cys Arg Lys Cys Gly Arg Gly Phe Ser Arg Lys Ser Asn
65                  70                  75                  80

Leu Ile Arg His Gln Arg Thr His Thr Gly Glu Lys Pro Phe Gln Cys
                85                  90                  95

Arg Ile Cys Met Arg Asn Phe Ser Gln Arg Gly Thr Leu Thr Arg His
                100                 105                 110

Ile Arg Thr His Thr Gly Glu Lys Pro Tyr Val Cys Arg Glu Cys Gly
                115                 120                 125

Arg Gly Phe Arg Gln His Ser His Leu Val Arg His Lys Arg Thr His
                130                 135                 140

Ala Ala Ala Ala Asn Ser Ala Ser Ser Ser Thr Lys Leu Asp Asp Asp
145                 150                 155                 160

Leu Gly Thr Ala Ala Val Leu Ser Asn Met Arg Ser Ser Pro Tyr
                165                 170                 175

Arg Thr His Asp Lys Pro Ile Ser Asn Val Asn Asp Met Asn Asn Thr
                180                 185                 190

Asn Ala Leu Gly Val Pro Ala Ser Arg Pro His Ser Ser Ser Phe Pro
                195                 200                 205

Ser Lys Gly Val Leu Arg Pro Ile Leu Leu Arg Ile His Asn Ser Glu
        210                 215                 220

Gln Gln Pro Ile Phe Glu Ser Asn Asn Ser Thr Ala Cys Ile
225                 230                 235

<210> SEQ ID NO 224
<211> LENGTH: 238
```

```
<212> TYPE: PRT
<213> ORGANISM: Artificial Sequence
<220> FEATURE:
<223> OTHER INFORMATION: plasmid sequence

<400> SEQUENCE: 224

Met Gly Lys Pro Ile Pro Asn Pro Leu Leu Gly Leu Asn Ser Thr Gln
1               5                   10                  15

Ala Met Gly Ala Pro Pro Lys Lys Arg Lys Val Gly Ile Arg Ile
            20                  25                  30

Pro Gly Glu Lys Pro Tyr Ile Cys Arg Lys Cys Gly Arg Gly Phe Ser
        35                  40                  45

Arg Lys Ser Asn Leu Ile Arg His Gln Arg Thr His Thr Gly Glu Lys
    50                  55                  60

Pro Tyr Ile Cys Arg Lys Cys Gly Arg Gly Phe Ser Arg Lys Ser Asn
65                  70                  75                  80

Leu Ile Arg His Gln Arg Thr His Thr Gly Glu Lys Pro Phe Gln Cys
                85                  90                  95

Arg Ile Cys Met Arg Asn Phe Ser Gln Arg Gly Thr Leu Thr Arg His
            100                 105                 110

Ile Arg Thr His Thr Gly Glu Lys Pro Tyr Glu Cys His Asp Cys Gly
        115                 120                 125

Lys Ser Phe Arg Gln Ser Thr His Leu Thr Gln His Arg Arg Ile His
    130                 135                 140

Ala Ala Ala Ala Asn Ser Ala Ser Ser Thr Lys Leu Asp Asp Asp
145                 150                 155                 160

Leu Gly Thr Ala Ala Ala Val Leu Ser Asn Met Arg Ser Ser Pro Tyr
                165                 170                 175

Arg Thr His Asp Lys Pro Ile Ser Asn Val Asn Asp Met Asn Asn Thr
            180                 185                 190

Asn Ala Leu Gly Val Pro Ala Ser Arg Pro His Ser Ser Ser Phe Pro
        195                 200                 205

Ser Lys Gly Val Leu Arg Pro Ile Leu Leu Arg Ile His Asn Ser Glu
    210                 215                 220

Gln Gln Pro Ile Phe Glu Ser Asn Asn Ser Thr Ala Cys Ile
225                 230                 235

<210> SEQ ID NO 225
<211> LENGTH: 274
<212> TYPE: PRT
<213> ORGANISM: Artificial Sequence
<220> FEATURE:
<223> OTHER INFORMATION: plasmid sequence

<400> SEQUENCE: 225

Met Gly Lys Pro Ile Pro Asn Pro Leu Leu Gly Leu Asn Ser Thr Gln
1               5                   10                  15

Ala Met Gly Ala Pro Pro Lys Lys Arg Lys Val Gly Ile Arg Ile
            20                  25                  30

Pro Gly Glu Lys Pro Tyr Thr Cys Lys Gln Cys Gly Lys Ala Phe Ser
        35                  40                  45

Val Ser Ser Ser Leu Arg Arg His Glu Thr Thr His Thr Gly Glu Lys
    50                  55                  60

Pro Phe Gln Cys Arg Ile Cys Met Arg Asn Phe Ser Asp Ser Gly Asn
65                  70                  75                  80

Leu Arg Val His Ile Arg Thr His Thr Gly Glu Lys Pro Tyr Thr Cys
                85                  90                  95
```

```
Lys Gln Cys Gly Lys Ala Phe Ser Val Ser Ser Ser Leu Arg Arg His
                100                 105                 110

Glu Thr Thr His Thr Gly Glu Lys Pro Phe His Cys Gly Tyr Cys Glu
            115                 120                 125

Lys Ser Phe Ser Val Lys Asp Tyr Leu Thr Lys Ile Arg Thr His Ala
    130                 135                 140

Ala Ala Ala Asn Phe Asn Gln Ser Gly Asn Ile Ala Asp Ser Ser Leu
145                 150                 155                 160

Ser Phe Thr Phe Thr Asn Ser Ser Asn Gly Pro Asn Leu Ile Thr Thr
                165                 170                 175

Gln Thr Asn Ser Gln Ala Leu Ser Gln Pro Ile Ala Ser Ser Asn Val
            180                 185                 190

His Asp Asn Phe Met Asn Asn Glu Ile Thr Ala Ser Lys Ile Asp Asp
                195                 200                 205

Gly Asn Asn Ser Lys Pro Leu Ser Pro Gly Trp Thr Asp Gln Thr Ala
210                 215                 220

Tyr Asn Ala Phe Gly Ile Thr Thr Gly Met Phe Asn Thr Thr Thr Met
225                 230                 235                 240

Asp Asp Val Tyr Asn Tyr Leu Phe Asp Asp Glu Asp Thr Pro Pro Asn
                245                 250                 255

Pro Lys Lys Glu Ile Ser Met Ala Tyr Pro Tyr Asp Val Pro Asp Tyr
            260                 265                 270

Ala Ser

<210> SEQ ID NO 226
<211> LENGTH: 277
<212> TYPE: PRT
<213> ORGANISM: Artificial Sequence
<220> FEATURE:
<223> OTHER INFORMATION: plasmid sequence

<400> SEQUENCE: 226

Met Gly Lys Pro Ile Pro Asn Pro Leu Leu Gly Leu Asn Ser Thr Gln
1               5                   10                  15

Ala Met Gly Ala Pro Lys Lys Arg Lys Val Gly Ile Arg Ile
            20                  25                  30

Pro Gly Glu Lys Pro Tyr Ala Cys Pro Val Glu Ser Cys Asp Arg Arg
            35                  40                  45

Phe Ser Met Ser His His Leu Lys Glu His Ile Arg Thr His Thr Gly
    50                  55                  60

Glu Lys Pro Phe Glu Cys Lys Asp Cys Gly Lys Ala Phe Ile Gln Lys
65                  70                  75                  80

Ser Asn Leu Ile Arg His Gln Arg Thr His Thr Gly Glu Lys Pro Tyr
                85                  90                  95

Thr Cys Lys Gln Cys Gly Lys Ala Phe Ser Val Ser Ser Ser Leu Arg
            100                 105                 110

Arg His Glu Thr Thr His Thr Gly Glu Lys Pro Phe Gln Cys Arg Ile
    115                 120                 125

Cys Met Arg Asn Phe Ser Gln Ser Gly Asp Leu Arg Arg His Ile Arg
130                 135                 140

Thr His Ala Ala Ala Asn Phe Asn Gln Ser Gly Asn Ile Ala Asp
145                 150                 155                 160

Ser Ser Leu Ser Phe Thr Phe Thr Asn Ser Ser Asn Gly Pro Asn Leu
                165                 170                 175
```

Ile Thr Thr Gln Thr Asn Ser Gln Ala Leu Ser Gln Pro Ile Ala Ser
            180                 185                 190

Ser Asn Val His Asp Asn Phe Met Asn Asn Glu Ile Thr Ala Ser Lys
        195                 200                 205

Ile Asp Asp Gly Asn Asn Ser Lys Pro Leu Ser Pro Gly Trp Thr Asp
    210                 215                 220

Gln Thr Ala Tyr Asn Ala Phe Gly Ile Thr Thr Gly Met Phe Asn Thr
225                 230                 235                 240

Thr Thr Met Asp Asp Val Tyr Asn Tyr Leu Phe Asp Asp Glu Asp Thr
                245                 250                 255

Pro Pro Asn Pro Lys Lys Glu Ile Ser Met Ala Tyr Pro Tyr Asp Val
            260                 265                 270

Pro Asp Tyr Ala Ser
            275

<210> SEQ ID NO 227
<211> LENGTH: 275
<212> TYPE: PRT
<213> ORGANISM: Artificial Sequence
<220> FEATURE:
<223> OTHER INFORMATION: plasmid sequence

<400> SEQUENCE: 227

Met Gly Lys Pro Ile Pro Asn Pro Leu Leu Gly Leu Asn Ser Thr Gln
1               5                   10                  15

Ala Met Gly Ala Pro Lys Lys Lys Arg Lys Val Gly Ile Arg Ile
            20                  25                  30

Pro Gly Glu Lys Pro Phe Gln Cys Arg Ile Cys Met Arg Asn Phe Ser
            35                  40                  45

Asp Ser Gly Asn Leu Arg Val His Ile Arg Thr His Thr Gly Glu Lys
    50                  55                  60

Pro Tyr Lys Cys Glu Glu Cys Gly Lys Ala Phe Arg Gln Ser Ser His
65                  70                  75                  80

Leu Thr Thr His Lys Ile Ile His Thr Gly Glu Lys Pro Tyr Lys Cys
                85                  90                  95

Pro Asp Cys Gly Lys Ser Phe Ser Gln Ser Ser Ser Leu Ile Arg His
            100                 105                 110

Gln Arg Thr His Thr Gly Glu Lys Pro Phe Gln Cys Arg Ile Cys Met
            115                 120                 125

Arg Asn Phe Ser Asp Pro Gly His Leu Val Arg His Ile Arg Thr His
    130                 135                 140

Ala Ala Ala Ala Asn Phe Asn Gln Ser Gly Asn Ile Ala Asp Ser Ser
145                 150                 155                 160

Leu Ser Phe Thr Phe Thr Asn Ser Ser Asn Gly Pro Asn Leu Ile Thr
                165                 170                 175

Thr Gln Thr Asn Ser Gln Ala Leu Ser Gln Pro Ile Ala Ser Ser Asn
            180                 185                 190

Val His Asp Asn Phe Met Asn Asn Glu Ile Thr Ala Ser Lys Ile Asp
        195                 200                 205

Asp Gly Asn Asn Ser Lys Pro Leu Ser Pro Gly Trp Thr Asp Gln Thr
    210                 215                 220

Ala Tyr Asn Ala Phe Gly Ile Thr Thr Gly Met Phe Asn Thr Thr Thr
225                 230                 235                 240

Met Asp Asp Val Tyr Asn Tyr Leu Phe Asp Asp Glu Asp Thr Pro Pro
                245                 250                 255

Asn Pro Lys Lys Glu Ile Ser Met Ala Tyr Pro Tyr Asp Val Pro Asp
            260                 265                 270

Tyr Ala Ser
        275

<210> SEQ ID NO 228
<211> LENGTH: 158
<212> TYPE: PRT
<213> ORGANISM: Artificial Sequence
<220> FEATURE:
<223> OTHER INFORMATION: plasmid sequence

<400> SEQUENCE: 228

Met Gly Lys Pro Ile Pro Asn Pro Leu Leu Gly Leu Asn Ser Thr Gln
1               5                   10                  15

Ala Met Gly Ala Pro Pro Lys Lys Arg Lys Val Gly Ile Arg Ile
            20                  25                  30

Pro Gly Glu Lys Pro Phe Gln Cys Arg Ile Cys Met Arg Asn Phe Ser
            35                  40                  45

Asp Pro Gly Ala Leu Val Arg His Ile Arg Thr His Thr Gly Glu Lys
        50                  55                  60

Pro Phe Gln Cys Arg Ile Cys Met Arg Asn Phe Ser Arg Ser Asp Thr
65                  70                  75                  80

Leu Ser Asn His Ile Arg Thr His Thr Gly Glu Lys Pro Tyr Glu Cys
                85                  90                  95

His Asp Cys Gly Lys Ser Phe Arg Gln Ser Thr His Leu Thr Gln His
            100                 105                 110

Arg Arg Ile His Thr Gly Glu Lys Pro Phe Gln Cys Arg Ile Cys Met
        115                 120                 125

Arg Asn Phe Ser Arg Ser Asp Thr Leu Ser Asn His Ile Arg Thr His
    130                 135                 140

Ala Ala Ala Ala Arg Gly Met His Leu Glu Gly Arg Ile Met
145                 150                 155

<210> SEQ ID NO 229
<211> LENGTH: 158
<212> TYPE: PRT
<213> ORGANISM: Artificial Sequence
<220> FEATURE:
<223> OTHER INFORMATION: plasmid sequence

<400> SEQUENCE: 229

Met Gly Lys Pro Ile Pro Asn Pro Leu Leu Gly Leu Asn Ser Thr Gln
1               5                   10                  15

Ala Met Gly Ala Pro Pro Lys Lys Arg Lys Val Gly Ile Arg Ile
            20                  25                  30

Pro Gly Glu Lys Pro Phe Gln Cys Lys Thr Cys Gln Arg Lys Phe Ser
            35                  40                  45

Arg Ser Asp His Leu Lys Thr His Thr Arg Thr His Thr Gly Glu Lys
        50                  55                  60

Pro Tyr Glu Cys His Asp Cys Gly Lys Ser Phe Arg Gln Ser Thr His
65                  70                  75                  80

Leu Thr Gln His Arg Arg Ile His Thr Gly Glu Lys Pro Tyr Lys Cys
                85                  90                  95

Glu Glu Cys Gly Lys Ala Phe Arg Gln Ser Ser His Leu Thr Thr His
            100                 105                 110

Lys Ile Ile His Thr Gly Glu Lys Pro Phe Gln Cys Arg Ile Cys Met
        115                 120                 125

```
Arg Asn Phe Ser Asp Ser Gly Asn Leu Arg Val His Ile Arg Thr His
    130                 135                 140

Ala Ala Ala Ala Arg Gly Met His Leu Glu Gly Arg Ile Met
145                 150                 155

<210> SEQ ID NO 230
<211> LENGTH: 130
<212> TYPE: PRT
<213> ORGANISM: Artificial Sequence
<220> FEATURE:
<223> OTHER INFORMATION: plasmid sequence

<400> SEQUENCE: 230

Met Gly Lys Pro Ile Pro Asn Pro Leu Leu Gly Leu Asn Ser Thr Gln
  1               5                  10                  15

Ala Met Gly Ala Pro Pro Lys Lys Arg Lys Val Gly Ile Arg Ile
             20                  25                  30

Pro Gly Glu Lys Pro Phe Gln Cys Lys Thr Cys Gln Arg Lys Phe Ser
             35                  40                  45

Arg Ser Asp His Leu Lys Thr His Thr Arg Thr His Thr Gly Glu Lys
 50                  55                  60

Pro Tyr Glu Cys His Asp Cys Gly Lys Ser Phe Arg Gln Ser Thr His
65                  70                  75                  80

Leu Thr Gln His Arg Arg Ile His Thr Gly Glu Lys Pro Tyr Lys Cys
                 85                  90                  95

Glu Glu Cys Gly Lys Ala Phe Arg Gln Ser Ser His Leu Thr Thr His
            100                 105                 110

Lys Ile Ile His Ala Ala Ala Ala Arg Gly Met His Leu Glu Gly Arg
            115                 120                 125

Ile Met
    130

<210> SEQ ID NO 231
<211> LENGTH: 130
<212> TYPE: PRT
<213> ORGANISM: Artificial Sequence
<220> FEATURE:
<223> OTHER INFORMATION: plasmid sequence

<400> SEQUENCE: 231

Met Gly Lys Pro Ile Pro Asn Pro Leu Leu Gly Leu Asn Ser Thr Gln
  1               5                  10                  15

Ala Met Gly Ala Pro Pro Lys Lys Arg Lys Val Gly Ile Arg Ile
             20                  25                  30

Pro Gly Glu Lys Pro Phe Gln Cys Lys Thr Cys Gln Arg Lys Phe Ser
             35                  40                  45

Arg Ser Asp His Leu Lys Thr His Thr Arg Thr His Thr Gly Glu Lys
 50                  55                  60

Pro Tyr Glu Cys Asp His Cys Gly Lys Ser Phe Ser Gln Ser Ser His
65                  70                  75                  80

Leu Asn Val His Lys Arg Thr His Thr Gly Glu Lys Pro Tyr Glu Cys
                 85                  90                  95

Asp His Cys Gly Lys Ser Phe Ser Gln Ser Ser His Leu Asn Val His
            100                 105                 110

Lys Arg Thr His Ala Ala Ala Ala Arg Gly Met His Leu Glu Gly Arg
            115                 120                 125

Ile Met
```

130

<210> SEQ ID NO 232
<211> LENGTH: 152
<212> TYPE: PRT
<213> ORGANISM: Saccharomyces cerevisiae

<400> SEQUENCE: 232

Met Trp Phe Pro Gln Ile Ile Ala Gly Met Ala Ala Gly Gly Ala Ala
1               5                   10                  15

Ser Ala Met Thr Pro Gly Lys Val Leu Phe Thr Asn Ala Leu Gly Leu
            20                  25                  30

Gly Cys Ser Arg Ser Arg Gly Leu Phe Leu Glu Met Phe Gly Thr Ala
        35                  40                  45

Val Leu Cys Leu Thr Val Leu Met Thr Ala Val Glu Lys Arg Glu Thr
50                  55                  60

Asn Phe Met Ala Ala Leu Pro Ile Gly Ile Ser Leu Phe Met Ala His
65                  70                  75                  80

Met Ala Leu Thr Gly Tyr Thr Gly Thr Gly Val Asn Pro Ala Arg Ser
                85                  90                  95

Leu Gly Ala Ala Val Ala Ala Arg Tyr Phe Pro His Tyr His Trp Ile
            100                 105                 110

Tyr Trp Ile Ser Pro Leu Leu Gly Ala Phe Leu Ala Trp Ser Val Trp
        115                 120                 125

Gln Leu Leu Gln Ile Leu Asp Tyr Thr Thr Tyr Val Asn Ala Glu Lys
130                 135                 140

Ala Ala Gly Gln Lys Lys Glu Asp
145                 150

<210> SEQ ID NO 233
<211> LENGTH: 273
<212> TYPE: PRT
<213> ORGANISM: Candida albicans

<400> SEQUENCE: 233

Met Val Ala Glu Ser Ser Ser Ile Asp Asn Thr Pro Asn Asp Val Glu
1               5                   10                  15

Ala Gln Arg Pro Val Tyr Glu Pro Lys Tyr Asp Asp Ser Val Asn Val
            20                  25                  30

Ser Pro Leu Lys Asn His Met Ile Ala Phe Leu Gly Glu Phe Phe Gly
        35                  40                  45

Thr Phe Ile Phe Leu Trp Val Ala Phe Val Ile Ala Gln Ile Ala Asn
50                  55                  60

Gln Asp Pro Thr Ile Pro Asp Lys Gly Ser Asp Pro Met Gln Leu Ile
65                  70                  75                  80

Met Ile Ser Phe Gly Phe Gly Phe Gly Val Met Met Gly Val Phe Met
                85                  90                  95

Phe Phe Arg Val Ser Gly Gly Asn Leu Asn Pro Ala Val Thr Leu Thr
            100                 105                 110

Leu Val Leu Ala Gln Ala Val Pro Pro Ile Arg Gly Leu Phe Met Met
        115                 120                 125

Val Ala Gln Met Ile Ala Gly Met Ala Ala Gly Ala Ala Ser Ala
130                 135                 140

Met Thr Pro Gly Pro Ile Ala Phe Thr Asn Gly Leu Gly Gly Gly Ala
145                 150                 155                 160

Ser Lys Ala Arg Gly Val Phe Leu Glu Ala Phe Gly Thr Cys Ile Leu

|           |           |           |           | 165       |           |           |           | 170       |           |           |           | 175       |
|-----------|-----------|-----------|-----------|-----------|-----------|-----------|-----------|-----------|-----------|-----------|-----------|-----------|

Cys Leu Thr Val Leu Met Met Ala Val Glu Lys Ser Arg Ala Thr Phe
                    180                 185                 190

Met Ala Pro Phe Val Ile Gly Ile Ser Leu Phe Leu Gly His Leu Ile
            195                 200                 205

Cys Val Tyr Tyr Thr Gly Ala Gly Leu Asn Pro Ala Arg Ser Phe Gly
        210                 215                 220

Pro Cys Val Ala Ala Arg Ser Phe Pro Val Tyr His Trp Ile Tyr Trp
225                 230                 235                 240

Val Gly Pro Ile Leu Gly Ser Val Ile Ala Phe Ala Ile Trp Lys Ile
                245                 250                 255

Phe Lys Ile Leu Lys Tyr Glu Thr Cys Asn Pro Gly Gln Asp Ser Asp
            260                 265                 270

Ala

<210> SEQ ID NO 234
<211> LENGTH: 12
<212> TYPE: DNA
<213> ORGANISM: Artificial Sequence
<220> FEATURE:
<223> OTHER INFORMATION: recognition element

<400> SEQUENCE: 234
ggggcwrgag gg                                                              12

<210> SEQ ID NO 235
<211> LENGTH: 12
<212> TYPE: DNA
<213> ORGANISM: Artificial Sequence
<220> FEATURE:
<223> OTHER INFORMATION: target sequence
<220> FEATURE:
<221> NAME/KEY: misc_feature
<222> LOCATION: (1)...(12)
<223> OTHER INFORMATION: n = A,T,C or G

<400> SEQUENCE: 235
gctgranggg ah                                                              12

<210> SEQ ID NO 236
<211> LENGTH: 31
<212> TYPE: DNA
<213> ORGANISM: Artificial Sequence
<220> FEATURE:
<223> OTHER INFORMATION: primer

<400> SEQUENCE: 236
gacaaccggt catcgataag ctaattctca c                                         31

<210> SEQ ID NO 237
<211> LENGTH: 29
<212> TYPE: DNA
<213> ORGANISM: Artificial Sequence
<220> FEATURE:
<223> OTHER INFORMATION: primer

<400> SEQUENCE: 237
ttgtccatgg acgctgtttc ctggtgaaa                                            29

<210> SEQ ID NO 238
<211> LENGTH: 12
<212> TYPE: DNA
<213> ORGANISM: Artificial Sequence

```
<220> FEATURE:
<223> OTHER INFORMATION: target sequence

<400> SEQUENCE: 238
daadaaaath ga                                                         12

<210> SEQ ID NO 239
<211> LENGTH: 13
<212> TYPE: DNA
<213> ORGANISM: Artificial Sequence
<220> FEATURE:
<223> OTHER INFORMATION: target sequence
<220> FEATURE:
<221> NAME/KEY: misc_feature
<222> LOCATION: (1)...(13)
<223> OTHER INFORMATION: n = A,T,C or G

<400> SEQUENCE: 239
gyagrahgan ggk                                                        13

<210> SEQ ID NO 240
<211> LENGTH: 12
<212> TYPE: DNA
<213> ORGANISM: Artificial Sequence
<220> FEATURE:
<223> OTHER INFORMATION: target sequence

<400> SEQUENCE: 240
hgaaathgag gt                                                         12

<210> SEQ ID NO 241
<211> LENGTH: 12
<212> TYPE: DNA
<213> ORGANISM: Artificial Sequence
<220> FEATURE:
<223> OTHER INFORMATION: target sequence

<400> SEQUENCE: 241
gragragggg ra                                                         12

<210> SEQ ID NO 242
<211> LENGTH: 12
<212> TYPE: DNA
<213> ORGANISM: Artificial Sequence
<220> FEATURE:
<223> OTHER INFORMATION: target sequence
<220> FEATURE:
<221> NAME/KEY: misc_feature
<222> LOCATION: (1)...(12)
<223> OTHER INFORMATION: n = A,T,C or G

<400> SEQUENCE: 242
grahganggg tc                                                         12

<210> SEQ ID NO 243
<211> LENGTH: 12
<212> TYPE: DNA
<213> ORGANISM: Artificial Sequence
<220> FEATURE:
<223> OTHER INFORMATION: target sequence

<400> SEQUENCE: 243
gragragggh ga                                                         12

<210> SEQ ID NO 244
<211> LENGTH: 12
<212> TYPE: DNA
```

```
<213> ORGANISM: Artificial Sequence
<220> FEATURE:
<223> OTHER INFORMATION: target sequence

<400> SEQUENCE: 244
gavgaaaath ga                                                           12

<210> SEQ ID NO 245
<211> LENGTH: 12
<212> TYPE: DNA
<213> ORGANISM: Artificial Sequence
<220> FEATURE:
<223> OTHER INFORMATION: target sequence
<220> FEATURE:
<221> NAME/KEY: misc_feature
<222> LOCATION: (1)...(12)
<223> OTHER INFORMATION: n = A,T,C or G

<400> SEQUENCE: 245
ngggyagraa at                                                           12

<210> SEQ ID NO 246
<211> LENGTH: 13
<212> TYPE: DNA
<213> ORGANISM: Artificial Sequence
<220> FEATURE:
<223> OTHER INFORMATION: target sequence
<220> FEATURE:
<221> NAME/KEY: misc_feature
<222> LOCATION: (1)...(13)
<223> OTHER INFORMATION: n = A,T,C or G

<400> SEQUENCE: 246
gaagrahgan ggk                                                          13

<210> SEQ ID NO 247
<211> LENGTH: 12
<212> TYPE: DNA
<213> ORGANISM: Artificial Sequence
<220> FEATURE:
<223> OTHER INFORMATION: target sequence
<220> FEATURE:
<221> NAME/KEY: misc_feature
<222> LOCATION: (1)...(12)
<223> OTHER INFORMATION: n = A,T,C or G

<400> SEQUENCE: 247
gradaanggg tc                                                           12

<210> SEQ ID NO 248
<211> LENGTH: 12
<212> TYPE: DNA
<213> ORGANISM: Artificial Sequence
<220> FEATURE:
<223> OTHER INFORMATION: target sequence
<220> FEATURE:
<221> NAME/KEY: misc_feature
<222> LOCATION: (1)...(12)
<223> OTHER INFORMATION: n = A,T,C or G

<400> SEQUENCE: 248
ggtngggtcg ya                                                           12

<210> SEQ ID NO 249
<211> LENGTH: 12
<212> TYPE: DNA
<213> ORGANISM: Artificial Sequence
<220> FEATURE:
<223> OTHER INFORMATION: target sequence
```

```
<400> SEQUENCE: 249
daagaaaacg ct                                                          12

<210> SEQ ID NO 250
<211> LENGTH: 26
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: 11
<223> OTHER INFORMATION: Xaa = Phe or Tyr
<220> FEATURE:
<221> NAME/KEY: VARIANT
<222> LOCATION: 17
<223> OTHER INFORMATION: Xaa = hydrophobic residue
<220> FEATURE:
<221> NAME/KEY: VARIANT
<222> LOCATION: 2-6, 8-10, 12, 14, 18, 21-25
<223> OTHER INFORMATION: Xaa = any amino acid

<400> SEQUENCE: 250

Cys Xaa Xaa Xaa Xaa Xaa Cys Xaa Xaa Xaa Xaa Xaa Gln Xaa Ser Asn
 1               5                  10                  15

Xaa Xaa Arg His Xaa Xaa Xaa Xaa Xaa His
            20                  25

<210> SEQ ID NO 251
<211> LENGTH: 26
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: 11
<223> OTHER INFORMATION: Xaa = Phe or Tyr
<220> FEATURE:
<221> NAME/KEY: VARIANT
<222> LOCATION: 17
<223> OTHER INFORMATION: Xaa = hydrophobic residue
<220> FEATURE:
<221> NAME/KEY: VARIANT
<222> LOCATION: 2-6,8-10, 12, 14, 18, 21-25
<223> OTHER INFORMATION: Xaa = any amino acid

<400> SEQUENCE: 251

Cys Xaa Xaa Xaa Xaa Xaa Cys Xaa Xaa Xaa Xaa Xaa Gln Xaa Ser Asn
 1               5                  10                  15

Xaa Xaa Lys His Xaa Xaa Xaa Xaa Xaa His
            20                  25

<210> SEQ ID NO 252
<211> LENGTH: 26
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: 11
<223> OTHER INFORMATION: Xaa = Phe or Tyr
<220> FEATURE:
<221> NAME/KEY: VARIANT
<222> LOCATION: 17
<223> OTHER INFORMATION: Xaa = hydrophobic residue
<220> FEATURE:
<221> NAME/KEY: VARIANT
<222> LOCATION: 2-6, 8-10, 12, 14, 18, 21-25
```

```
<223> OTHER INFORMATION: Xaa = any amino acid

<400> SEQUENCE: 252

Cys Xaa Xaa Xaa Xaa Cys Xaa Xaa Xaa Xaa Xaa Cys Xaa Ser Asn
 1               5                  10                  15

Xaa Xaa Arg His Xaa Xaa Xaa Xaa Xaa His
            20                  25

<210> SEQ ID NO 253
<211> LENGTH: 94
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: 11, 33, 45, 67, 79
<223> OTHER INFORMATION: Xaa = Phe or Tyr
<220> FEATURE:
<221> NAME/KEY: VARIANT
<222> LOCATION: 17, 51, 85
<223> OTHER INFORMATION: Xaa = hydrophobic residue
<220> FEATURE:
<221> NAME/KEY: VARIANT
<222> LOCATION: 2-6,8-10, 12, 14, 18, 21-25, 27-32, 34, 36-40, 42-44,
      46, 48, 52, 55-59, 61-66, 68, 70-74, 76-78, 80, 82, 86, 89-93
<223> OTHER INFORMATION: Xaa = any amino acid

<400> SEQUENCE: 253

Cys Xaa Xaa Xaa Xaa Cys Xaa Xaa Xaa Xaa Xaa Gln Xaa Ser Asn
 1               5                  10                  15

Xaa Xaa Arg His Xaa Xaa Xaa Xaa Xaa His Xaa Xaa Xaa Xaa Xaa
            20                  25                  30

Xaa Xaa Cys Xaa Xaa Xaa Xaa Cys Xaa Xaa Xaa Xaa Xaa Gln Xaa
                35                  40                  45

Ser Asn Xaa Xaa Lys His Xaa Xaa Xaa Xaa Xaa His Xaa Xaa Xaa Xaa
 50                  55                  60

Xaa Xaa Xaa Xaa Cys Xaa Xaa Xaa Xaa Cys Xaa Xaa Xaa Xaa Xaa
 65                  70                  75                  80

Cys Xaa Ser Asn Xaa Xaa Arg His Xaa Xaa Xaa Xaa Xaa His
                 85                  90

<210> SEQ ID NO 254
<211> LENGTH: 26
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: 11
<223> OTHER INFORMATION: Xaa = Phe or Tyr
<220> FEATURE:
<221> NAME/KEY: VARIANT
<222> LOCATION: 17
<223> OTHER INFORMATION: Xaa = hydrophobic residue
<220> FEATURE:
<221> NAME/KEY: VARIANT
<222> LOCATION: 2-6, 8-10,12,14,18, 21-25
<223> OTHER INFORMATION: Xaa = any amino acid

<400> SEQUENCE: 254

Cys Xaa Xaa Xaa Xaa Cys Xaa Xaa Xaa Xaa Xaa Arg Xaa Asp Lys
 1               5                  10                  15

Xaa Xaa Arg His Xaa Xaa Xaa Xaa Xaa His
            20                  25
```

```
<210> SEQ ID NO 255
<211> LENGTH: 26
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: 11
<223> OTHER INFORMATION: Xaa = Phe or Tyr
<220> FEATURE:
<221> NAME/KEY: VARIANT
<222> LOCATION: 17
<223> OTHER INFORMATION: Xaa = hydrophobic residue
<220> FEATURE:
<221> NAME/KEY: VARIANT
<222> LOCATION: 2-6, 8-10, 12, 14, 18, 21-25
<223> OTHER INFORMATION: Xaa = any amino acid

<400> SEQUENCE: 255

Cys Xaa Xaa Xaa Xaa Xaa Cys Xaa Xaa Xaa Xaa Xaa Gln Xaa Thr His
 1               5                  10                  15

Xaa Xaa Arg His Xaa Xaa Xaa Xaa Xaa His
            20                  25

<210> SEQ ID NO 256
<211> LENGTH: 26
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: 11
<223> OTHER INFORMATION: Xaa = Phe or Tyr
<220> FEATURE:
<221> NAME/KEY: VARIANT
<222> LOCATION: 17
<223> OTHER INFORMATION: Xaa = hydrophobic residue
<220> FEATURE:
<221> NAME/KEY: VARIANT
<222> LOCATION: 2-6, 8-10, 12, 14, 18, 21-25
<223> OTHER INFORMATION: Xaa = any amino acid

<400> SEQUENCE: 256

Cys Xaa Xaa Xaa Xaa Xaa Cys Xaa Xaa Xaa Xaa Xaa Val Xaa Ser Thr
 1               5                  10                  15

Xaa Xaa Arg His Xaa Xaa Xaa Xaa Xaa His
            20                  25

<210> SEQ ID NO 257
<211> LENGTH: 26
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: 11
<223> OTHER INFORMATION: Xaa = Phe or Tyr
<220> FEATURE:
<221> NAME/KEY: VARIANT
<222> LOCATION: 17
<223> OTHER INFORMATION: Xaa = hydrophobic residue
<220> FEATURE:
<221> NAME/KEY: VARIANT
<222> LOCATION: 2-6, 8-10, 12, 14, 18, 21-25
<223> OTHER INFORMATION: Xaa = any amino acid

<400> SEQUENCE: 257

Cys Xaa Xaa Xaa Xaa Xaa Cys Xaa Xaa Xaa Xaa Xaa Arg Xaa Asp Lys
```

-continued

```
                1               5                  10                 15
Xaa Xaa Arg His Xaa Xaa Xaa Xaa Xaa His
        20                  25
```

<210> SEQ ID NO 258
<211> LENGTH: 128
<212> TYPE: PRT
<213> ORGANISM: Artificial Sequence
<220> FEATURE:
<223> OTHER INFORMATION: purified polypeptide
<220> FEATURE:
<221> NAME/KEY: VARIANT
<222> LOCATION: 11, 33, 45, 67, 79,101, 113
<223> OTHER INFORMATION: Xaa = Phe or Tyr
<220> FEATURE:
<221> NAME/KEY: VARIANT
<222> LOCATION: 17, 51, 85, 119
<223> OTHER INFORMATION: Xaa = hydrophobic residue
<220> FEATURE:
<221> NAME/KEY: VARIANT
<222> LOCATION: 2-6, 8-10, 12, 14, 18, 21-25, 27-32, 34, 36-40, 42-44,
       46, 48, 52, 55-59, 61-66, 68, 70-74, 76-78, 80, 82, 86, 89-93,
       95-100,102,104-108, 110-112, 114, 116, 120, 123-127
<223> OTHER INFORMATION: Xaa = any amino acid

<400> SEQUENCE: 258

```
Cys Xaa Xaa Xaa Xaa Cys Xaa Xaa Xaa Xaa Xaa Arg Xaa Asp Lys
 1               5                  10                 15

Xaa Xaa Arg His Xaa Xaa Xaa Xaa His Xaa Xaa Xaa Xaa Xaa
        20                  25                  30

Xaa Xaa Cys Xaa Xaa Xaa Xaa Cys Xaa Xaa Xaa Xaa Gln Xaa
        35                  40                  45

Thr His Xaa Xaa Arg His Xaa Xaa Xaa Xaa Xaa His Xaa Xaa Xaa Xaa
 50                  55                  60

Xaa Xaa Xaa Xaa Cys Xaa Xaa Xaa Xaa Cys Xaa Xaa Xaa Xaa
65                  70                  75                  80

Val Xaa Ser Thr Xaa Arg His Xaa Xaa Xaa Xaa His Xaa Xaa
        85                  90                  95

Xaa Xaa Xaa Xaa Xaa Xaa Cys Xaa Xaa Xaa Xaa Cys Xaa Xaa Xaa
        100                 105                 110

Xaa Xaa Arg Xaa Asp Lys Xaa Xaa Arg His Xaa Xaa Xaa Xaa Xaa His
        115                 120                 125
```

<210> SEQ ID NO 259
<211> LENGTH: 630
<212> TYPE: DNA
<213> ORGANISM: Artificial Sequence
<220> FEATURE:
<223> OTHER INFORMATION: plasmid sequence
<220> FEATURE:
<221> NAME/KEY: CDS
<222> LOCATION: (1)...(627)

<400> SEQUENCE: 259

```
atg gtg tac ccc tac gac gtg ccc gac tac gcc gaa ttg cct cca aaa      48
Met Val Tyr Pro Tyr Asp Val Pro Asp Tyr Ala Glu Leu Pro Pro Lys
 1               5                  10                 15 aag aag aga aag gta ggg atc cga att ccc ggg gaa aaa ccg ttc cag      96
Lys Lys Arg Lys Val Gly Ile Arg Ile Pro Gly Glu Lys Pro Phe Gln
            20                  25                  30 tgt aaa act tgt cag cga aag ttc tcc cgg tcc gac cac ctg aag acc     144
Cys Lys Thr Cys Gln Arg Lys Phe Ser Arg Ser Asp His Leu Lys Thr
        35                  40                  45 cac acc agg act cat acc ggg gaa aaa ccg tat gtt tgc tca aaa tgt     192
```

```
His Thr Arg Thr His Thr Gly Glu Lys Pro Tyr Val Cys Ser Lys Cys
    50                  55                  60 ggg aaa gcc ttc act cag agt tca aat ctg act gta cat caa aaa atc    240
Gly Lys Ala Phe Thr Gln Ser Ser Asn Leu Thr Val His Gln Lys Ile
 65                  70                  75                  80 cac acc ggg gaa aaa ccg tat gag tgt cac gat tgc gga aag tcc ttt    288
His Thr Gly Glu Lys Pro Tyr Glu Cys His Asp Cys Gly Lys Ser Phe
                 85                  90                  95 agg cag agc acc cac ctc act cgg cac cgg agg atc cac acc ggg gaa    336
Arg Gln Ser Thr His Leu Thr Arg His Arg Arg Ile His Thr Gly Glu
            100                 105                 110 aaa ccg tat aag tgt cat caa tgt ggg aaa gcc ttt att caa tcc ttt    384
Lys Pro Tyr Lys Cys His Gln Cys Gly Lys Ala Phe Ile Gln Ser Phe
        115                 120                 125 aac ctt cga aga cat gag aga act cac acc ggt gaa aaa gcg gcc gct    432
Asn Leu Arg Arg His Glu Arg Thr His Thr Gly Glu Lys Ala Ala Ala
    130                 135                 140 aaa ttc gtg tca gtg aca ttt gaa gat gtg gct gtg ctc ttt act cgg    480
Lys Phe Val Ser Val Thr Phe Glu Asp Val Ala Val Leu Phe Thr Arg
145                 150                 155                 160 gac gag tgg aag aag ctg gat ctg tct cag aga agc ctg tac cgt gag    528
Asp Glu Trp Lys Lys Leu Asp Leu Ser Gln Arg Ser Leu Tyr Arg Glu
                165                 170                 175 gtg atg ctg gag aat tac agc aac ctg gcc tcc atg gca gga ttc ctg    576
Val Met Leu Glu Asn Tyr Ser Asn Leu Ala Ser Met Ala Gly Phe Leu
            180                 185                 190 ttt acc aaa cca aag gtg atc tcc ctg ttg cag caa gga gag gat ccc    624
Phe Thr Lys Pro Lys Val Ile Ser Leu Leu Gln Gln Gly Glu Asp Pro
        195                 200                 205 tgg taa                                                             630
Trp

<210> SEQ ID NO 260
<211> LENGTH: 209
<212> TYPE: PRT
<213> ORGANISM: Artificial Sequence
<220> FEATURE:
<223> OTHER INFORMATION: plasmid sequence

<400> SEQUENCE: 260

Met Val Tyr Pro Tyr Asp Val Pro Asp Tyr Ala Glu Leu Pro Pro Lys
  1               5                  10                  15

Lys Lys Arg Lys Val Gly Ile Arg Ile Pro Gly Glu Lys Pro Phe Gln
                 20                  25                  30

Cys Lys Thr Cys Gln Arg Lys Phe Ser Arg Ser Asp His Leu Lys Thr
             35                  40                  45

His Thr Arg Thr His Thr Gly Glu Lys Pro Tyr Val Cys Ser Lys Cys
    50                  55                  60

Gly Lys Ala Phe Thr Gln Ser Ser Asn Leu Thr Val His Gln Lys Ile
 65                  70                  75                  80

His Thr Gly Glu Lys Pro Tyr Glu Cys His Asp Cys Gly Lys Ser Phe
                 85                  90                  95

Arg Gln Ser Thr His Leu Thr Arg His Arg Arg Ile His Thr Gly Glu
            100                 105                 110

Lys Pro Tyr Lys Cys His Gln Cys Gly Lys Ala Phe Ile Gln Ser Phe
        115                 120                 125

Asn Leu Arg Arg His Glu Arg Thr His Thr Gly Glu Lys Ala Ala Ala
    130                 135                 140
```

```
Lys Phe Val Ser Val Thr Phe Glu Asp Val Ala Val Leu Phe Thr Arg
145                 150                 155                 160

Asp Glu Trp Lys Lys Leu Asp Leu Ser Gln Arg Ser Leu Tyr Arg Glu
            165                 170                 175

Val Met Leu Glu Asn Tyr Ser Asn Leu Ala Ser Met Ala Gly Phe Leu
        180                 185                 190

Phe Thr Lys Pro Lys Val Ile Ser Leu Leu Gln Gln Gly Glu Asp Pro
    195                 200                 205

Trp

<210> SEQ ID NO 261
<211> LENGTH: 546
<212> TYPE: DNA
<213> ORGANISM: Artificial Sequence
<220> FEATURE:
<223> OTHER INFORMATION: plasmid sequence
<220> FEATURE:
<221> NAME/KEY: CDS
<222> LOCATION: (1)...(543)

<400> SEQUENCE: 261 atg gtg tac ccc tac gac gtg ccc gac tac gcc gaa ttg cct cca aaa      48
Met Val Tyr Pro Tyr Asp Val Pro Asp Tyr Ala Glu Leu Pro Pro Lys
1               5                   10                  15 aag aag aga aag gta ggg atc cga att ccc ggg gaa aaa ccg tat gag      96
Lys Lys Arg Lys Val Gly Ile Arg Ile Pro Gly Glu Lys Pro Tyr Glu
            20                  25                  30 tgt gat cac tgt gga aaa tcc ttt agc cag agc tct cat ctg aat gtg     144
Cys Asp His Cys Gly Lys Ser Phe Ser Gln Ser Ser His Leu Asn Val
        35                  40                  45 cac aaa aga act cac acc ggg gaa aaa ccg tat aag tgc cct gat tgt     192
His Lys Arg Thr His Thr Gly Glu Lys Pro Tyr Lys Cys Pro Asp Cys
    50                  55                  60 ggg aag agt ttt agt cag agt tcc agc ctc att cgc cac cag cgg aca     240
Gly Lys Ser Phe Ser Gln Ser Ser Ser Leu Ile Arg His Gln Arg Thr
65                  70                  75                  80 cac acc ggg gaa aaa ccg tat gag tgt cac gat tgc gga aag tcc ttt     288
His Thr Gly Glu Lys Pro Tyr Glu Cys His Asp Cys Gly Lys Ser Phe
                85                  90                  95 agg cag agc acc cac ctc act cgg cac cgg agg atc cac acc ggt gaa     336
Arg Gln Ser Thr His Leu Thr Arg His Arg Arg Ile His Thr Gly Glu
            100                 105                 110 aaa gcg gcc gct aaa ttc gtg tca gtg aca ttt gaa gat gtg gct gtg     384
Lys Ala Ala Ala Lys Phe Val Ser Val Thr Phe Glu Asp Val Ala Val
        115                 120                 125 ctc ttt act cgg gac gag tgg aag aag ctg gat ctg tct cag aga agc     432
Leu Phe Thr Arg Asp Glu Trp Lys Lys Leu Asp Leu Ser Gln Arg Ser
    130                 135                 140 ctg tac cgt gag gtg atg ctg gag aat tac agc aac ctg gcc tcc atg     480
Leu Tyr Arg Glu Val Met Leu Glu Asn Tyr Ser Asn Leu Ala Ser Met
145                 150                 155                 160 gca gga ttc ctg ttt acc aaa cca aag gtg atc tcc ctg ttg cag caa     528
Ala Gly Phe Leu Phe Thr Lys Pro Lys Val Ile Ser Leu Leu Gln Gln
                165                 170                 175 gga gag gat ccc tgg taa                                              546
Gly Glu Asp Pro Trp
            180
```